(12) United States Patent
Jenkins et al.

(10) Patent No.: US 11,572,590 B2
(45) Date of Patent: *Feb. 7, 2023

(54) METHODS FOR EVALUATING TUMOR CELL SPHEROIDS USING 3D MICROFLUIDIC CELL CULTURE DEVICE

(71) Applicant: Dana-Farber Cancer Institute, Inc., Boston, MA (US)

(72) Inventors: Russell W. Jenkins, Boston, MA (US); David Barbie, Andover, MA (US); Cloud P. Paweletz, Boston, MA (US); Elena Ivanova, Brookline, MA (US); Amir Aref, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 427 days.

This patent is subject to a terminal disclaimer.

(21) Appl. No.: 16/498,907

(22) PCT Filed: Mar. 30, 2018

(86) PCT No.: PCT/US2018/025390
§ 371 (c)(1),
(2) Date: Sep. 27, 2019

(87) PCT Pub. No.: WO2018/183839
PCT Pub. Date: Oct. 4, 2018

(65) Prior Publication Data
US 2021/0087635 A1    Mar. 25, 2021

Related U.S. Application Data

(60) Provisional application No. 62/480,192, filed on Mar. 31, 2017.

(51) Int. Cl.
*C12Q 1/6886* (2018.01)
*G01N 33/50* (2006.01)
(Continued)

(52) U.S. Cl.
CPC .......... *C12Q 1/6886* (2013.01); *C12M 23/16* (2013.01); *C12N 1/04* (2013.01); *C12N 9/6491* (2013.01);
(Continued)

(58) Field of Classification Search
CPC .......................... C12Q 1/6886; C12N 9/6491
See application file for complete search history.

(56) References Cited

U.S. PATENT DOCUMENTS

| 5,726,009 A | 3/1998 | Connors et al. |
| 8,748,180 B2 | 6/2014 | Shuler et al. |

(Continued)

FOREIGN PATENT DOCUMENTS

| EP | 2741083 A1 | 6/2014 |
| JP | 2013-507922 A | 3/2013 |

(Continued)

OTHER PUBLICATIONS

Astolfi et al. Lab Chip. 2016. 16:312-325. First published on Dec. 2, 2015. (Year: 2015).*

(Continued)

*Primary Examiner* — Joseph G. Dauner
(74) *Attorney, Agent, or Firm* — Wolf, Greenfield & Sacks, P.C.

(57) ABSTRACT

Provided herein are methods for evaluating tumor cell spheroids in a three-dimensional microfluidic device by determining changes in the relative levels of live cells and dead cells in aliquots cultured under different conditions. Methods described herein allow ex vivo recapitulation of the tumor microenvironment such that the in vivo effectiveness of a test compound in treating tumor tissue may be predicted.

20 Claims, 87 Drawing Sheets

Specification includes a Sequence Listing.

(51) Int. Cl.

| | |
|---|---|
| C12M 3/06 | (2006.01) |
| C12N 1/04 | (2006.01) |
| C12N 9/64 | (2006.01) |
| C12Q 1/6869 | (2018.01) |
| C12Q 1/6881 | (2018.01) |
| G01N 33/58 | (2006.01) |

(52) U.S. Cl.
CPC ......... *C12Q 1/6869* (2013.01); *C12Q 1/6881* (2013.01); *G01N 33/5082* (2013.01); *G01N 33/582* (2013.01); *C12Y 304/24007* (2013.01)

(56) References Cited

U.S. PATENT DOCUMENTS

| | | | |
|---|---|---|---|
| 10,472,599 | B2 | 11/2019 | Barbie et al. |
| 11,098,369 | B2 * | 8/2021 | Barbie ................. C12Q 1/6881 |
| 2009/0081639 | A1 | 3/2009 | Hill et al. |
| 2010/0111768 | A1 | 5/2010 | Banerjee et al. |
| 2010/0291584 | A1 | 11/2010 | Tseng et al. |
| 2011/0159522 | A1 | 6/2011 | Kamm et al. |
| 2012/0135452 | A1 | 5/2012 | Shuler et al. |
| 2013/0143230 | A1 | 6/2013 | Tolias et al. |
| 2014/0057311 | A1 | 2/2014 | Kamm et al. |
| 2014/0221225 | A1 | 8/2014 | Danen et al. |
| 2015/0344473 | A1 | 12/2015 | Du et al. |
| 2017/0369829 | A1 | 12/2017 | Barbie et al. |
| 2019/0112666 | A1 | 4/2019 | Barbie et al. |
| 2020/0032187 | A1 | 1/2020 | Barbie et al. |

FOREIGN PATENT DOCUMENTS

| | | | |
|---|---|---|---|
| JP | H06-505636 B2 | 3/2013 | |
| WO | WO 92/15700 A1 | 9/1992 | |
| WO | WO 2011/046884 A2 | 4/2011 | |
| WO | WO 2014/164464 A1 | 10/2014 | |
| WO | WO 2015/200832 A1 | 12/2015 | |
| WO | WO 2016/069493 A2 | 5/2016 | |
| WO | WO-2016112172 A1 * | 7/2016 | ........... C12N 5/0693 |
| WO | WO 2018/090375 A1 | 5/2018 | |

OTHER PUBLICATIONS

Nakamura et al. Life Sciences. 2002. 70:791-798. (Year: 2002).*
International Search Report and Written Opinion for Application No. PCT/US2018/025390, dated Jun. 25, 2018.
International Search Report and Written Opinion for PCT/US2016/012450 dated Apr. 8, 2016.
International Preliminary Report on Patentability for PCT/US2016/012450 dated Jul. 20, 2017.
Extended European Search Report for EP 167354301.8 dated Dec. 19, 2018.
Corrected European Search Report for EP 167354301.8 dated Aug. 7, 2019.
International Preliminary Report on Patentability for PCT/US2018/025390 dated Oct. 10, 2019.
Extended European Search Report for EP 18775414.8 dated Nov. 25, 2020.
Adams et al., Molecular regulation of angiogenesis and lymphangiogenesis. Nat Rev Mol Cell Biol. Jun. 2007;8(6):464-78.
Amman et al., Development of an innovative 3D cell culture system to study tumour—stroma interactions in non-small cell lung cancer cells. PLoS One. Mar. 24, 2014;9(3):e92511. doi: 10.1371/journal.pone.0092511. eCollection 2014.
Aref et al., Screening therapeutic EMT blocking agents in a three-dimensional microenvironment. Integr Biol (Camb). Feb. 2013;5(2):381-9. doi: 10.1039/c2ib20209c.
Botchkina et al., New-generation taxoid SB-T-1214 inhibits stem cell-related gene expression in 3D cancer spheroids induced by purified colon tumor-initiating cells. Mol Cancer. Jul. 14, 2010;9:192. doi:10.1186/1476-4598-9-192.
Carbognin et al., Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. Jun. 18, 2015;10(6):e0130142. doi: 10.1371/journal.pone.0130142. eCollection 2015.
Crystal et al., Patient-derived models of acquired resistance can identify effective drug combinations for cancer. Science. Dec. 19, 2014;346(6216):1480-6. doi: 10.1126/science.1254721. Epub Nov. 13, 2014.
Gao et al., Organoid cultures derived from patients with advanced prostate cancer. Cell. Sep. 25, 2014;159(1):176-87. doi: 10.1016/j.cell.2014.08.016. Epub Sep. 4, 2014.
Gerdes et al., Highly multiplexed single-cell analysis of formalin-fixed, paraffin-embedded cancer tissue. Proc Natl Acad Sci U S A. Jul. 16, 2013;110(29):11982-7. doi: 10.1073/pnas.1300136110. Epub Jul. 1, 2013.
Hasan et al., A Low-Cost Digital Microscope with Real-Time Fluorescent Imaging Capability. PLoS One. Dec. 15, 2016;11(12):e0167863. doi: 10.1371/journal.pone.0167863. eCollection 2016.
Hasan et al.,Cutting Edge: Inhibiting TBK1 by Compound II Ameliorates Autoimmune Disease in Mice. J Immunol Nov. 15, 2015, 195 (10) 4573-4577.
Hsieh et al., The effect of primary cancer cell culture models on the results of drug chemosensitivity assays: the application of perfusion microbioreactor system as cell culture vessel. Biomed Res Int. 2015;2015:470283. doi: 10.1155/2015/470283. Epub Jan. 14, 2015.
Kondo et al., Retaining cell-cell contact enables preparation and culture of spheroids composed of pure primary cancer cells from colorectal cancer. Proc Natl Acad Sci U S A. Apr. 12, 2011;108(15):6235-40. doi: 10.1073/pnas.1015938108. Epub Mar. 28, 2011.
Lash et al., Comparison of three multiplex cytokine analysis systems: Luminex, SearchLight and FAST Quant. J Immunol Methods. Feb. 20, 2006;309(1-2):205-8. Epub Jan. 18, 2006.
Li et al., Microfluidic 3D cell culture: potential application for tissue-based bioassays. Bioanalysis. 2012;4(12):1509-1525. doi:10.4155/bio.12.133.
Lo et al.,The melanoma revolution: from UV carcinogenesis to a new era in therapeutics. Science. Nov. 21, 2014;346(6212):945-9. doi: 10.1126/science.1253735.
Loessner et al., Bioengineered 3D platform to explore cell-ECM interactions and drug resistance of epithelial ovarian cancer cells. Biomaterials. Nov. 2010;31(32):8494-506. doi: 10.1016/j.biomaterials.2010.07.064. Epub Aug. 14, 2010.
Morton et al., Establishment of human tumor xenografts in immunodeficient mice. Nat Protoc. 2007;2(2):247-50.
Niles et al., Monitor the Ratio of Live and Dead Cells Within a Population. MultiTox Fluor Multiplex Cytotoxicity Assay. Promega Notes. 2006;94:22-26.
Perfetto et al., Amine reactive dyes: an effective tool to discriminate live and dead cells in polychromatic flow cytometry. J Immunol Methods. Jun. 30, 2006;313(1-2):199-208. Epub May 19, 2006.
Sabhachandani et al., Generation and functional assessment of 3D multicellular spheroids in droplet based microfluidics platform. Lab Chip. Feb. 7, 2016;16(3):497-505. doi: 10.1039/c5lc01139f.
Seguin et al., An integrin $\beta_3$-KRAS-Ra1B complex drives tumour sternness and resistance to EGFR inhibition. Nat Cell Biol. May 2014;16(5):457-68. doi: 10.1038/ncb2953. Epub Apr. 20, 2014.
Shin et al., Integration of intra- and extravasation in one cell-based microfluidic chip for the study of cancer metastasis. Lab Chip. Nov. 21, 2011;11(22):3880-7. doi: 10.1039/c11c20671k. Epub Oct. 5, 2011.
Shinohara et al., Structure and chromosomal localization of the human PD-1 gene (PDCD1).Genomics. Oct. 1994;23(3):704-6.
Siolas et al., Patient-derived tumor xenografts: transforming clinical samples into mouse models. Cancer Res. Sep. 1, 2013;73(17):5315-9. doi: 10.1158/0008-5472.CAN-13-1069. Epub Jun. 3, 2013.
Stanton et al., Current methods for assaying angiogenesis in vitro and in vivo. Int J Exp Pathol. Oct. 2004;85(5):233-48.

(56) References Cited

OTHER PUBLICATIONS

Sundlisaeter et al., Primary glioma spheroids maintain tumourogenicity and essential phenotypic traits after cryopreservation. Neuropathol Appl Neurobiol. Aug. 2006;32(4):419-27. doi: 10.1111/j.1365-2990.2006.00744.x. PMID: 16866987.

Taube et al., Differential Expression of Immune-Regulatory Genes Associated with PD-L1 Display in Melanoma: Implications for PD-1 Pathway Blockade. Clin Cancer Res. Sep. 1, 2015;21(17):3969-76. doi: 10.1158/1078-0432.CCR-15-0244. Epub May 5, 2015.

Tentler et al., Patient-derived tumour xenografts as models for oncology drug development. Nat Rev Clin Oncol. Apr. 17, 2012;9(6):338-50. doi: 10.1038/nrclinonc.2012.61.

Thiery, Epithelial-mesenchymal transitions in tumour progression. Nat Rev Cancer. Jun. 2002;2(6):442-54.

Yao et al., TGF-beta IL-6 axis mediates selective and adaptive mechanisms of resistance to molecular targeted therapy in lung cancer. Proc Natl Acad Sci U S A. Aug. 31, 2010;107(35):15535-40. doi: 10.1073/pnas.1009472107. Epub Aug. 16, 2010.

Yu et al., Cancer therapy. Ex vivo culture of circulating breast tumor cells for individualized testing of drug susceptibility. Science. Jul. 11, 2014;345(6193):216-20. doi: 10.1126/science.1253533.

Yu et al., TBK1 inhibitors: a review of patent literature (2011-2014). Expert Opin Ther Pat. 2015;25(12):1385-96. doi: 10.1517/13543776.2015.1081168. Epub Aug. 19, 2015.

Zhu et al., Inhibition of KRAS-driven tumorigenicity by interruption of an autocrine cytokine circuit. Cancer Discov. Apr. 2014;4(4):452-65. doi: 10.1158/2159-8290.CD-13-0646. Epub Jan. 20, 2014.

\* cited by examiner

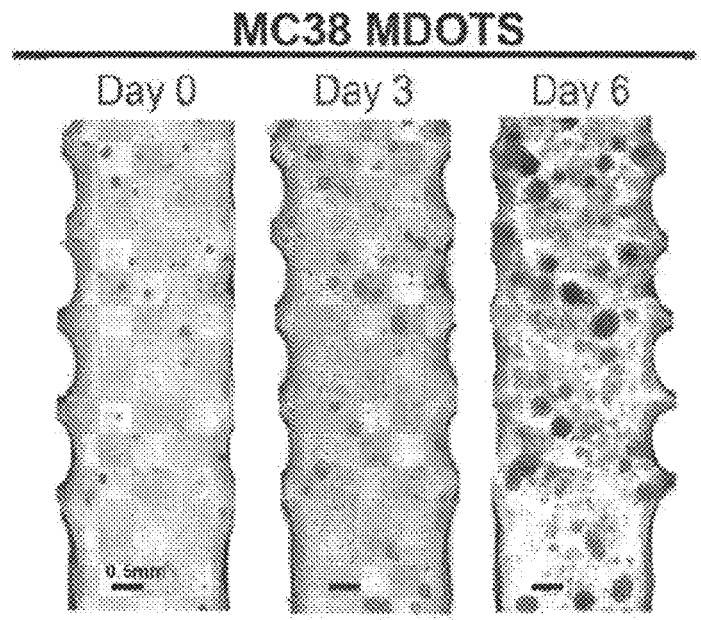
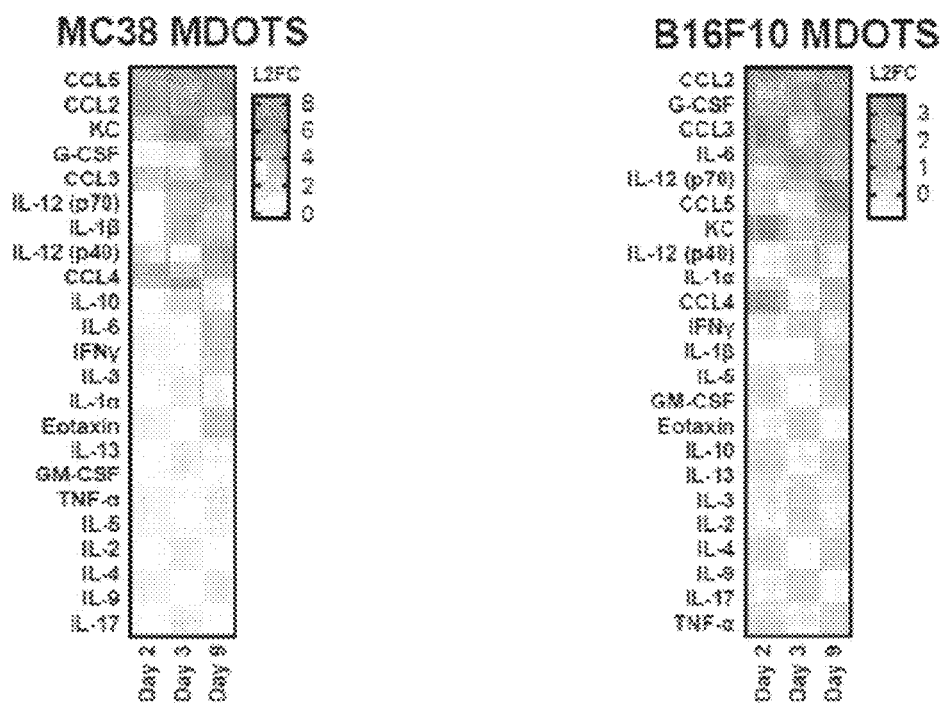
FIG. 2A
FIG. 2B
FIG. 2C

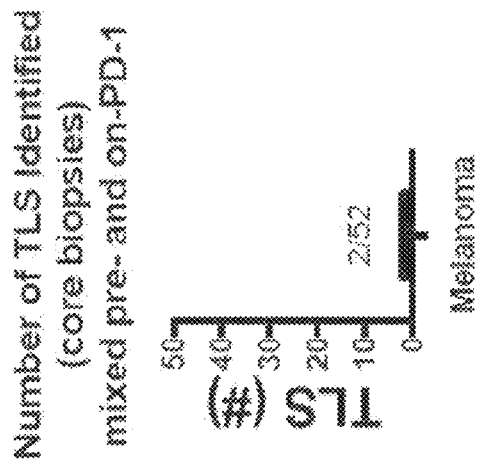
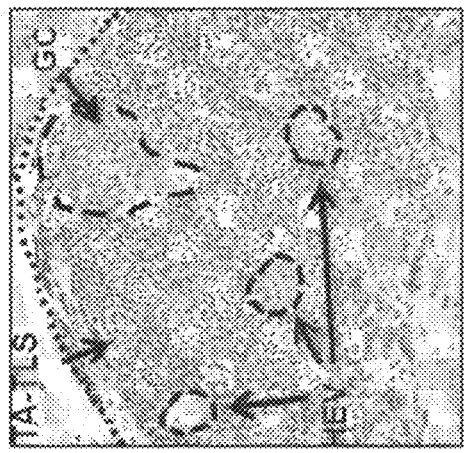
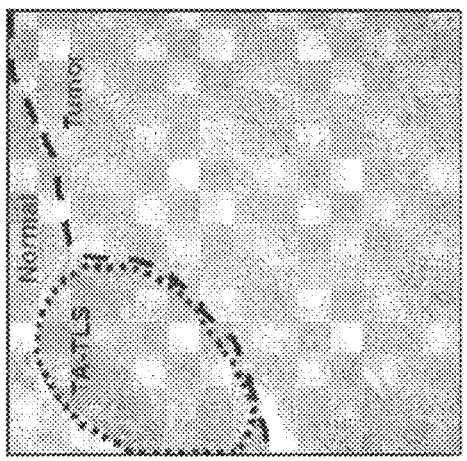
FIG. 11A

METHODS FOR EVALUATING TUMOR CELL SPHEROIDS USING 3D MICROFLUIDIC CELL CULTURE DEVICE

RELATED APPLICATIONS

This application is a national stage filing under 35 U.S.C. 371 of International Patent Application Serial No. PCT/US2018/025390, filed Mar. 30, 2018, which claims the benefit of U.S. provisional application No. 62/480,192, filed on Mar. 31, 2017. The entire contents of each of these applications are incorporated herein by reference in their entirety.

FEDERALLY SPONSORED RESEARCH

This invention was made with government support under K08 CA138918-01A1 and R01 CA190394-01 awarded by the National Institutes of Health. The government has certain rights in the invention.

REFERENCE TO A SEQUENCE LISTING SUBMITTED AS A TEXT FILE VIA EFS-WEB RELATED APPLICATIONS

The present application contains a Sequence Listing which has been submitted in ASCII format via EFS-Web and is hereby incorporated by reference in its entirety. Said ASCII copy, created on Sep. 27, 2019, is named D050470136US01-SEQ-CB and is 2,763 bytes in size.

BACKGROUND

Existing patient-derived cancer models, including circulating tumor cells (CTCs), organoid cultures, and patient-derived xenografts (PDXs) can guide precision cancer therapy, but take weeks to months to generate and lack the native tumor immune microenvironment. Current approaches to study anti-tumor immune responses in patients are also limited by remote measurements in whole blood or plasma, or static assessment of biopsies.

Recently there has been developed a 3D microfluidic device for the short-term culture of murine- and patient-derived organotypic tumor spheroids. Cultured tumor spheroids are believed by some to more closely resemble the native immune microenvironment.

It would be desirable to be able to assess the effects of single drugs and combinations of drugs on tumor cells in the tumor micro-environment. It would be particularly helpful if there were a way to evaluate simultaneously the effects of a combination of immune blockade and anticancer compounds ex vivo. To date, efforts to evaluate tumor cells have been confounded by (i) the tumor cells changing when removed from the body, (ii) the absence of an intact immune system communicating with the tumor microenvironment when the tumor cells are removed from the body, (iii) the inability to distinguish the effects of tumor removal and culturing from the effects of a drug applied in vitro, and (iv) the complexity of measuring at a molecular level immune based markers and other markers which might predict whether a drug might work in vivo based on experiments conducted in vitro. To date, there is no simple assay for evaluating in in a high throughput manner the effects of drugs on human cancer cells in a native tumor microenvironment.

SUMMARY

It has been discovered, surprisingly, that the tumor microenvironment of a cultured tumor spheroid contains sufficient immune components to be predictive of a drug's activity when administered in vivo. It has been discovered, surprisingly, that the tumor microenvironment of a cultured tumor spheroid contains sufficient immune components such that combinations of immune blockade compounds and anti-cancer drugs can be assessed, the results being predictive of administering the drugs in vivo. It has been discovered, surprisingly, that the tumor microenvironment of a cultured tumor spheroid can be evaluated optically and reproducibly, to establish the effects of drugs on the tumor cells within the spheroids, while distinguishing the effects on tumor cells resulting from the act of culturing the tumor cells. It has been discovered, surprisingly, that such techniques for evaluating tumor spheroids can be utilized in a high throughput method for determining the relative amounts of live and dead cells in an environment mimicking that occurring in vivo.

In one aspect, the invention involves a novel approach for evaluating ex vivo response to Immune Checkpoint Blockade (ICB) using murine- and patient-derived organotypic tumor spheroids (MDOTS/PDOTS) cultured in a 3-dimensional microfluidic system. Spheroids isolated from fresh mouse and human tumor samples retain autologous lymphoid and myeloid cell populations, including antigen-experienced tumor infiltrating CD4 and CD8 T lymphocytes, and respond to ICB in short-term ex vivo culture. Tumor killing was recapitulated ex vivo using MDOTS derived from the anti-PD-1 sensitive MC38 syngeneic mouse cancer model, whereas relative resistance to anti-PD-1 therapy was preserved in the CT26 and B16F10 syngeneic models. Systematic cytokine/chemokine profiling following PD-1 blockade in PDOTS from patients with melanoma and other tumors identified significant induction of the immunoattractants CCL19 and CXCL13, which was confirmed in vivo and correlated with evidence of intratumoral immune cell infiltration. Resistance to anti-PD1 treatment in MDOTS and PDOTS also tracked with conduction of immune suppressive chemokines. Ex vivo profiling revealed a combination therapy as a novel therapeutic strategy to enhance sensitivity to PD-1 blockade in this setting, which effectively predicted tumor response in vivo. These findings demonstrate feasibility of ex vivo profiling of PD-1 blockade, and offer a novel functional approach to facilitate precision immunooncology and develop novel therapeutic combinations.

According to one aspect of the invention, a method for evaluating tumor cell spheroids in a three-dimensional microfluidic device is provided. The method involves:

obtaining tumor spheroids from an enzyme treated tumor sample, suspending a first aliquot of the tumor spheroids in biocompatible gel;

suspending a second aliquot of the tumor spheroids in biocompatible gel;

placing the first aliquot of the tumor spheroids in biocompatible gel in a first three-dimensional device, contacting the first aliquot with a first fluorophore dye selective for dead cells, the first fluorophore dye emitting fluorescence at a first wavelength when bound to a dead cell, contacting the first aliquot with a second fluorophore dye selective for live cells, the second fluorophore dye emitting fluorescence at a second wavelength different from the first wavelength when bound to a live cell, measuring total fluorescence emitted by each of the first and second fluorophore dyes in the first aliquot, culturing the second aliquot in a second three-dimensional device, contacting the second aliquot with the first fluorophore dye, contacting the second aliquot with the second fluorophore dye, wherein the contacting of the second aliquot with the first fluorophore dye and second fluorophore dye is carried out at least 24 hours after the contacting of the first aliquot with the first fluorophore dye and second fluorophore dye, measuring total fluorescence emitted by each of the first and second fluorophore dyes in the second aliquot, wherein an increase or decrease in the ratio of live cells to dead cells in each of the aliquots may be assessed.

In one embodiment, the total fluorescence emitted by each of the first and second fluorophore dyes is measured using a camera, preferably at a resolution of at least 2×, at least 3×, at least 4× or more, from directly above or below each three-dimensional device, and preferably wherein the three-dimensional devices are placed on a moveable stage permitting the camera to capture the total fluorescence in each aliquot.

In some embodiments, the dead cell fluorescence and the live cell fluorescence can be added together to yield a live and dead cell total. The amount of dead cells may be expressed as a percentage of the dead cell fluorescence to the total fluorescence. The amount of live cells can be expressed as a percentage of the live cell fluorescence to the total. In some embodiments, the dead cell fluorescence and the live cell fluorescence can be expressed as a ratio, that is, dead cells/live cells or live cells/dead cells. In this manner, changes to the number of dead cells to live cells can be tracked over time, wherein an initial ratio is established prior to culturing and changes to the ratio are determined over time.

In some embodiments, there are multiple aliquots of tumor spheroids, for example three, or four, or five, or six or more than six, and the contacting of the third, fourth, fifth, sixth or more than sixth such aliquots with the first fluorophore dye and second fluorophore dye is carried out, for example, two days, three days, four days, five days, and more than five days, respectively, after the contacting of the first aliquot with the first fluorophore dye and second fluorophore dye. The timing of testing aliquots may be separated by any time period, such as one day, less than a day, two days or three or more days. In one embodiment, an aliquot is tested six days after placing the spheroids in the gel.

In any of the embodiments, the second (or any subsequent) aliquot is contacted with at least one test compound during the culturing of the second aliquot and wherein said culturing of the second aliquot in the presence of the test compound occurs for at least 24 hours, at least two days, at least three days, at least four days, at least five days, or at least 6 days or more.

In any of the foregoing embodiments, the second aliquot can be contacted with at least two test compounds during the culturing of the second aliquot and wherein said culturing of the second aliquot in the presence of the test compounds occurs for at least 24 hours, at least two days, at least three days, at least four days, at least five days, or at least 6 days, and preferably wherein at least one of the test compounds is an immune checkpoint inhibitor.

The number of spheroids can be any number of spheroids convenient and available to the researcher, but in the system described below, the number of spheroids in the first and the second aliquots each contain between about 15 and 30 spheroids, preferably between about 20 and 25 spheroids.

In some embodiments, the first three-dimensional device can be a first three-dimensional microfluidic device and the second three-dimensional device can be a second three-dimensional microfluidic device. In some embodiments, the culturing of the first aliquot in the first three-dimensional microfluidic device, is for less than 6 hours, less than 3 hours, less than 2 hours and even less than 1 hour prior to contacting the first aliquot with the first and second fluorophore dyes. In particular, it may be desirable to contact the first aliquot with the dyes prior to culturing the spheroids at all, that is essentially upon introducing the spheroids into the three dimensional device.

In any of the foregoing embodiments, the enzyme can be collagenase.

In any of the foregoing embodiments, the first fluorophore dye can be propidium iodide, DRAQ7, 7-AAD, eBioscience Fixable Viability Dye EFLUOR® 455UV, eBioscience Fixable Viability Dye EFLUOR® 450, eBioscience Fixable Viability Dye EFLUOR® 506, eBioscience Fixable Viability Dye EFLUOR® 520, eBioscience Fixable Viability Dye EFLUOR® 660, eBioscience Fixable Viability Dye EFLUOR® 780, BioLegend Zombie AQUA™, BioLegend Zombie NIR™, BioLegend Zombie RED™, BioLegend Zombie VIOLET™, BioLegend Zombie UV™, or BioLegend Zombie YELLOW™, and/or the second fluorophore dye can be acridine orange, nuclear green LCS1 (ab138904), DRAQ5 (ab108410), CyTRAK ORANGE™ NUCLEAR-ID Red DNA stain (ENZ-52406), SiR700-DNA, calcein AM, calcein violet AM, calcein blue AM, VYBRANT® DYECYCLE™ Violet, VYBRANT® DYECYCLE™ Green, VYBRANT® DYECYCLE™ Orange, or VYBRANT® DYECYCLE™ Ruby.

In any of the foregoing embodiments, the tumor spheroids can be obtained by mincing a primary tumor sample in a medium supplemented with serum; treating the minced primary tumor sample with an enzyme; and harvesting tumor spheroids from the enzyme treated sample. In some embodiments, the minced primary tumor sample is treated with the enzyme in an amount and/or for a time sufficient to yield a partial digestion of the minced primary tumor sample, and preferably wherein the treatment is for between 10 minutes and 60 minutes, and more preferably between 15 minutes and 45 minutes at a temperature of 25° C. to 39° C.

In any of the foregoing embodiments, the biocompatible gel can be collagen, BD Matrigel™ Matrix Basement Membrane, or fibrin hydrogel.

In any of the foregoing embodiments, the tumor sample can be derived from a murine model. In some embodiments, the murine model is a syngeneic model selected from the group consisting of Bladder MBT-2, Breast 4T1, EMT6, Colon, Colon26, CT-26, MC38, Fibrosarcoma WEHI-164, Kidney Renca, Leukemia C1498, L1210, Liver H22, KLN205, LL/2, LewisLung, Lymphoma A20 S, E.G7-OVA, EL4, Mastocytoma P815, Melanoma B16-BL6, B16-F10, S91, Myeloma MPC-11, Neuroblastoma Neuro-2a, Ovarian: IDB, Pancreatic Pan02, Plasmacytoma J558, and Prostate RM-1.

In any of the foregoing embodiments, the tumor sample can be a human tumor sample.

In any of the foregoing embodiments, the tumor sample can be a patient derived xenograft (PDX).

In any of the foregoing embodiments, the three-dimensional device can include one or more fluid channels flanked by one or more gel cage regions, wherein the one or more gel cage regions comprises the biocompatible gel in which the tumor spheroids are embedded, and wherein the device recapitulates in vivo tumor microenvironment. In any of the foregoing embodiments, the three-dimensional device can include: a substrate comprised of an optically transparent material and further comprising i) one or more fluid channels; ii) one or more fluid channel inlets; iii) one or more fluid channel outlets; iv) one or more gel cage regions; and v) a plurality of posts; wherein all or a portion of each gel cage region is flanked by all or a portion of one or more fluid channels, thereby creating one or more gel cage region-fluid channel interface regions; each gel cage region comprises at least one row of posts which forms the gel cage region; and the one or more gel cage region has a height of less than 500 µm.

In any of the foregoing embodiments, the test compound can be a small molecule, a nucleic acid molecule, an RNAi compound, an aptamer, a protein or a peptide, an antibody or antigen-binding antibody fragment, a ligand or receptor-binding protein, a gene therapy vector, or a combination thereof. In any of the foregoing embodiments, the first test compound can be a chemotherapeutic compound, an immunomodulatory compound, or radiation. In any of the foregoing embodiments, the first test compound can be an alkylating compound, an antimetabolite, an anthracycline, a proteasome inhibitor, or an mTOR inhibitor. In any of the foregoing embodiments, the first test compound can be an immune modulator.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures and further described for the purpose of illustration throughout the application describe non-limiting embodiments, and in some cases may simplify certain processes or omit features or steps for the purpose of clearer illustration.

Figure 1A:
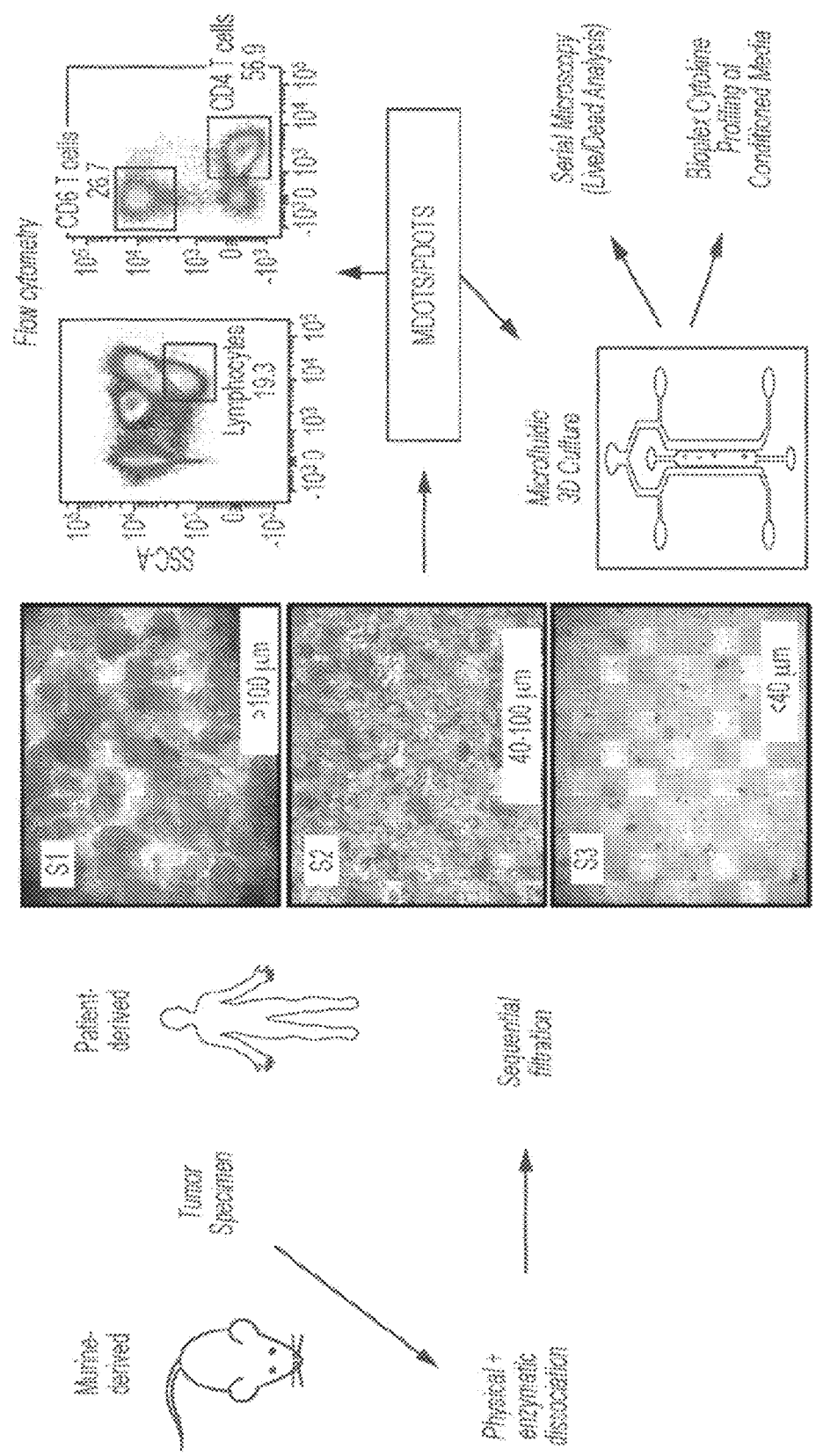

FIG. 1A is a schematic for preparation and analysis of MDOTS/PDOTS (S2 fraction) from murine or patient-derived tumor specimens.

Figure 1B:
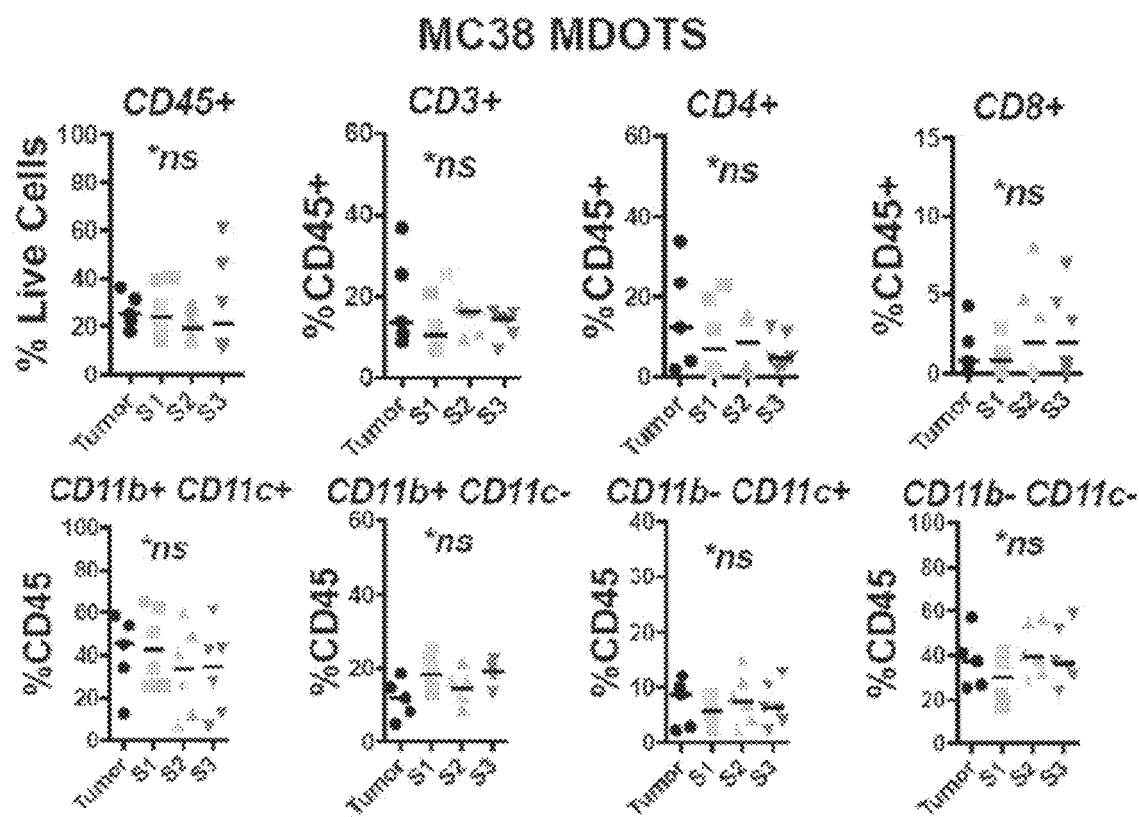

FIG. 1B depicts MC38 allograft immune profiling by flow cytometry comparing bulk tumor (n=5) to S1, S2, S3 (n=6) spheroid fractions (Kruskal-Wallis with Dunn's multiple comparisons test, α=0.05; ns=not significant).

Figure 1C:
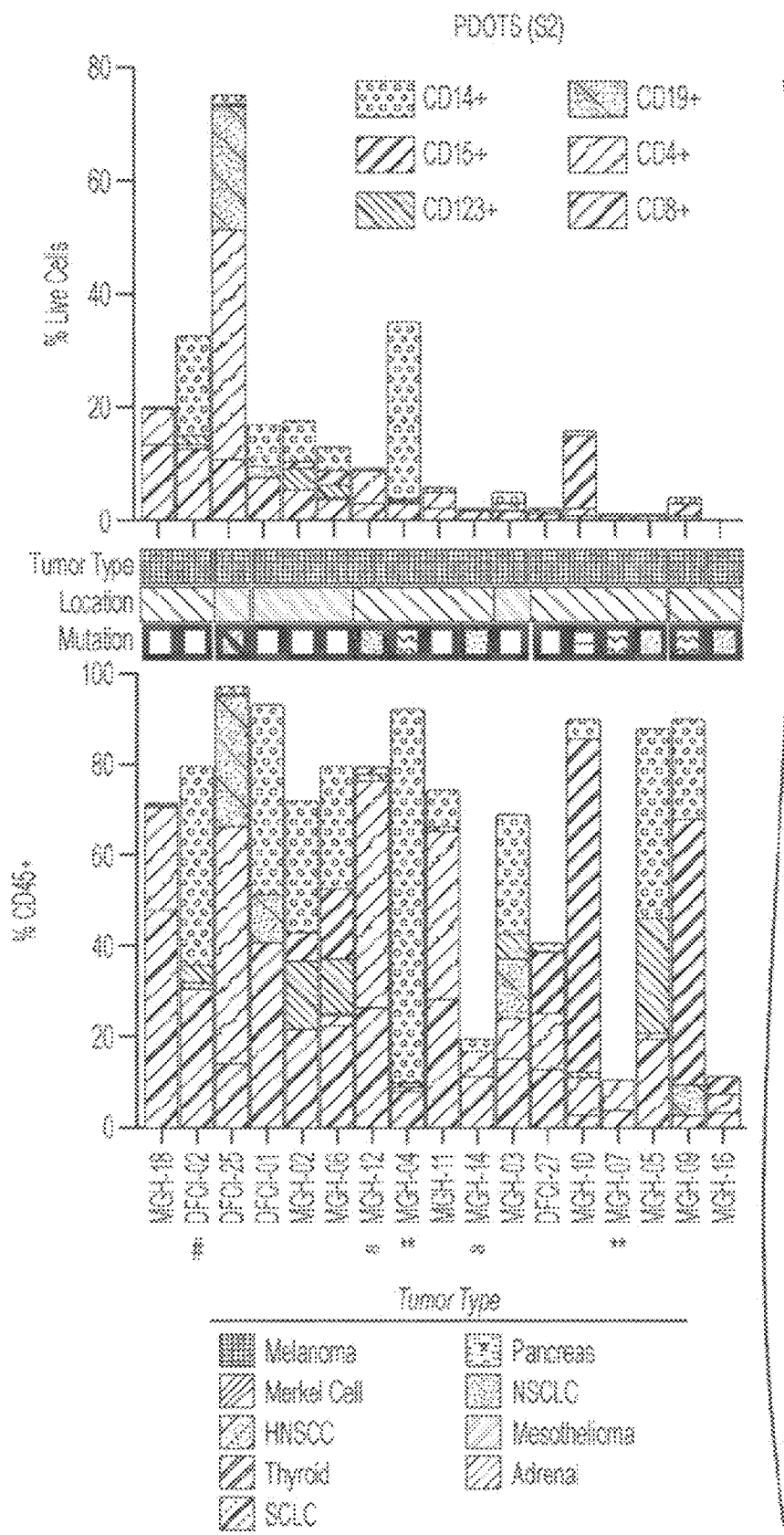
Figure 1D:
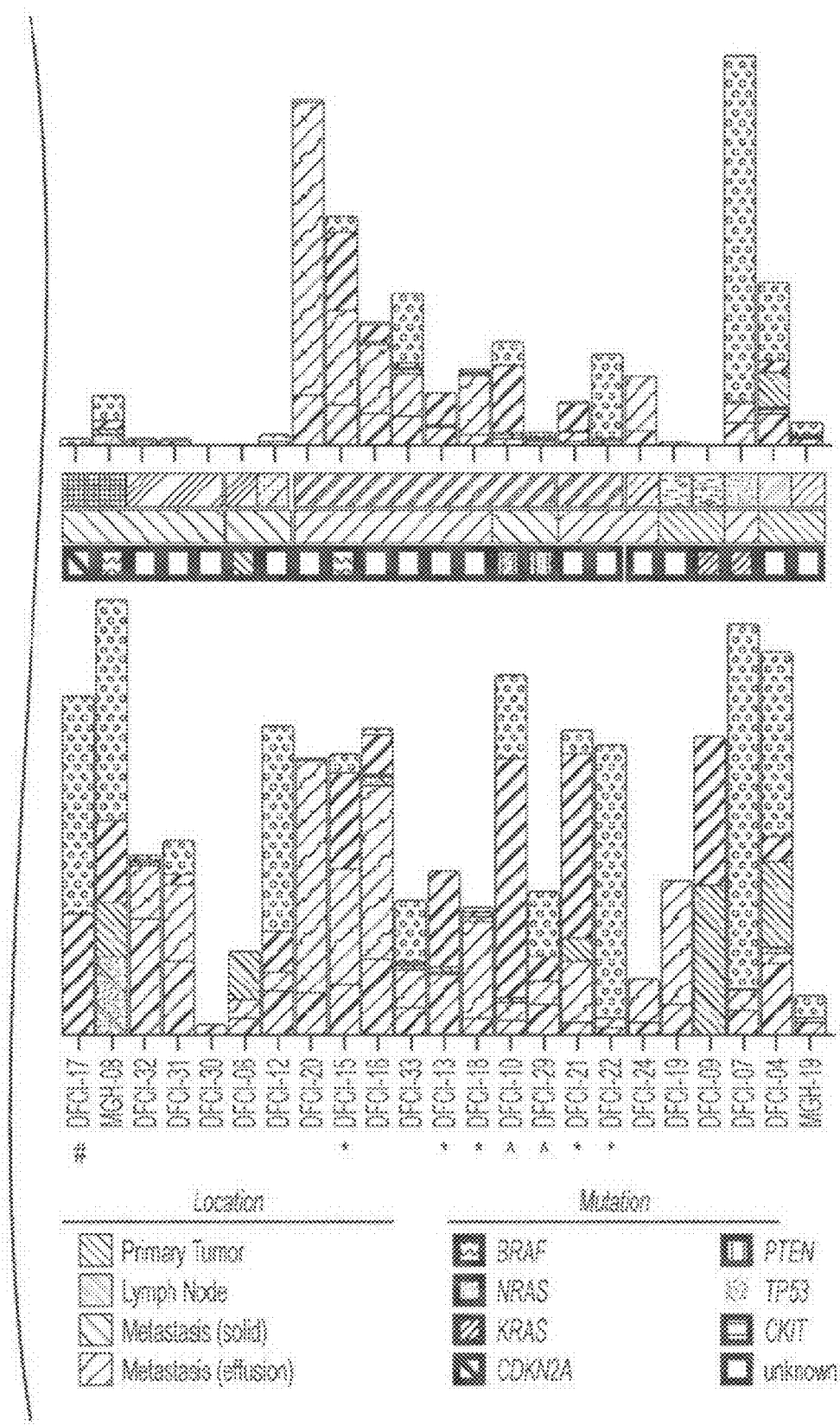

FIGS. 1C-1D depict immune profiling of PDOTS (S2; n=40) (upper panel=% live cells, lower panel=% CD45+ cells) with indicated patient/tumor characteristics, grouped by tumor type and ranked by % CD8+ T cells.

Figure 1E:
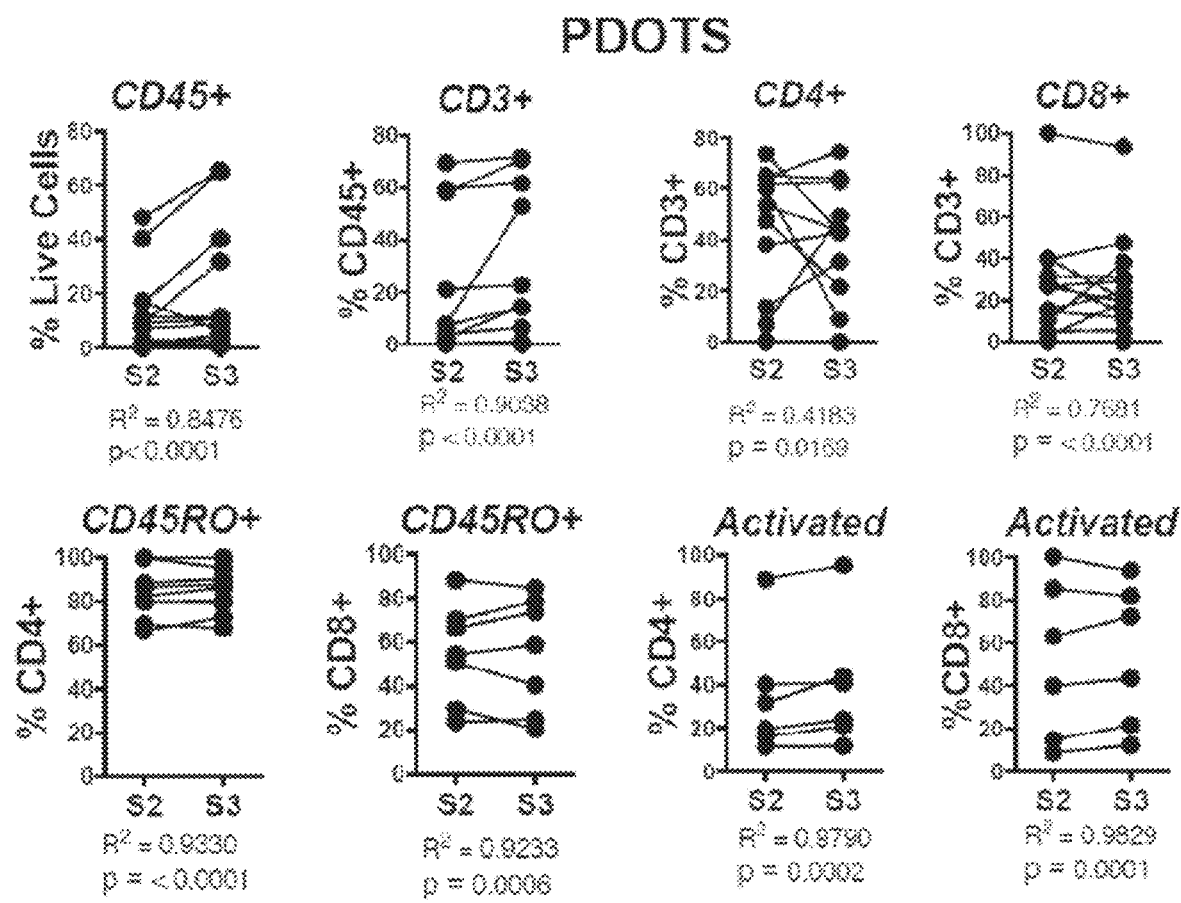

FIG. 1E depicts immune cell correlation of S2/S3 fractions (CD45, n=14; CD3, n=15; CD4/CD8, n=13; CD4+CD45RO+, n=9; CD8+CD45RO+, n=8; activated=CD38+ and/or CD69+, n=6), R2 significant for all comparisons.

Figure 1F:
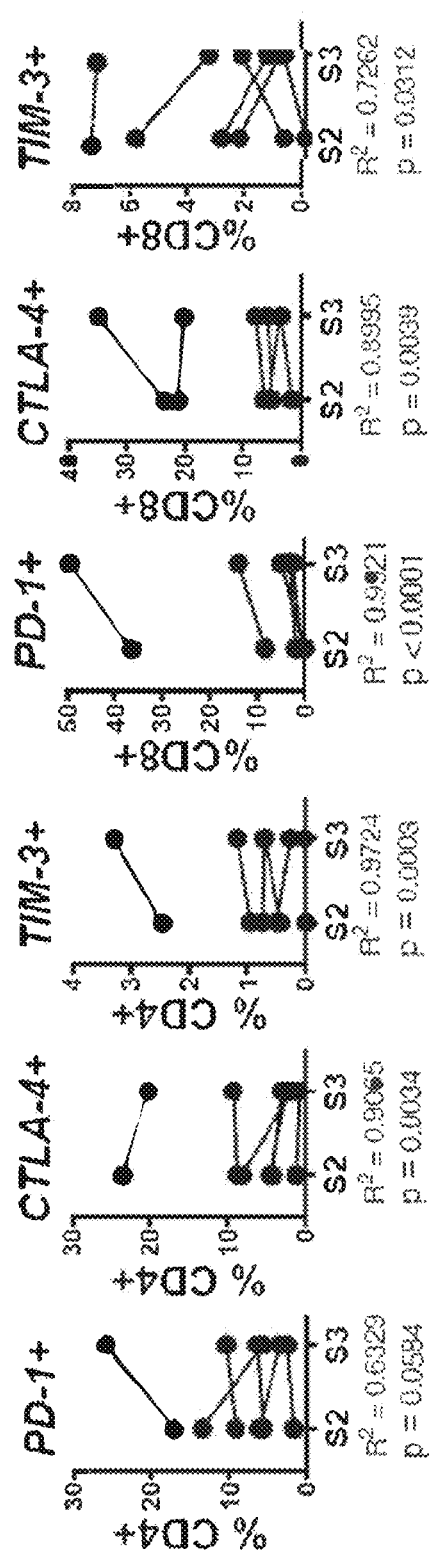

FIG. 1F depicts PD-1, CTLA-4, TIM-3 expression on CD4 and CD8 T cell populations in S2/S3 fractions (n=6), R2 significant for all comparisons.

FIG. 2A depicts phase-contrast imaging (4×) of MC38 MDOTS in 3D microfluidic culture.

FIG. 2B is a cytokine heatmap from cultured MC38 MDOTS expressed as log-2 fold change relative to Day 1.

FIG. 2C is a cytokine heatmap from cultured B16F10 MDOTS expressed as log-2 fold change relative to Day 1.

Figure 2D:
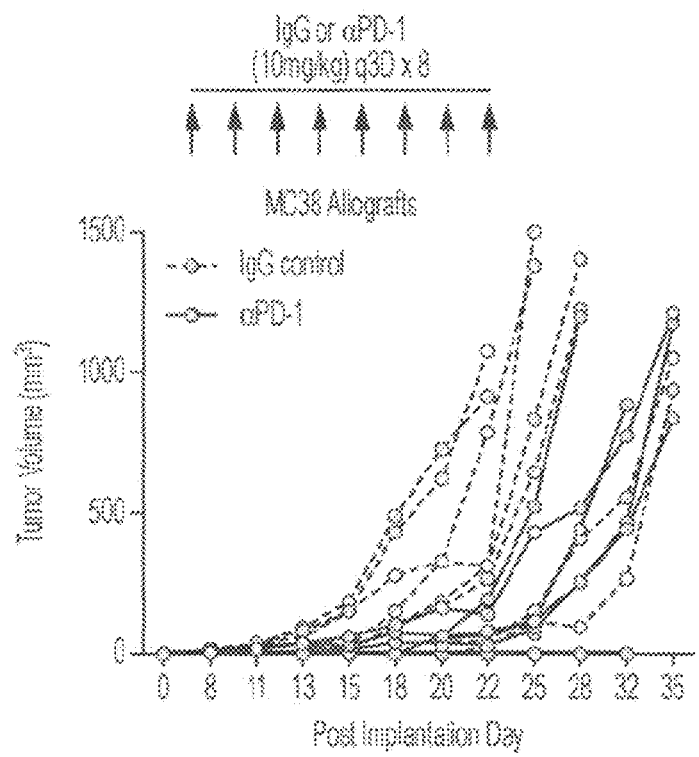

FIG. 2D illustrates MC38 allograft tumor volume following isotype control IgG (n=10) or rat-anti-mouse anti-PD-1 antibody (n=10) treatment.

Figure 2E:
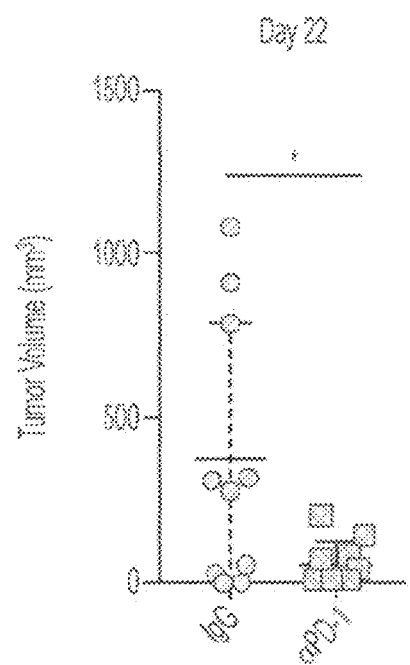

FIG. 2E illustrates Day 22 MC38 tumor volumes (unpaired 2-sided t-test, p<0.05).

Figure 2F:
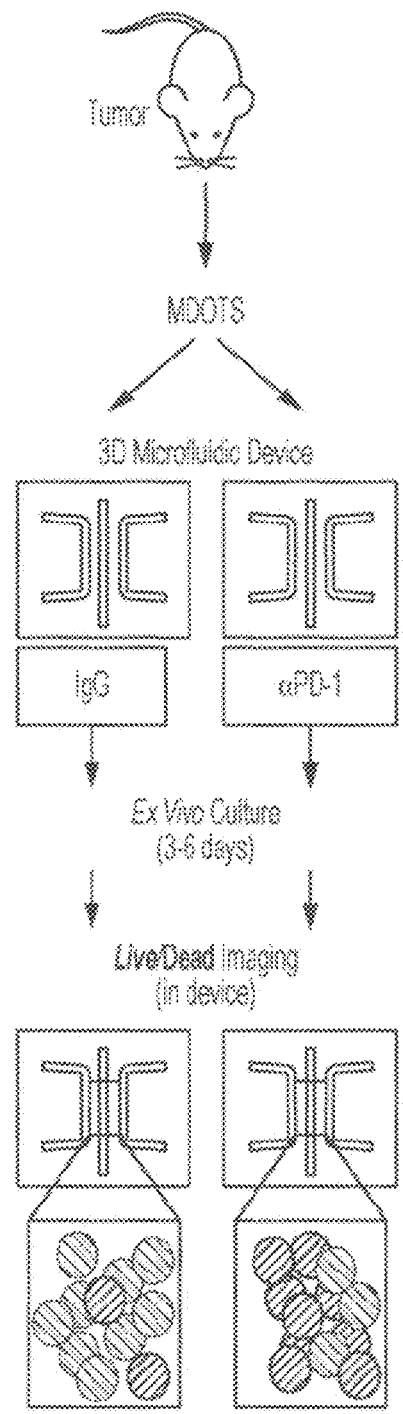

FIG. 2F is a schematic of MDOTS Live/Dead Imaging workflow.

Figure 2G:
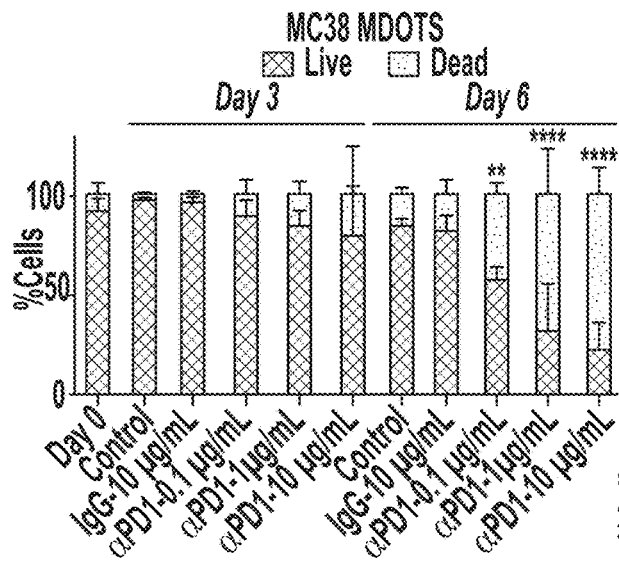

FIG. 2G illustrates Live (AO=green)/dead (PI=red) quantification of MC38 MDOTS Day 0 (immediately after loading), Day 3, and Day 6 following IgG control or indicated anti-PD-1 antibody doses; n=4, biological replicates, p<0.01, **p<0.0001, Kruskal-Wallis Dunnett's with multiple comparisons test).

Figure 2H:
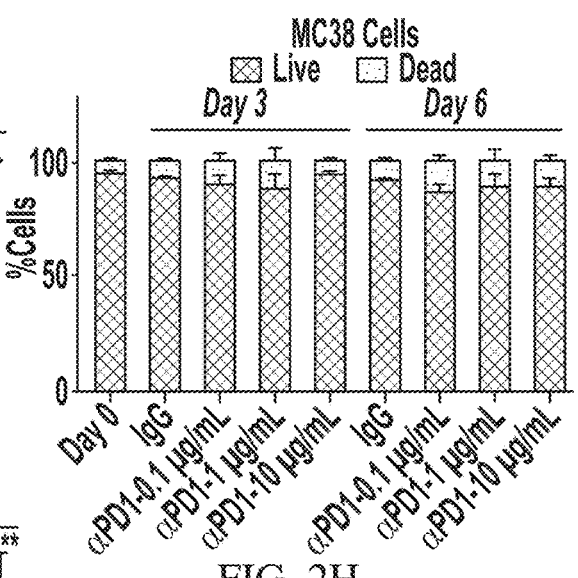

FIG. 2H illustrates Live/dead analysis of MC38 spheroids lacking immune cells±anti-PD1 (n=4, biological replicates).

Figure 2I:
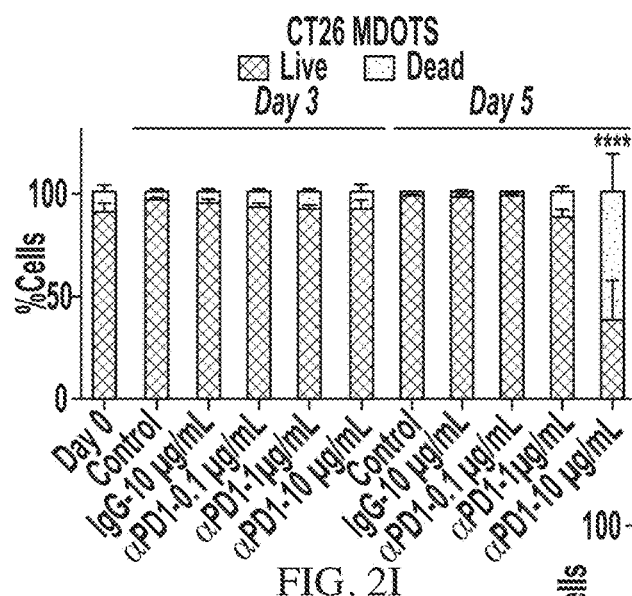

FIG. 2I illustrates Live/dead analysis of CT26 MDOTS±anti-PD1 (n=3, biological replicates, ****p<0.0001).

Figure 2J:
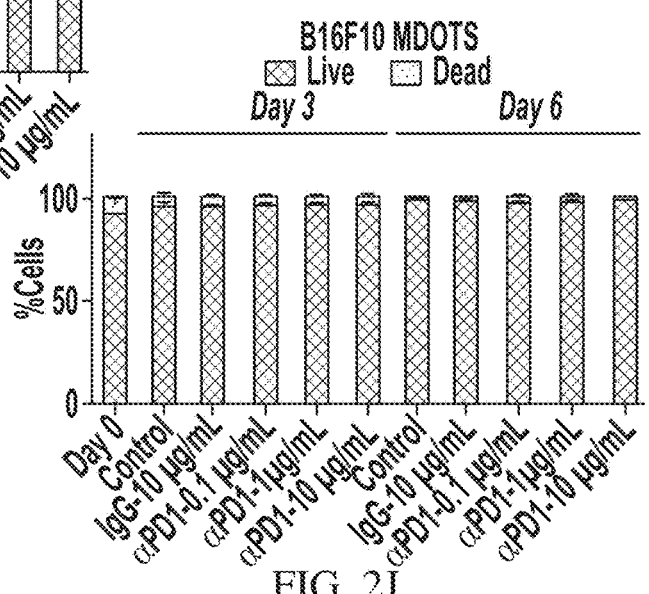

FIG. 2J illustrates Live/dead analysis of B16F10 MDOTS±anti-PD1 (n=3, biological replicates).

Figure 2K:
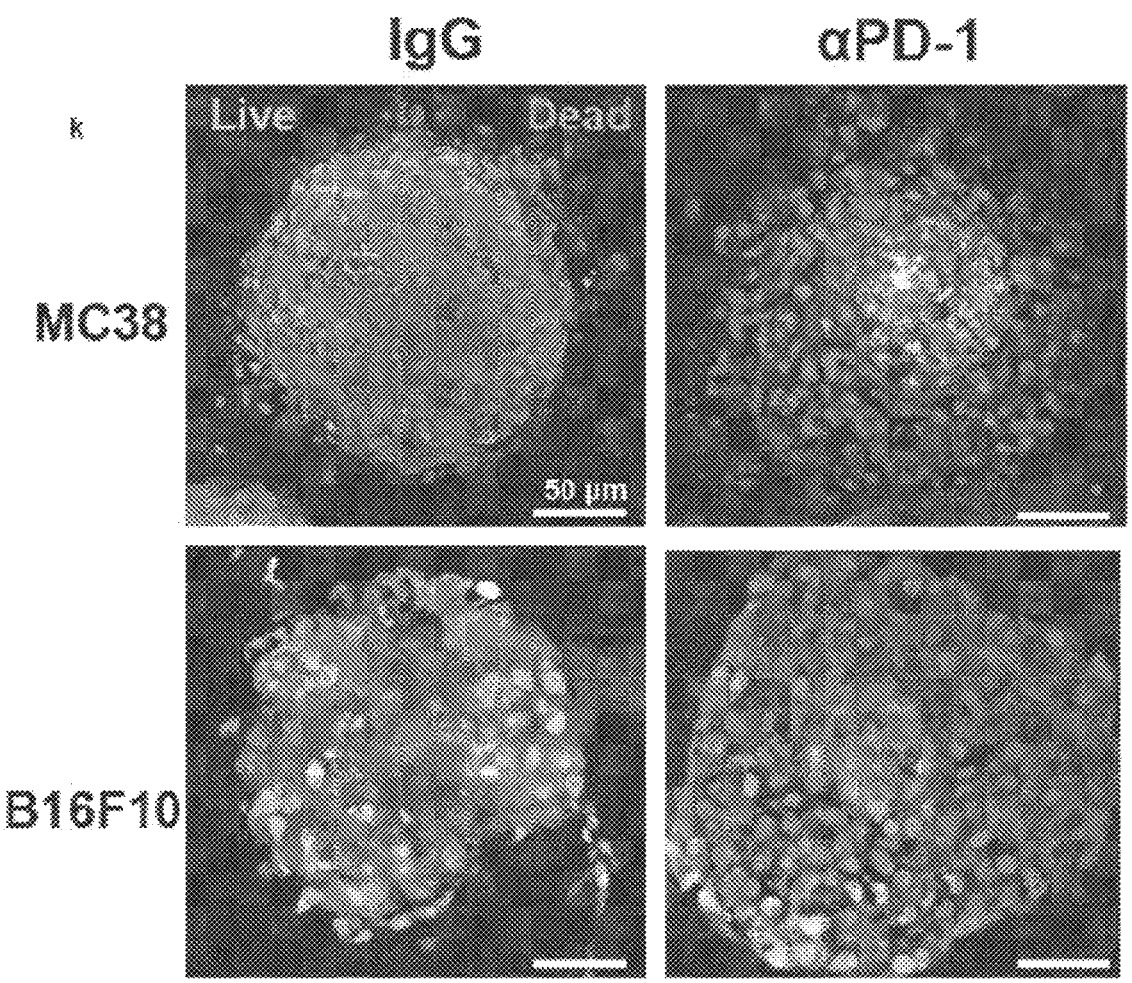

FIG. 2K depicts deconvolution fluorescence microscopy of MC38 and B16F10 MDOTS Day 6±anti-PD1 (representative images shown).

Figure 3A:
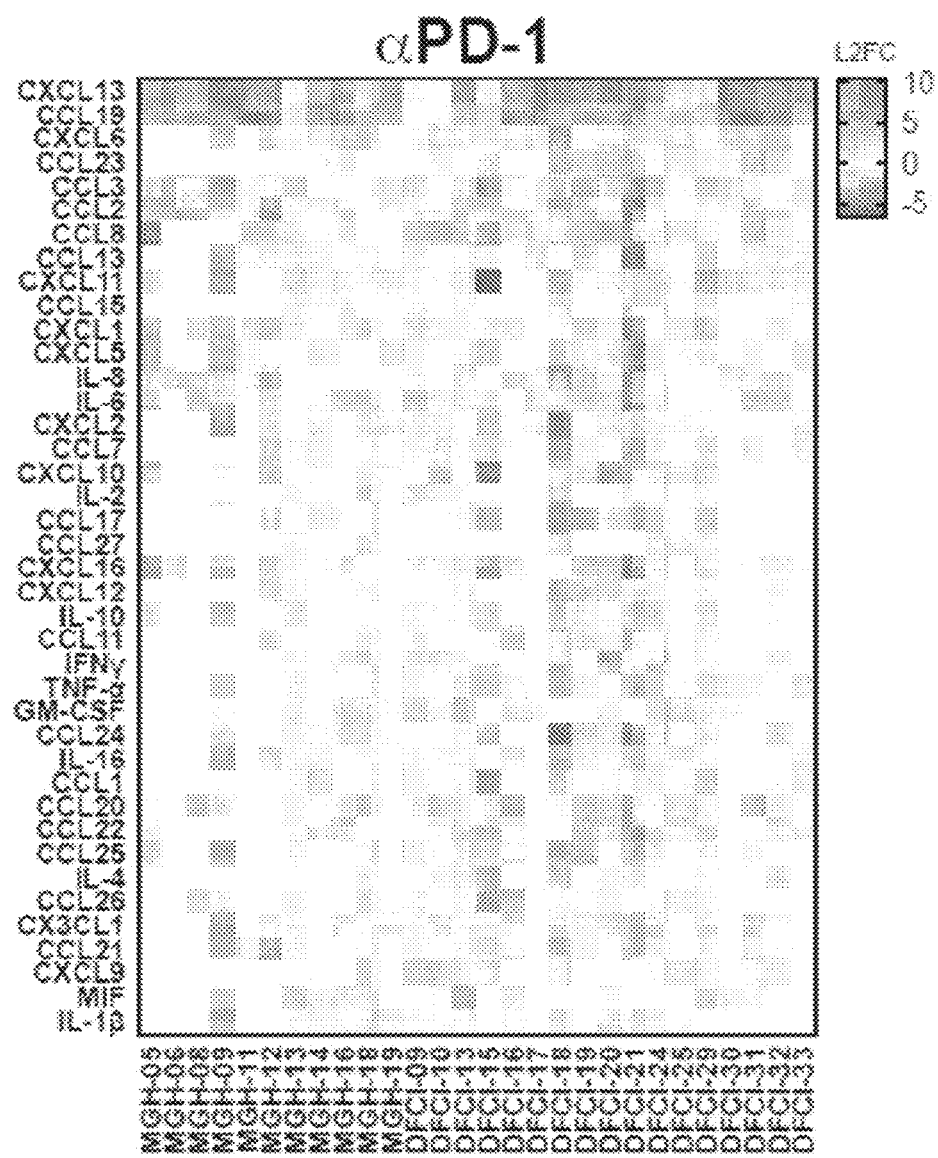

FIG. 3A is a cytokine heatmap that illustrates day 3±anti-PD-1 (n=28) expressed as log 2 fold-change (L2FC) relative to untreated control.

Figure 3B:
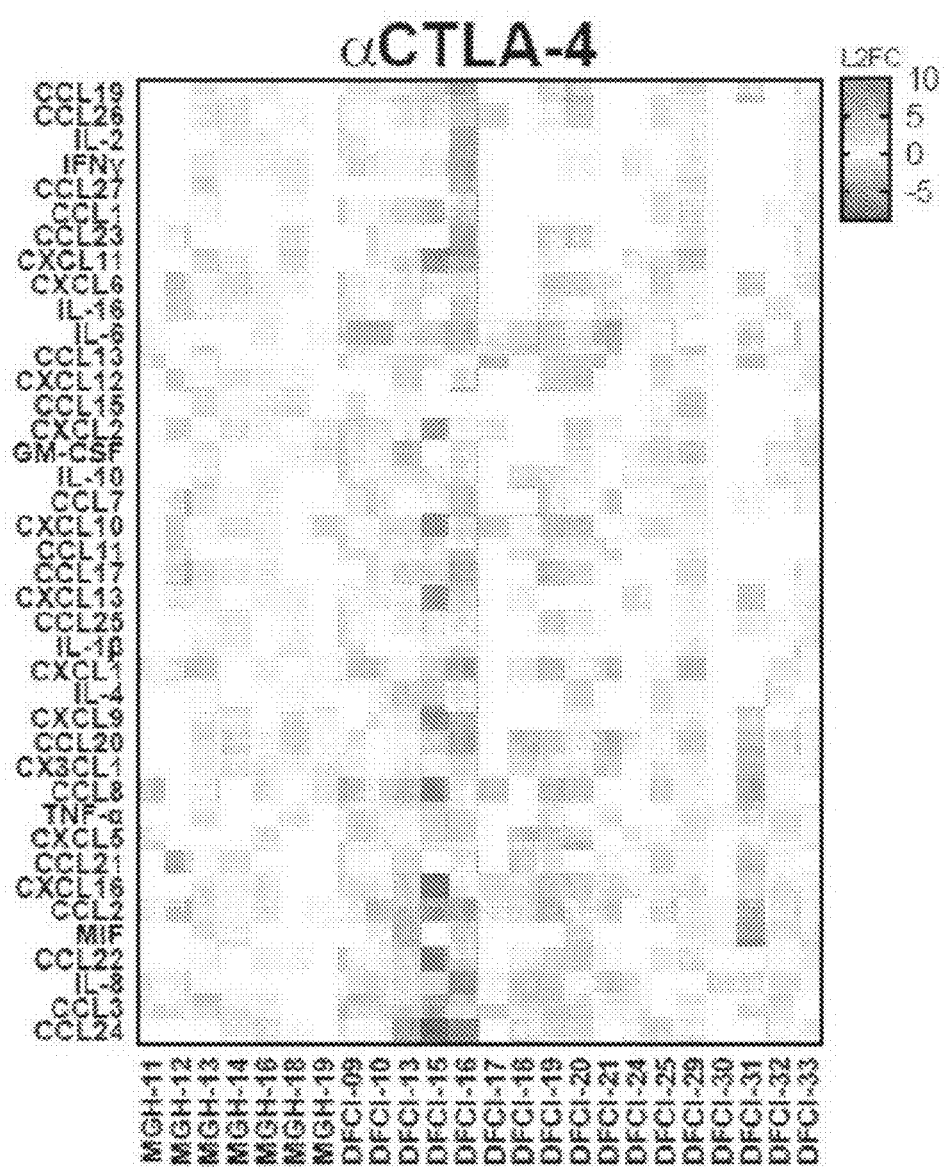

FIG. 3B is a cytokine heatmap that illustrates day 3±anti-CTLA-4 (n=24) expressed as log 2 fold-change (L2FC) relative to untreated control.

Figure 3C:
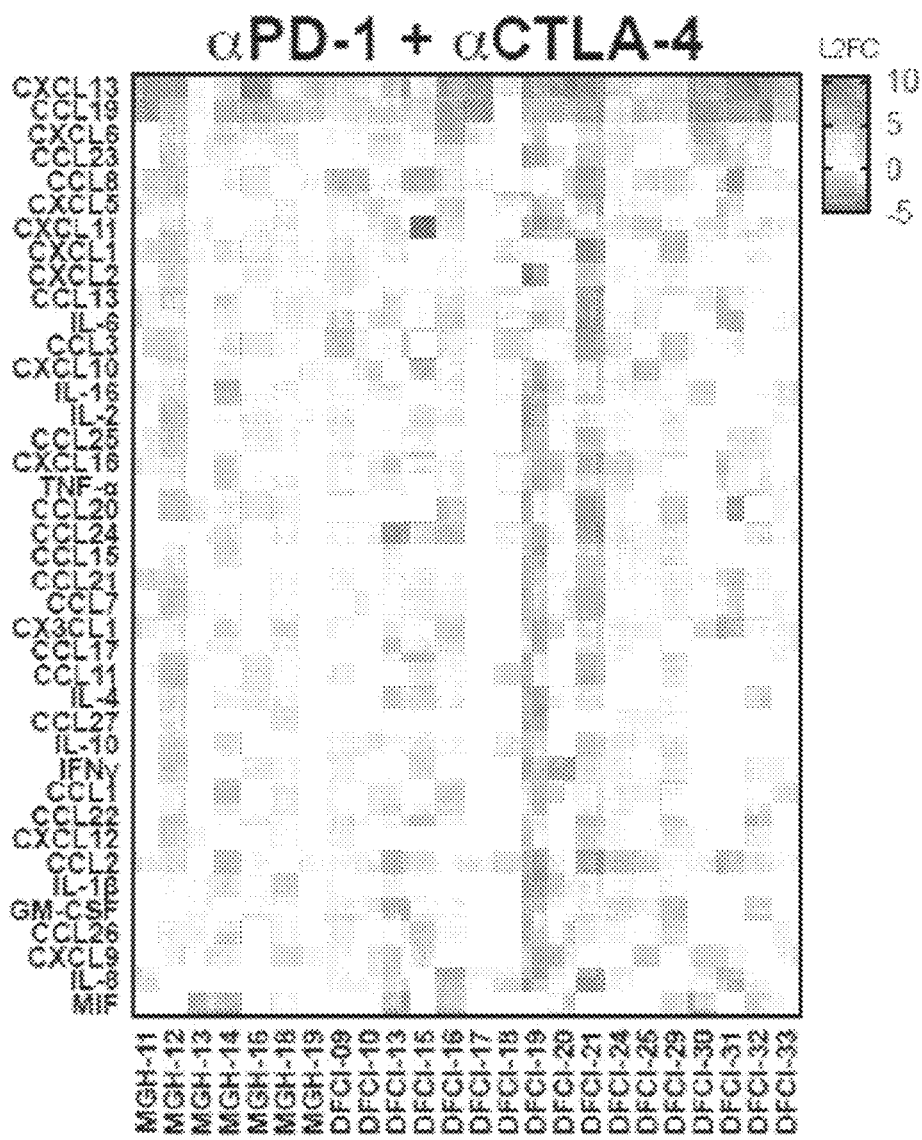

FIG. 3C is a cytokine heatmap that illustrates day 3±anti-PD-1+anti-CTLA-4 (n=24) expressed as log 2 fold-change (L2FC) relative to untreated control.

Figure 3D:
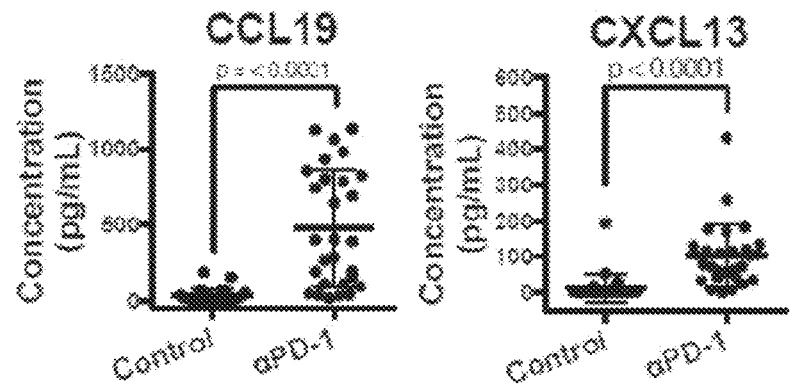

FIG. 3D depicts absolute CCL19/CXCL13 levels following single checkpoint blockade (2-sided, paired, t-test, α=0.05).

Figure 3E:
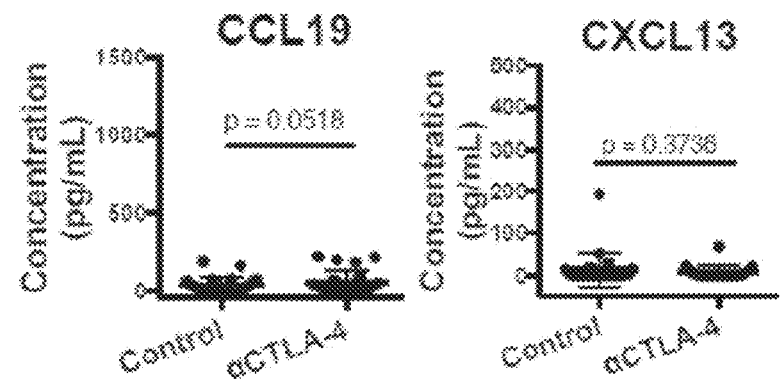

FIG. 3E depicts absolute CCL19/CXCL13 levels following single checkpoint blockade (2-sided, paired, t-test, α=0.05).

Figure 3F:
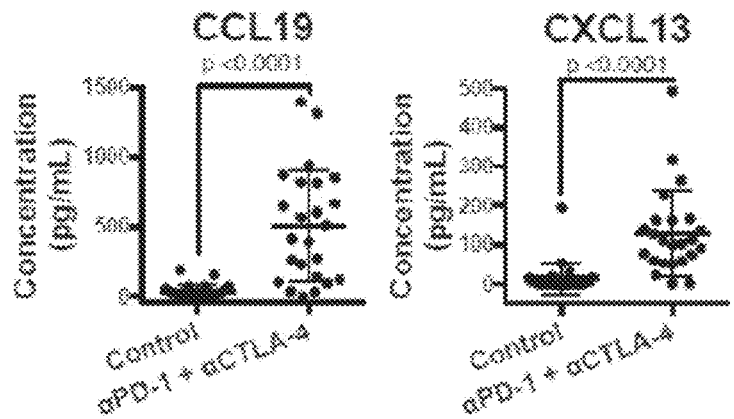

FIG. 3F depicts absolute CCL19/CXCL13 levels following dual checkpoint blockade (2-sided, paired, t-test, α=0.05).

Figure 3G:
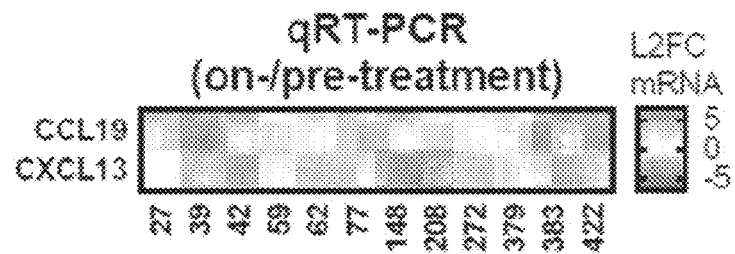

FIG. 3G is a heatmap that illustrates CCL19/CXCL13 mRNA levels from melanoma biopsy samples on anti-PD1 treatment relative to pre-PD-1 (L2FC) by qRT-PCR (n=12).

Figure 3H:
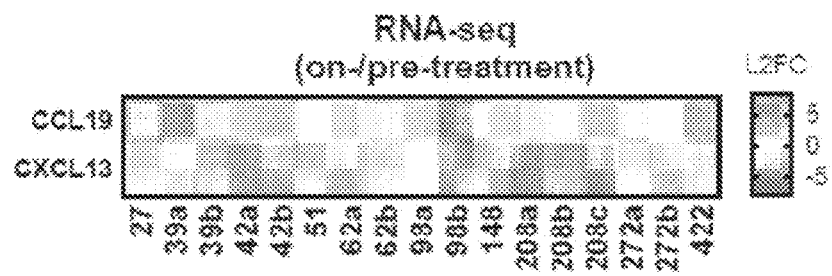

FIG. 3H is a heatmap that illustrates CCL19/CXCL13 mRNA levels from melanoma biopsy samples on anti-PD1 treatment relative to pre-PD-1 (L2FC) by RNA-seq (n=17 from 10 patients).

Figure 3I:
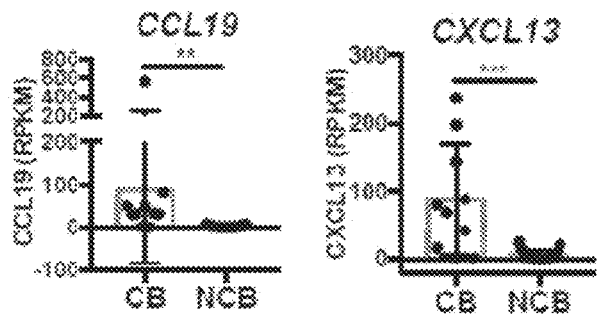

FIG. 3I depicts absolute expression (RPKM) for CCL19 and CXCL13 in melanoma biopsy specimens (pre- and on-treatment) from patients with established clinical benefit (CB) or no clinical benefit (NCB) from checkpoint blockade.

Figure 3J:
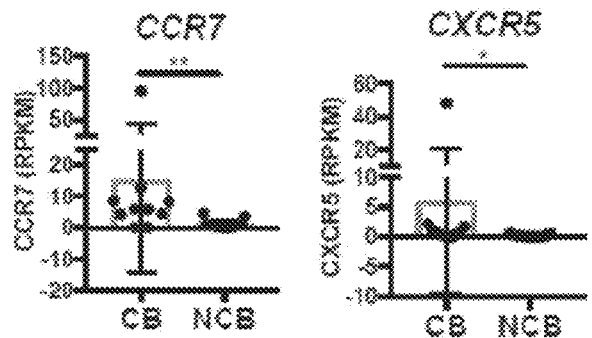

FIG. 3J depicts absolute expression (RPKM) for CCR7 and CXCR5, the respective receptors for CCL19 and CXCL13, in melanoma biopsy specimens (pre- and on-treatment) from patients with established clinical benefit (CB) or no clinical benefit (NCB) from checkpoint blockade.

Figure 3K:
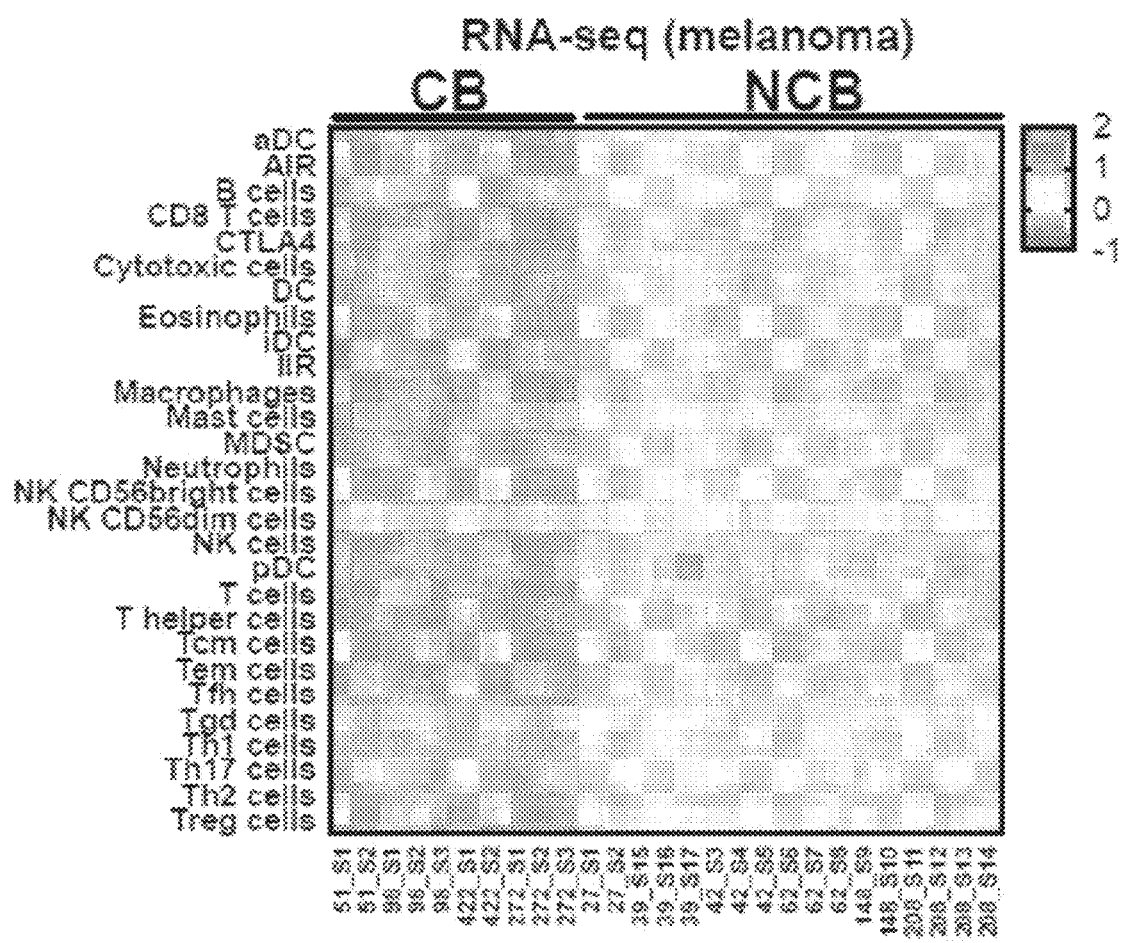

FIG. 3K is a heat map that illustrates immune signatures (GSEA) in melanoma biopsy specimens (pre- and on-treatment) from patients with established clinical benefit (CB, n=10 samples from 4 patients) or no clinical benefit (NCB, n=17 samples from 6 patients).

Figure 3L:
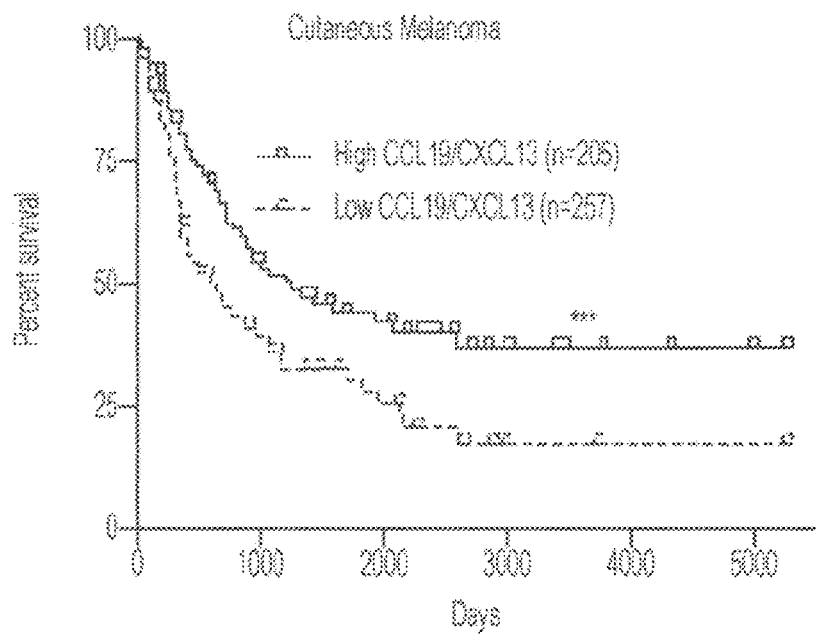

FIG. 3L depicts a Kaplan-Meier survival curve by CCL19/CXCL13 expression (high vs. low).

Figure 3M:
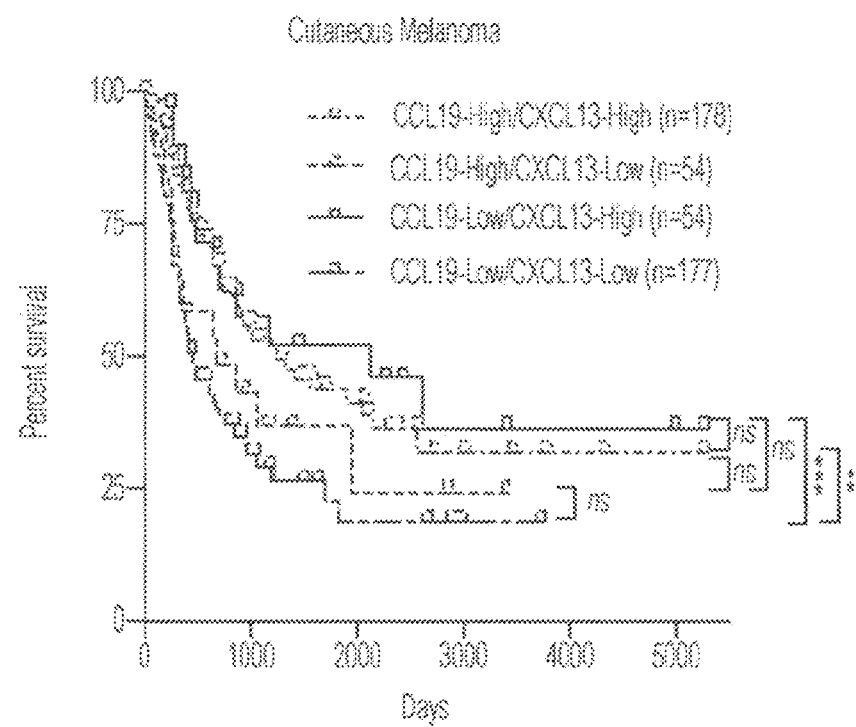

FIG. 3M depicts a Kaplan-Meier survival curve by four-way sorting using cutaneous melanoma (SKCM) TCGA data20 (logrank Mantel-Cox test).

Figure 3N:
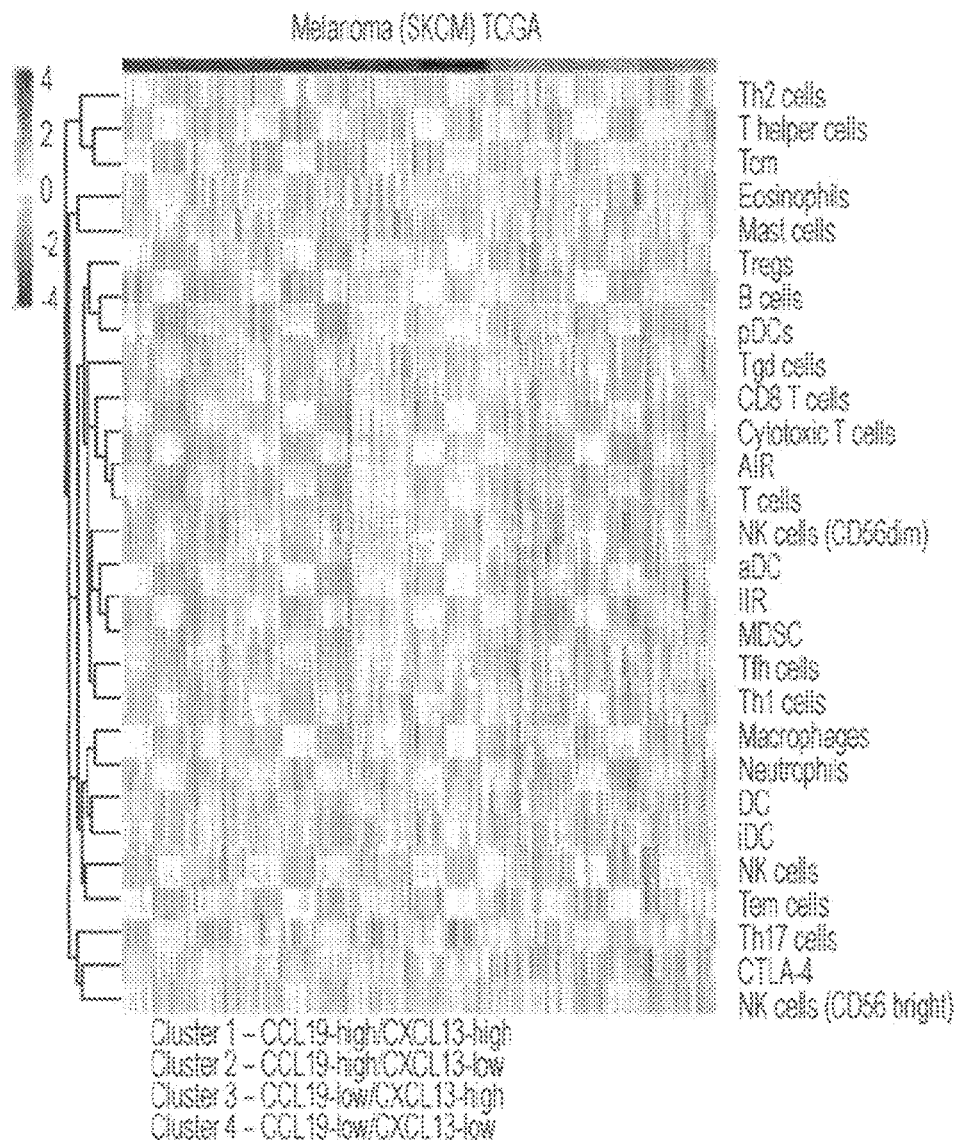

FIG. 3N illustrates immune signatures (GSEA) in melanoma biopsy specimens (pre- and on-treatment) in clusters of patients with varying expression of CCL19 and CXCL13 in cutaneous melanoma (SKCM) TCGA.

Figure 3O:
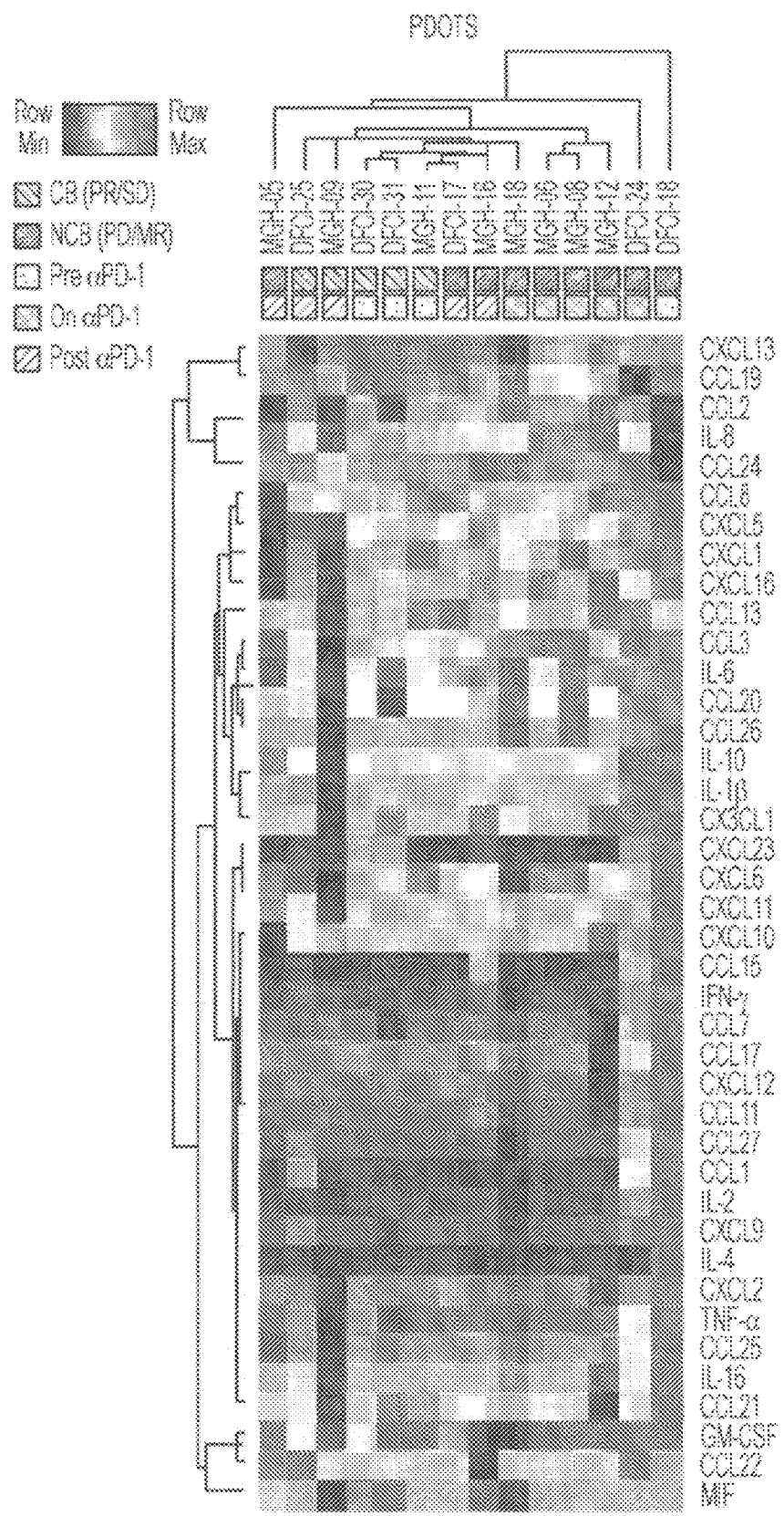

FIG. 3O is a heatmap that illustrates an unsupervised hierarchical clustering of Day 3 PDOTS anti-PD1 induced cytokines, expressed as row normalized (L2FC; n=14), annotated by response to anti-PD-1 therapy and timing of sample collection.

Figure 4A:
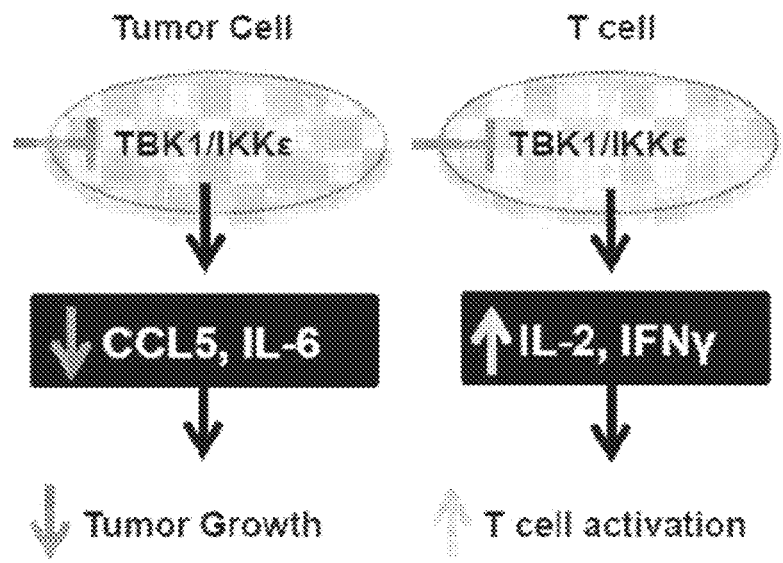

FIG. 4A depicts a scheme of impact of TBK1/IKKε inhibition on cytokine production from tumor cells and T cells.

Figure 4B:
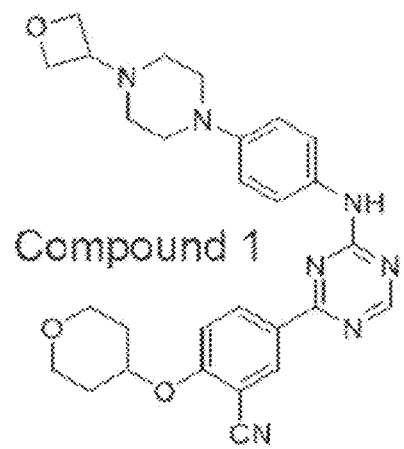

FIG. 4B depicts the chemical structure of Compound 1 with $IC_{50}$ towards TBK1/IKKε, and $EC_{50}$ in HCT116 cells.

Figure 4C:
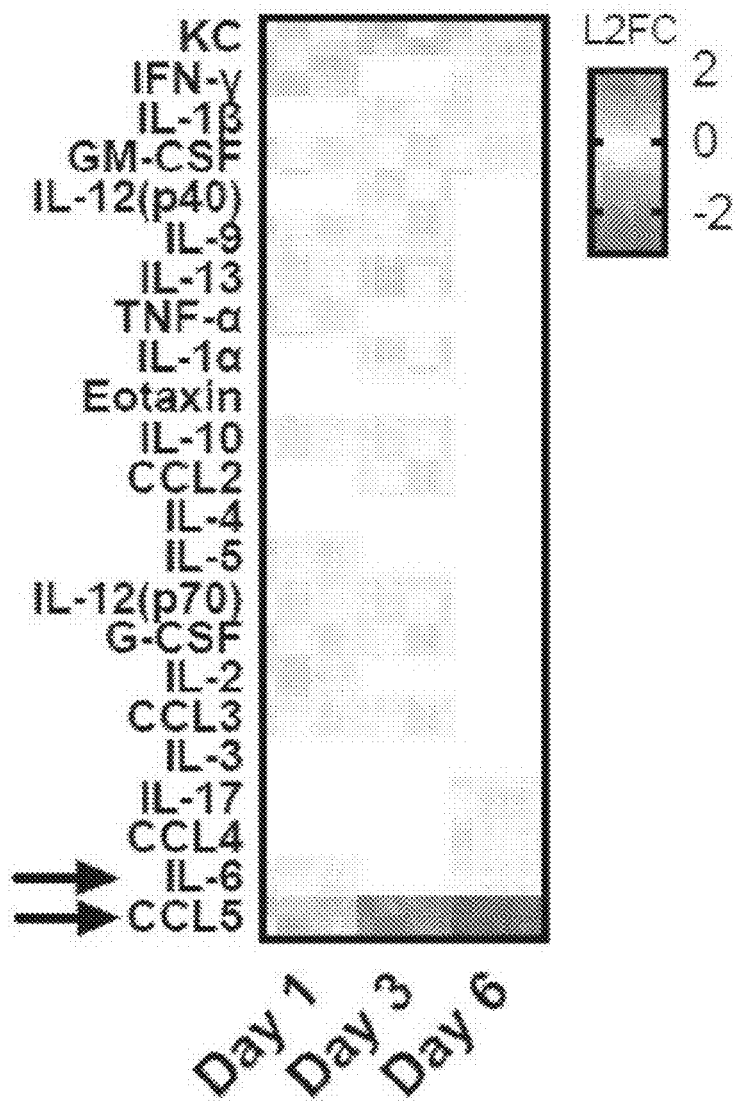

FIG. 4C depicts cytokine heatmaps for CT26 spheroids (lacking immune cells) on Day 1, 3, and 6±Compound 1 (n=3, biological replicates) expressed as log 2 fold-change (L2FC) relative to vehicle control.

Figure 4D:
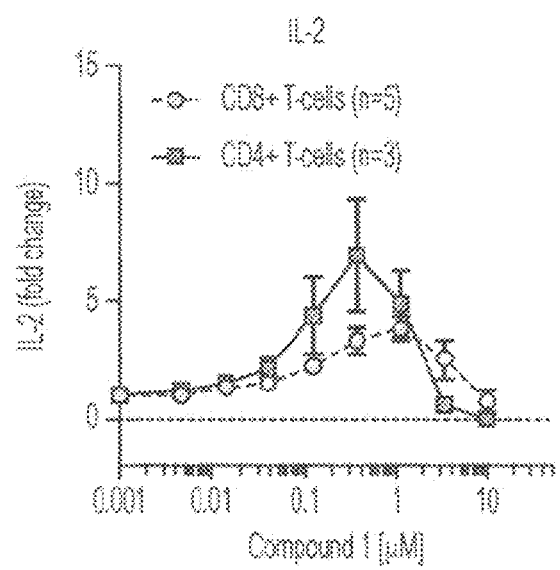

FIG. 4D is a dose-response curve for Compound 1 on IL-2 in human CD4 (n=3) and CD8 (n=5) T cells.

Figure 4E:
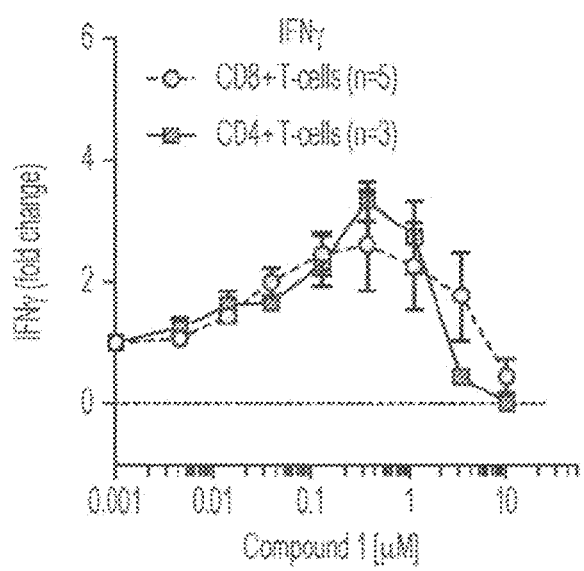

FIG. 4E is a dose-response curve for Compound 1 on IFNγ in human CD4 (n=3) and CD8 (n=5) T cells.

Figure 4F:
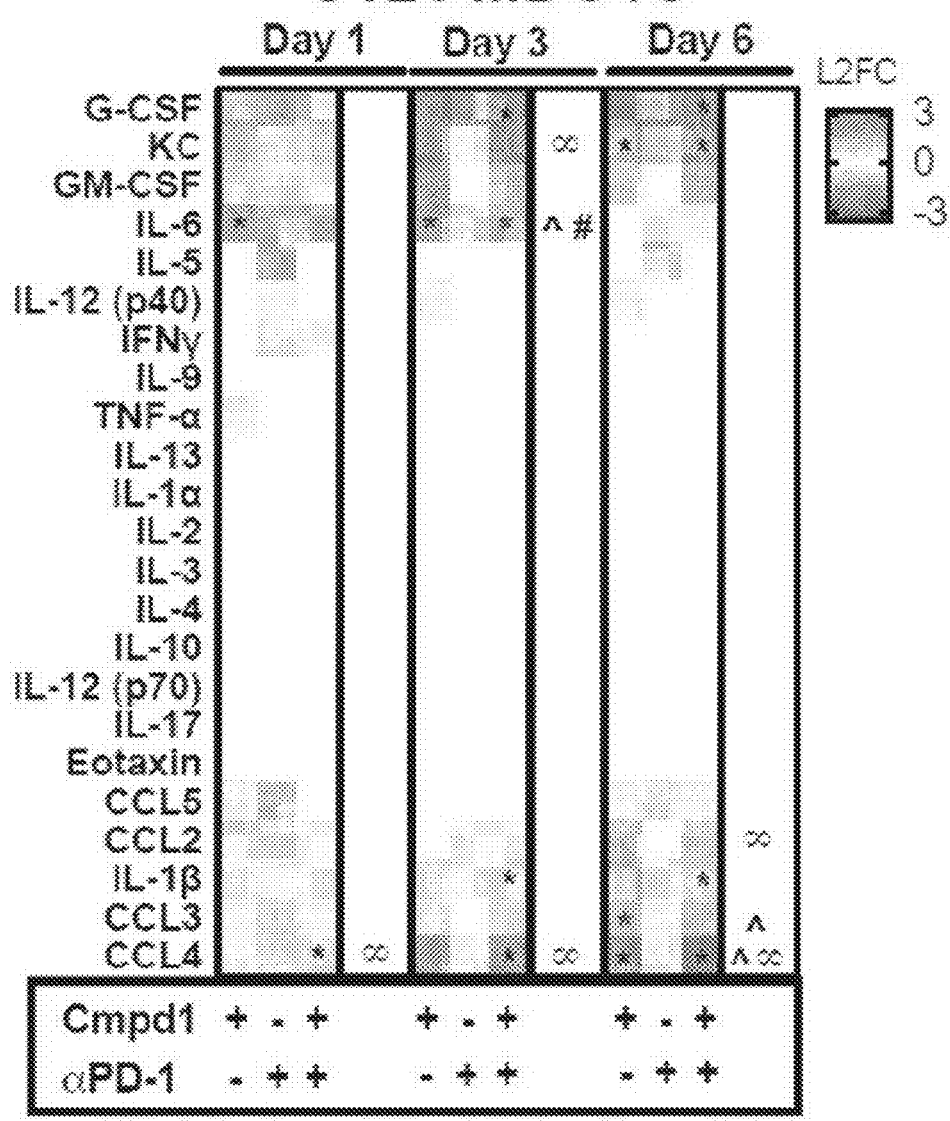

FIG. 4F depicts cytokine heatmaps for CT26 MDOTS treated with IgG+Cmpd1 (1 µM), αPD-1 (10 µg/mL), or αPD-1+Cmpd1 (1 µM) from the mean of n=3 biological replicates, plotted as L2FC relative to isotype control IgG with vehicle control. 2-sided Welch's 2-sample t-test with unequal variance (α=0.05).

Figure 4G:
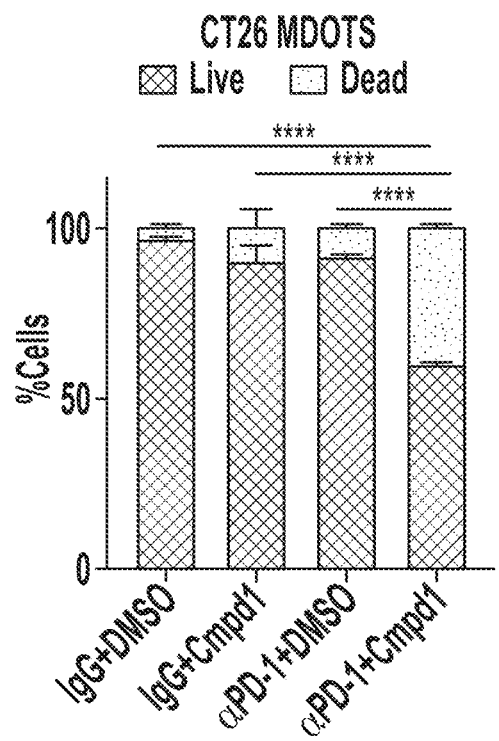

FIG. 4G is a chart that depicts live (AO=green)/dead (PI=red) quantification of CT26 MDOTS after 6 days treated with IgG-DMSO, Cmpd1 (1 µM), αPD-1, and αPD-1+Cmpd1 (*p<0.05, Kruskal-Wallis ANOVA with multiple comparisons; n=3).

Figure 4H:
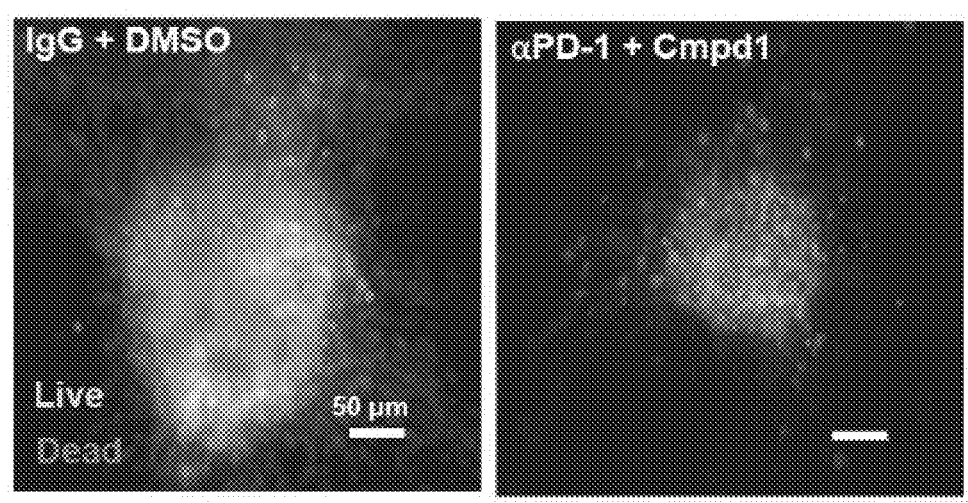

FIG. 4H depicts imaging results corresponding to live (AO=green)/dead (PI=red) quantification of CT26 MDOTS after 6 days treated with IgG-DMSO, Cmpd1 (1 µM), αPD-1, and αPD-1+Cmpd1 (*p<0.05, Kruskal-Wallis ANOVA with multiple comparisons; n=3).

Figure 4I:
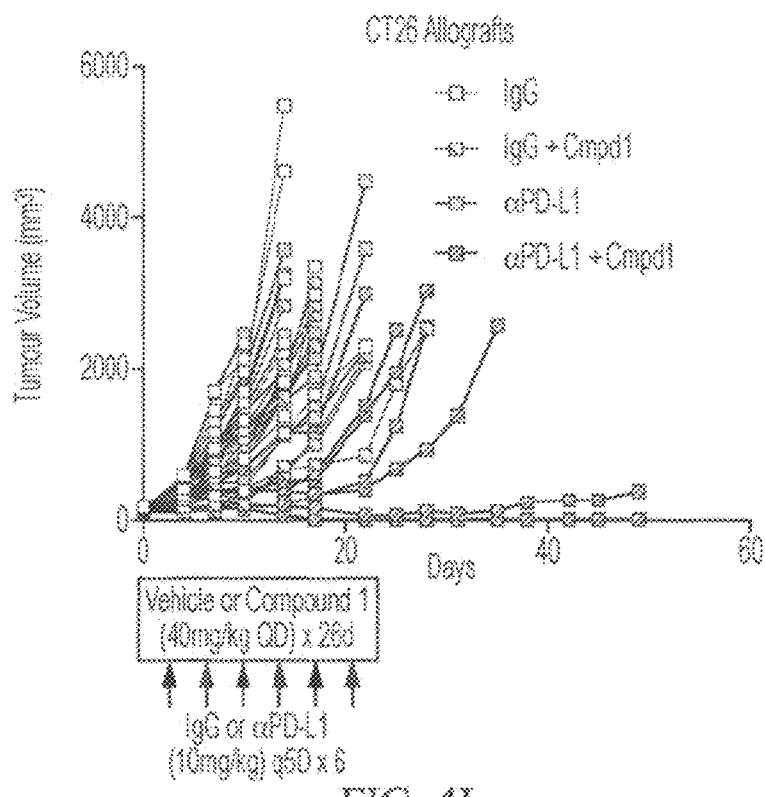

FIG. 4I depicts CT26 allograft tumor volume over time following IgG+vehicle, IgG+Cmpd1, αPD-L1+vehicle, and αPD-L1+Cmpd1 (n=10 per group, **p<0.01, 1-way ANOVA with Tukey's multiple comparison's test for tumor volume, log-rank Mantel-Cox test for Kaplan-Meier analysis for entire group and pairwise comparisons).

Figure 4J:
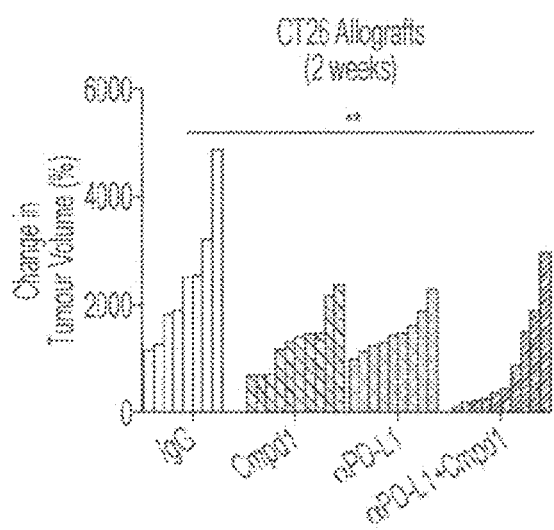

FIG. 4J depicts CT26 allograft percent change in tumor volume following IgG+vehicle, IgG+Cmpd1, αPD-L1+vehicle, and αPD-L1+Cmpd1 (n=10 per group, **p<0.01, 1-way ANOVA with Tukey's multiple comparison's test for tumor volume, log-rank Mantel-Cox test for Kaplan-Meier analysis for entire group and pairwise comparisons).

Figure 4K:
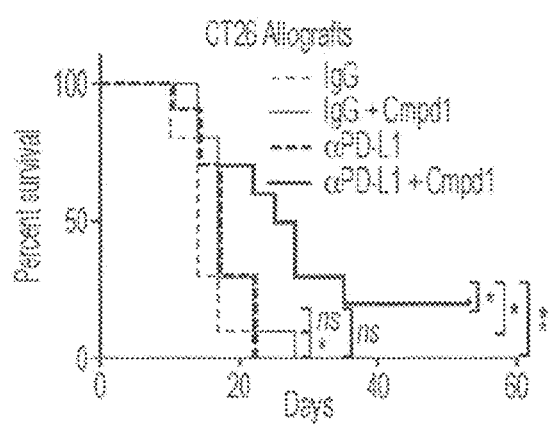

FIG. 4K depicts CT26 allograft percent survival following IgG+vehicle, IgG+Cmpd1, αPD-L1+vehicle, and αPD-L1+Cmpd1 (n=10 per group, **p<0.01, 1-way ANOVA with Tukey's multiple comparison's test for tumor volume, log-rank Mantel-Cox test for Kaplan-Meier analysis for entire group and pairwise comparisons).

Figure 5A:
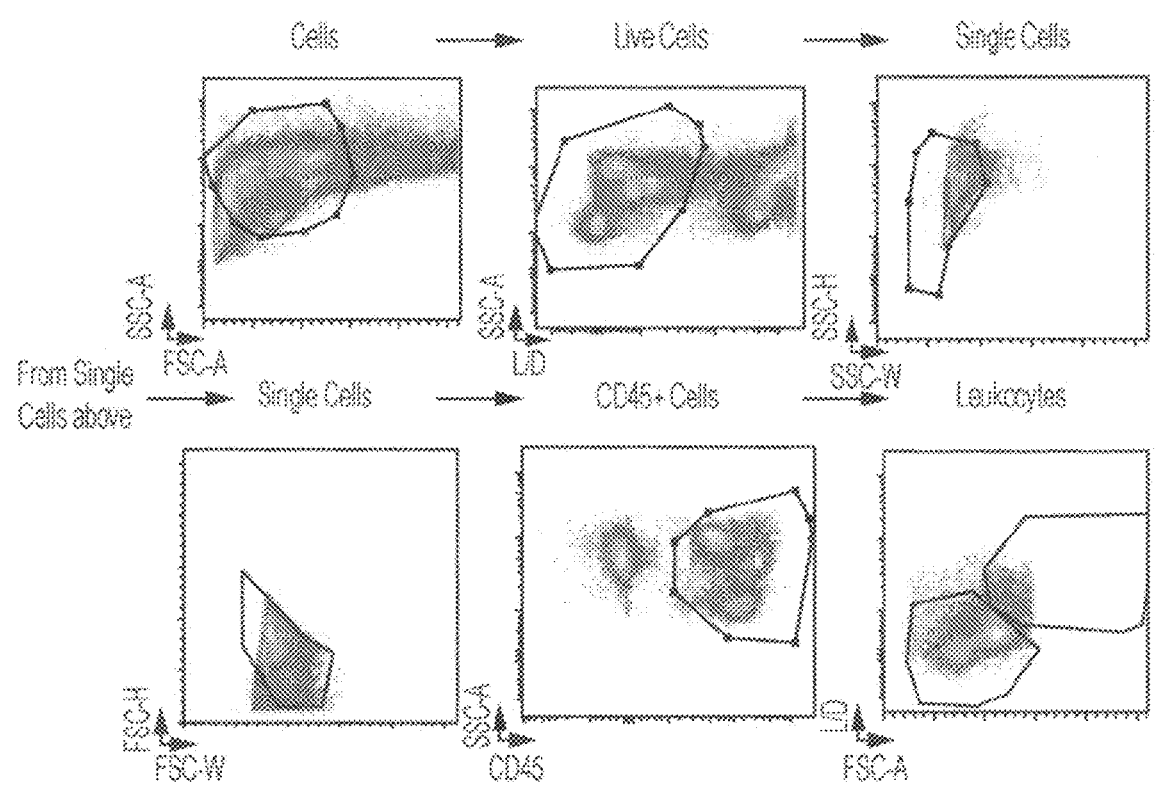

FIG. 5A depicts common gating for viable CD45+ cells in immune cell profiling by multi-color flow cytometry experiments.

Figure 5B:
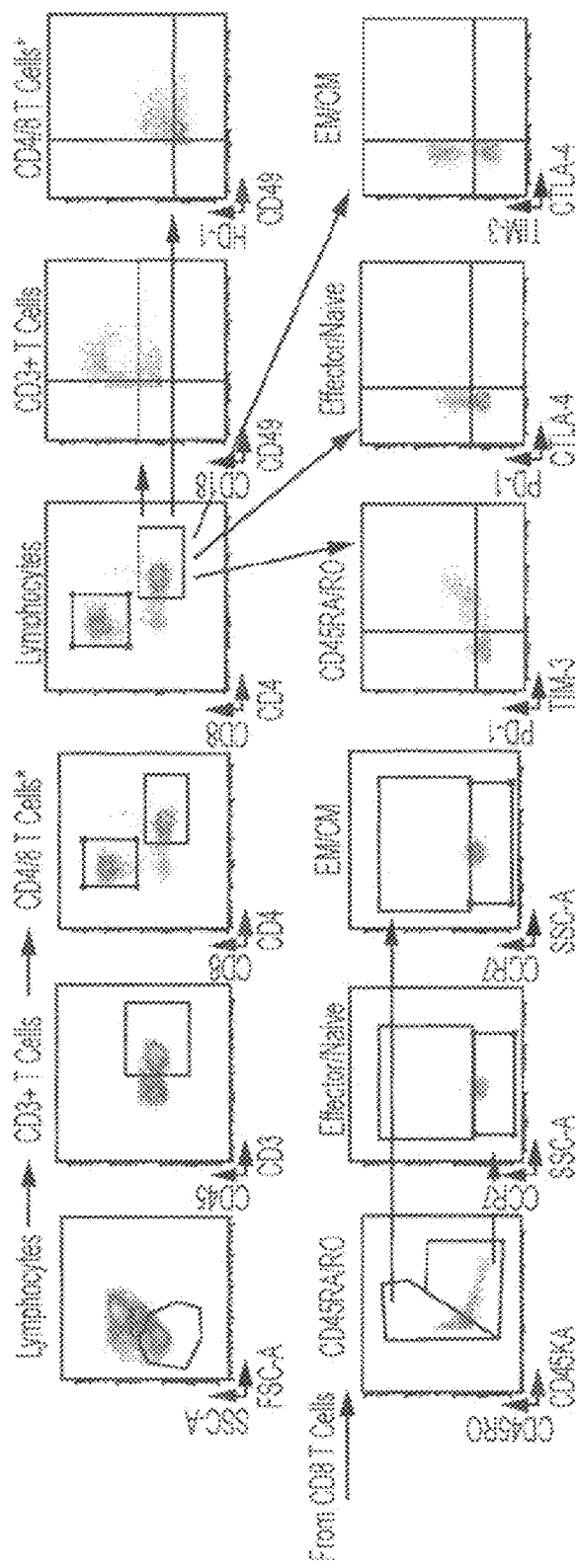

FIG. 5B depicts gating hierarchy for T cell lineage and phenotypic marker in immune cell profiling by multi-color flow cytometry experiments.

Figure 5C:
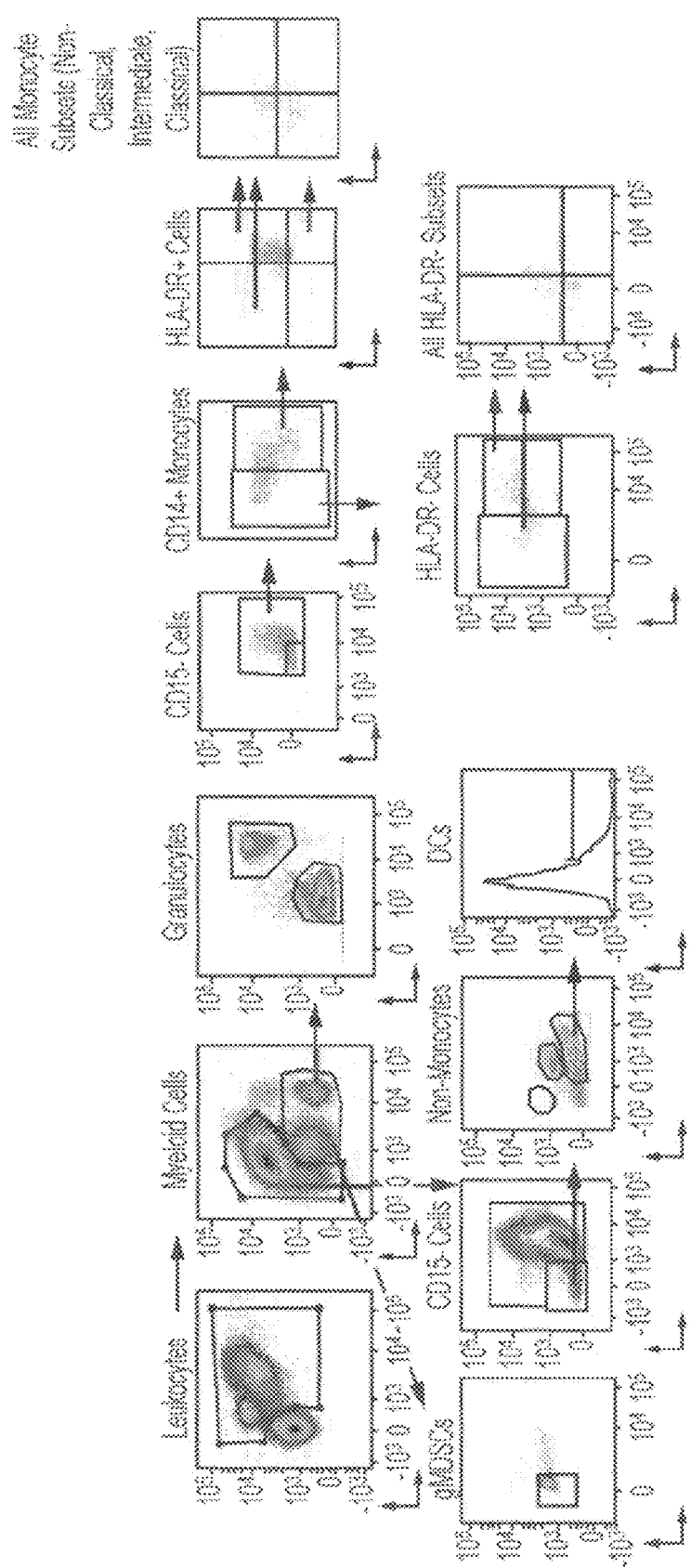

FIG. 5C depicts myeloid cell gating hierarchy in immune cell profiling by multi-color flow cytometry experiments.

Figure 5D:
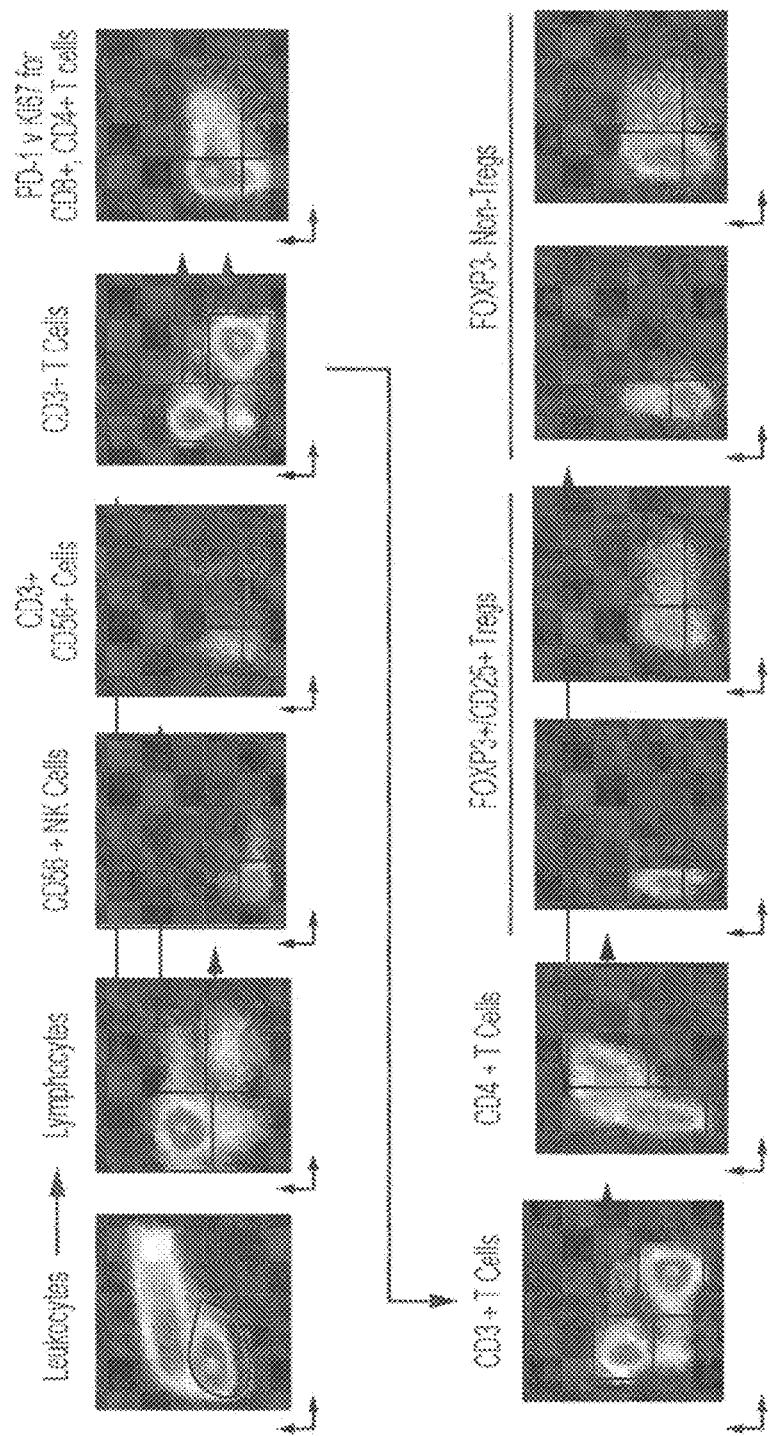

FIG. 5D depicts gating for NK lineage and Tregs in immune cell profiling by multi-color flow cytometry experiments.

Figure 6A:
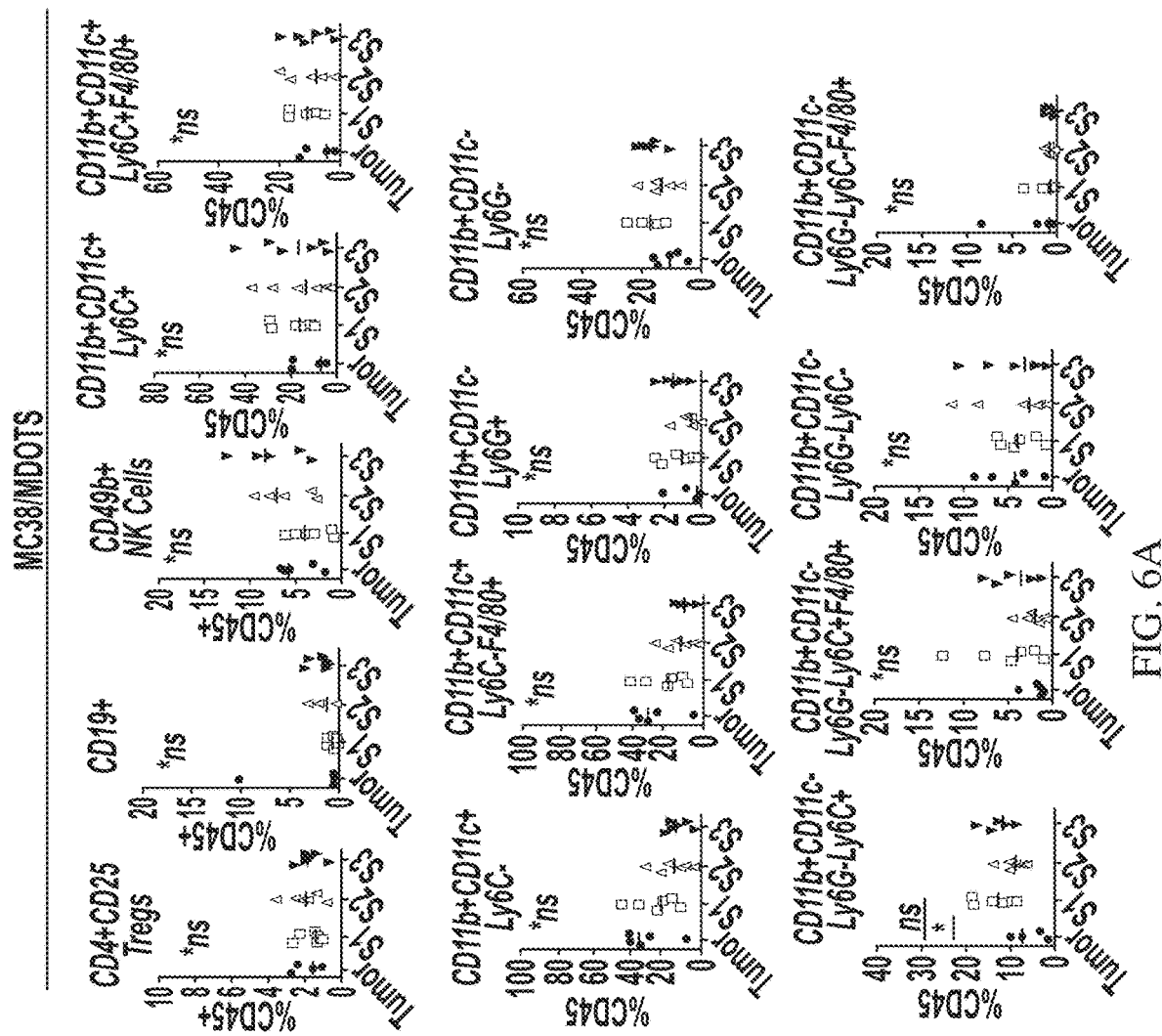

FIG. 6A depicts immune cell sub-populations in MC38 tumors and/or spheroids from immune cell profiling of MDOTS. Immune cell sub-populations from MC38 (a) bulk tumor (n=5) to S1, S2, S3 (n=6) were evaluated by flow cytometry, as in FIG. 1b (Kruskal-Wallis test with Dunn's multiple comparisons test, α=0.05; *p<0.05; ns=not significant).

Figure 6B:
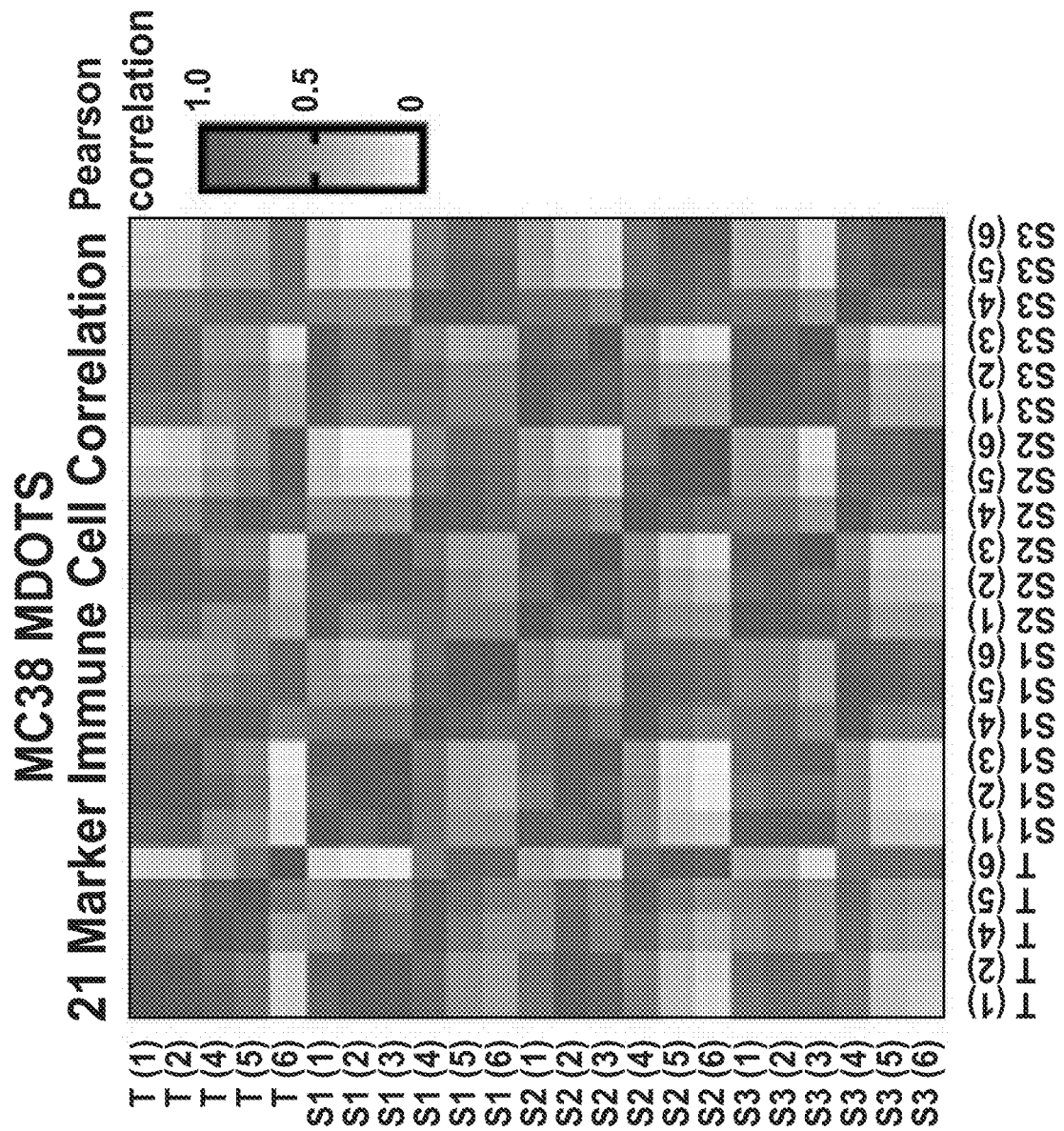

FIG. 6B depicts a Pearson correlation matrix using composite of 21 cell surface markers in MC38 tumor, S1, S2, and S3 spheroids.

Figure 6C:
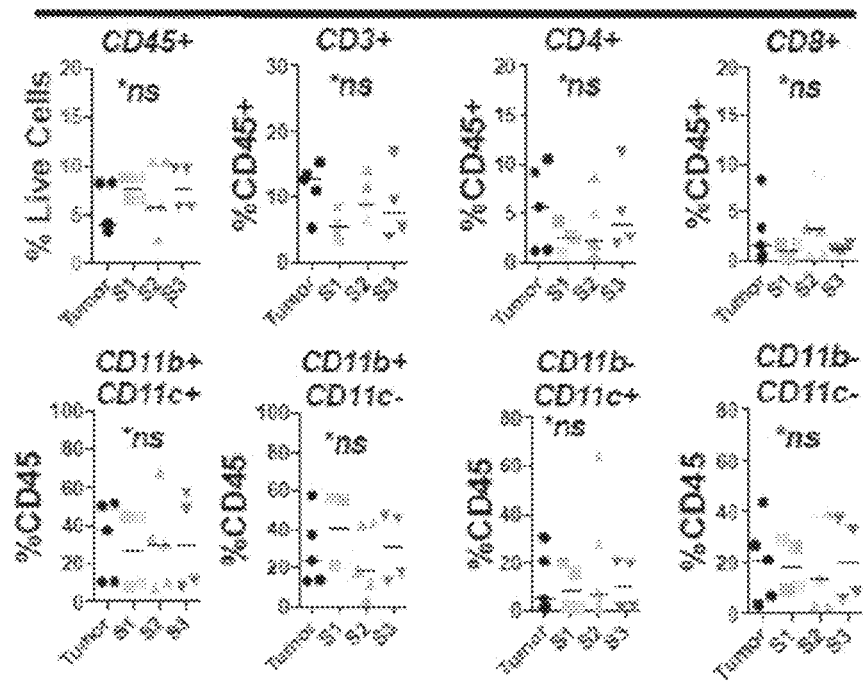

FIG. 6C depicts immune cell sub-populations in B16F10 tumors and/or spheroids from immune cell profiling of MDOTS. Immune cell sub-populations from B 16F10 (a) bulk tumor (n=5) to S1 (n=4), S2 (n=5), and S3 (n=4) evaluated by flow cytometry (Kruskal-Wallis test with Dunn's multiple comparisons test, α=0.05; *p<0.05; ns=not significant).

Figure 6D:
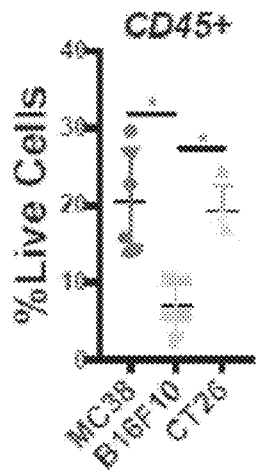

FIG. 6D depicts CD45+ cells (% live cells) in MC38 (n=6), B16F10 (n=5), and CT26 (n=5) MDOTS (S2). Kruskal-Wallis test with Dunn's multiple comparisons test, α=0.05; *p<0.05.

Figure 6E:
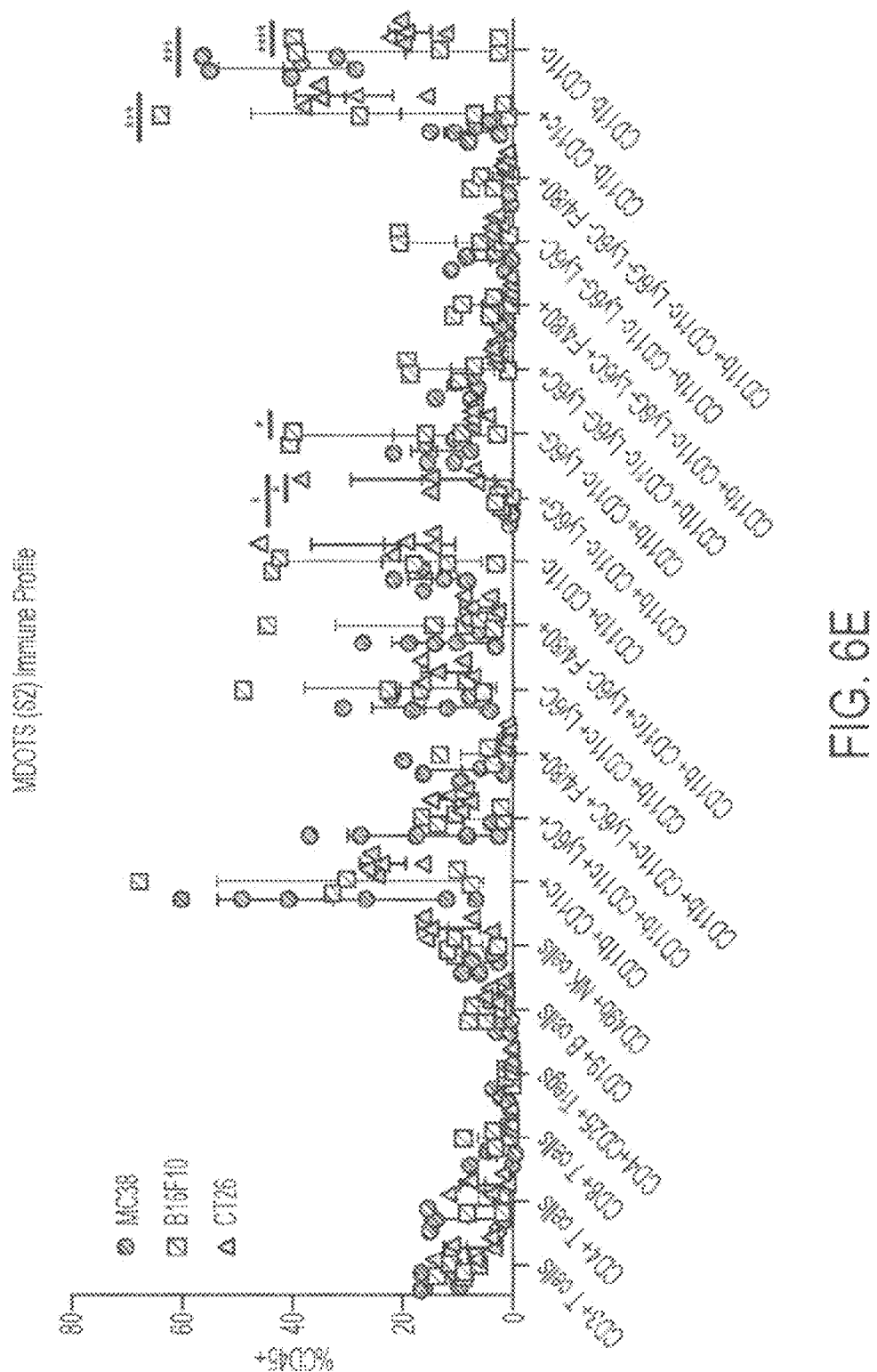

FIG. 6E depicts immune sub-populations (% CD45+ cells) in MC38 (n=6), B16F10 (n=5), and CT26 (n=5) MDOTS (S2). 2-way ANOVA with Tukey's multiple comparisons test, α=0.05; *p<0.05, *p<0.001, **p<0.0001).

Figures 6F, 6G:
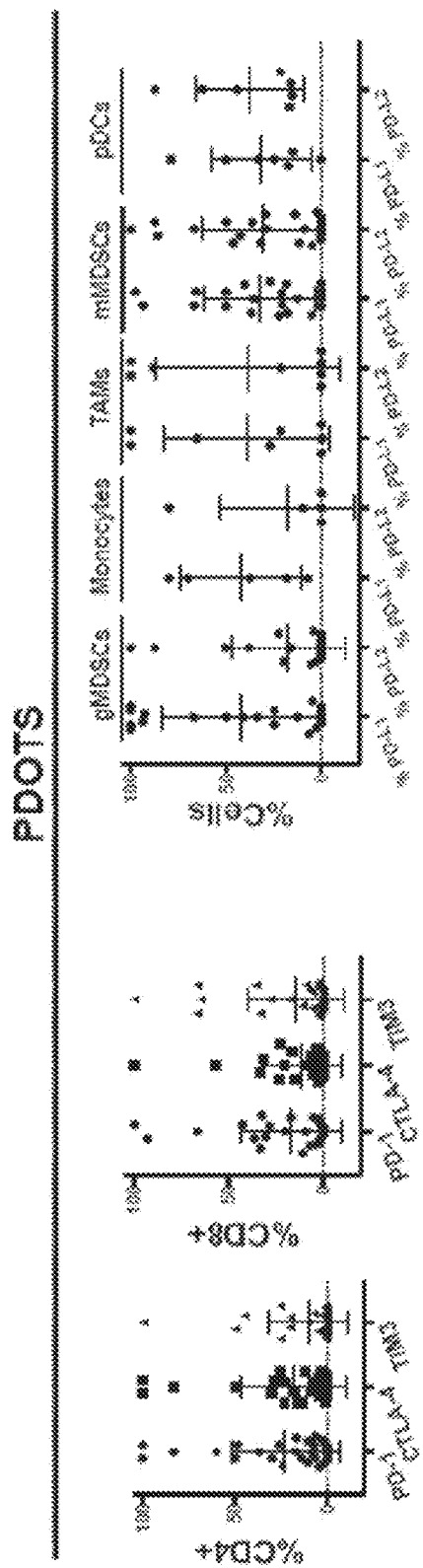

FIG. 6F depicts surface expression of T cell exhaustion markers (PD-1, CTLA-4, TIM-3) on CD4 and CD8 populations in PDOTS (n=40) from immune cell profiling of PDOTS.

FIG. 6G depicts surface expression of PD-L1 and PD-L2 on myeloid sub-populations, including granulocytic myeloid-derived suppressor cells (gMDSCs), monocytes, tumor-associated macrophages (TAMs), monocytic myeloid-derived suppressor cells (mMDSCs), and plasmacytoid dendritic cells (pDCs).

Figure 6H:
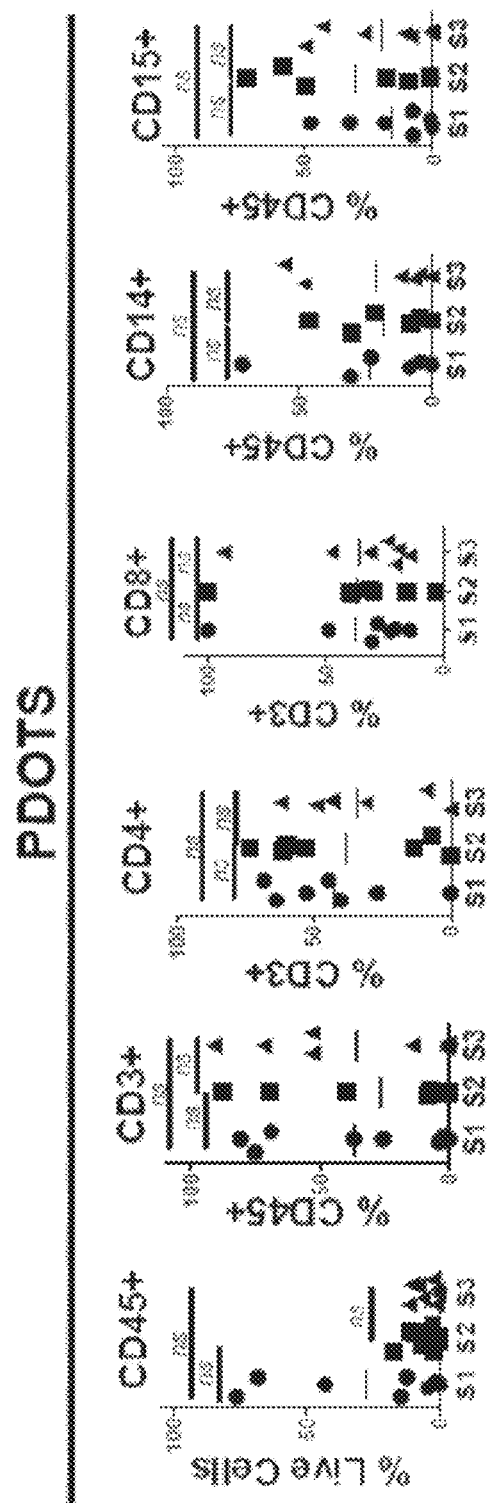

FIG. 6H depicts immune cell sub-populations of PDOTS fractions (S1, S2, S3) evaluated by flow cytometry, for CD45+(n=8), CD3+(n=8), CD4+(n=7), CD8+(n=7), CD14+ (n=7), and CD15+(n=6). Kruskal-Wallis test with Dunn's multiple comparisons test, α=0.05; ns=not significant.

Figure 6I:
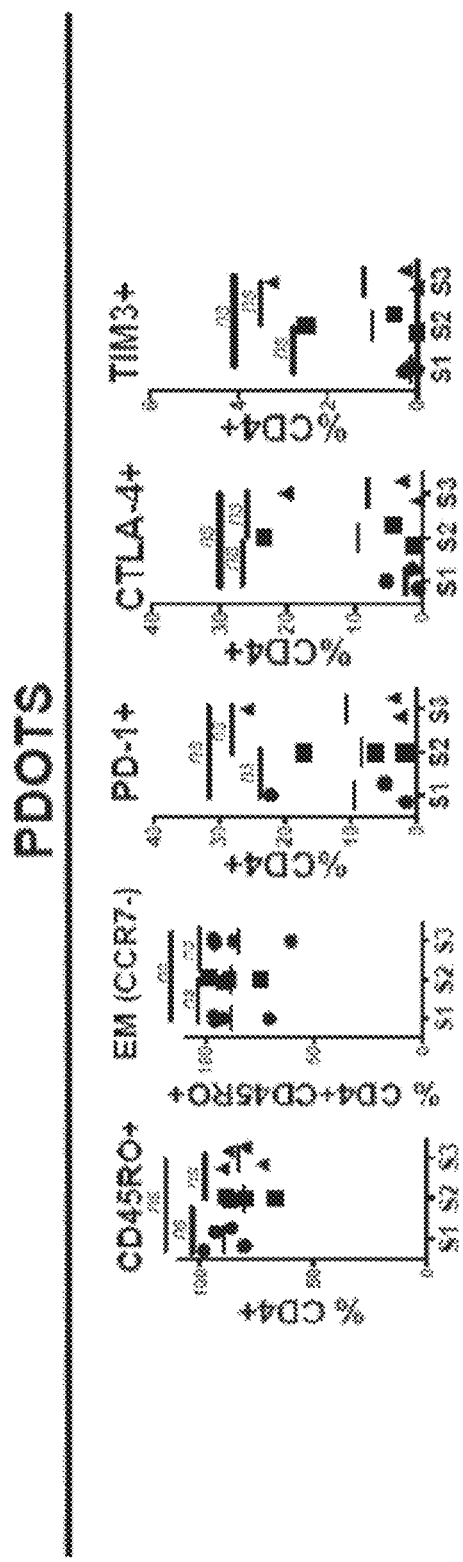

FIG. 6I depicts antigen-experienced sub-population (CD45RO+), effector memory (CD45RO+CCR7−) subtype, and surface expression of T cell exhaustion markers (PD-1, CTLA-4, TIM-3) on CD4 populations in PDOTS fractions (n≥3; Kruskal-Wallis test with Dunn's multiple comparisons test, α=0.05; ns=not significant).

Figure 6J:
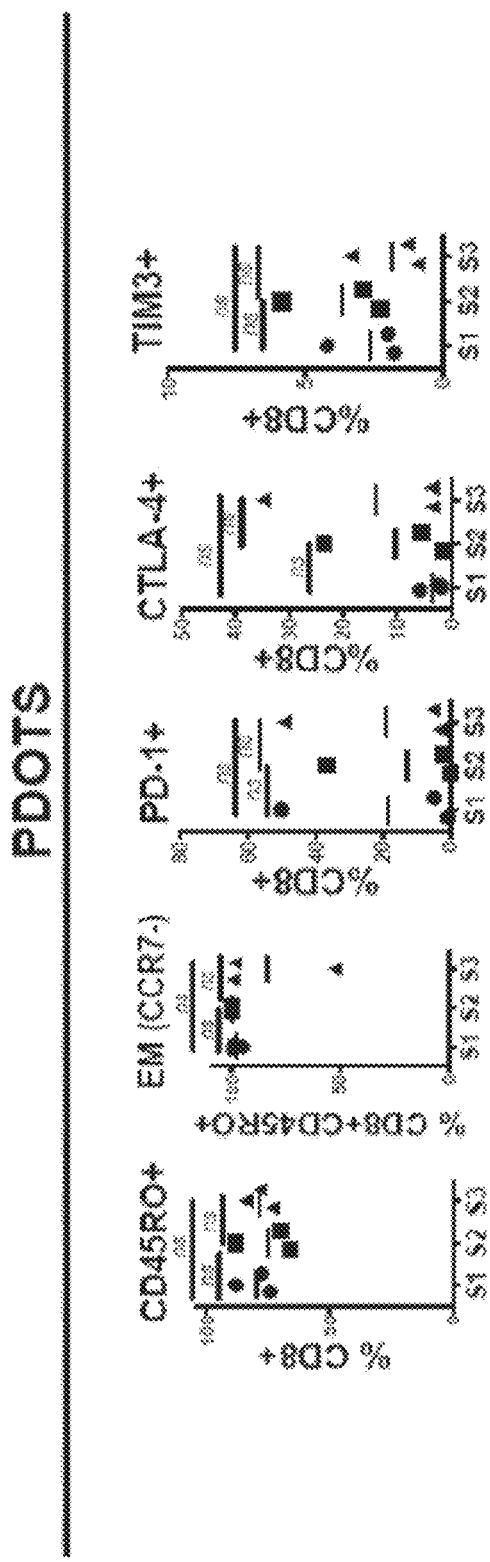

FIG. 6J depicts antigen-experienced sub-population (CD45RO+), effector memory (CD45RO+CCR7−) subtype, and surface expression of T cell exhaustion markers (PD-1, CTLA-4, TIM-3) on CD8 populations in PDOTS fractions (n≥3; Kruskal-Wallis test with Dunn's multiple comparisons test, α=0.05; ns=not significant).

Figures 7A, 7B, 7C:
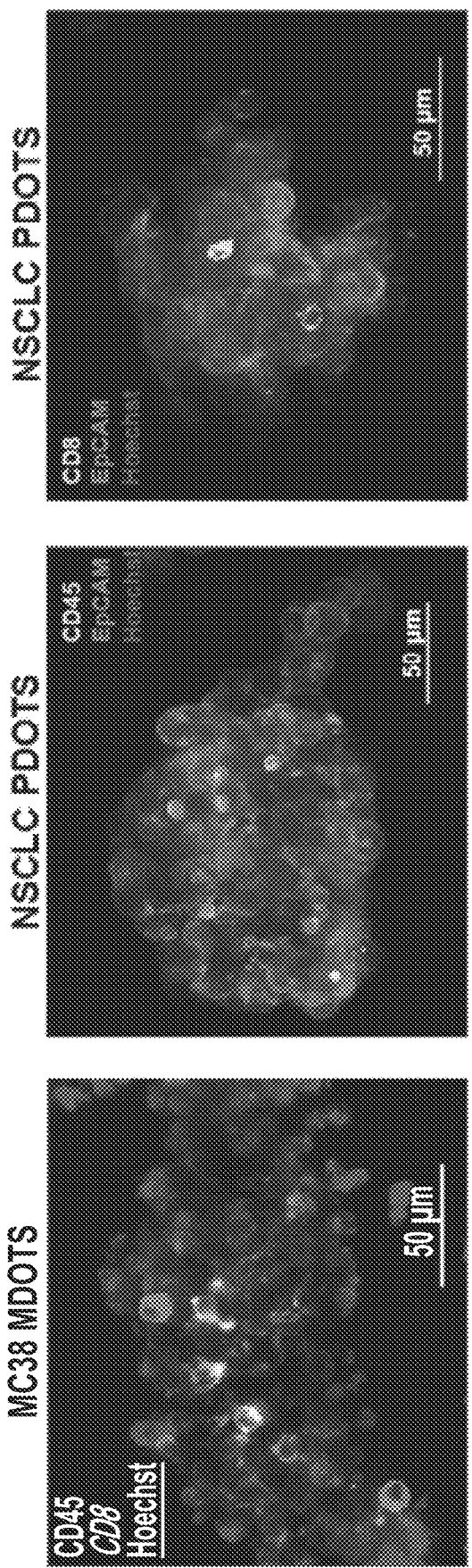

FIG. 7A depicts immunofluorescence staining of MC38 MDOTS.

FIG. 7B depicts immunofluorescence staining of NSCLC PDOTS.

FIG. 7C depicts immunofluorescence staining of NSCLC PDOTS.

Figure 7D:
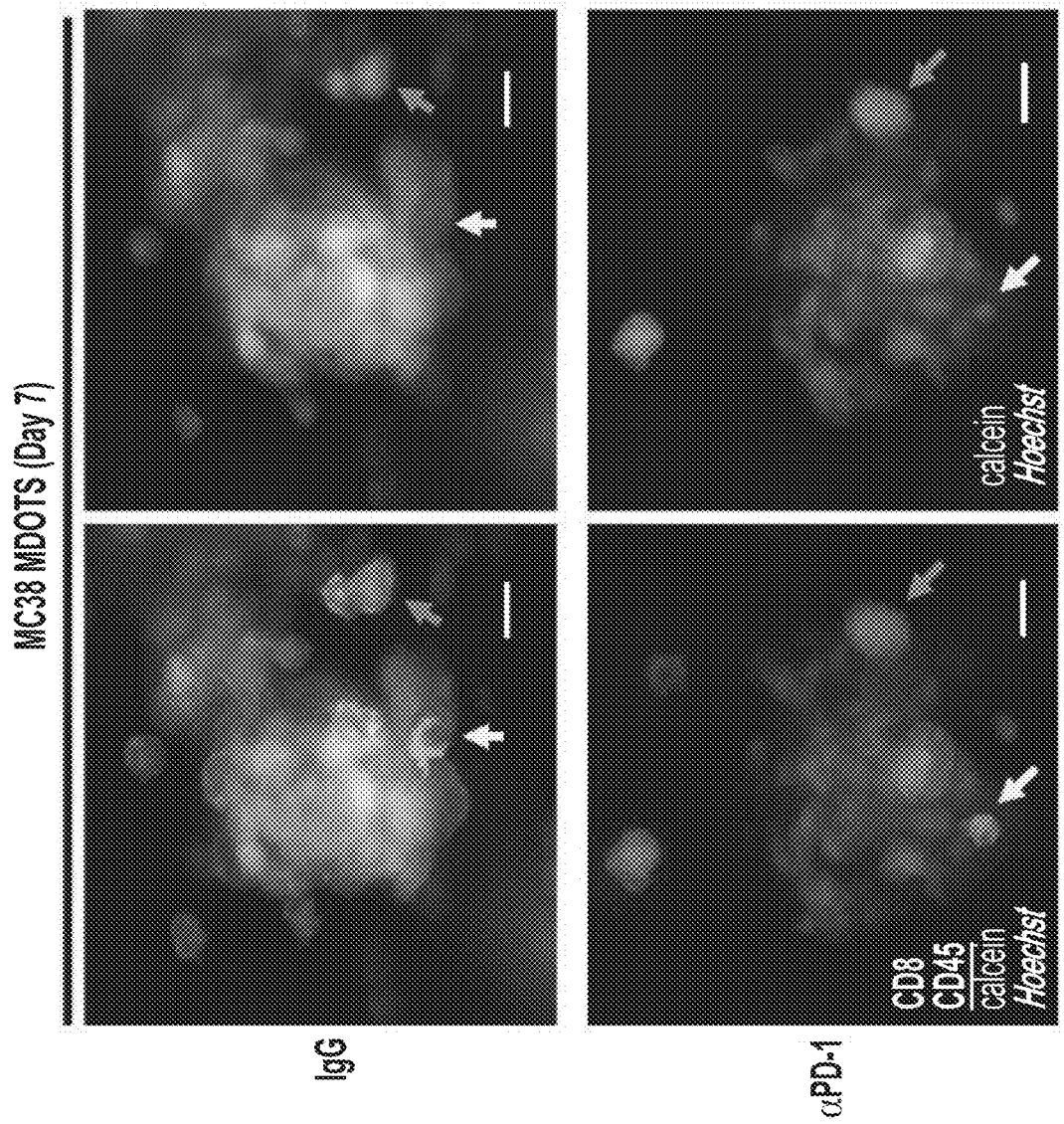

FIG. 7D depicts immunofluorescence staining for MC38 MDOTS stained for CD45+ immune cells (purple) and CD8+ T cells (yellow) with calcein (green) staining live cells and Hoechst (blue) staining all cell nuclei at Day 7 after treatment with IgG (10 µg/mL) or anti-PD-1 (10 µg/mL) (scale bar=20 µm).

Figure 7E:
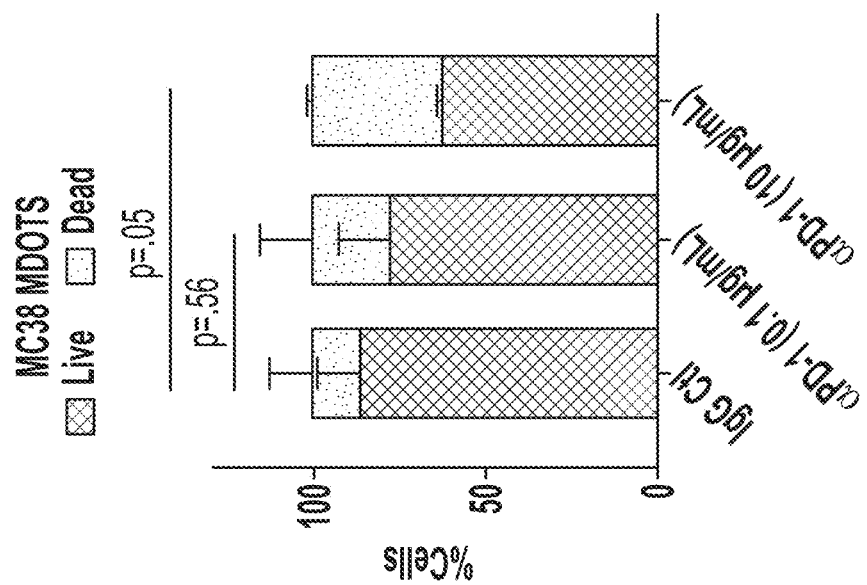

FIG. 7E is a chart that depicts live/dead analysis of MC38 MDOTS±anti-PD-1 performed by independent lab (n=3, biological replicates).

Figure 7F:
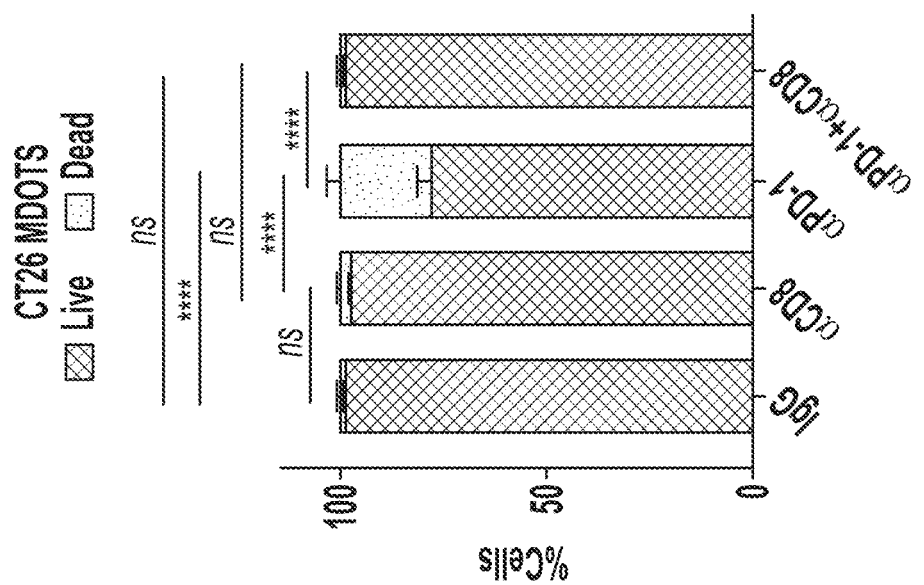

FIG. 7F is a chart that depicts live/dead analysis of CT26 MDOTS performed on Day 6 following treatment with isotype IgG control (10 µg/mL) or anti-PD-1 (10 µg/mL)±anti-CD8 (10 µg/mL) (n=6, biological replicates; 2-way ANOVA with Tukey's multiple comparisons test; ****p<0.0001, ns=not significant).

Figure 7G:
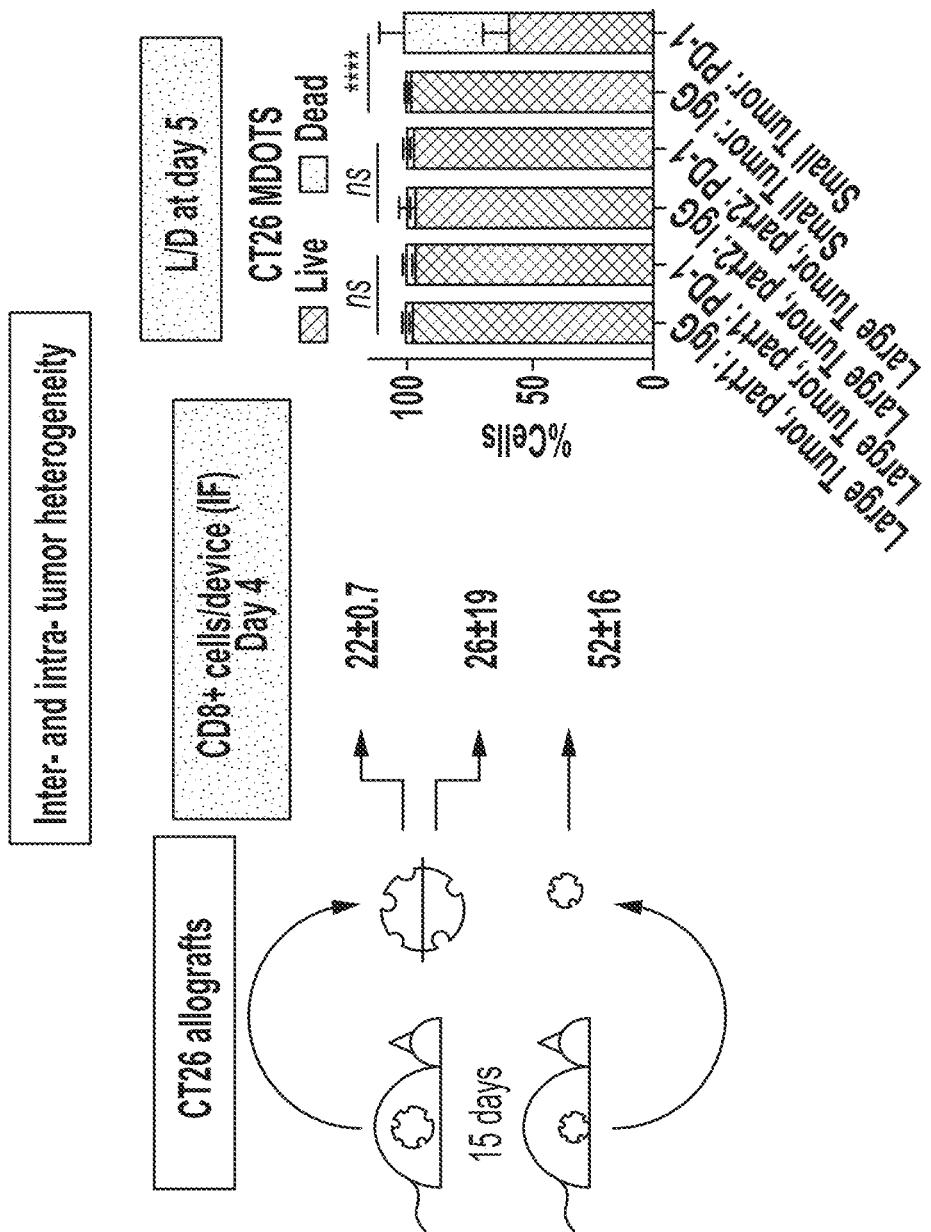

FIG. 7G depicts a comparison of intratumoral and intertumoral heterogeneity evaluating CD8+ T cell counts (IF, performed on Day 4) and live/dead analysis (AO/PI staining) of CT26 MDOTS (Day 5).

Figure 8A:
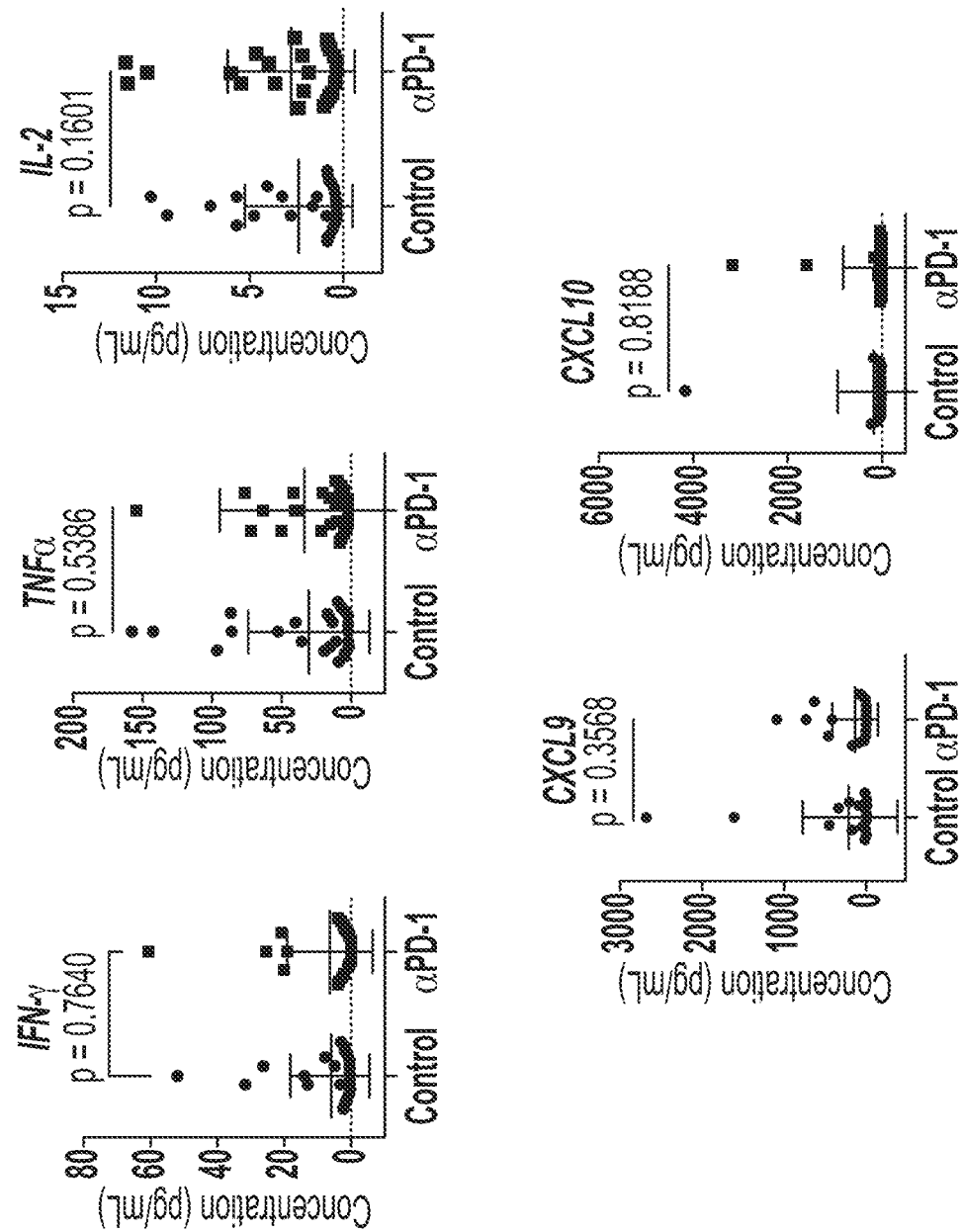

FIG. 8A depicts absolute cytokine levels (pg/mL) obtained by bead-based cytokine profiling of PDOTS under control conditions or in response to αPD-1 grouped by Th1 and IFN-γ effector cytokines, (n=28; 2-sided, paired, t-test, α=0.05).

Figure 8B:
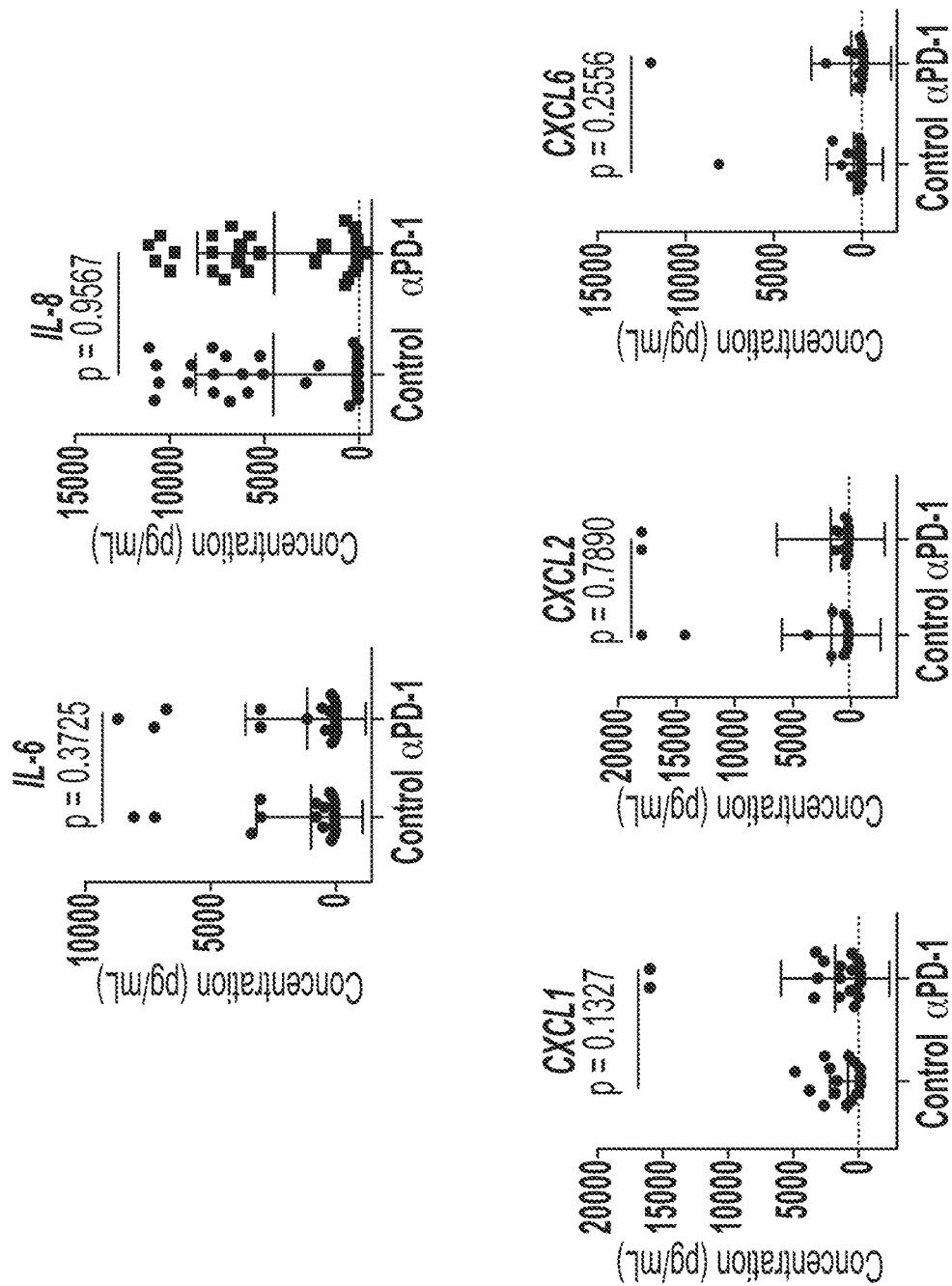

FIG. 8B depicts absolute cytokine levels (pg/mL) obtained by bead-based cytokine profiling of PDOTS under control conditions or in response to αPD-1 grouped by granulocyte chemoattractants, (n=28; 2-sided, paired, t-test, α=0.05).

Figure 8C:
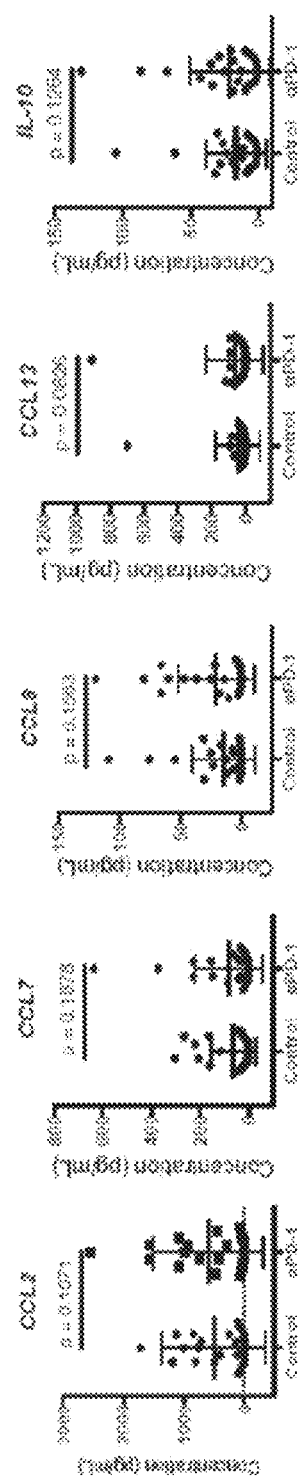

FIG. 8C depicts absolute cytokine levels (pg/mL) obtained by bead-based cytokine profiling of PDOTS under control conditions or in response to αPD-1 grouped by IPRES immune suppressive cytokines, (n=28; 2-sided, paired, t-test, α=0.05).

Figure 8D:
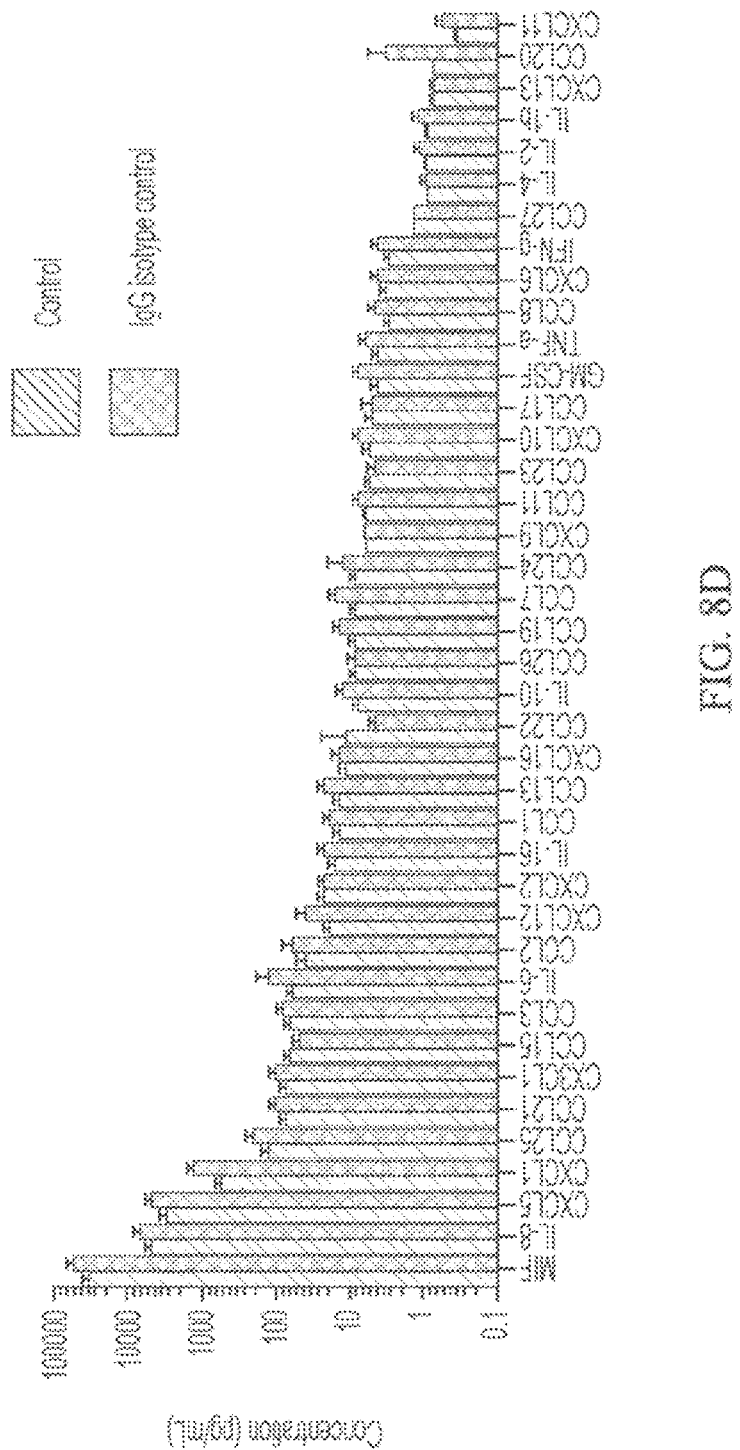

FIG. 8D illustrates a comparison of PDOTS cytokine profiles after 3 days in standard growth conditions with and without isotype control IgG antibody (50 µg/mL) (n=2), performed using PDOTS derived from sample MGH-16 (melanoma).

Figure 8E:
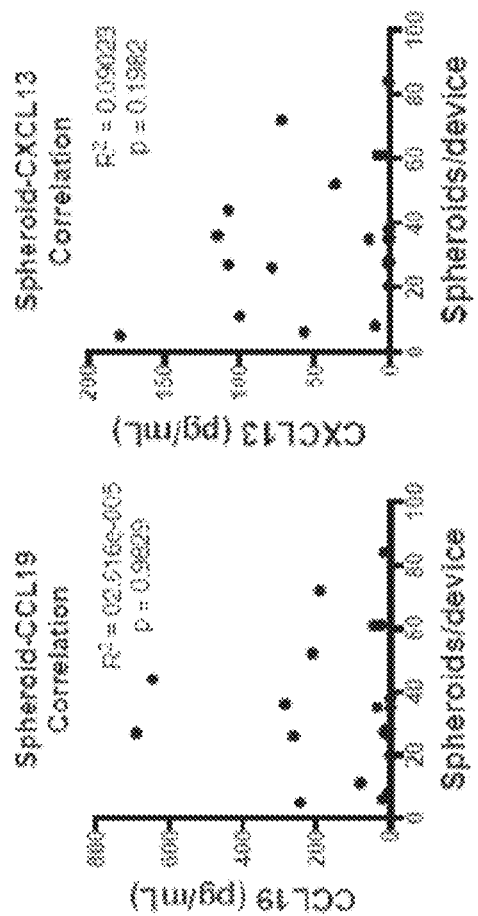

FIG. 8E depicts CCL19 and CXCL13 levels (pg/mL) relative to the number of spheroids per device in control and treatment (αPD-1) conditions (R2=Pearson correlation coefficient).

Figure 8F:
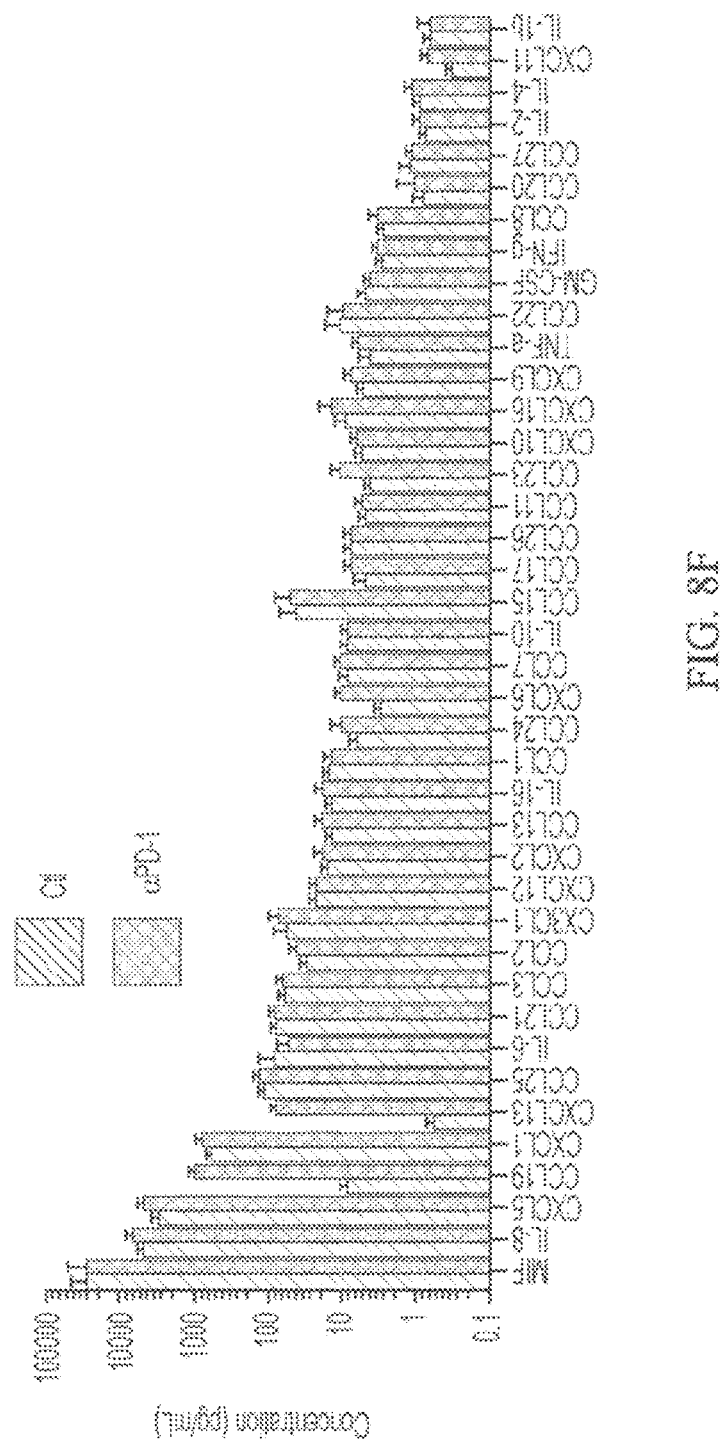

FIG. 8F depicts results of biological replicates for MGH-16 PDOTS in response to PD-1 blockade (n=3, L2FC relative to untreated control on Day 3).

Figure 8G:
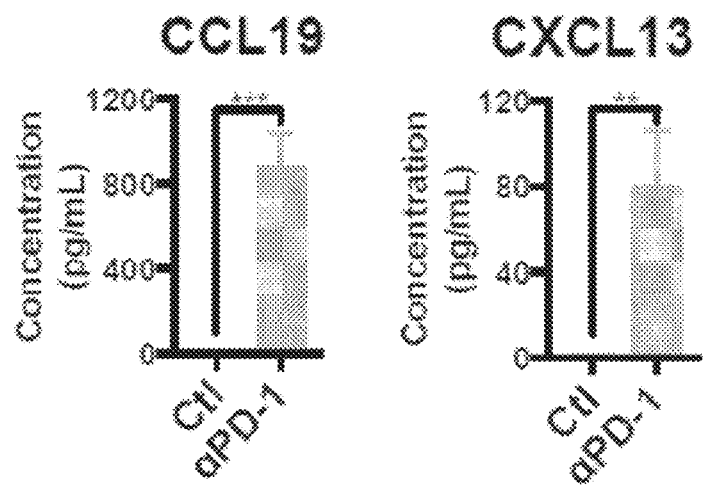

FIG. 8G depicts CCL19 and CXCL13 levels (pg/mL) from biological replicates for MGH-16 PDOTS in response to PD-1 blockade (n=3, L2FC relative to untreated control on Day 3).

Figure 8H:
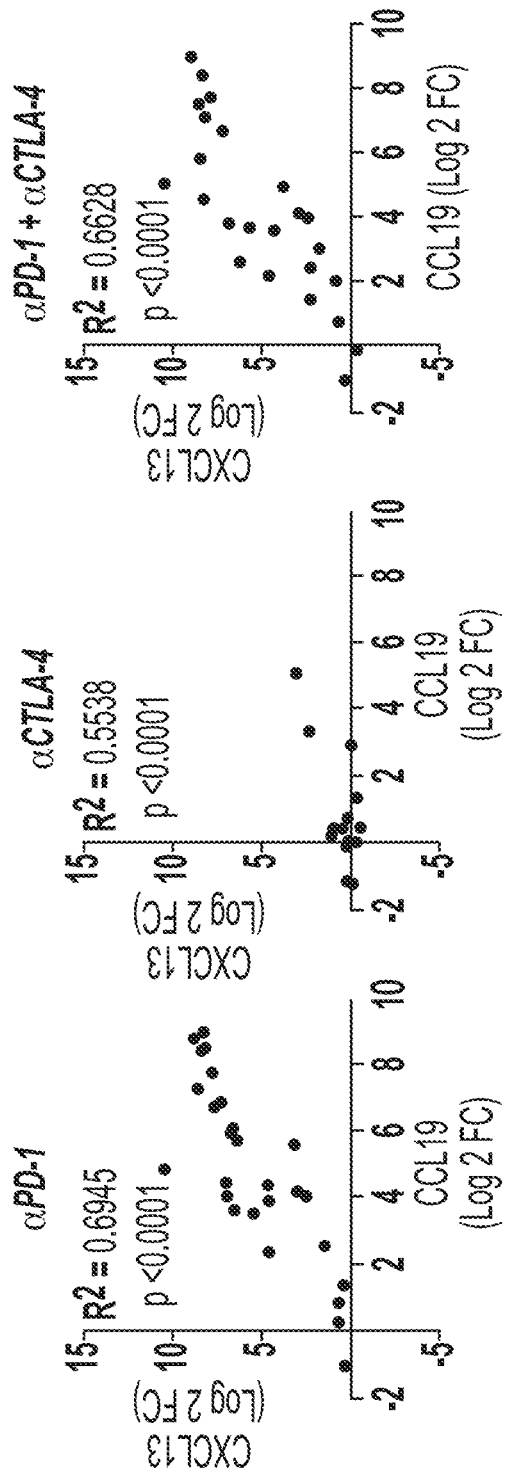
Figure 81:

FIG. 8H depicts the correlation between CCL19 and CXCL13 upregulation (log 2 fold-change relative to untreated control) in response to αPD-1, αCTLA-4, or αPD-1+αCTLA-4 (R2=Pearson correlation coefficient).

FIG. 8I illustrates the effect of culture in the microfluidic device on cytokine profile following αPD-1 treatment. Equal volumes of PDOTS from patient MGH-16 (in collagen hydrogels) were loaded for microfluidic device (or into a single well of a 96-well plate in equal volumes of culture media. Media was collected on Day 3 (control and αPD-1) for cytokine profiling. Induction of cytokines represented as fold-change relative to the untreated control.

Figure 9A:
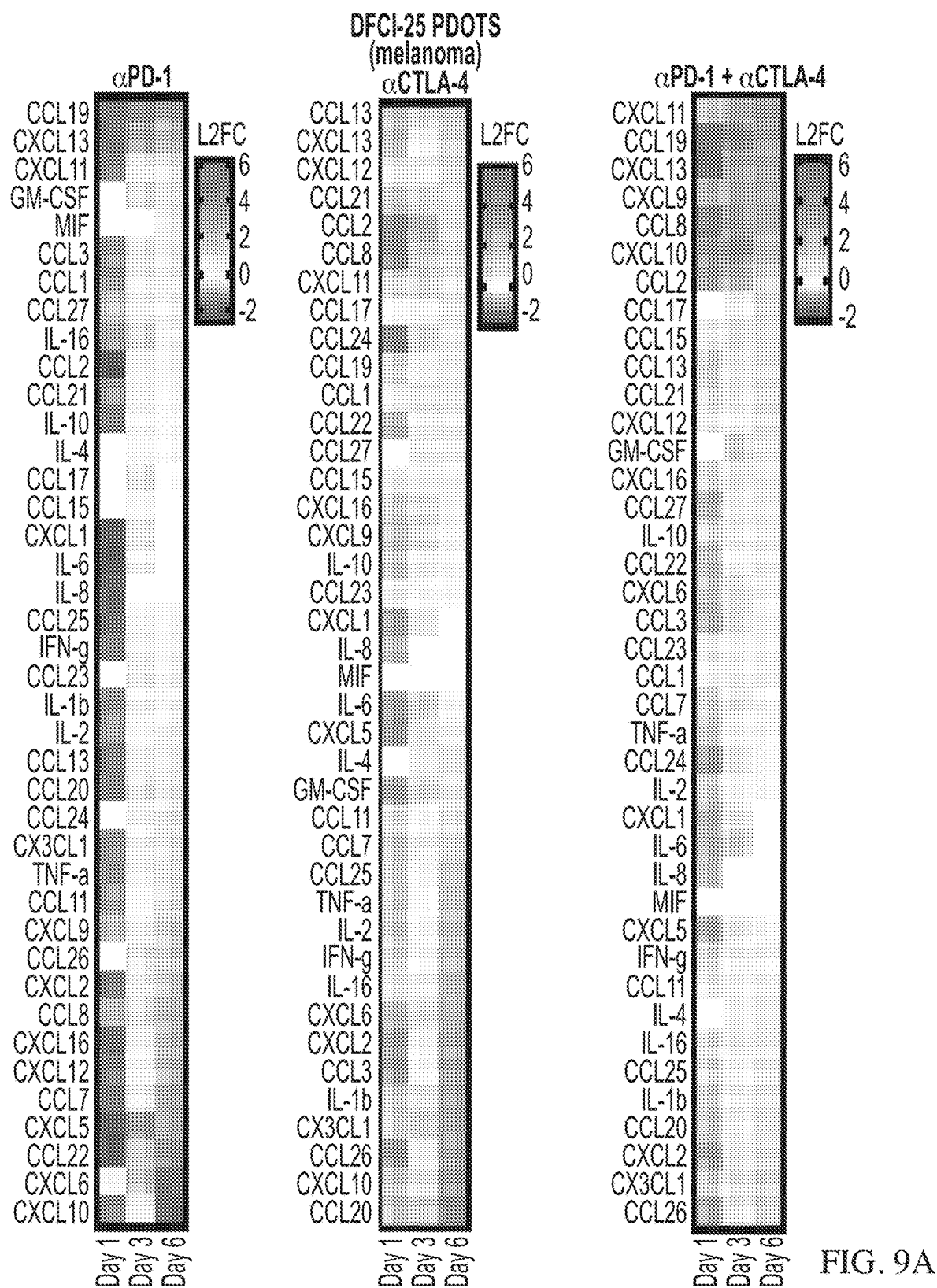

FIG. 9A is a heatmap demonstrating log(2) fold-change (relative to untreated control, ranked highest to lowest) in cytokine profiles using conditioned media obtained at indicated time points of ex vivo microfluidic culture with αPD-1, αCTLA-4, or αPD-1+αCTLA-4 in DFCI-25 (melanoma PDOTS). Arrows denote effector cytokines (e.g. IFN-γ, IL-2) associated with immune-mediated cytolysis.

Figure 9B:
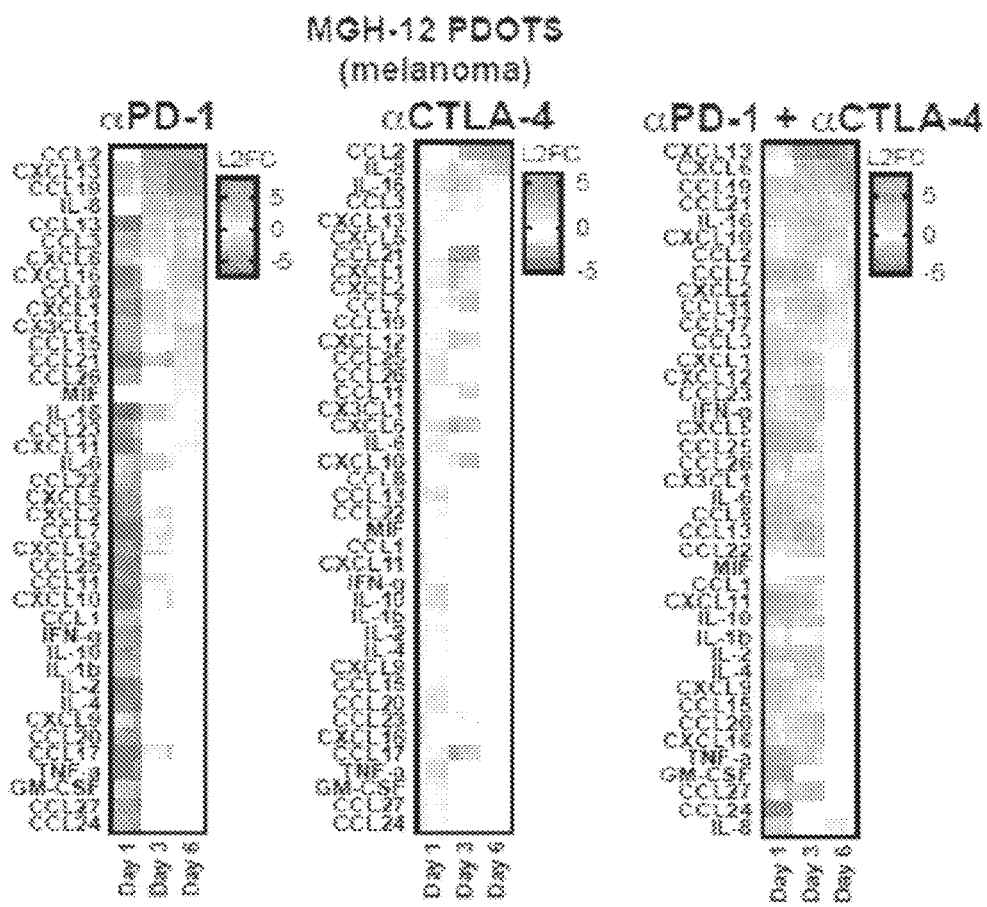

FIG. 9B is a heatmap demonstrating log(2) fold-change (relative to untreated control, ranked highest to lowest) in cytokine profiles using conditioned media obtained at indicated time points of ex vivo microfluidic culture with αPD-1, αCTLA-4, or αPD-1+αCTLA-4 in MGH-12 (melanoma PDOTS). Arrows denote effector cytokines (e.g. IFN-γ, IL-2) associated with immune-mediated cytolysis.

Figure 9C:
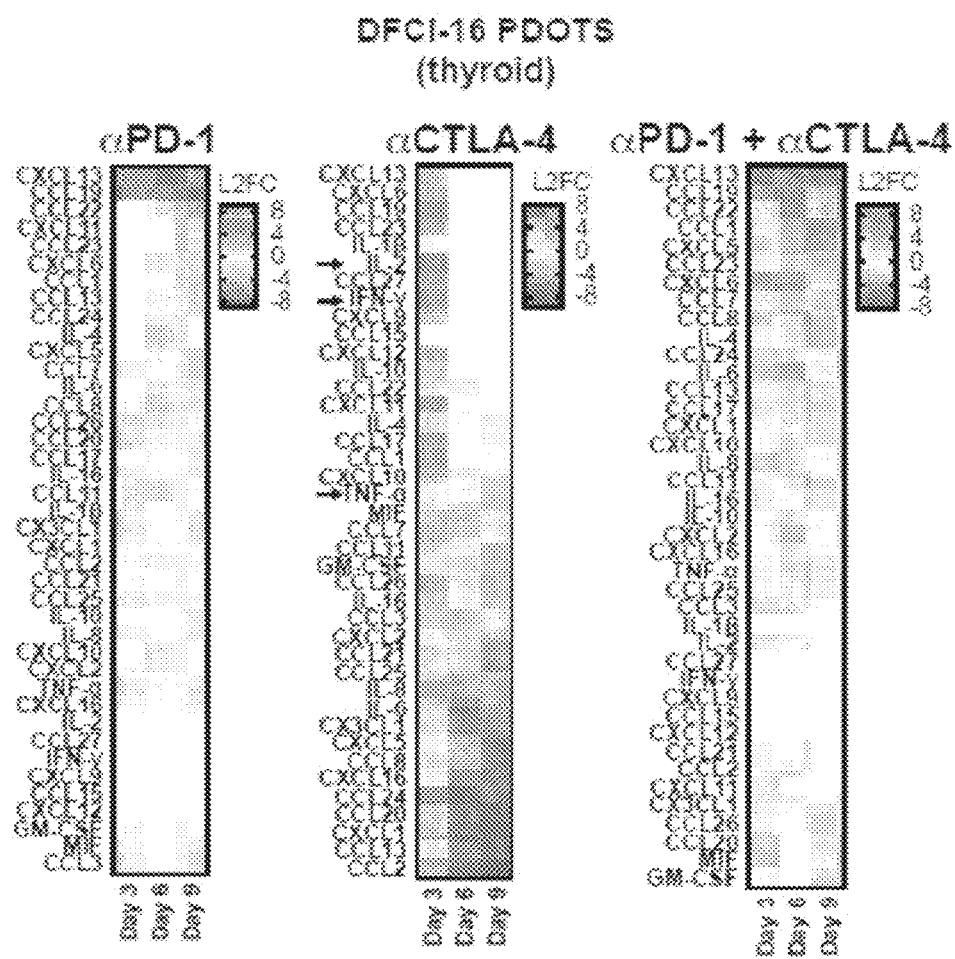

FIG. 9C is a heatmap demonstrating log(2) fold-change (relative to untreated control, ranked highest to lowest) in cytokine profiles using conditioned media obtained at indicated time points of ex vivo microfluidic culture with αPD-1, αCTLA-4, or αPD-1+αCTLA-4 in DFCI-16 (thyroid carcinoma PDOTS). Arrows denote effector cytokines (e.g. IFN-γ, IL-2) associated with immune-mediated cytolysis.

Figure 9D:
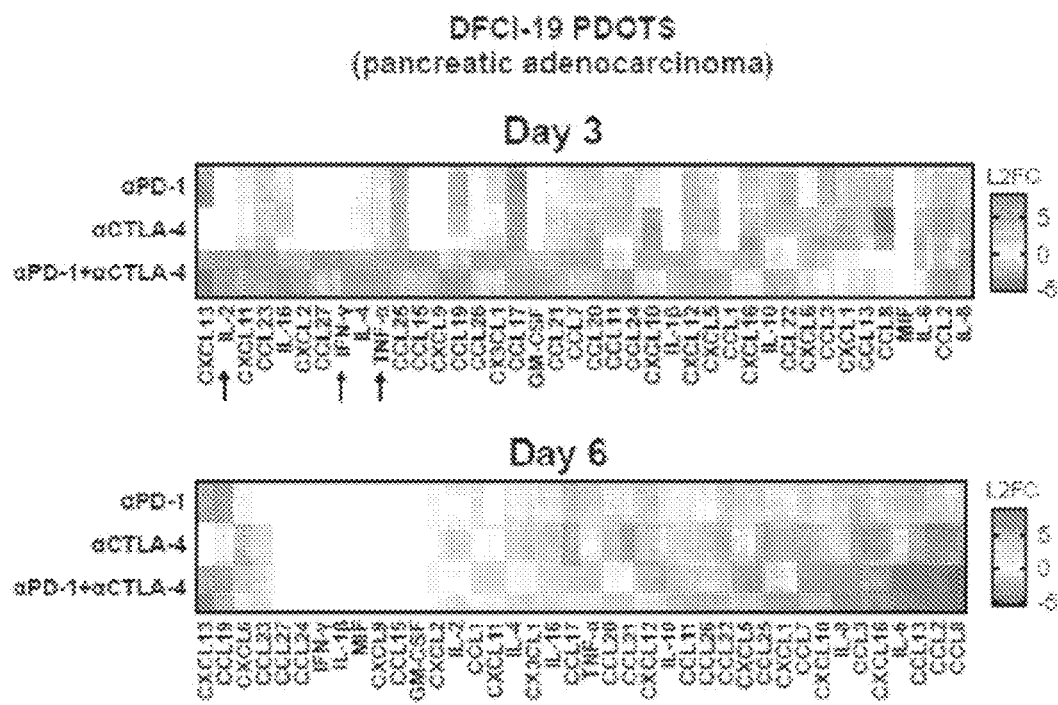

FIG. 9D is a heatmap demonstrating log(2) fold-change (relative to untreated control, ranked highest to lowest) in cytokine profiles using conditioned media obtained at indicated time points of ex vivo microfluidic culture with αPD-1, αCTLA-4, or αPD-1+αCTLA-4 in DFCI-19 (pancreatic adenocarcinoma PDOTS). Arrows denote effector cytokines (e.g. IFN-γ, IL-2) associated with immune-mediated cytolysis.

Figure 10A:
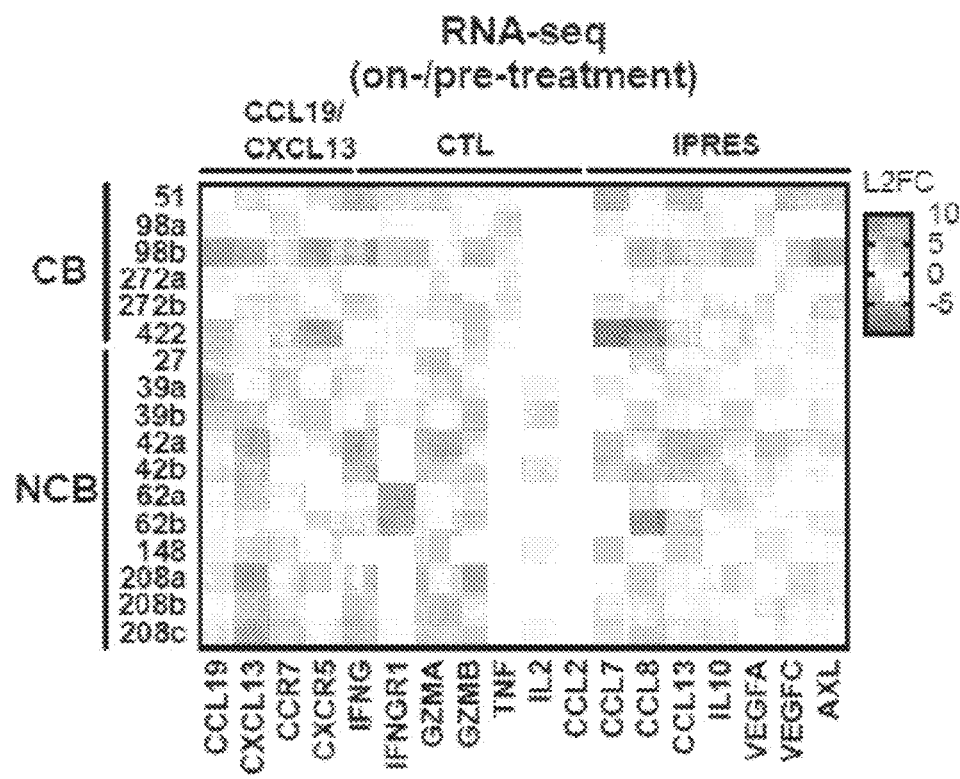

FIG. 10A depicts RNA-seq showing select cytokines, cytokine receptors, cytotoxic T cell (CTL) associated genes, and IPRES transcripts (L2FC relative to pre-treatment control in 10 sets of patient samples).

Figure 10B:
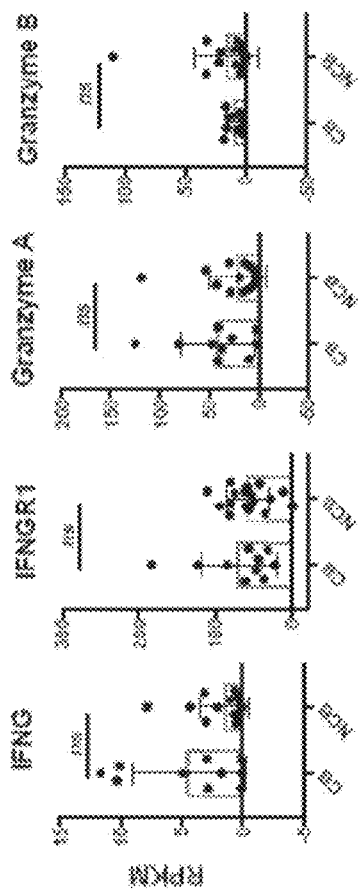

FIG. 10B depicts RNA-seq absolute expression (RPKM) for cytotoxic T cell effector associated genes (IFNG, IFNGR1, granzyme A, granzyme B) from patients with established clinical benefit (CB, n=10 samples from 4 patients) or no clinical benefit (NCB, n=17 samples from 6 patients) from checkpoint blockade.

Figure 10C:
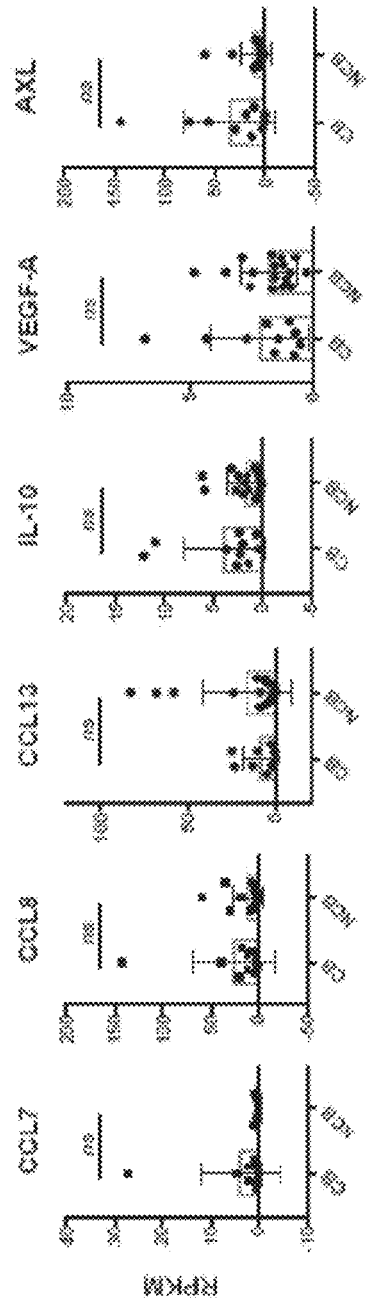

FIG. 10C depicts RNA-seq absolute expression (RPKM) for select IPRES genes in melanoma biopsy specimens (pre- and on-treatment) from patients with established clinical benefit (CB, n=10 samples from 4 patients) or no clinical benefit (NCB, n=17 samples from 6 patients) from checkpoint blockade.

Figure 10D:
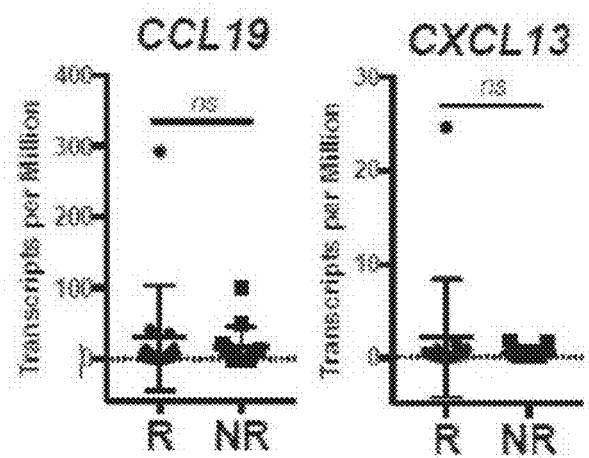

FIG. 10D depicts pre-treatment expression of CCL19 and CXCL13 in responders (n=15) and non-responders (n=13) to PD-1 blockade. Expression data is represented as transcripts per million (TPM) with error bars indicating standard deviation (ns=not significant; unpaired, 2-sided, Mann-Whitney test, α=0.05).

Figure 10E:
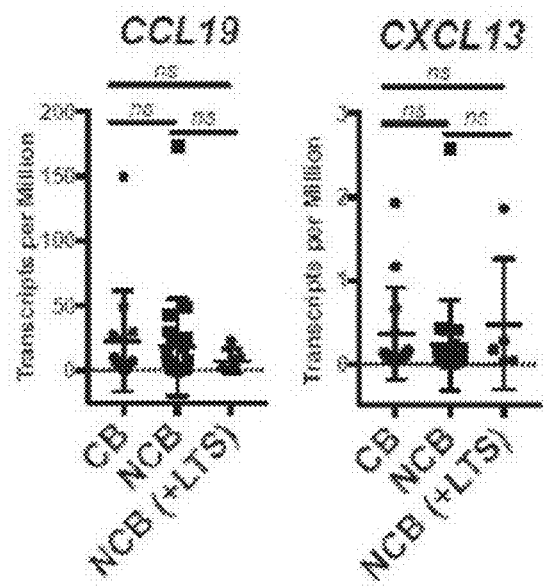

FIG. 10E depicts pre-treatment expression of CCL19 and CXCL13 in patients who experienced clinical benefit (CB, n=14), no clinical benefit (NCB, n=22), and no clinical benefit, but long-term survival (NCB+LTS, n=5) from ipilimumab (αCTLA-4). Expression data is represented as transcripts per million (TPM) with error bars indicating standard deviation (ns=not significant; Kruskal-Wallis with Dunn's multiple comparisons test, α=0.05).

Figure 10F:
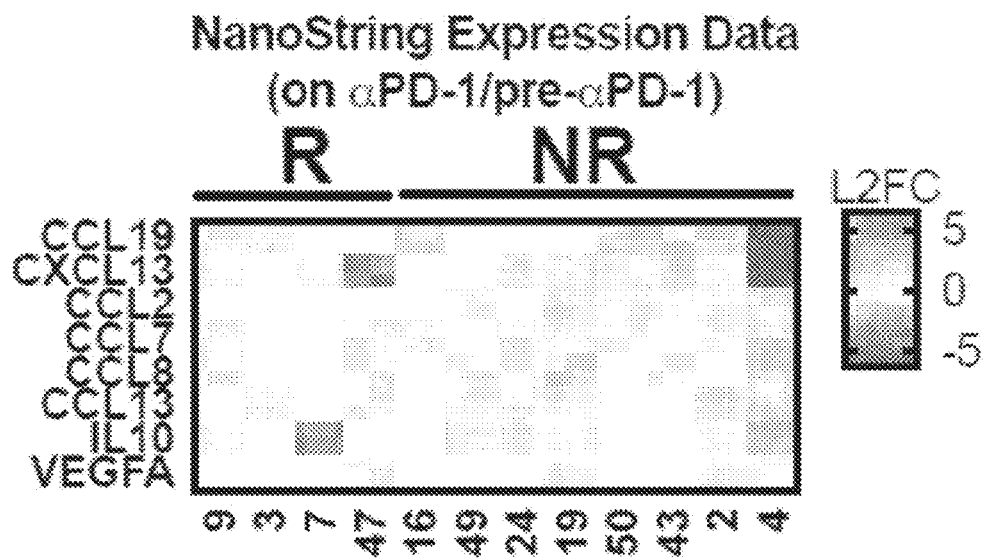

FIG. 10F is a heatmap demonstrating log(2) fold change (on-αPD-1/pre-αPD-1) in expression of indicated cytokines.

Figure 10G:
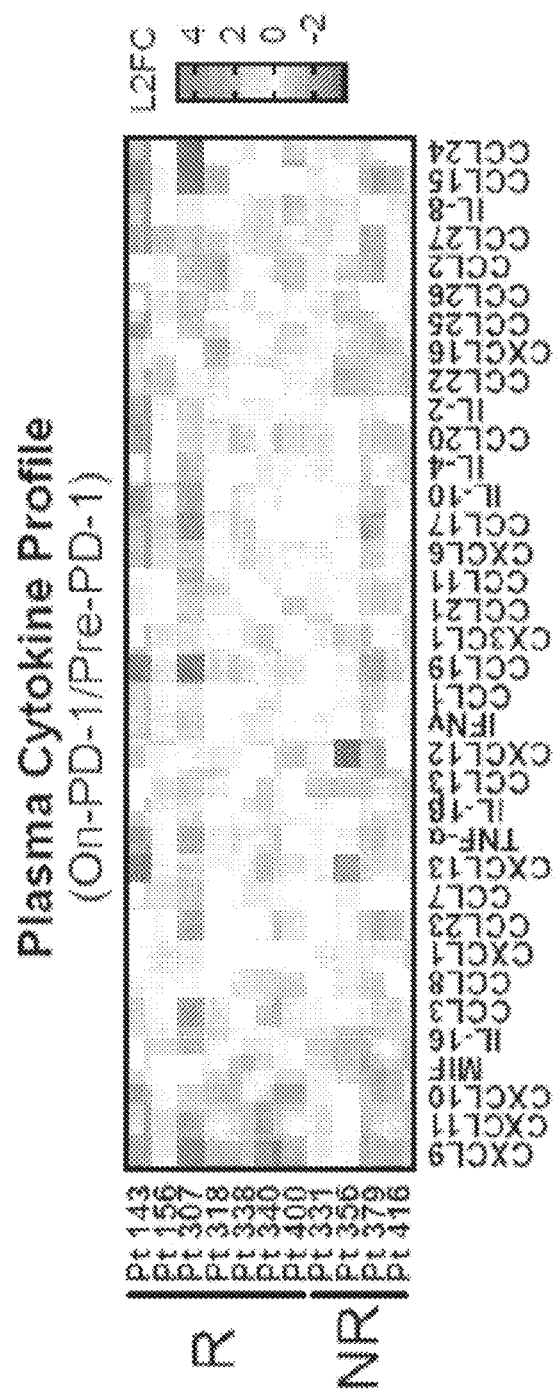

FIG. 10G is a heatmap demonstrating log(2) fold change of plasma cytokines using matched plasma samples (on-treatment/pre-treatment) for responders (R; n=7) and non-responders (NR; n=4) to anti-PD-1 therapy.

Figure 10H:
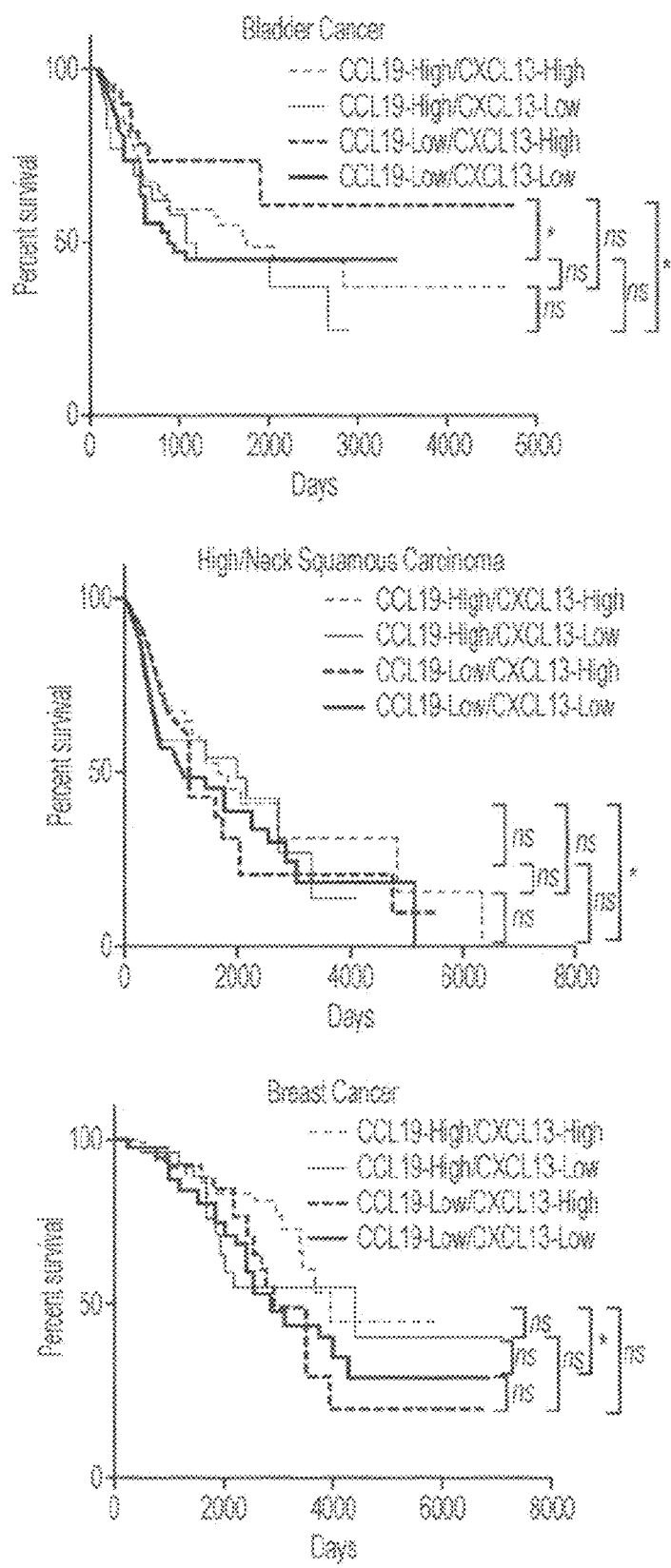

FIG. 10H depicts four-way Kaplan-Meier survival curves by CCL19/CXCL13 expression (high-high, high-low, low-high, and low-low) using urothelial bladder carcinoma (BLCA), head & neck squamous cell carcinoma (HNSC), and breast carcinoma (BRCA) TCGA data (pairwise analysis using log-rank Mantel-Cox test, *p<0.05).

FIG. 11A depicts H&E imaging (10× objective) of tumor-associated tertiary lymphoid structure (TA-TLS), higher magnification (40× objective), and quantitation of TA-TLS identified in 52 H&E slides.

Figure 11B:
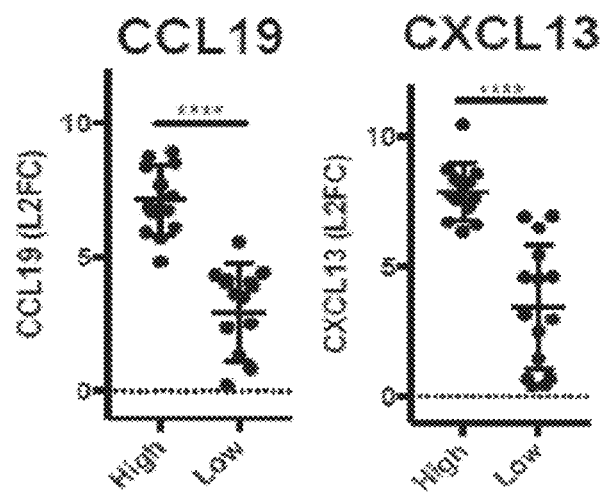

FIG. 11B depicts PDOTS divided into CCL19/CXCL13-high (n=14) and CCL19/CXCL13-low (n=14) by median L2FC (Mann-Whitney test, ****p<0.0001).

Figure 11C:
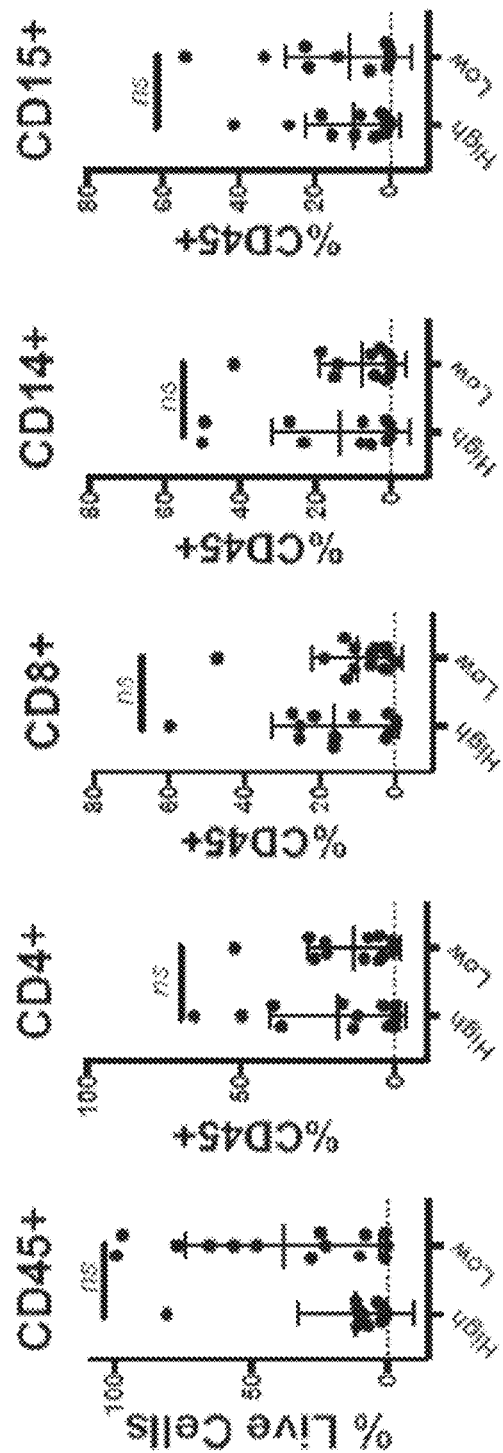

FIG. 11C depicts median immune cell composition (CD45+, CD4+, CD8+, CD14+, CD15+) between PDOTS with distinct ex vivo expression of CCL19/CXCL13 (high vs. low).

Figure 11D:
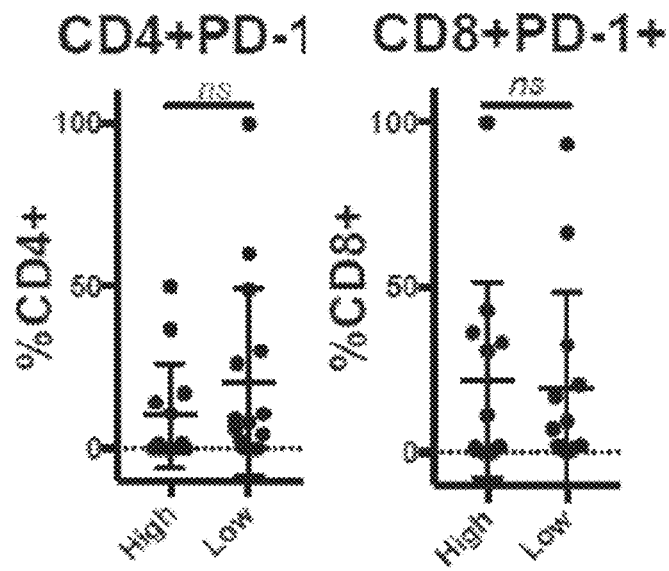

FIG. 11D depicts median immune cell composition (CD4+PD1+ and CD8+PD-1+) in CCL19/CXCL13 high vs. low PDOTS.

Figure 11E:
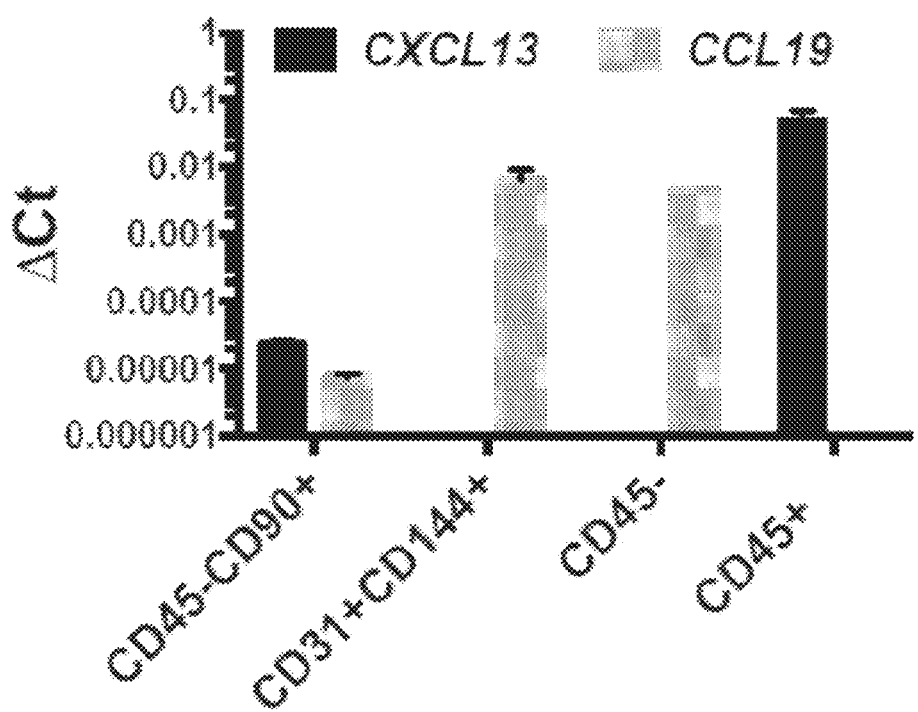

FIG. 11E depicts relative expression of CCL19 and CXCL13 by qRT-PCR in cancer-associated fibroblasts (CD45-CD90+), cancer-associated endothelial cells (CD31+ CD144+), CD45- (cancer cells, etc.) and CD45+ immune cells following 4-way cell sorting (n=2, technical replicates from MGH-16).

Figure 11F:
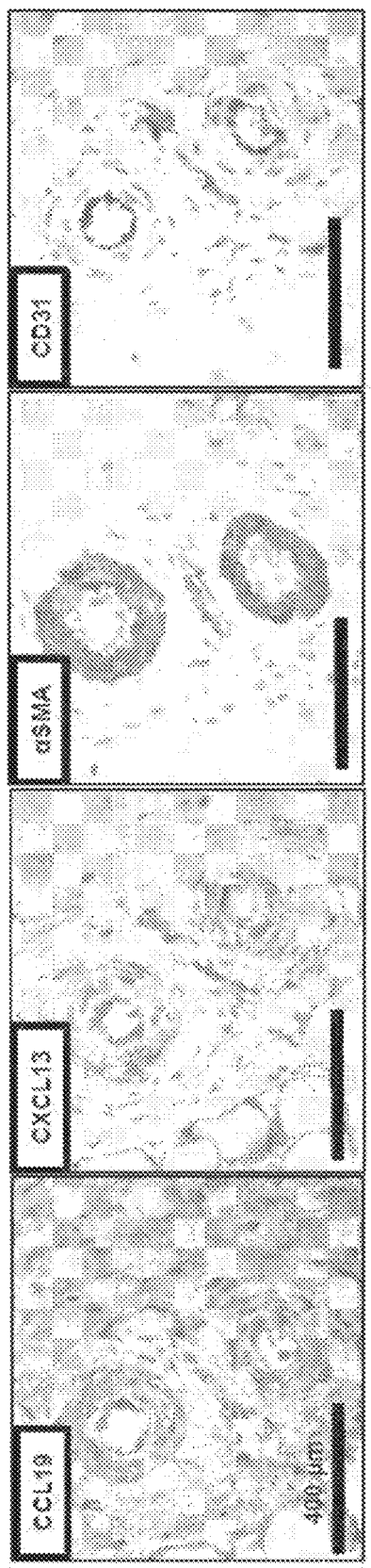

FIG. 11F depicts immunohistochemical staining of CCL19, CXCL13, αSMA (cancer-associated fibroblasts), and CD31 (endothelial cells) in melanoma specimen (pt 422, on-treatment; 40× magnification, scale bar 400 μm).

Figure 12A:
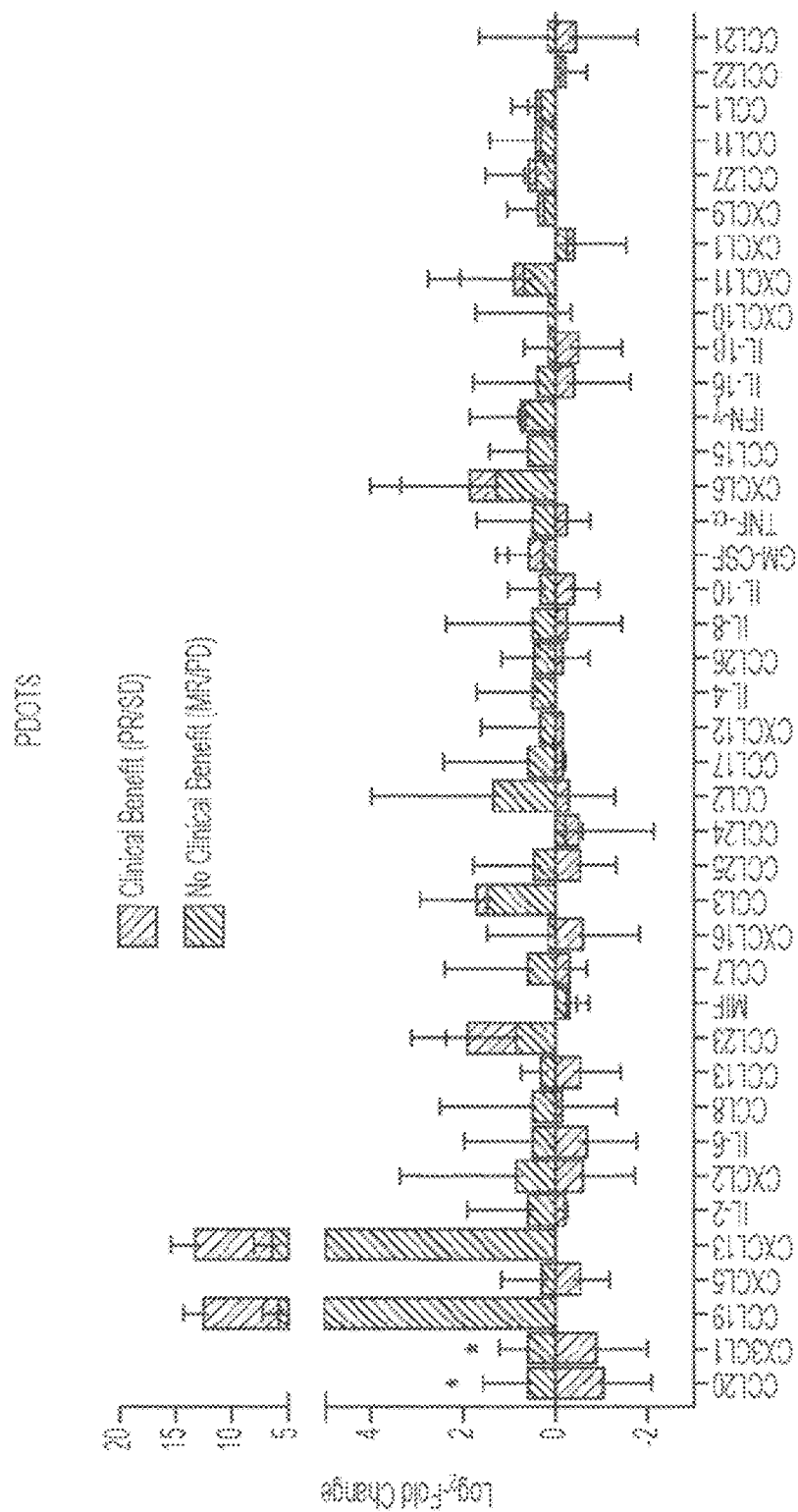

FIG. 12A depicts mean cytokine changes from PDOTS following ex vivo PD-1 blockade in patients with clinical benefit (n=5; PR/SD) and without clinical benefit (n=9; MR/PD) from PD-1 blockade (*p<0.05).

Figure 12B:
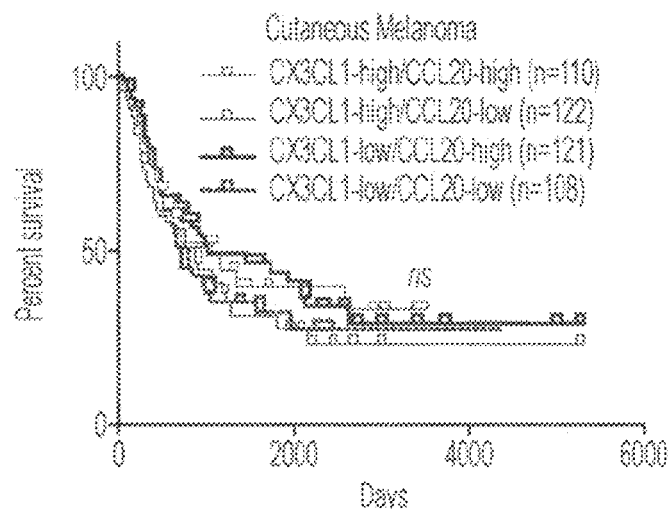

FIG. 12B depicts four-way Kaplan-Meier survival curves by CX3CL1/CCL20 expression (high-high, high-low, low-high, and low-low) using melanoma TCGA data (pairwise analysis using log-rank Mantel-Cox test, α=0.05, ns=not significant).

Figure 12C:
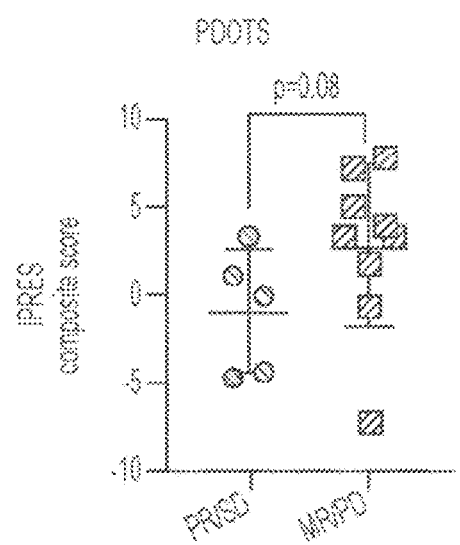

FIG. 12C depicts composite IPRES6 score (sum of L2FC for CCL2, CCL7, CCL8, CCL13, IL-10) in response to ex vivo PD-1 blockade in PDOTS samples from patients with clinical benefit (PR/SD) and without clinical benefit (MR/PD) from PD-1 blockade.

Figure 12D:
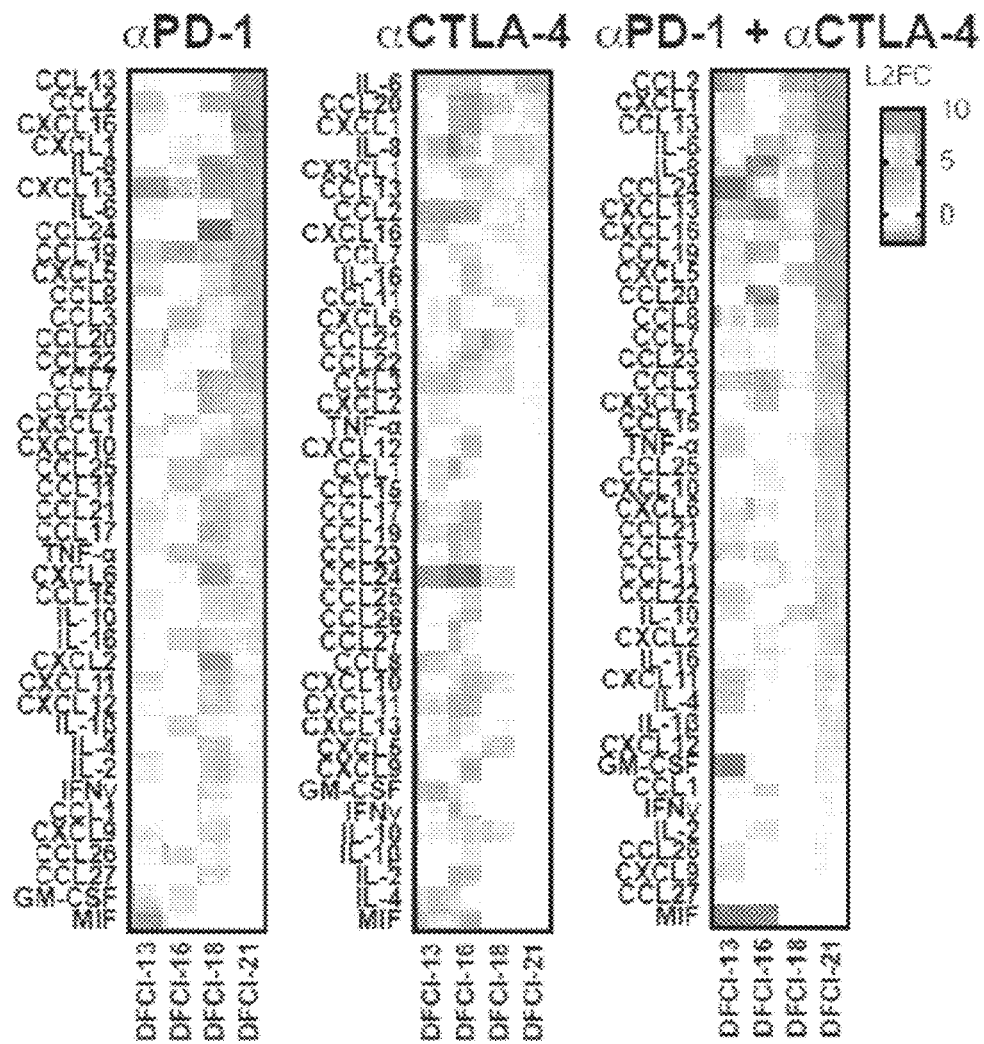

FIG. 12D depicts heatmaps of Day 3 PDOTS anti-PD1 induced cytokines for samples DFCI-13, -16, -18, and -21 (serial sampling from same patient with metastatic papillary thyroid cancer), expressed as L2FC relative to untreated control.

Figure 12E:
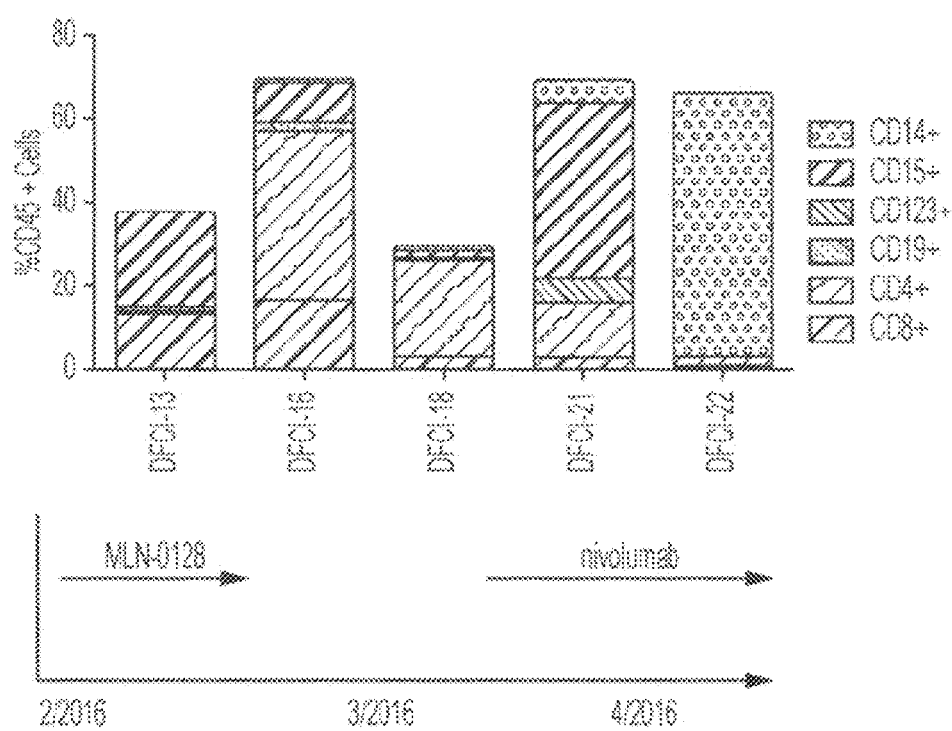

FIG. 12E is a chart that depicts serial immune profiling of samples DFCI-13, -16, -18, -21, and -22 from the same patient undergoing indicated treatments.

Figure 12F:
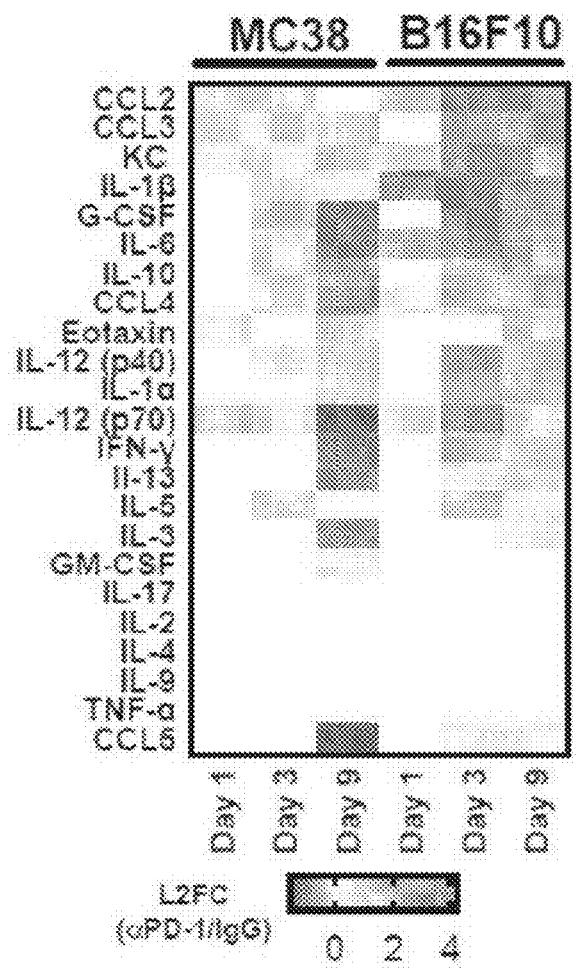

FIG. 12F is a heatmap of relative anti-PD1 induced cytokine changes from MC38 and B16F10 MDOTS (L2FC relative to isotype control; n=3, biological replicates).

Figure 12G:
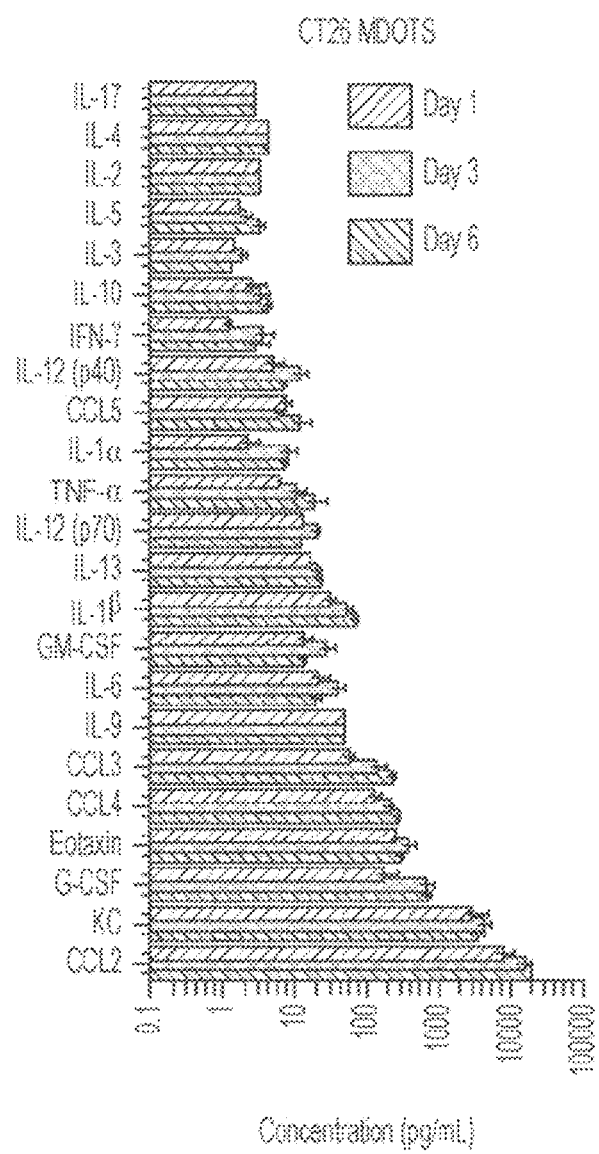

FIG. 12G is a chart that depicts absolute cytokine levels in CT26 MDOTS over time (n=3, biological replicates).

Figure 12H:
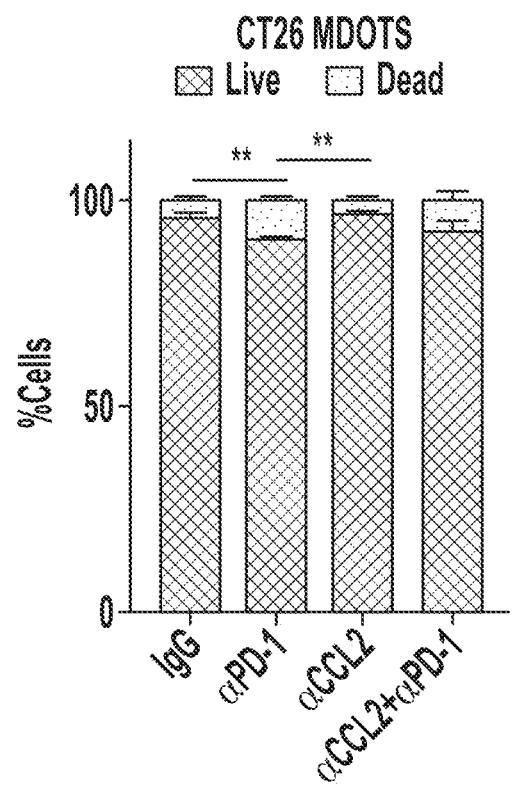

FIG. 12H depicts Live/Dead analysis at Day 6 in CT26 MDOTS treated with anti-CCL2±anti-PD-1 at Days 1, 3, and 6 (L2FC relative to isotype control; n=3, biological replicates).

Figure 12I:
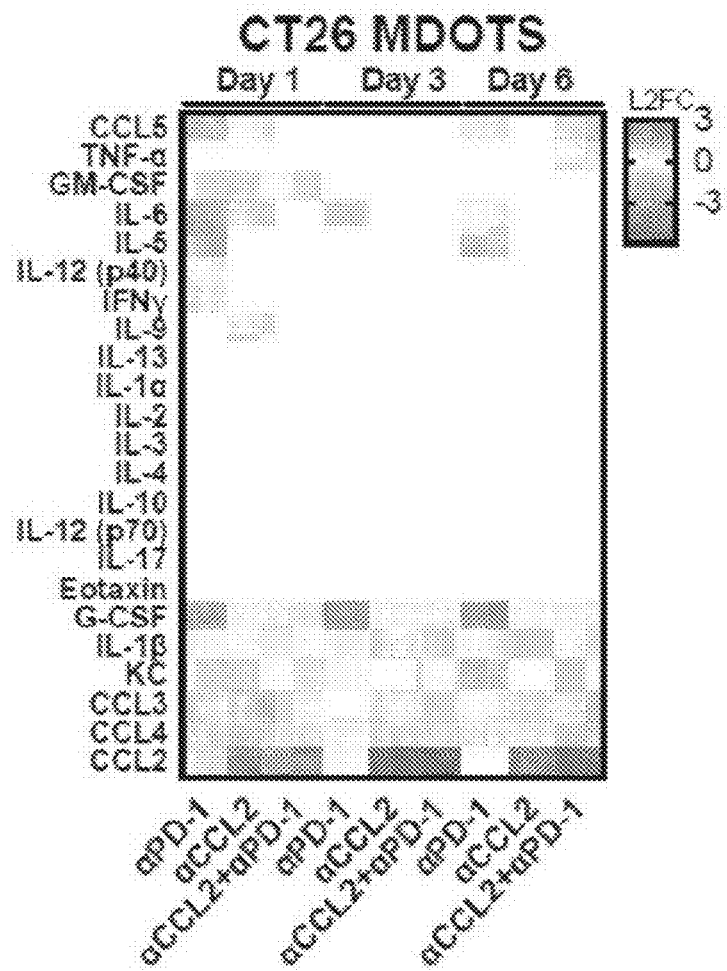

FIG. 12I is a heatmap of relative cytokine changes in CT26 MDOTS treated with anti-CCL2±anti-PD-1 at Days 1, 3, and 6 (L2FC relative to isotype control; n=3, biological replicates).

Figure 13A:
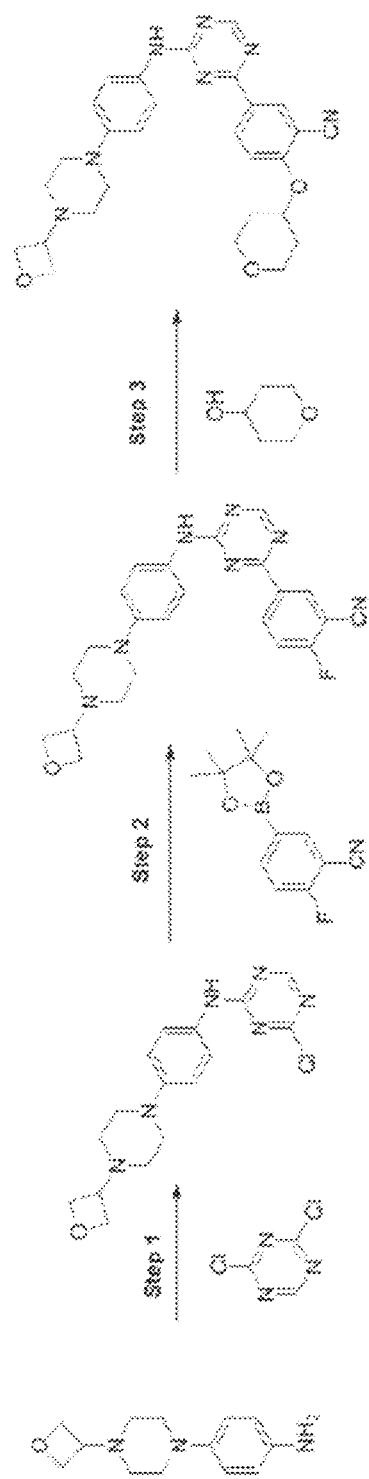

FIG. 13A is a scheme that depicts chemical synthesis of Compound 1.

Figure 13B:
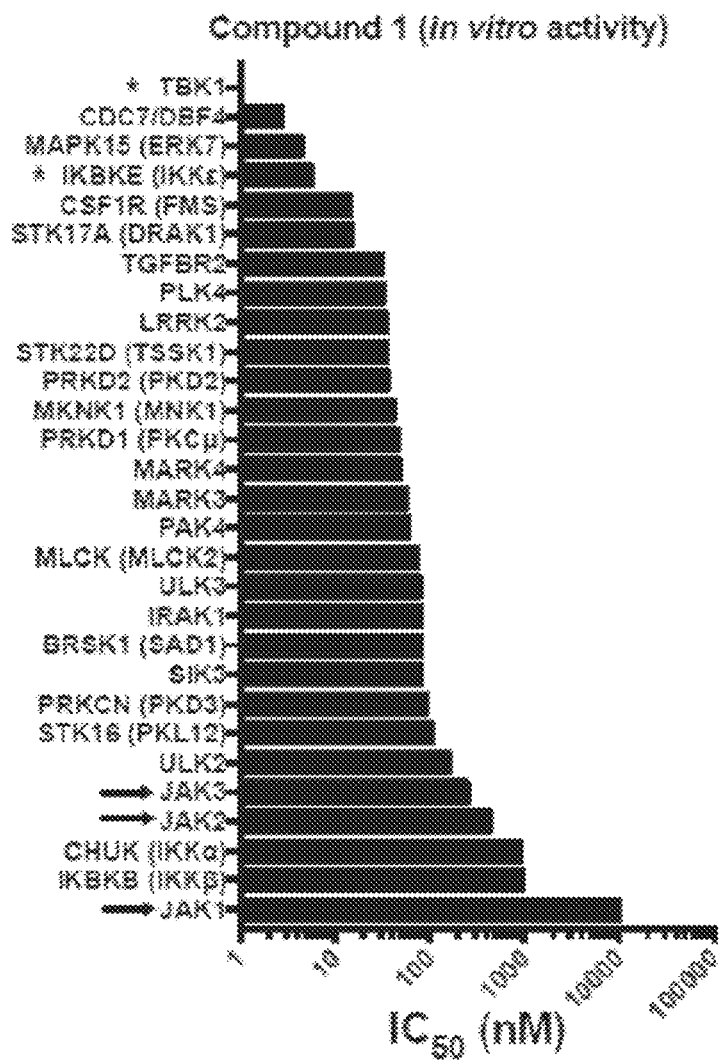

FIG. 13B is a chart that depicts $IC_{50}$ values for indicated enzymes treated with Compound 1.

Figure 13C:
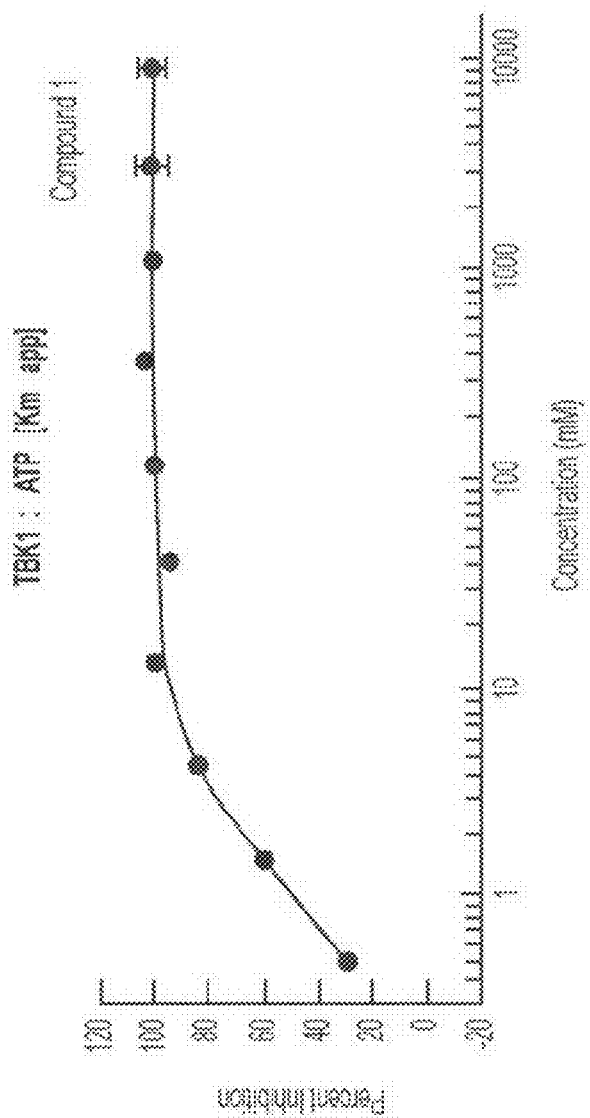

FIG. 13C depicts an $IC_{50}$ curve for TBK1.

Figure 13D:
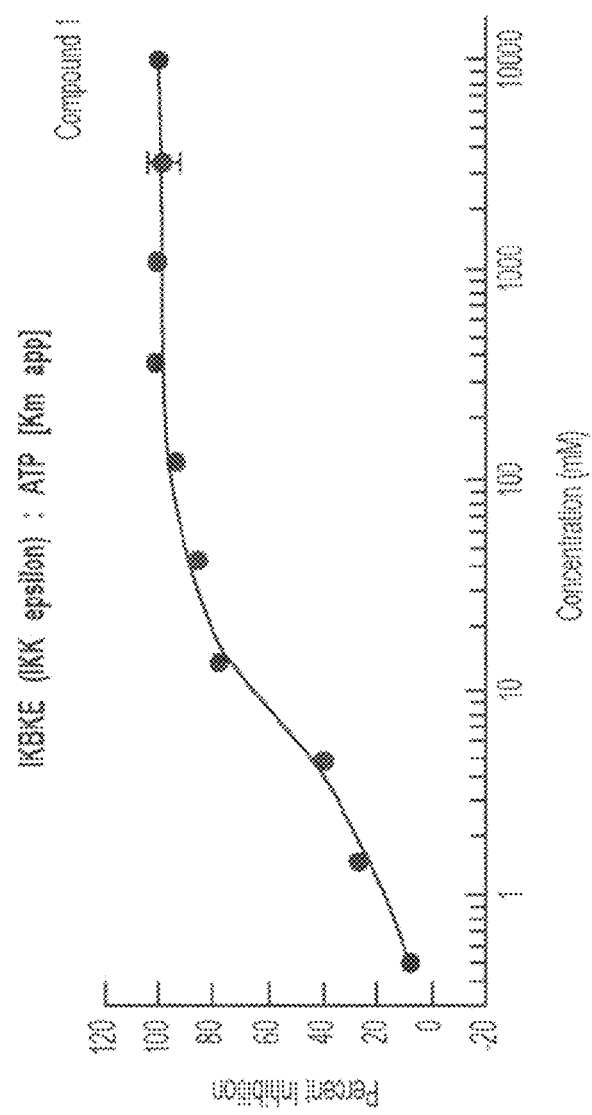

FIG. 13D depicts an $IC_{50}$ curve for IKKε (IKBKE).

Figure 13E:
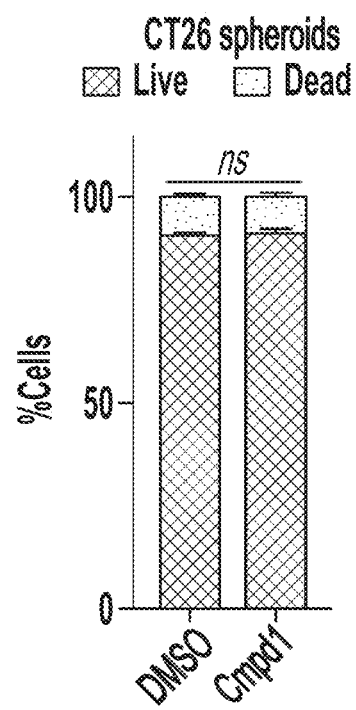

FIG. 13E is a chart that depicts effect of Compound 1 on viability of CT26 spheroids lacking immune cells (n=3, biological replicates).

Figure 13F:
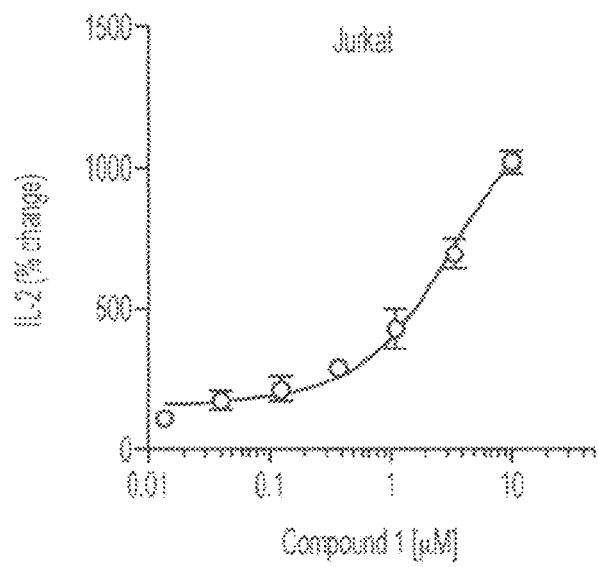

FIG. 13F illustrates fold-change in IL-2 levels produced by Jurkat cells with increasing doses of Compound 1.

Figure 13G:
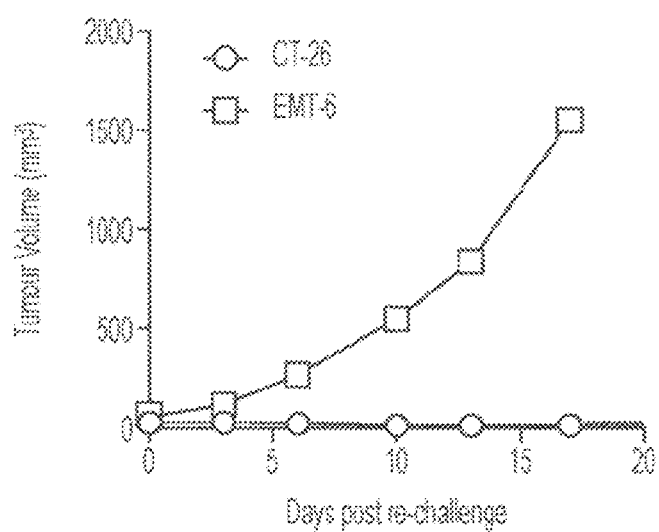

FIG. 13G depicts change in tumor volume following re-implantation of CT26 and EMT-6 cells into the flanks of mice previously treated with anti-PD-L1+Compound 1.

Figure 14A:
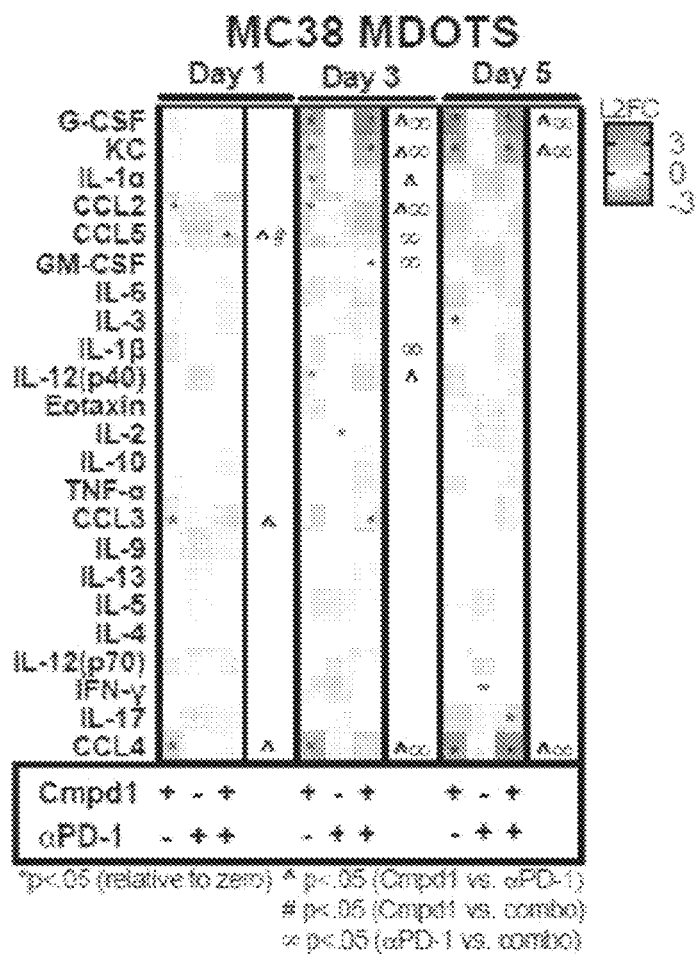

FIG. 14A is a cytokine heatmap for MC38 MDOTS treated with IgG+Cmpd1 (1 μM), αPD-1 (10 μg/mL), or αPD-1+Cmpd1 (1 μM) from the mean of n=3 biological replicates, plotted as L2FC relative to isotype control IgG (10 μg/mL) with vehicle control (DMSO 0.1%). 2-sided Welch's 2-sample t-test with unequal variance (α=0.05).

Figure 14B:
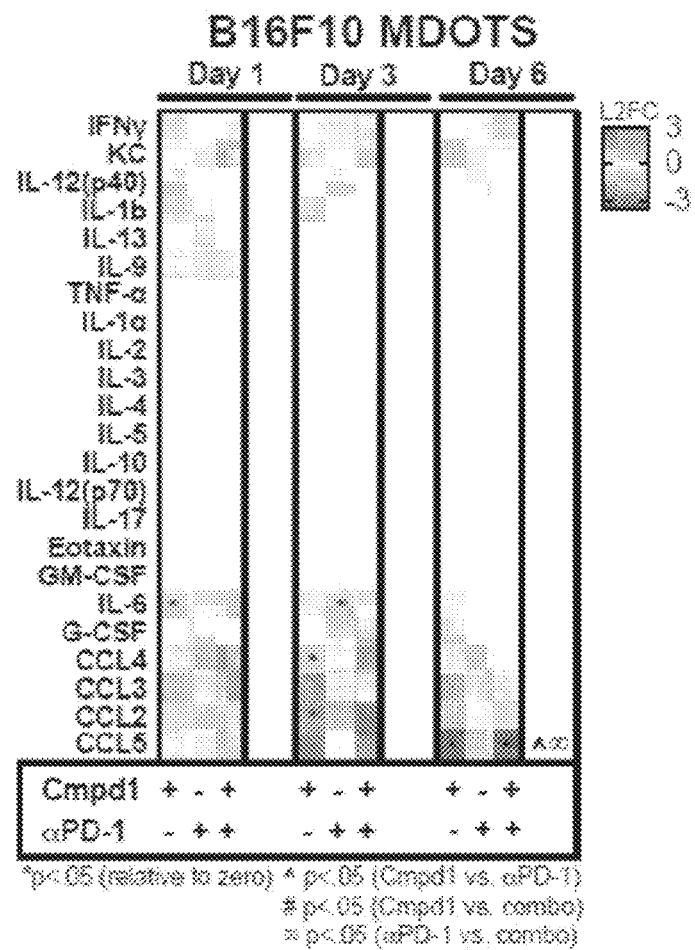

FIG. 14B is a cytokine heatmap for B 16F10 MDOTS treated with IgG+Cmpd1 (1 μM), αPD-1 (10 μg/mL), or αPD-1+Cmpd1 (1 μM) from the mean of n=3 biological replicates, plotted as L2FC relative to isotype control IgG (10 μg/mL) with vehicle control (DMSO 0.1%). 2-sided Welch's 2-sample t-test with unequal variance (α=0.05).

Figure 14C:
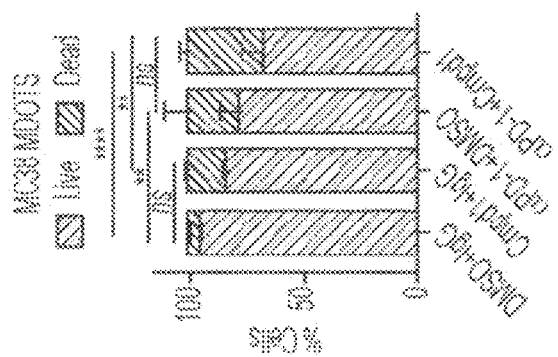

FIG. 14C is a chart that depicts live (AO=green)/dead (PI=red) quantification of MC38 MDOTS after 5 days treated with IgG-DMSO, Cmpd1 (1 μM), αPD-1, and αPD-1+Cmpd1 (*p<0.05, Kruskal-Wallis ANOVA with multiple comparisons; n=3).

Figure 14D:
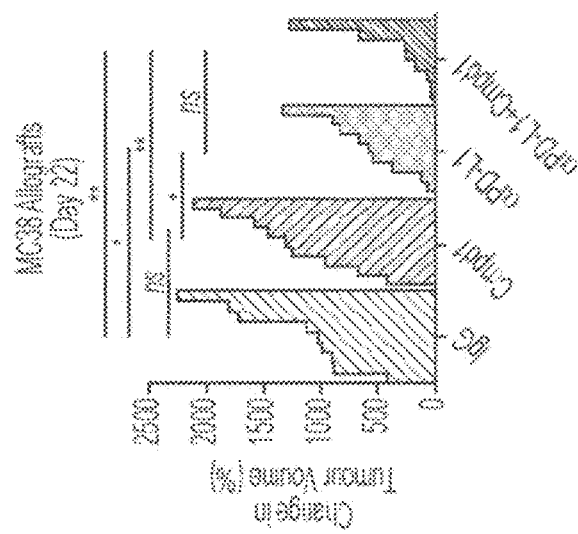

FIG. 14D depicts MC38 allograft tumor volume waterfall plot following IgG+vehicle, IgG+Cmpd1, αPD-L1+vehicle, and αPD-L1+Cmpd1 (n=10 per group, *p<0.05, **p<0.01, 1-way ANOVA with Tukey's multiple comparison's test for tumor volume, log-rank Mantel-Cox test for Kaplan-Meier analysis for entire group and pairwise comparisons).

Figure 14E:
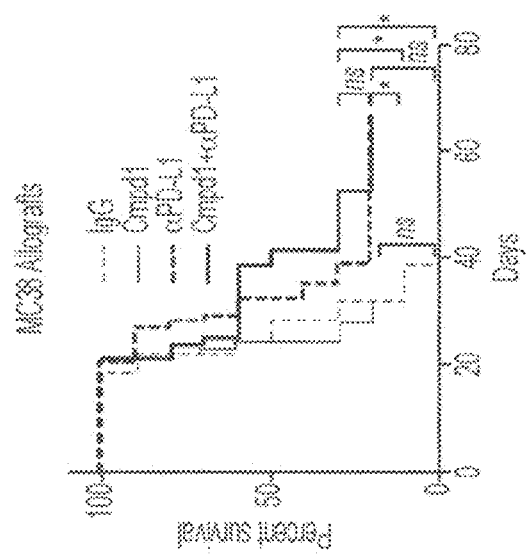

FIG. 14E depicts percent survival following IgG+vehicle, IgG+Cmpd1, αPD-L1+vehicle, and αPD-L1+Cmpd1 (n=10 per group, *p<0.05, **p<0.01, 1-way ANOVA with Tukey's multiple comparison's test for tumor volume, log-rank Mantel-Cox test for Kaplan-Meier analysis for entire group and pairwise comparisons).

Figure 14H:
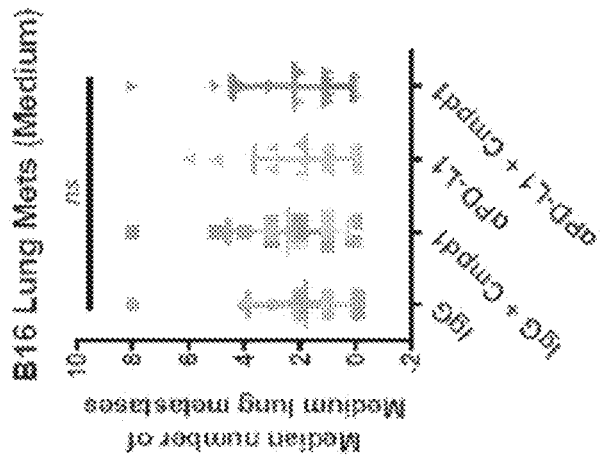
Figure 14G:
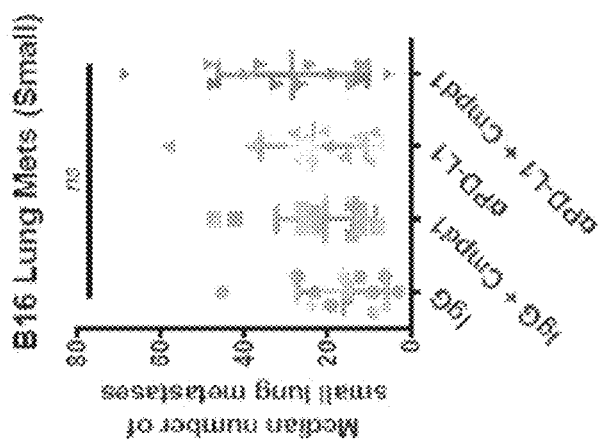
Figure 14F:
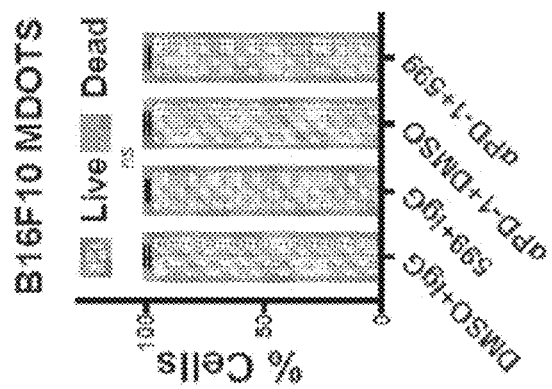

FIG. 14F is a chart that depicts live (AO=green)/dead (PI=red) quantification of B16F10 MDOTS after 6 days treated with IgG-DMSO, Cmpd1 (1 μM), αPD-1, and αPD-1+Cmpd1 (α=0.05, ns=not significant. Kruskal-Wallis ANOVA with multiple comparisons; n=3).

FIG. 14G depicts quantification of small lung metastases in B 16F10 tail vein injection model following IgG+vehicle, IgG+Cmpd1, αPD-L1+vehicle, and αPD-L1+Cmpd1 (n=10 per group, 1-way ANOVA with Tukey's multiple comparison's test, ns=not significant).

FIG. 14H depicts quantification of medium lung metastases in B16F10 tail vein injection model following IgG+vehicle, IgG+Cmpd1, αPD-L1+vehicle, and αPD-L1+Cmpd1 (n=10 per group, 1-way ANOVA with Tukey's multiple comparison's test, ns=not significant).

Figures 14I, 14J, 14K:
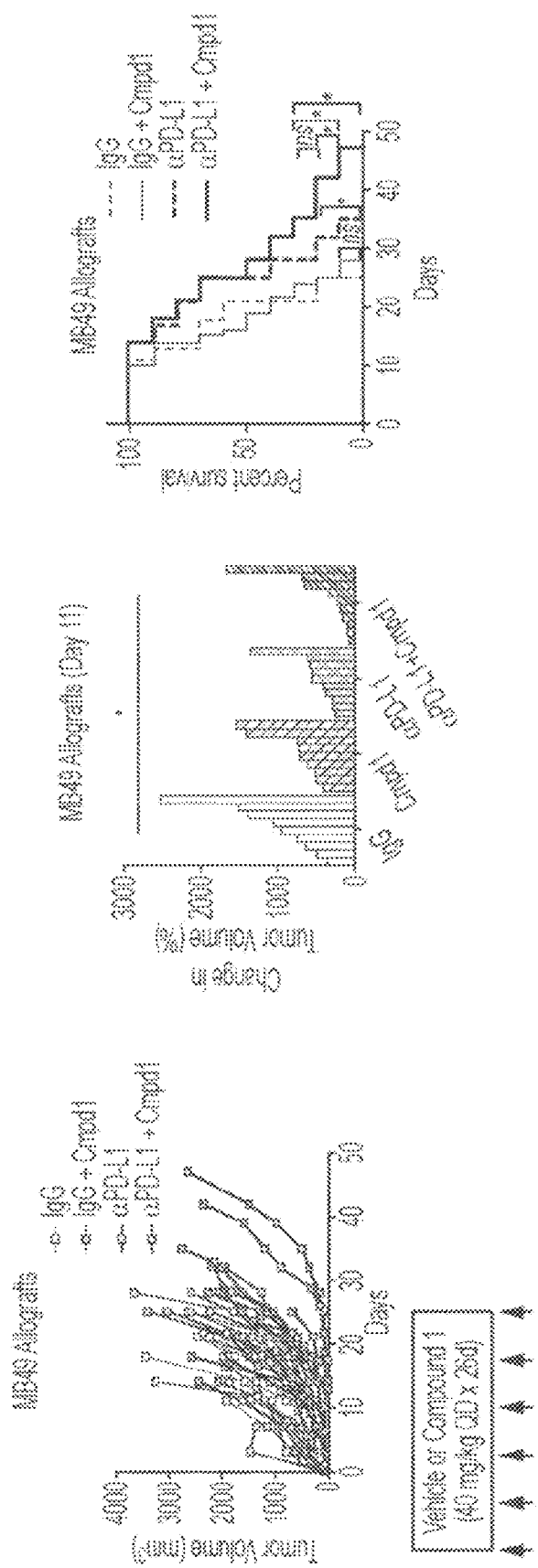

FIG. 14I depicts MB49 allograft tumor volume waterfall plot following IgG+vehicle, IgG+Cmpd1, αPD-L1+vehicle, and αPD-L1+Cmpd1 (n=10 per group, *p<0.05, 1-way ANOVA with Tukey's multiple comparison's test for tumor volume, log-rank Mantel-Cox test for Kaplan-Meier analysis for entire group and pairwise comparisons).

FIG. 14J depicts MB49 allograft tumor volume waterfall plot as a bar chart following IgG+vehicle, IgG+Cmpd1, αPD-L1+vehicle, and αPD-L1+Cmpd1 (n=10 per group,

*p<0.05, 1-way ANOVA with Tukey's multiple comparison's test for tumor volume, log-rank Mantel-Cox test for Kaplan-Meier analysis for entire group and pairwise comparisons).

FIG. 14K depicts percent survival following IgG+vehicle, IgG+Cmpd1, αPD-L1+vehicle, and αPD-L1+Cmpd1 (n=10 per group, *p<0.05, 1-way ANOVA with Tukey's multiple comparison's test for tumor volume, log-rank Mantel-Cox test for Kaplan-Meier analysis for entire group and pairwise comparisons).

Figure 15:
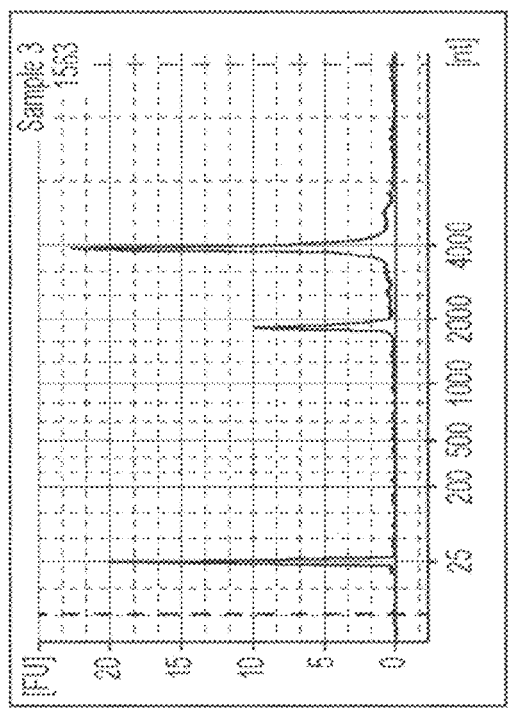

FIG. 15 depicts a table summary of Pilot RNA Extraction, QC, and Quantitation (left), and a representation bioanalyzer trac showing fully intact total RNA from MDOTS (right).

DETAILED DESCRIPTION

Among other aspects, the disclosure provides methods for evaluating tumor cell spheroids in a three-dimensional microfluidic device by monitoring a ratio of live cells to dead cells. In some aspects, the methods include steps of exposing separate aliquots of a tumor spheroid sample to different conditions, such as the inclusion or exclusion of a test compound. As such, in some embodiments, the effects of a test compound can be evaluated by monitoring its effects on the ratio of live cells to dead cells. It has been discovered, surprisingly, that the tumor microenvironment of a cultured tumor spheroid can be evaluated optically and reproducibly, to establish the effects of drugs on the tumor cells within the spheroids, while distinguishing the effects on tumor cells resulting from the act of culturing the tumor cells.

As used herein, the term "tumor" refers to a neoplasm, i.e., an abnormal growth of cells or tissue and is understood to include benign, i.e., non-cancerous growths, and malignant; i.e., cancerous growths including primary or metastatic cancerous growths.

Examples of neoplasms include, but are not limited to, mesothelioma, lung cancer (e.g., small-cell lung cancer, non-small cell lung cancer), skin cancer (e.g., melanoma), stomach cancer, liver cancer, colorectal cancer, breast cancer, pancreatic cancer, prostate cancer, blood cancer, bone cancer, bone marrow cancer, and other cancers.

The term "tumor spheroid," or "tumor cell spheroid" as used herein, refers to an aggregation of tumor cells constituting a small mass, or lump of tumor cells. In some embodiments, tumor spheroids are less than about 3 cm, less than about 2 cm, less than about 1 cm, less than about 5 mm, less than about 2.5 mm, less than about 1 mm, less than about 100 μm, less than about 50 μm, less than about 25 μm, less than about 10 μm, or less than about 5 μm in diameter. In some embodiments, the tumor spheroids have a diameter of 10 μm to 500 μm. In some embodiments, the tumor spheroids have a diameter of 40 μm to 100 μm. In some embodiments, the tumor spheroids have a diameter of 40 μm to 70 μm.

The term "primary tumor sample" as used herein refers to a sample comprising tumor material obtained from a subject having cancer. The term encompasses tumor tissue samples, for example, tissue obtained by surgical resection and tissue obtained by biopsy, such as for example, a core biopsy or a fine needle biopsy. The term also encompasses patient derived xenograft (PDX). Patient derived xenografts are created when cancerous tissue from a patient's primary tumor is implanted directly into an immunodeficient mouse (see, for example, Morton C L, Houghton P J (2007). "Establishment of human tumor xenografts in immunodeficient mice". Nature Protocols 2 (2): 247-50; Siolas D, Hannon G J (September 2013). "Patient-derived tumor xenografts: transforming clinical samples into mouse models". Cancer Research 73 (17): 5315-9). PDX mirrors patients' histopathological and genetic profiles. It has improved predictive power as preclinical cancer models, and enables the true individualized therapy and discovery of predictive biomarkers.

In some embodiments, the subject is a human. In some embodiments, the subject is a non-human mammal or a non-human vertebrate. In some embodiments, the subject is laboratory animal, a mouse, a rat, a rodent, a farm animal, a pig, a cattle, a horse, a goat, a sheep, a companion animal, a dog a cat, or a guinea pig.

In some embodiments, a tumor sample as used herein is derived from a subject known to have resistance or sensitivity to a particular therapeutic treatment. For example, in some embodiments, methods provided herein can identify novel combination therapies and/or novel single therapies that overcome resistance to a specified treatment, e.g., PD-1 inhibition in the treatment of cancer. In some embodiments, where PD-1 combination therapies are to be evaluated, tumor samples may be derived from one or more subjects having the same or varied levels of sensitivity to PD-1 inhibition therapy. In some embodiments, the tumor sample is derived from a B16F10 murine model. B16F10 is a murine model that is minimally sensitive to PD-1 blockade. In some embodiments, the tumor sample is derived from an MC38 murine model. MC38 is a murine model that is highly sensitive to PD-1 blockade relative to B16F10. In some embodiments, the tumor sample is derived from a CT26 murine model. CT26 is a murine model that is of an intermediate sensitivity relative to B16F10 and MC38 models. In some embodiments, methods provided herein comprises steps of evaluating a combination of two or more of tumor samples derived from B16F10, MC38, or CT26 models.

Tumor cell spheroids can be prepared by any method known in the art. Exemplary methods for preparing tumor cell spheroids are described in WO 2016/112172, the disclosure of which is incorporated herein by reference.

In some embodiments, the primary tumor sample is collected in a serum-supplemented medium, for example but not limited to, RPMI medium supplemented with 10% fetal bovine serum. The sample is then minced, i.e., cut or chopped into tiny pieces. In some embodiments, the sample is minced on ice. In some embodiments, the minced primary tumor sample comprises tumor pieces in the size of about 3 mm, 2.5 mm, 2.0 mm, 1.5 mm, 1.0 mm, 0.5, or 0.25 mm.

In some embodiments, the primary tumor sample is not frozen and thawed.

In some embodiments, minced primary tumor sample is frozen in a medium supplemented with serum and thawed prior to treating with the composition comprising the enzyme. In some embodiments, the minced primary tumor sample is frozen for at least 6 hours 12 hours, 24 hours, 2 days, 1 week or one month. In some embodiments, the minced primary tumor sample is frozen at −80° C. In some embodiments, the minced primary tumor sample is frozen in liquid nitrogen. In some embodiments, the minced primary tumor sample is frozen in a medium supplemented with serum. In some embodiments, the minced primary tumor sample is frozen in a mixture containing serum and solvent such as Dimethyl sulfoxide (DMSO). In some embodiments, the minced primary tumor sample is frozen in a mixture containing fetal bovine serum and Dimethyl sulfoxide (DMSO).

In some embodiments, the frozen minced primary tumor sample is thawed, i.e., defrosted, before treating the sample with a composition comprising an enzyme. In some embodiments, the minced primary tumor sample is thawed in a water bath kept at about 37° C. (e.g., 35° C., 36° C., 37° C., 38° C., or 39° C.). In some embodiments, the minced primary tumor sample is thawed at room temperature.

The minced primary tumor sample is treated with an enzyme mix to digest the tumor samples. In some embodiments, the composition comprising an enzyme includes collagenase. In some embodiments, the composition comprising an enzyme includes a serum-supplemented culture medium, insulin, one or more corticosteroids, one or more antibiotics, collagenase and optionally one or more growth factors. Serum-supplemented culture media, corticosteroids, antibiotics, and growth factors are well-known in the art. In some embodiments, the composition comprising an enzyme comprises DMEM or RPMI, fetal bovine serum, insulin, epidermal growth factor, hydrocortisone, Penicillin and/or Streptomycin, and collagenase. In some embodiments, the composition comprising an enzyme comprises further comprises a buffering agent such as 4-(2-hydroxyethyl)-1-piperazineethanesulfonic acid (HEPES).

"Treating the minced primary tumor sample with a composition comprising an enzyme" comprises incubating the minced tumor samples with the enzyme composition for at least 1 hour. In some embodiments, the minced tumor samples are incubated with the enzyme mix for at least 2 hours, at least 4 hours, at least 6 hours, at least 8 hours, at least 10 hours, at least 12 hours, at least 15 hours or at least 24 hours. In some embodiments, the minced primary tumor sample is incubated with the enzyme mix at 25° C., 26° C., 27° C., 28° C., 29° C., 30° C., 31° C., 32° C., 33° C., 34° C., 35° C., 36° C., 37° C., 38° C., or 39° C. In some embodiments, the minced primary tumor sample is incubated with the enzyme mix at 37° C.

In some embodiments, the minced primary tumor sample is treated with the composition comprising the enzyme in an amount or for a time sufficient yield a partial digestion of the minced primary tumor sample. In some embodiments, the minced primary tumor sample is treated with the composition comprising the enzyme for 30 minutes to 15 hours at a temperature of 25° C. to 39° C.

Collecting tumor spheroids from the enzyme mix treated sample comprises centrifuging and washing the sample at least twice followed by isolating the digested tumor spheroids of the desired size. In some embodiments, the enzyme mix treated sample is centrifuged and washed using phosphate buffered saline (PBS) at least twice. Tumor spheroids of the desired size are collected using sieves. In some embodiments, the tumor spheroids having a diameter of 10 μm, 50 μm, 100 μm, 200 μm, 300 μm, 400 μm, 450 μm, and 500 μm are collected from the enzyme mix treated sample with the use of a sieve. In some embodiments, the tumor spheroids having a diameter of 40 μm to 100 μm are collected from the enzyme mix treated sample with the use of a sieve. In some embodiments, the tumor spheroids having a diameter of 40 μm, 50 μm, 60 μm and 70 μm are collected from the enzyme mix treated sample with the use of a sieve.

The tumor spheroids having a desired diameter are collected by sieving the enzyme mix treated sample through cell strainers. In some embodiments, the tumor spheroids having a diameter of 10 μm to 500 μm are collected by sieving the enzyme mix treated sample via 500 μm and 10 μm cell strainers to yield tumor spheroids having a diameter of 10 μm to 500 μm. In some embodiments, the tumor spheroids having a diameter of 40 μm to 100 μm are collected by sieving the enzyme mix treated sample via 100 μm and 40 μm cell strainers to yield tumor spheroids having a diameter of 10 μm to 500 μm. The tumor spheroids of the desired diameter are collected and suspended in a biocompatible gel. Examples of biocompatible gel include collagen, BD Matrigel™ Matrix Basement Membrane, or fibrin hydrogel (e.g., fibrin hydrogel generated from thrombin treatment of fibrinogen).

In some embodiments, the collected tumor spheroids are not frozen and then thawed before suspending in the biocompatible gel. In some embodiments, the collected tumor spheroids are introduced into the three-dimensional cell culture device within less than 2 hours, less than 1 hour, less than 30 minutes, less than 20 minutes, less than 10 minutes, or less after collection.

In some embodiments, the collected tumor spheroids are frozen in a freezing medium and then thawed before suspending in the biocompatible gel. In some embodiments, the collected tumor spheroids are frozen for at least 6 hours 12 hours, 24 hours, 2 days, 1 week or one month. In some embodiments, the collected tumor spheroids are frozen at −80° C. In some embodiments, the collected tumor spheroids are frozen in liquid nitrogen. In some embodiments, the collected tumor spheroids are frozen at −80° C. overnight, and then transferred to liquid nitrogen for storage. In some embodiments, the collected tumor spheroids are frozen in a medium supplemented with serum. In some embodiments, the collected tumor spheroids are frozen in a mixture containing culture medium such as DMEM or RPMI, fetal bovine serum and solvent such as Dimethyl sulfoxide (DMSO). The frozen spheroids are thawed, for example overnight at 4° C., and then suspended in the biocompatible gel.

The tumor spheroids are cultured, i.e., grown, in a three dimensional (3D) microfluidic device. In some embodiments, the tumor spheroids are cultured with endothelial cells, such as human umbilical vein endothelial cells (HUVECs). In some embodiments, the tumor spheroids are cultured without endothelial cells. In some embodiments, the tumor spheroids are cultured with or without endothelial cells for at least 1 day, at least 2 days, at least 4 days, at least 6 days, at least 1 week, or at least 2 weeks.

3D microfluidic devices are known in the art and include, for example, but not limited to, the devices described in US 2013/0143230, EP2741083, US 2014/0057311, U.S. Pat. No. 8,748,180, and WO 2016/112172, the disclosures of which are incorporated by reference herein.

In some embodiments, a 3D microfluidic device refers to a device that comprises one or more fluid channels flanked by one or more gel cage regions, wherein the one or more gel cage regions comprises the biocompatible gel in which the tumor spheroids are embedded, and wherein the device recapitulates, i.e., mimics, the in vivo tumor microenvironment. In order to facilitate visualization, the microfluidic device is typically comprised of a substrate that is transparent to light, referred to herein as "an optically transparent material". As will be appreciated by those of skill in the art, suitable optically transparent materials include polymers, plastic, and glass. Examples of suitable polymers are polydimethylsiloxane (PDMS), poly(methyl methacrylate) (PMMA), polystyrene (PS), SU-8, and cyclic olefin copolymer (COC). In some embodiments, all or a portion of the device is made of a biocompatible material, e.g., the material is compatible with, or not toxic or injurious to, living material (e.g., cells, tissue).

The fluid channel can be used to contain a (one or more) fluid (e.g., cell culture media), cells such as endothelial cells, cellular material, tissue, fluorophore dyes, and/or compounds (e.g., drugs) to be assessed, while the gel cage regions may be used to contain a gel (e.g., biologically relevant gel, such as collagen, Matrigel™, or fibrin hydrogel (e.g., fibrin hydrogel generated from thrombin treatment of fibrinogen)). In some embodiments, the 3D microfluidic device comprises the device described in US 2014/0057311, the disclosure of which is incorporated by reference herein. In particular, paragraphs [0056] to [0107] which describe the regions, channels, chambers, posts, and arrangement of posts, and paragraphs [0127] to [0130] which describe the methods of making the device are incorporated by reference herein.

In some embodiments, the method for identifying a compound for treating cancer, comprises culturing a first and second aliquot of tumor cell spheroids in a three-dimensional microfluidic device as described herein in the presence and absence of one or more test compounds, detecting a change in the ratio of live cells to dead cells in the aliquots of tumor cell spheroids.

In some embodiments, the change in the ratio of live cells to dead cells in the aliquots of tumor cell spheroids is monitored by measuring the total fluorescence emitted by each of the first and second fluorophore dyes. Accordingly, in some embodiments, the dead cell fluorescence and the live cell fluorescence can be added together to yield a live and dead cell total. In some embodiments, the amount of dead cells may be expressed as a percentage of the dead cell fluorescence to the total fluorescence. In some embodiments, the amount of live cells can be expressed as a percentage of the live cell fluorescence to the total. In some embodiments, the dead cell fluorescence and the live cell fluorescence can be expressed as a ratio. For example, in some embodiments, the ratio is expressed as dead cells/live cells or live cells/dead cells. In this manner, expressing as a ratio provides a standardized method of evaluating tumor cell spheroids.

In some embodiments, proliferation and/or dispersion of the tumor cell spheroids are also assessed.

In some embodiments, the method for identifying a compound or combination of compounds for treating cancer, comprises obtaining tumor spheroids from an enzyme treated tumor sample, suspending a first aliquot of the tumor spheroids in biocompatible gel, and suspending a second aliquot of the tumor spheroids in biocompatible gel. In some embodiments, the method further comprises placing the first aliquot of the tumor spheroids in biocompatible gel in a first three-dimensional device, and contacting the first aliquot with a first fluorophore dye selective for dead cells and a second fluorophore dye selective for live cells, where the first fluorophore dye emits fluorescence at a first wavelength when bound to a dead cell and the second fluorophore dye emits fluorescence at a second wavelength different from the first wavelength when bound to a live cell. In some embodiments, the method further comprises measuring total fluorescence emitted by each of the first and second fluorophore dyes in the first aliquot. In some embodiments, the method further comprises culturing the second aliquot in a second three-dimensional device, contacting the second aliquot with the first fluorophore dye and the second fluorophore dye, wherein the contacting of the second aliquot with the first fluorophore dye and second fluorophore dye is carried out at least 24 hours after the contacting of the first aliquot with the first fluorophore dye and second fluorophore dye. In some embodiments, the method further comprises measuring total fluorescence emitted by each of the first and second fluorophore dyes in the second aliquot, wherein an increase or decrease in the ratio of live cells to dead cells in each of the aliquots may be assessed.

"Culturing patient-derived tumor cell spheroids in the presence of the test compound" comprises introducing the test compound into the one or more fluid channels of the device described herein, wherein the one or more gel cage regions of the device comprises a gel in which the tumor spheroids are embedded; and culturing the tumor spheroids under suitable culture conditions. Suitable conditions include growing the tumor cell spheroids under standard cell culture conditions (e.g. at 37° C. in a humidified atmosphere of >80% relative humidity air and 5 to 10% $CO_2$).

In some embodiments, techniques provided herein relate to evaluating the effects of one or more therapeutic treatments in a tumor cell spheroid culture. In some embodiments, changes in the tumor cell spheroid culture are evaluated using one or more luminescent probes (e.g., one or more fluorescent dyes). For example, in some embodiments, methods described herein comprise steps of contacting a tumor cell spheroid culture with a first fluorophore dye and a second fluorophore dye that each selectively bind to a cell type that is different from the other, and where the fluorophore dyes emit fluorescence at different wavelengths when bound to the respective cell types. In some embodiments, the first fluorophore dye is selective for dead cells and the second fluorophore dye is selective for live cells. In some embodiments, the first fluorophore dye is selective for live cells and the second fluorophore dye is selective for dead cells.

In some embodiments, one or more fluorophore dye (e.g., one or more of a first fluorophore dye, one or more of a second fluorophore dye) is introduced into the one or more fluid channels of the cell culture device. The techniques provided in the present disclosure are envisioned to be compatible with any suitable fluorophore dye (e.g., fluorophore-containing dyes, stains, fluorescent labels, etc.). Suitable fluorophore dyes are known in the art and can be selected by a practitioner in view of a desired application of the techniques described herein. For example, in some embodiments, the one or more fluorophore dyes utilized in the techniques described herein can be compatible with staining under fixed or non-fixed conditions.

Fluorophore dyes that can be used for the detection of dead cells in non-fixed conditions include, by way of example and not limitation, DNA-dependent stains such as propidium iodide, DRAQ7, and 7-AAD. Fluorophore dyes that can be used for the detection of dead cells in either fixed or non-fixed conditions include, by way of example and not limitation, dyes listed in Table 1.

TABLE 1

Examples of dyes to stain for dead cells

| Dye | Excitation (max) | Emission (max) |
|---|---|---|
| Propidium iodide | 540 nm | 620 nm |
| DRAQ7 | 600 nm | 697 nm |
| 7-AAD | 550 nm | 645 nm |
| eBioscience Fixable Viability Dye eFluor ® 455 UV | 350 nm | 455 nm |
| eBioscience Fixable Viability Dye eFluor ® 450 | 405 nm | 450 nm |
| eBioscience Fixable Viability Dye eFluor ® 506 | 405 nm | 506 nm |
| eBioscience Fixable Viability Dye eFluor ® 520 | 488 nm | 522 nm |

TABLE 1-continued

Examples of dyes to stain for dead cells

| Dye | Excitation (max) | Emission (max) |
|---|---|---|
| eBioscience Fixable Viability Dye eFluor ® 660 | 633 nm | 660 nm |
| eBioscience Fixable Viability Dye eFluor ® 780 | 780 nm | 633 nm |
| BioLegend Zombie Aqua ™ | 382 nm | 510 nm |
| BioLegend Zombie NIR ™ | 718 nm | 746 nm |
| BioLegend Zombie Red ™ | 600 nm | 624 nm |
| BioLegend Zombie Violet ™ | 400 nm | 423 nm |
| BioLegend Zombie UV ™ | 362 nm | 459 nm |
| BioLegend Zombie Yellow ™ | 396 nm | 572 nm |

The techniques provided in the present disclosure are envisioned to be compatible with any suitable fluorophore dye selective for live cells known in the art. Fluorophore dyes that can be used for the detection of live or fixed cells include, by way of example and not limitation, DNA-dependent stains such as acridine orange, nuclear green LCS1 (ab138904), DRAQ5 (ab108410), CyTRAK Orange, NUCLEAR-ID Red DNA stain (ENZ-52406), and SiR700-DNA. Examples of non-DNA-dependent fluorophore dyes that stain for live cells are known in the art and include, by way of example and not limitation, calcein AM, calcein violet AM, and calcein blue AM. Fluorophore dyes that can be used for the detection of live or fixed cells include, by way of example and not limitation, dyes shown in Table 2.

TABLE 2

Examples of dyes to stain for live cells

| Dye | Excitation | Emission |
|---|---|---|
| Vybrant ® DyeCycle ™ Violet | UV, 405 nm | 437 |
| Vybrant ® DyeCycle ™ Green | 488 nm | 534 |
| Vybrant ® DyeCycle ™ Orange | 488, 532 nm | 563 |
| Vybrant ® DyeCycle ™ Ruby | 488, 633/5 nm | 686 |
| acridine orange | 500 nm | 526 nm |
| nuclear green LCS1 (ab138904) | 503 nm | 526 nm |
| DRAQ5 (ab108410) | 647 nm | 681 nm |
| CyTRAK Orange | 488-550 nm | 610 nm |
| NUCLEAR-ID Red DNA stain (ENZ-52406) | 566 nm | 650 nm |
| SiR700-DNA | 689 nm | 716 nm |
| calcein AM | 495 nm | 515 nm |
| calcein violet AM | 408 nm | 450 nm |
| calcein blue AM | 360 nm | 445 nm |

Additionally, two-color cell viability assays are available and may be used with the techniques described herein. Examples of live/dead cytotoxicity kits include, by way of example and not limitation, kits shown in Table 3.

TABLE 3

Examples of kits containing dyes to stain for both live/dead cells

| Kit Name | Platform | Fluorescent Dyes | Ex/Em (nm) | Em Colors |
|---|---|---|---|---|
| LIVE/DEAD Viability/Cytotoxicity Kit for mammalian cells | FC, FM, M | calcein AM ethidium homodimer-1 | 494/517 517/617 | Green (Live) Red (Dead) |
| LIVE/DEAD Cell-Mediated Cytotoxicity Kit for animal cells, 2000 assays | FC, FM, M | $DiOC_{18}(3)$ propidium iodide | 484/501 536/617 | Green (Live) Red (Dead) |
| LIVE/DEAD Sperm Viability Kit 200-1,000 assays | FC, FM | SYBR ™ 14 dye propidium iodide | 485/517 536/617 | Green (Live) Red (Dead) |
| LIVE/DEAD Cell Vitality Assay Kit $C_{12}$— resazurin/ SYTOX ™ Green 1,000 assays | FC, FM, M | SYTOX ™ Green C12-resazurin | 488/530 488/575 | Green (Dead) Red (Live) |

Changes in the tumor cell spheroid culture which predict or demonstrate a reduction in proliferation and/or dispersion of the tumor cell spheroids in the presence or absence of the test compound can be detected using known methods in the art, such as, chemical or physical methods, or a combination thereof.

As described herein, a tumor cell spheroid sample is evaluated by analyzing the relative amounts of live cells and dead cells in separate aliquots of the sample. In some embodiments, the relative amounts of live cells and dead cells in an aliquot is determined by fluorescence measurement. For example, in some embodiments, fluorescence measurement comprises total fluorescence acquisition of the emissions detected from a first fluorophore dye that selectively binds dead cells and a second fluorophore dye that selectively binds live cells. Based on such measurements, the relative emission levels can be parsed out to provide the amount of live cells relative to the amount of dead cells in the aliquot.

In some embodiments, the relative amounts or ratio of live cells to dead cells in an aliquot can be expressed as a percentage of the total fluorescence, such that:

$$[(\% \text{ live cells}) + (\% \text{ dead cells}) = 100\%]$$

In some embodiments, the relative levels of live cells and dead cells in a first aliquot is compared to a similar measurement obtained for a second aliquot that has been treated with a test compound. An increase in (% dead cells) in the presence of the test compound compared to the first aliquot is indicative that the test compound is effective for inducing cell death. In some embodiments, the percentage of dead cells in the presence of an effective test compound is increased relative to the absence of the test compound by about 5%, by about 10%, by about 15%, by about 20%, by about 25%, by about 30%, by about 35%, by about 40%, by about 50%, by about 60%, by about 70%, by about 80%, by about 90%, or greater.

In some embodiments, a change in the tumor cell spheroid culture can further be detected visually, e.g., using confocal microscopy imaging. The images obtained can be analyzed as described in Aref et al. Integr Biol (Camb). 2013 February; 5(2):381-9, the disclosure of which is incorporated by reference in its entirety. In particular, the paragraphs on pages 387-388 relating to image acquisition and analysis (normalized dispersion, $\Delta/\Delta 0$, and normalized cell number (N/N0)) are incorporated by reference in their entireties.

In some embodiments, the change in the tumor cell spheroid culture is a clustering of immune cells around one or more tumor cell spheroids in the culture. In some embodiments, the change in the tumor cell spheroid culture is a decrease in size and/or number of cells of one or more tumor cell spheroids in the culture.

In some embodiments, the change in the tumor cell culture is further detected chemically. For example, in some embodiments, the change in the tumor cell spheroid culture is determined by detection of the presence of a biological molecule secreted into the culture supernatant. In some embodiments, the biological molecule is a protein, carbohydrate, lipid, nucleic acid, metabolite, or a combination thereof. In some embodiments, the biological molecule is a chemokine or a cytokine. In some embodiments, the biological molecule is known to be associated with activation of the immune system or otherwise an enhancement of the immune response.

In some embodiments, the detected biological molecule(s) involves single cell sequencing of T cell receptors on tumor spheroid associated CD4 and CD8 T cells that become activated in the device.

In some embodiments, a sample of tumor cell spheroid culture supernatant may be obtained from the 3D culture device. In some embodiments, a secreted biological molecule or a profile of secreted biological molecules, e.g., a cytokine profile or chemokine profile, may be detected in the tumor cell spheroid culture supernatant.

Methods for detecting secreted biological molecules are known in the art. Exemplary assays and cytokines are disclosed, for example, in WO 2016/112172, the disclosure of which is incorporated herein by reference.

In some embodiments, a sample of tumor cell spheroid is analyzed by nucleic acid content. For example, it is possible to analyze extracellular nucleic acids, e.g., nucleic acids present in a culture medium of a tumor cell spheroid sample using methods known in the art. Alternatively, nucleic acids can be isolated from cells in a cultured sample using methods known in the art. In some embodiments, such analysis can be used to assess gene expression, e.g., to evaluate the expression of genes associated with cytotoxicity, such as cytokines and cytokine receptors. In some embodiments, DNA and/or RNA (e.g., mRNA, rRNA, tRNA, etc.) from a sample may be analyzed. In some embodiments, RNA content of a sample is analyzed using RNA-seq.

In some embodiments, the test compound inhibits epithelial-mesenchymal transition (EMT). In some embodiments, the test compound is a small molecule compound. In some embodiments, the methods described herein are used to screen a library of test compounds, for example, a library of chemical compounds. In some embodiments, the test compound comprises a nucleic acid molecule, for example, a DNA molecule, an RNA molecule, or a DNA/RNA hybrid molecule, single-stranded, or double-stranded. In some embodiments, the test compound comprises an RNAi compound, for example, an antisense-RNA, an siRNA, an shRNA, a snoRNA, a microRNA (miRNA), or a small temporal RNA (stRNA). In some embodiments, the test compound comprises an aptamer. In some embodiments, the test compound comprises a protein or peptide. In some embodiments, the test compound comprises an antibody or an antigen-binding antibody fragment, e.g., a F(ab')2 fragment, a Fab fragment, a Fab' fragment, or an scFv fragment. In some embodiments, the antibody is a single domain antibody. In some embodiments, the compound comprises a ligand- or receptor-binding protein. In some embodiments, the compound comprises a gene therapy vector.

In some embodiments, more primary tumor cell spheroids are cultured in the presence of more than one compound, e.g., a first test compound and a second test compound, optionally a third test compound, fourth compound, etc.

In some embodiments, a test compound is an anti-cancer compound. In some embodiments a test compound is a chemotherapeutic compound, an immunomodulatory compound, or radiation.

Exemplary chemotherapeutic compounds include asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, a test compound is a vinca alkaloid, e.g., vinblastine, vincristine, vindesine, vinorelbine. In some embodiments, a test compound is an alkylating compound, e.g., cyclophosphamide, decarbazine, melphalan, ifosfamide, temozolomide. In some embodiments, a test compound is an antimetabolite, e.g., folic acid antagonists, pyrimidine analogs, purine analogs or adenosine deaminase inhibitor, e.g., fludarabine. In some embodiments, a test compound is an mTOR inhibitor. In some embodiments, a test compound is a proteasome inhibitor, e.g., aclacinomycin A, gliotoxin or bortezomib.

In some embodiments, a test compound is a small molecule inhibitor, e.g., a TBK1 inhibitor, a MEK inhibitor, a FAK inhibitor, a BRD/BET inhibitor, a CDK 4/6 inhibitor, an HDAC inhibitor, a DNMT inhibitor (or hypomethylating compound), a MET inhibitor, an EGFR inhibitor, or a BRAF inhibitor. In some embodiments, a test compound is a kinase inhibitor, e.g., a TBK1 inhibitor, a MEK inhibitor, a FAK inhibitor, or a CDK 4/6 inhibitor. For example, TBK-1 inhibitors are known in the art, e.g., Yu, T., et al. "TBK1 inhibitors: a review of patent literature (2011-2014)" Exp. Opin. On Ther. Patents 25(12); Hasan, M., et al. J. Immunol. 195(10):4573-77; and US20150344473, the contents of each of which are incorporated herein by reference.

Exemplary immunomodulatory compounds include immune activating compounds or inhibitors of an immune checkpoint protein selected from the group consisting of: CTLA-4, PD-1, PD-L1, TIM3, LAG3, B7-H3 (CD276), B7-H4, 4-1BB (CD137), OX40, ICOS, CD27, CD28, PD-L2, CD80, CD86, B7RP1, HVEM, BTLA, CD137L, OX40L, CD70, CD40, CD40L, GALS, A2aR, and VISTA. In some embodiments, the immune checkpoint inhibitor is a peptide, antibody, interfering RNA, or small molecule. In some embodiments, the immune checkpoint inhibitor, e.g., inhibitor, is a monoclonal antibody, or an Ig fusion protein. In some embodiments, the immune checkpoint inhibitor is an antibody or an antigen binding fragment thereof. In some embodiments, the immune checkpoint inhibitor is an anti-PD-1 antibody.

In some embodiments, the immune checkpoint inhibitor inhibits PD1. In humans, programmed cell death protein 1 (PD-1) is encoded by the PDCD1 gene. PDCD1 has also been designated as CD279 (cluster of differentiation 279). This gene encodes a cell surface membrane protein of the immunoglobulin superfamily. PD-1 is a 288 amino acid cell surface protein molecule. PD-1 has two ligands, PDL1 and PD-L2, which are members of the B7 family. PD-1 is expressed on the surface of activated T cells, B cells, and macrophages. PD-1 is expressed in pro-B cells and is thought to play a role in their differentiation. See T. Shinohara 5 et al., Genomics 23 (3): 704-6 (1995). PD-1 is a member of the extended CD28/CTLA-4 family of T cell regulators. (Y. Ishida et al., "EMBO J. 11 (11): 3887-95, (1992)). PD-1 may negatively regulate immune responses. PD1 limits autoimmunity and the activity of T cells in peripheral tissues at the time of an inflammatory response to infection.

An immune checkpoint inhibitor that inhibits PD-1, or a PD-1 antagonist, as used herein is a molecule that binds to PD-1 and inhibits or prevents PD-1 activation. Without wishing to be bound by theory, it is believed that such molecules block the interaction of PD-1 with its ligand(s) PD-L1 and/or PD-L2.

PD-1 activity may be interfered with by antibodies that bind selectively to and block the activity of PD-1. The activity of PD-1 can also be inhibited or blocked by molecules other than antibodies that bind PD-1. Such molecules can be small molecules or can be peptide mimetics of PD-L1 and PD-L2 that bind PD-1 but do not activate PD-1. Molecules that antagonize PD-1 activity include those described in U.S. Publications 20130280265, 20130237580, 20130230514, 20130109843, 20130108651, 20130017199, and 20120251537, 2011/0271358, EP 2170959B1, the entire disclosures of which are incorporated herein by reference. See also M. A. Curran, et al., Proc. Natl. Acad. Sci. USA 107, 4275 (2010); S. L. Topalian, et al., New Engl. J. Med. 366, 2443 (2012); J. R. Brahmer, et al., New Engl. J. Med. 366, 2455 (2012); and D. E. Dolan et al., Cancer Control 21, 3 (2014). Herein, PD-1 antagonists include: nivolumab, also known as BMS-936558 (Bristol-Meyers Squibb, and also known as MDX-1106 or ONO-4538), a fully human IgG4 monoclonal antibody against PD-1; pidilizumab, also known as CT-011 (CureTech), a humanized IgG1 monoclonal antibody that binds PD-1; MK-3475 (Merck, and also known as SCH 900475), an anti-PD-1 antibody; and pembrolizumab (Merck, also known as MK-3475, lambrolizumab, or Keytruda), a humanized IgG4-kappa monoclonal antibody with activity against PD-1. Compounds that interfere bind to the DNA or mRNA encoding PD-1 also can act as PD-1 inhibitors. Examples include a small inhibitory anti-PD-1 RNAi, an anti-PD-1 antisense RNA, or a dominant negative protein. PD-L2 fusion protein AMP-224 (codeveloped by Glaxo Smith Kline and Amplimmune) is believed to bind to and block PD-1.

In some embodiments, the immune checkpoint inhibitor inhibits PD-L1. In humans, programmed death-ligand 1 (PD-L1), also known as B7 homolog 1 (B7-H1) or cluster of differentiation 274 (CD274), is a 40 kDa type 1 transmembrane protein that is encoded by the CD274 gene. Foreign antigens normally induce an immune response triggering proliferation of antigen-specific T cells, such as antigen-specific CD8+ T cells. PD-L1 is an immune checkpoint inhibitor that may block or lower such an immune response. PD-L1 may play a major role in suppressing the immune system during events such as pregnancy, tissue allografts, autoimmune disease, and other disease states, such as hepatitis and cancer. The PD-L1 ligand binds to its receptor, PD-1, found on activated T cells, B cells, and myeloid cells, thereby modulating activation or inhibition. In addition to PD-1, PD-L1 also has an affinity for the costimulatory molecule CD80 (B7-1). Upon IFN-γ stimulation, PDL1 is expressed on T cells, natural killer (NK) cells, macrophages, myeloid dendritic cells (DCs), B cells, epithelial cells, and vascular endothelial cells.

PD-L1 activity may be blocked by molecules that selectively bind to and block the activity of PD-L1. Anti-PD-L1 antibodies block interactions between PD-L1 and both PD-1 and B7-1 (also known as CD80). Block means inhibit or prevent the transmission of an inhibitory signal mediated via PD-L1. PD-L1 antagonists include, for example: BMS-30 936559, also known as MDX-1105 (Bristol-Meyers Squibb), a fully human, high affinity, immunoglobulin (Ig) G4 monoclonal antibody to PD-L1; MPDL3280A, also known as RG7446 or atezolizumab (Genentech/Roche), an engineered human monoclonal antibody targeting PDL1; MSB0010718C, also known as avelumab (Merck), a fully human IgG1 monoclonal antibody that binds to PD-L1; and MEDI473 (AstraZeneca/MedImmune), a human immunoglobulin (Ig) G1κ monoclonal antibody that blocks PD-L1 binding to its 5 receptors. Compounds that bind to the DNA or mRNA encoding PD-L1 also can act as PD-L1 inhibitors, e.g., small inhibitory anti-PDL1 RNAi, small inhibitory anti-PD-L1 RNA, anti-PD-L1 antisense RNA, or dominant negative PD-L1 protein. Antagonists of or compounds that antagonize PD-L1, e.g., anti-PD-L1 antibodies and PD-L1 antagonists, may include, but are not limited to those previously mentioned and any of those that are disclosed in Stewart et al., 2015, 3(9):1052-62; Herbst et al., 2014, Nature 515:563-567; Brahmer et al., N Engl J Med 2012; 366:2455-2465; U.S. Pat. No. 8,168,179; US20150320859; and/or US20130309250, all incorporated herein by reference.

In some embodiments, the immune checkpoint inhibitor inhibits CTLA-4. CTLA-4 (also known as CTLA-4 or cluster of differentiation 152 (CD152)), is a transmembrane glycoprotein that, in humans, is encoded by the CTLA-4 gene. CTLA-5 4 is a member of the immunoglobulin superfamily, which is expressed on the surface of helper T cells and is present in regulatory T cells, where it may be important for immune function. CTLA-4, like the homologous CD28, binds to B7 molecules, particularly CD80/B7-1 and CD86/B7-2 on antigen-presenting cells (APCs), thereby sending an inhibitory signal to T cells. CTLA-4 functions as an immune checkpoint that inhibits the immune system and is important for maintenance of immune tolerance.

CTLA-4 activity may be blocked by molecules that bind selectively to and block the activity of CTLA-4 or that bind selectively to its counter-receptors, e.g., CD80, CD86, etc. and block activity of CTLA-4. Blocking means inhibit or prevent the transmission of an inhibitory signal via CTLA-4. CTLA-4 antagonists include, for example, inhibitory antibodies directed to CD80, CD86, and/or CTLA-4; small molecule inhibitors of CD80, CD86, and CTLA-4; antisense molecules directed against CD80, CD86, and/or CTLA-4; adnectins directed against CD80, CD86, and/or CTLA-4; and RNAi inhibitors (both single and double stranded) of CD80, CD86, and/or CTLA-4.

Suitable CTLA-4 antagonists and/or anti-CTLA-4 antibodies include humanized anti-CTLA-4 antibodies, such as MDX-010/ipilimumab (Bristol-Meyers Squibb), tremelimumab/CP-675,206 (Pfizer; AstraZeneca), and antibodies that are disclosed in PCT Publication No. WO 2001/014424, PCT Publication No. WO 2004/035607, U.S. Publication No. 2005/0201994, European Patent No. EP 1212422 B1, U.S. Pat. Nos. 5,811,097, 5,855,887, 6,051,227, 6,984,720, 7,034,121, 8,475,790, U.S. Publication Nos. 2002/0039581 and/or 2002/086014, the entire disclosures of which are incorporated herein by reference. Other anti-CTLA-4 antibodies and/or CTLA-4 antagonists that can be used in a method of the present disclosure include, for example, those disclosed in Hurwitz et al., Proc. Natl. Acad. Sci. USA, 95(17):10067-10071 (1998); Camacho et al., J. Clin. Oncology, 22(145): Abstract No. 2505 (2004) (antibody CP9675206); Mokyr et al., Cancer Res., 58:5301-5304 (1998), and Lipson and Drake, Clin Cancer Res; 17(22) Nov. 15, 2011; U.S. Pat. No. 8,318,916; and/or EP1212422B1, all of which are herein incorporated by reference, in their entireties.

In some embodiments, the immune checkpoint inhibitor inhibits VISTA. V-domain Ig suppressor of T cell activation (VISTA), (also known as PD-H1, PD-1 homolog, or Dies1), is a negative regulator of T cell function. VISTA is a 309 aa type I transmembrane protein that is composed of seven exons, it has one Ig-V like domain, and its sequence is similar to the Ig-V domains of members of CD28 and B7 families. VISTA is highly expressed in the tumor microenvironment (TME) and on hematopoietic cells. It is also expressed on macrophages, dendritic cells, neutrophils, natural killer cells, and naive and activated T cells. Its expression is highly regulated on myeloid antigen-presenting cells (APCs) and T cells, while lower levels are found on CD4+ T cells, CD8+ T cells, and Treg cells. VISTA shows some sequence homology to the PD-1 ligand, PD-L1, however the two immune checkpoint inhibitors are structurally different and have different signaling pathways. VISTA blockade has been shown to enhance antitumor immune responses in mice, while in humans, blockade of the related PD-1 pathway has shown great potential in clinical immunotherapy trials. VISTA is a negative checkpoint regulator that suppresses T-cell activation and its blockade may be an efficacious immunotherapeutic strategy for human cancer. VISTA (Wang et al., 2011. JEM. 208(3):577-92; Lines et al., 2014. Cancer Res. 74(7):1924-32; Kondo et al. 2015. J. of Immuno.V194; WO2011120013; US20140105912; US20140220012; US20130177557, US20130177557, incorporated by reference herein, in their entireties).

VISTA activity may be blocked by molecules that selectively bind to and block the activity of VISTA. Molecules or compounds that are VISTA antagonists include peptides that bind VISTA, antisense molecules directed against VISTA, single- or doublestranded RNAi molecules targeted to degrade or inhibit VISTA, small molecule inhibitors of VISTA, anti-VISTA antibodies, inhibitory antibodies directed to VISTA, and humanized antibodies that selectively bind and inhibit VISTA. Antagonists of or compounds that antagonize VISTA, e.g., anti-VISTA antibodies and VISTA antagonists, are not limited to, but may include any of those that are disclosed in Liu et al. 2015. PNAS. 112(21):6682-6687; Wang et al., 2011. JEM. 208(3):577-92; Lines et al., 2014. Cancer Res. 74(7):1924-32; Kondo et al. 2015. J. of Immuno.V194; WO2015097536, EP2552947, WO2011120013, US20140056892, U.S. Pat. No. 8,236,304, WO2014039983, US20140105912, US20140220012, US20130177557; WO2015191881; US20140341920; CN105246507; and/or US20130177557, all of which are incorporated by reference herein, in their entireties.

In some embodiments, the immune checkpoint inhibitor inhibits TIM-3. In some embodiments, the immune checkpoint inhibitor inhibits LAG-3.

In some embodiments, a combination of test compounds are tested in the cell culture. In some embodiments, the combination of immune checkpoint inhibitors includes a PD1 inhibitor and a CTLA-4 inhibitor. In some embodiments, the combination of immune checkpoint inhibitors includes a PD1 inhibitor and a TIM-3 inhibitor. In some embodiments, the combination of immune checkpoint inhibitors includes a PD1 inhibitor and a LAG-3 inhibitor. In some embodiments, the combination of immune checkpoint inhibitors includes a PD-L1 inhibitor and a CTLA-4 inhibitor. In some embodiments, the combination of immune checkpoint inhibitors includes a PD-L1 inhibitor and a TIM-3 inhibitor. In some embodiments, the combination of immune checkpoint inhibitors includes a PD-L1 inhibitor and a LAG-3 inhibitor. In some embodiments, the combination of immune checkpoint inhibitors includes a CTLA-4 inhibitor and a TIM-3 inhibitor. In some embodiments, the combination of immune checkpoint inhibitors includes a CTLA-4 inhibitor and a LAG-3 inhibitor. In some embodiments, the combination of immune checkpoint inhibitors includes a TIM-3 inhibitor and a LAG-3 inhibitor. In some embodiments, the combination of immune checkpoint inhibitors includes a PD1 inhibitor, a CTLA-4 inhibitor, and a TIM-3 inhibitor. In some embodiments, the combination of immune checkpoint inhibitors includes a PD1 inhibitor, a CTLA-4 inhibitor, and a LAG-3 inhibitor. In some embodiments, the combination of immune checkpoint inhibitors includes a PD1 inhibitor, a TIM-3 inhibitor, and a LAG-3 inhibitor. In some embodiments, the combination of immune checkpoint inhibitors includes a CTLA-4 inhibitor, a TIM-3 inhibitor, and a LAG-3 inhibitor.

In some embodiments, the combination of test compounds includes an immune checkpoint inhibitor and a small molecule compound. In some embodiments, the combination of test compounds includes an immune checkpoint inhibitor and a TB K-1 inhibitor. In some embodiments, the combination of test compounds includes a PD-1 inhibitor and a TB K-1 inhibitor. In some embodiments, the combination of test compounds includes a PD-L1 inhibitor and a TB K-1 inhibitor. In some embodiments, the combination of test compounds includes a CTLA-4 inhibitor and a TB K-1 inhibitor. In some embodiments, the combination of test compounds includes a VISTA inhibitor and a TBK-1 inhibitor. In some embodiments, the combination of test compounds includes a TIM-3 inhibitor and a TB K-1 inhibitor. In some embodiments, the combination of test compounds includes a LAG-3 inhibitor and a TB K-1 inhibitor.

In some embodiments, an immune activating compound is a CD28 antagonist, e.g., an anti-CD28 antibody. An antibody, or immunoglobulin, is a glycoprotein containing two identical light chains (L chains), each containing approximately 200 amino acids, and two identical heavy chains (H chains), which generally are at least twice as long as the L chains. The paratope of the antibody is specific for a particular epitope of an antigen, and their spacial complementarity (binding) "tags" the microbe for further action or neutralize its actions directly. The antibody communicates with other components of the immune response via its crystallizable fragment (Fc) region, which includes a conserved glycosylation site. There are five Fc regions, resulting in the five different antibody isotypes: IgA, IgD, IgE, IgG, and IgM. IgD functions as an antigen receptor on B cells that have not been exposed to antigens, and activates basophils and mast cells, resulting in the production of antimicrobial factors. IgG, expressed in four forms, provides the majority of antibody-based immunity against invading pathogens. IgM is expressed on the surface of B cells as a monomer, and in a secreted form as a pentamer. It eliminates pathogens during the early phases of humoral (B cell-mediated) immunity before there 5 are sufficient levels of IgG. IgG is often used in immunotherapy.

The term antibody is used in the broadest sense and specifically includes, for example, single monoclonal antibodies, antibody compositions with polyepitopic specificity, single chain antibodies, and antigen-binding fragments of antibodies. An antibody may include an immunoglobulin constant domain from any immunoglobulin, such as IgG1, IgG2, IgG3, or IgG4 subtypes, IgA (including IgA1 and IgA2), IgE, IgD or IgM.

A fluorescence light source provides an excitation wavelength to excite a fluorophore. A fluorescent light source can be used in connection with a photosensitive detector capable of detecting total fluorescence emitted by the excited fluorophore to generate an image. A fluorescence microscope can be configured to include a fluorescence light source and a photosensitive detector. Fluorescence microscopes are available in the art and are commercially available. A skilled artisan would be able to select a microscope with appropriate capabilities for the desired imaging and/or analysis.

Fluorescence microscopes are available in upright or inverted configurations, either of which are suitable for use with the provided methods. In an upright microscope configuration, the objective and photosensitive detector, e.g., camera, is disposed above the stage, pointing down. Exemplary upright fluorescent microscopes include, but are not limited to, Nikon Eclipse 80i Fluorescent Microscope. In an inverted microscope configuration, the light source is disposed above the stage pointing down, and the objective is disposed below the stage pointing up.

In some embodiments, a fluorescence microscope is an epifluorescence microscope, in which light of the appropriate excitation wavelength is passed through the objective lens onto the sample to be examined. In some such embodiments, fluorescence is emitted from the sample through the same objective lens through which the light initially passed, and is then detected via a photosensitive detector, e.g., a camera. In some instances, a dichroic beam splitter may be used to filter the emitted fluorescence by permitting fluorescence of a particular wavelength to pass through, while reflecting the remaining fluorescence, to increase the signal-to-noise ratio. In some embodiments, a fluorescence microscope is a confocal microscope. Confocal microscopes can be used, for example, to generate three dimensional structures from a series of optical section images. In some embodiments, a fluorescence microscope is a total internal reflection fluorescence microscope.

In some embodiments, the fluorescence microscope is configured to permit measurement of emission of fluorescence from two or more distinct fluorophore dyes at distinct wavelengths. For example, in some embodiments, the fluorescence microscope contains a filter arrangement that allows separation of the fluorescence emitted by the two or more distinct fluorophore dyes.

In some embodiments, the microscope is configured to permit measurement of multiple capture images of the same microfluidic device by moving the stage on which the microfluidic device is disposed. In some embodiments, the stage is a motorized stage. Motorized stages are known in the art and are commercially available. In some embodiments, the stage is configured to move one dimensionally, e.g., to move in the x-axis. In some embodiments, the stage is configured to move two dimensionally, e.g., to move in the x- and y-axes. In some embodiments, the stage is configured not to move in three dimensions, e.g., to not move in the z-axis. In some such embodiments, the focal plane of the tumor cell spheroids in the three-dimensional microfluidic device remains the same throughout the fluorescence detection.

In some embodiments, a three dimensional analysis of the tumor cell spheroids is performed. For example, in some embodiments, the stage is configured to move in three dimensions, e.g., moves in x-, y-, and z-axes. In such embodiments, images of multiple sections (e.g., focal planes) can be obtained to generate a Z stack using microscopes, photosensitive detectors, and software available in the art. For example, commercially available ProScan controller and TTL Breakout Box (Prior Scientific, Rockland, Mass.) can be used to control a CCD camera for Z-stack image acquisition.

The overall resolution of the fluorescence emission detection depends on the magnification of the objective lens through which the detectable signal passes, and/or the magnification of the photosensitive detection device, e.g., camera. In some embodiments, the magnification of the objective lens is at least 2×, at least 3×, at least 4×, at least 10×, at least 40×, at least 100×, or more. In some embodiments, the magnification of the photosensitive detection device, e.g., camera, is 0×. In some embodiments, the magnification of the photosensitive detection device, e.g., camera, is at least 2×, at least 3×, at least 4×, at least 10×, or more. In some embodiments, the overall resolution of the fluorescence detection is at least 2×, at least 3×, at least 4×, at least 10×, at least 40×, at least 100×, at least 400×, at least 1000×, or more. In some embodiments, the resolution at which the fluorescence is detected is such that the entire field of the three dimensional device containing the tumor cell spheroids can be imaged without adjusting the focal plane.

Images of the fluorescence emitted by the fluorophore dyes are detected and/or captured using a photosensitive detector. Photosensitive detectors capable of detecting total fluorescence are known in the art and commercially available. In some embodiments, a photosensitive detector is a camera or a photodiode. In some embodiments, the camera is a CCD camera. Exemplary cameras include, but are not limited to CoolSNAP CCD Camera (Roper Scientific). In some embodiments, the photodiode is an avalanche photodiode.

Images can be acquired by the photosensitive detector and analyzed, e.g., using commercially available software. Exemplary image capture and analysis software includes, but is not limited to NIS-Elements AR software package (Nikon). In some embodiments, multiple images of a microfluidic device are captured by the detector and stitched together. Images may be deconvoluted using available programs such as AutoQuant (Media Cybernetics).

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1. Materials and Methods for Ex Vivo Profiling

Patient Samples.

A cohort of patients (Tables S1-1 and S1-2) treated at Massachusetts General Hospital and Dana-Farber Cancer Institute was assembled for PDOTS profiling and culture between August 2015 and August 2016. Informed consent was obtained from all subjects. Tumor samples were collected and analyzed according to Dana-Farber/Harvard Cancer Center IRB-approved protocols. These studies were conducted according to the Declaration of Helsinki and approved by the MGH and DFCI IRBs. De-identified archival matched plasma and tissue samples from the MGH Melanoma Tissue Bank were obtained from patients pre- or on-treatment with anti-PD-1 therapy as indicated. Mutational analysis performed on clinically validated next-generation sequencing (NGS) platforms at MGH and DFCI. Clinical benefit (CB) to PD-1 was defined as absence of disease, decrease in tumor volume (radiographic or clinical), or stable disease, whereas patients with no clinical benefit (NCB) included patients with mixed response, progression on treatment, and primary non-responders.

TABLE S1-1

| ID | Age/Sex | Diagnosis | Stage | Mutational Status |
|---|---|---|---|---|
| MGH-01 | 78/M | Melanoma (cutaneous) | IV | $BRAF^{WT}$, $NRAS^{WT}$ |
| MGH-02 | 69/M | Melanoma (cutaneous) | IIIB | N/A |
| MGH-03 | 49/M | Melanoma (cutaneous) | IV | N/A |
| MGH-04 (**) | 28/M | Melanoma (cutaneous) | IV | $BRAF^{V600E}$ |
| MGH-05 | 70/M | Melanoma (cutaneous) | IV | $BRAF^{WT}$, $NRAS^{G13V}$ |
| MGH-06 | 78/M | Melanoma (cutaneous) | IV | $BRAF^{WT}$, $NRAS^{wT}$ |
| MGH-07 (**) | 28/M | Melanoma (cutaneous) | IV | $BRAF^{V600E}$ |
| MGH-08 | 80/M | Melanoma (cutaneous) | IV | $BRAF^{V600K}$ |
| MGH-09 | 69/F | Melanoma (cutaneous) | IV | $BRAF^{V600E}$ |
| MGH-10 | 74/F | Melanoma (mucosal) | IV | $KIT^{D816A}$ |
| MGH-11 | 63/F | Melanoma (cutaneous) | IV | N/A |
| MGH-12 (□) | 61/M | Melanoma (cutaneous) | IV | TP53 |
| MGH-13 | 65/F | Thyroid cancer (papillary) | IV | $BRAF^{V600E}$ |
| MGH-14 (□) | 61/M | Melanoma (cutaneous) | IV | TP53 |
| MGH-16 | 62/M | Melanoma (sino-nasal) | IV | $NRAS^{G12D}$ |
| MGH-18 | 68/M | Melanoma (cutaneous) | IV | $NRAS^{Q61R}$ |
| MGH-19 | 24/F | Adreno-cortical carcinoma | II | N/A |
| DFCI-01 | 73/F | Melanoma (cutaneous) | III | Not tested |
| DFCI-02 (#) | 81/M | Melanoma (cutaneous) | IV | CDKN2A (Q50*) |
| DFCI-04 | 72/F | Mesothelioma | IV | 9p del, polysomy 22 |
| DFCI-06 | 42/F | Merkel cell carcinoma | IV | BRCA2 (F439V) |
| DFCI-07 | 58/M | NSCLC/lung adeno-carcinoma | IV | KRAS/LKB1 |
| DFCI-09 | 45/M | Pancreatic adenocarcinoma | IIB | $KRAS^{G12D}$, TP53 |
| DFCI-10 (^) | 55/M | Thyroid cancer (Hurthle cell) | IV | TP53, MSH2, PTEN |
| DFCI-12 | 58/F | Head/neck squamous cell carcinoma | IV | Unknown |
| DFCI-13 (*) | 76/M | Thyroid cancer (papillary) | IV | Unknown |
| DFCI-15 | 75/F | Thyroid cancer (papillary) | IV | $BRAF^{V600E}$ |
| DFCI-16 (*) | 76/M | Thyroid cancer (papillary) | IV | Unknown |
| DFCI-17 (#) | 81/M | Melanoma (cutaneous) | IV | CDKN2A (Q50*) |
| DFCI-18 (*) | 76/M | Thyroid cancer (papillary) | IV | Unknown |
| DFCI-19 | 67/M | Pancreatic adenocarcinoma | IIA | Unknown |
| DFCI-20 | 51/M | Thyroid cancer (papillary) | IV | None identified |
| DFCI-21 (*) | 76/M | Thyroid cancer (papillary) | IV | Unknown |
| DFCI-22 (*) | 76/M | Thyroid cancer (papillary) | IV | Unknown |
| DFCI-24 | 79/M | Small cell lung cancer | IV | Unknown |
| DFCI-25 | 68/M | Melanoma (cutaneous) | IV | $NRAS^{Q61K}$, CDKN2A (Q50*) |
| DFCI-27 | 72/M | Melanoma (cutaneous) | IV | $BRAF^{wT}$ |
| DFCI-29 (^) | 55/M | Thyroid cancer (Hurthle cell) | IV | TP53, MSH2, PTEN |
| DFCI-30 | 52/M | Merkel cell carcinoma | IV | Unknown |
| DFCI-31 | 67/M | Merkel cell carcinoma | IV | Unknown |
| DFCI-32 | 89/M | Merkel cell carcinoma | IIb | Unknown |
| DFCI-33 | 49/M | Thyroid cancer (differentiated) | IV | Unknown |

(*) DFCI-13, 16, 18, 21, 22 represent serial pleural effusion samples from same patient.
(**) MGH-04 and MGH-07 are serial biopsies from the same patient.
(#) DFCI-02 and -17 are samples from same patient.
(^) DFCI-10 and DFCI-29 are samples from the same patient.
(□) MGH-12 and MGH-14 are serial samples from a patient with a brain metastasis requiring resection and subsequent re-resection.

TABLE S1-2

| ID | Prior Therapy | Therapy at Time of Biopsy | Site | Subsequent Therapy | Response to | Status |
|---|---|---|---|---|---|---|
| MGH-01 | None | None | subcutaneous | None | N/A | Deceased; never treated |
| MGH-02 | None | None | lymph node | None | N/A | Alive; NED |
| MGH-03 | None | None | lymph node | BRAFi + MEKi → αPD-1 + αCTLA-4 | N/A | Deceased; progression |
| MGH-04 (**) | None | None | subcutaneous | αPD-1 + αCTLA-4 → αPD-1 maintenance | N/A | Alive; ongoing response |
| MGH-05 | αCTLA-4 → αPD-1 → clinical trial | None | subcutaneous | None | Progression | Deceased; progression |
| MGH-06 | αPD-1 | αPD-1 | lymph node | αPD-1 (irAE) → αCTLA-4 | Mixed | Alive; ongoing response |
| MGH-07 (**) | αPD-1 + αCTLA-4 | αPD-1 + αCTLA-4 | Subcutaneous | αPD-1 | Response | Alive; ongoing response |

TABLE S1-2-continued

| ID | Prior Therapy | Therapy at Time of Biopsy | Site | Subsequent Therapy | Response to | Status |
|---|---|---|---|---|---|---|
| MGH-08 | αPD-1+ | αPD-1 | Subcutaneous | αCTLA-4→ BRAFi + MEKi | Mixed Response | Alive; ongoing response to BRAFi + MEKi |
| MGH-09 | αPD-1 → irAE | None | Subcutaneous | BRAFi + MEKi | Response (SD × 4-5 mo) → PD off-therapy | Alive; ongoing response to BRAFi + MEKi |
| MGH-10 | Chemotherapy, radiation, surgery → αCTLA-4→ αPD-1 | None | Small bowel | None | Response (partial) - held for irAE | Alive; NED |
| MGH-11 | BRAFi/MEKi | None | Lymph node | αPD-1 | Response | Alive; ongoing treatment |
| MGH-12 (□) | αCTLA-4 (PD) → αPD-1 (MR) | αPD-1 | Brain metastasis | αPD-1 | Mixed Response | Alive; mixed response |
| MGH-13 | Radioactive iodine | None | Subcutaneous | Radiation | N/A | Alive; awaiting further therapy |
| MGH-14 (□) | αPD-1 | αPD-1 | Brain metastasis | αPD-1 + radiation | Mixed Response | Alive; stable disease |
| MGH-16 | Anti-PD-L1 + MEKi (PD) → high-dose IL-2 (AE) → αCTLA-4 (PD) → αPD-1(MR→PD) → SIRT (liver metastases) → pan-RAFi (PD) | None | Subcutaneous | None | Progression | Deceased |
| MGH-18 | Radiation → anti-PD-1 + anti-KIR (irAE) → αCTLA-4 (PD) →pan-RAFi (PD)→ αPD-1 + radiation | αPD-1 | Subcutaneous | αPD-1 | Progression (slow) | Alive; slowly progressive disease |
| MGH-19 | None | None | Primary | None | N/A | Alive |
| DFCI-01 | None | Unknown | Lymph node | N/A | Unknown | Unknown |
| DFCI-02 (#) | αCTLA-4, αPD-1 | αPD-1 | Subcutaneous | αPD-1 | Progression | Deceased |
| DFCI-04 | None | Unknown | Primary (partial pleurectomy) | None | N/A | Deceased |
| DFCI-06 | None | None | Subcutaneous | None | N/A | Deceased |
| DFCI-07 | Chemotherapy (PD) → αPD-1 | None | Peritoneal fluid | None | Progression | Deceased |
| DFCI-09 | None | None | Pancreas (Whipple) | None | N/A | Alive; recurrent disease |
| DFCI-10 (^) | None | None | Subcutaneous | lenvatinib | N/A | Alive |
| DFCI-12 | Cisplatin | None | Pleural biopsy (VATS) | αPD-1 | Progression | Deceased |
| DFCI-13 (*) | MLN-0128 | MLN-0128 | Pleural effusion | MLN-0128 | Progression | Deceased |
| DFCI-15 | MLN-0128 | MLN-0128 | Pleural effusion | None | N/A | Deceased |
| DFCI-16 (*) | MLN-0128 | None | Pleural effusion | nivolumab | N/A | Deceased |
| DFCI-17 (#) | RTA 408 + αCTLA-4 | RTA 408 + αCTLA-4 | Subcutaneous | N/A | Progression | Alive; Progressive Disease |
| DFCI-18 (*) | MLN-0128 | None | Pleural effusion | nivolumab | Progression | Deceased |
| DFCI-19 | FOLFIRINOX → capecitabine + radiation | None | Pancreas (Whipple) | 5-FU | N/A | Alive (NED) |

TABLE S1-2-continued

| ID | Prior Therapy | Therapy at Time of Biopsy | Site | Subsequent Therapy | Response to | Status |
|---|---|---|---|---|---|---|
| DFCI-20 | lenvatinib | lenvatinib | Pleural effusion | MLN-0128 | N/A | Progressive Disease |
| DFCI-21 (*) | αPD-1 | αPD-1 | Pleural effusion | αPD-1 | Progression | Deceased |
| DFCI-22 (*) | αPD-1 | αPD-1 | Pleural effusion | αPD-1 | Progression | Deceased |
| DFCI-24 | cisplatin-etoposide → αPD-1 | αPD-1 | Pleural effusion | None | Progression | Deceased |
| DFCI-25 | αCTLA-4 + αPD-1→ αPD-1 maintenance → irAE | None | Lymph node | N/A | Response (held for irAE) | Alive; awaiting further therapy |
| DFCI-27 | αPD-1 | αPD-1 | Subcutaneous | αPD-1 | Mixed Response | Alive; on treatment |
| DFCI-29 (^) | Lenvatinib → MLN-0128 → everolimus | everolimus | Subcutaneous | everolimus | N/A | Alive |
| DFCI-30 | carboplatin-etoposide, radiation (recurrence) | None | Lymph node | αPD-1 | Response | Alive; on treatment |
| DFCI-31 | carboplatin-etoposide | None | Subcutaneous | αPD-1 | Stable Disease | Alive; on treatment |
| DFCI-32 | None | None | Primary | Radiation | N/A | Alive; on treatment |
| DFCI-33 | Radioactive iodine | None | Pleural effusion | lenvatinib | N/A | Alive; on treatment |

(*) DFCI-13, 16, 18, 21, 22 represent serial pleural effusion samples from same patient.
(**) MGH-04 and MGH-07 are serial biopsies from the same patient.
(#) DFCI-02 and -17 are samples from same patient.
(^) DFCI-10 and DFCI-29 are samples from the same patient.
(□) MGH-12 and MGH-14 are serial samples from a patient with a brain metastasis requiring resection and subsequent re-resection.
AE = adverse event.
irAE = immune-related adverse event.
MR = mixed response.
PD = progressive disease Syngeneic Murine Models.

All animal experiments were performed in compliance with established ethical regulations and were approved by the Dana-Farber Animal Care and Use Committee. MC38 murine colon adenocarcinoma cells were generously provided by Dr. Gordon Freeman (DFCI) received under an MTA from Dr. Jeffrey Schlom of NCI (Bethesda, Md.). B16F10 melanoma cells, CT26 colon carcinoma cells, and EMT6 breast mammary carcinoma cells were obtained from ATCC. Cells were expanded, tested free for mycoplasma and mouse pathogens. Thawed cells were cultured for up to three passages in DMEM (MC38, B16F10) or RPMI 1640 (CT26) supplemented with 10% heat-inactivated FBS at 37° C. in a humidified incubator maintained at 5% $CO_2$. Cell counts were performed prior to implantation by both hemocytometer & Invitrogen Countess Cell Counter. MC38 colon carcinoma cells, CT26 colon carcinoma cells, and B 16F10 melanoma cells ($5 \times 10^5$ cells/mouse in 100 μL), re-suspended in sterile PBS ($Ca^+$, $Mg^+$ free), were injected into 8 week old female C57BL/6 albino mice or Balb/c (Jackson) and tumors were collected 2-3 weeks post-implantation or on reaching 2000 $mm^3$ in size (or if there were any humane reason, including decreased BW>15% for 1 week or moribund) and MDOTS were prepared as described below. Implantation of CT26 colon carcinoma cells was performed using BALB/c mice in identical fashion. For in vivo treatment studies, mice were randomized (using the deterministic method) and then injected with 10 mg/kg isotype control IgG (clone 2A3, BioXCell) or rat-anti-mouse PD-1 (clone RMP1-14, BioXCell) every 3 days×8 doses and tumor volume was measured as shown. Investigators were not blinded to treatment groups. Tumor volume (TV) was monitored on a weekly basis after the initial tumor volume is about 100 $mm^3$. TV was measured twice weekly during the exponential tumor growth phase, and body weight was monitored on a weekly basis after implantation.

Spheroid Preparation and Microfluidic Culture.

Fresh tumor specimens (murine and human patients) were received in media (DMEM) on ice and minced in a 10 cm dish (on ice) using sterile forceps and scalpel. Minced tumor was resuspended in DMEM (4.5 mM glucose, 100 mM sodium pyruvate, 1:100 penicillin-streptomycin) (Corning CellGro, Manassas, Va.) +10% FBS (Gemini Bio-Products, West Sacramento, Calif.), 100 U/mL collagenase type IV (Life Technologies, Carlsbad, Calif.), and 15 mM HEPES (Life Technologies, Carlsbad, Calif.), except for CT26 tumors that were prepared in RPMI. Samples were pelleted and resuspended in 10-20 mL media. Red blood cells were removed from visibly bloody samples using RBC Lysis Buffer (Boston Bio-Products, Ashland, Mass.). Samples were pelleted and then resuspended in fresh DMEM+10% FBS and strained over 100 μm filter and 40 μm filters to generate 51 (>100 μm), S2 (40-100 μm), and S3 (<40 μm) spheroid fractions, which were subsequently maintained in ultra low-attachment tissue culture plates. S2 fractions were used for ex vivo culture. An aliquot of the S2 fraction was pelleted and resuspended in type I rat tail collagen (Corning, Corning, N.Y.) at a concentration of 2.5 mg/mL following addition of 10×PBS with phenol red with pH adjusted using NaOH (pH 7.0-7.5 confirmed using PANPEHA Whatman paper (Sigma-Aldrich, St. Louis, Mo.)). The spheroid-collagen mixture was then injected into the center gel region of the 3D microfluidic culture device. Collagen hydrogels containing PDOTS/MDOTS were hydrated with media with or without indicated therapeutic monoclonal antibodies after 30 minutes at 37° C. MDOTS were treated with isotype control IgG (10 μg/mL, clone 2A3) or anti-PD-1 (0.1, 1.0, 10 μg/mL, clone RMP1-14). Monoclonal rat-anti-mouse-CCL2 (5 μg/mL, clone 123616, R&D Systems) was used for CCL2 neutralization in MDOTS. PDOTS were treated with anti-PD-1 (pembrolizumab, 250 μg/mL), anti-CTLA-4 (ipilimumab, 50 μg/mL), or combination (250 μg/mL pembrolizumab+50 μg/mL ipilimumab). Doses were selected (1:100 dilutions of stock concentrations used clinically) to correspond to reported peak plasma concentrations of each drug following administration of 10 mg/kg (FDA CDER application). In select experiments, PDOTS were treated with InVivoMAb human IgG isotype control (BioXCell). For spheroid cultures lacking immune cells, MC38 or CT26 cells ($1 \times 10^6$) were seeded in low attachment culture for 24 hours and were filtered (as above). The S2 fraction was pelleted and resuspended in collagen (as above) prior to microfluidic culture.

Flow Cytometric Immune Profiling of Murine Tumors and MDOTS.

Tumors from MC38 and B 16F10 syngeneic murine models were procured as described above. Cells were incubated for 20 minutes in the dark at room temperature using the Zombie NIR Fixable Viability Kit (Biolegend, 423105) at a dilution of 1:500 in PBS. FcR were blocked by incubation with the anti-mouse CD16/CD32 clone 2.4G2 blocking Ab (Fisher Scientific) for 15 minutes at 4° C. at a 1:100 dilution in flow cytometry staining buffer (PBS+5% FBS). Cell surface staining was performed by incubation for 20 minutes at 4° C. using the following Abs diluted in flow cytometry staining buffer (total staining volume of 100 uL): Lymphocyte Staining Panel—CD45 AF488 (BioLegend 103122), CD25 PE (BioLegend 101904), CD19 PE-Dazzle (115554), CD49b PE-Cy7 (BioLegend, 108922), CD3 BV421 (BioLegend, 100228), CD8 BV510 (BioLegend 100752), CD4 BV786 (Fisher Scientific #BDB563331); Myeloid Staining Panel—F4/80 AF488 (BioLegend #123120), MHCII PE (BioLegend #107608), CD11c BV421 (BioLegend #117330), Ly6G BV510 (BioLegend #127633), CD11b BV650 (BioLegend #101239), Ly6C BV711 (BioLegend #128037), CD45 BV786 (Fisher Scientific # BDB564225), CD19 APC-Cy7 (BioLegend #115530), and CD49b APC-Cy7 (BioLegend #108920) were included with the myeloid staining panel to be used as a dump channel along with the dead cells as determined by the Zombie NIR viability stain. After cell surface staining, cells were fixed by incubating in 200 μL IC Fixation Buffer (eBioscience #00-8222-49) for 10 minutes at room temperature. Cells were washed and resuspended in flow cytometry staining buffer and read the following day on a BD LSR Fortessa flow cytometer. Data were analyzed using FlowJo software version 10.0.8.

Flow Cytometric Immune Profiling of PDOTS and Human Tumor Samples.

Cells were incubated with Live/Dead Fixable Yellow Dead Cell Stain Kit (Life Technologies, Carlsbad, Calif.) for 8 minutes in the dark at room temperature or Live/Dead Fixable Zombie NIR™ (Biolegend, San Diego, Calif.) for 5 minutes in the dark at room temperature in FACS buffer (PBS+2% FBS) at a ratio of 250 μL/D 1× dilution per 100 mg of original sample weight. Surface marker and intracellular staining were performed according to the manufacturer's protocol (eBioscience, San Diego, Calif.). FcR were blocked prior to surface antibody staining using Human FcR Blocking Reagent (Miltenyi, San Diego, Calif.). Cells were fixed in 1% PBS+2% FBS and washed prior to analysis on a BD LSRFortessa with FACSDiva software (BD Biosciences, San Jose, Calif.). Data were analyzed using FlowJo (Ashland, Oreg.) software version 10.0.8. Cell viability was determined by negative live/dead staining. Antibodies were specific for the following human markers: CD3 (HIT3a; UCHT1), CD8 (RPA-T8), CD14 (M5E2; MphiP9), CD45 (HI30), CD56 (B159), CCR7 (150503), EpCAM (EBA-1), HLA-DR (G46-6), PD-1 (EH12.1), and IgG1 isotype control (MOPC-21) from BD Biosciences (San Jose, Calif.); CD3 (UCHT1), CD4 (RPA-T4), CD14 (M5E2), CD15 (W6D3), CD16 (3G8), CD19 (HIB19), CD25 (BC96), CD33 (WM53), CD38 (HIT2), CD40L (24-31), CD45 (HI30), CD45RA (HI100), CD45RO (UCHL1), CD56 (HCD56; 5.1H11), CD66b (G10F5), CD69 (FN50), CD123 (6H6), CD163 (GHI/61), CTLA-4 (L3D10), CXCR5 (J252D4), EpCAM (9C4), Ki-67 (Ki-67), PD-1 (EH12.2H7), PD-L1 (29E.2A3), PD-L2 (24F.10C12), TIM-3 (F38-2E2), IgG2a isotype control (MOPC-173), IgG2b isotype control (MPC-11), and IgG1 isotype control (MOPC-21) from BioLegend (San Diego, Calif.); Pan-cytokeratin (C11) and PD-L1 (E1L3N) from Cell Signaling Technologies (Danvers, Mass.); CD45 (2D1), FOXP3 (236A/E7), and IL-10 (236A/E7) from Affymetrix/eBioscience (San Diego, Calif.). Four-way flow sorting of immune cells (CD45+), tumor cells (CD45−CD31−CD90−), cancer-associated fibroblasts (CD45−CD31−CD90+), and endothelial cells (CD45−CD31+CD144+) was conducted on a BD Aria II SORP with gates set using single stain controls and manual compensation using the following antibodies: CD31-APC (Biolegend, 303115), CD45-BV711 Biolegend, 304050), CD90-PE/Cy7 (Biolegend, 328123), and CD144-PE (Biolegend, 348505). Cells were sorted into cold PBS and stored on ice before mRNA extraction using established techniques.

Microfluidic Device Design and Fabrication.

Microfluidic device design and fabrication was performed according to methods known in the art (e.g., Aref, A. R. et al., Integr. Biol. (Camb.) (2013), the content of which is incorporated herein by reference in entirety), with modifications of device dimensions to accommodate larger volumes of media. MDOTS were also evaluated using DAX-1 3D cell culture chip (AIM Biotech, Singapore), for select studies.

Live/Dead Staining.

Dual labeling was performed by loading microfluidic device with Nexcelom ViaStain™ AO/PI Staining Solution (Nexcelom, CS2-0106). Following incubation with the dyes (20 minutes at room temperature in the dark), images were captured on a Nikon Eclipse 80i fluorescence microscope equipped with Z-stack (Prior) and CoolSNAP CCD camera (Roper Scientific). Image capture and analysis was performed using NIS-Elements AR software package. Image deconvolution was done using AutoQuant Module. Whole device images were achieved by stitching in multiple captures. Live and dead cell quantitation was performed by measuring total cell area of each dye. Three different laboratories verified immune-mediated cell death of MC38 MDOTS following PD-1 blockade. To inhibit CD8+ T cell cytotoxicity, CT26 MDOTS were treated with 10 μg/mL anti-CD8a Ab (clone 53-6.72, BioXCell). Intertumoral and intratumoral heterogeneity experiments were performed using CT26 allografts as described above. MDOTS were prepared using separate pieces of a larger tumor alongside MDOTS prepared from a smaller allograft. MDOTS were processed, treated, and profiled as described above. Immunofluorescence for CD8+ T cells was performed as described below.

Immunofluorescence and Time-Lapse Imaging.

For immunofluorescence studies, PDOTS and MDOTS were washed with PBS and blocked with FcR blocking reagent (PDOTS—Miltenyi, Cambridge, Mass., MDOTS—BioLegend, San Diego, Calif.) for 30 minutes at room temperature. Directly conjugated antibodies for PDOTS were CD326 EpCAM-PE (clone 9C4), CD45-AlexaFluor-488 (HI30), CD8a-AlexaFluor488 (RPA-T8); for MDOTS—CD45-AlexaFluor488 or 647 (30-F11), CD8a-PE (53-6.7) (BioLegend, San Diego, Calif.). Antibodies were diluted 1:50 in 10 ug/mL solution of Hoechst 33342 (Thermo Fisher Scientific, Waltham, Mass.) in PBS and loaded into microfluidic devices for 1-hour incubation at room temp in the dark. Spheroids were washed twice with PBS with 0.1% Tween20 followed by PBS. For viability assessment, microfluidic devices were loaded with 1:1000 solution of calcein AM (Thermo Fisher Scientific, Waltham, Mass.) in PBS. Images were captured on a Nikon Eclipse 80i fluorescence microscope equipped with Z-stack (Prior) and CoolSNAP CCD camera (Roper Scientific). Image capture and analysis was performed using NIS-Elements AR software package. Brightfield time-lapse images were captured with a 10×NA 0.3 objective and cooled CCD camera (Orca R2, Hamamatsu) in a humidified, temperature-controlled chamber. Illumination was with a CoolLED pe-100 white light LED. Time lapse imaging of several fields of view over time was controlled by NISElements software of a Prior motorized stage along with the LED and camera.

Cytokine Profiling.

Two multiplex assays were performed utilizing a bead-based immunoassay approach, the Bio-Plex Pro™ Human Cytokine 40-plex Assay (Cat #171AK99MR2) and Bio-Plex Pro™ Mouse Cytokine Panel 1, 23-plex (Cat #M60009RDPD) on a Bio-plex 200 system (Cat #171000201). MDOT/PDOT conditioned media concentration levels [pg/mL] of each protein were derived from 5-parameter curve fitting models. Fold changes relative to the MDOT/PDOT control were calculated and plotted as log 2FC. Lower and upper limits of quantitation (LLOQ/ULOQ) were imputed from standard curves for cytokines above or below detection. Conditioned media from PDOTS were assayed neat and plasma was diluted 1:4.

Tertiary Lymphoid Structure Evaluation.

Fifty-two sections stained with hematoxylin & eosin (H&E) of melanoma pre- and on-therapy with anti-PD-1 were evaluated independently by two dermatopathologists for the presence of tertiary lymphoid structures (TLS) at the periphery of these tumors. These are characterized by prominent lymphocytic infiltrate, sometimes with germinal center formation and with associated high endothelial venules, as shown in FIG. 10A.

RNA-Seq.

Freshly isolated patient tumor samples (from patients consented to DF/HCC protocol 11-181) were snap frozen in liquid nitrogen and RNA was collected using the Qiagen RNeasy Mini kit. RNA libraries were prepared from 250 ng RNA per sample using standard Illumina protocols. RNA sequencing was performed at the Broad Institute (Illumina HiSeq2000) and the Wistar Institute (Illumina NextSeq 500). RNA samples were ribo-zero treated and then subjected to library prep using Epicentre's ScriptSeq Complete Gold kit. Quality check was done on the Bioanalyzer using the High Sensitivity DNA kit and quantification was carried out using KAPA Quantification kit. Raw RNA-Seq data (BAM files) read counts were summarized by featureCounts with parameters that only paired-ended, not chimeric and well mapped (mapping quality >/=20) reads are counted. Then normalization was applied to eliminate bias from sequencing depths and gene lengths by edgeR, thus RPKMs (Reads Per Kilobase of transcript per Million mapped reads).

Quantitative Real-Time PCR.

Analysis of expression levels of CCL19 and CXCL13 by quantitative reverse transcription polymerase chain reaction (qRT-PCR) was performed using tissue samples obtained from patients with metastatic melanoma. Samples were selected from patients treated with anti-PD-1 therapy with available tissue pre- and on-treatment. All patients provided written consent to DF/HCC protocol 11-181 (Melanoma Tissue and Blood Collection). Tissue samples were snap frozen in liquid nitrogen and processed to yield RNA, which was stored at −80° C. after extraction. Normal lymph node tissue was used as a positive control for expression of CCL19 and CXCL13. Primers were designed for CXCL13 (Fwd: 5'-GAGGCAGATGGAACTTGAGC-3' (SEQ ID NO: 1), Rev: 5'-CTGGGGATCTTCGAATGCTA-3' (SEQ ID NO: 2)) and CCL19 (Fwd: 5'-CCAACTCT-GAGTGGCACCAA-3' (SEQ ID NO: 3), Rev: 5'-TGAACACTACAGCAGGCACC-3' (SEQ ID NO: 4)), Total RNA was extracted via the QIAGEN RNeasy Mini Kit after being ground with the QIAGEN TissueRuptor. The extraction process was automated via the QIAGEN QIAcube. RNA was stored in 1.5 mL RNAse-free EP tubes and then quantified using the QIAGEN Qubit. cDNA was reverse-transcribed from RNA using the Invitrogen Superscript VILO kit run on an Applied Biosystems 2720 Thermo Cycler and then stored in 1.5 mL tubes in a −40° C. freezer until later use. For qPCR the samples were run in triplicate on a Roche LightCycler 96 using Bio-Rad's SsoAdvanced Universal SYBR Green Supermix in a total volume of 20 µL per well. β-tubulin (Fwd: 5'-CGCAGAAGAGGAGGAG-GATT-3' (SEQ ID NO: 5), Rev: 5'-GAG-GAAAGGGGCAGTTGAGT-3' (SEQ ID NO: 6)) were employed to normalize the expression of target genes. Four runs were performed. RT-PCR was performed in triplicate and values averaged. Effect of PD-1 blockade depicted as log 2 fold change in CCL19 or CXCL13 expression (normalized to β-tubulin) from on-treatment samples relative to pre-treatment samples. For analysis of CCL19/CXCL13 expression in sorted cell populations (FIG. 10H), qRT-PCR was performed according to methods known in the art (e.g., Zhu, Z. et al. Cancer Discov. (2014), the content of which is incorporated herein by reference in entirety) using the following primers: and CXCL13 (Fwd: 5'-CTCTGCTTCT-CATGCTGCTG-3' (SEQ ID NO: 7), Rev: 5-TGAGGGTC-CACACACACAAT-3' (SEQ ID NO: 8)) and CCL19 (Fwd: 5'-ATCCCTGGGTACATCGTGAG-3' (SEQ ID NO: 9), Rev: 5'-GCTTCATCTTGGCTGAGGTC-3' (SEQ ID NO: 10)), using 36B4 (Fwd: 5'-CAGATTGGCTACC-CAACTGTT-3' (SEQ ID NO: 11), Rev: 5'-GGAAGGTGTAATCCGTCTCCAC-3' (SEQ ID NO: 12)) to normalize gene expression.

Immunohistochemistry.

Immunohistochemistry staining was performed on 4 µm formalin-fixed paraffin-embedded sections. All procedures were done on the automated Ventana Discovery Ultra staining system. Sections were first deparaffinized using EZ prep solution and antigen retrieval was achieved using Cell Conditioning solution 1. Sections were blocked with Discovery Inhibitor (all from Ventana). Sections were incubated with primary antibodies for 16 minutes for population markers and 12 hours for CXCL13 and CCL19, then washed and incubated with OmniMap anti-Mouse or anti-Rabbit conjugated with horseradish peroxidase (HRP) (Ventana, cat #760-4310 and 760-4311) for an additional 16 minutes. Discovery Purple or OmiMAP DAB chromogen kits (cat #760-229 or 760-159) was then applied to generate a color reaction. Slides were then counterstained with hematoxylin II followed by bluing reagent (Ventana, cat #790-2208 and cat #760-2037). Primary antibodies used for staining were: anti-CCL19 (RD Systems, cat #MAB361-100; 1:200) and anti-CXCL13 (Abcam, cat #ab112521; 1:150), CD31 (Cell Marque, cat #131M-94; 1:500); αSMA (Abcam, cat #ab5694; 1:400).

Source Data.

Data for differential CCL19 and CXCL13 gene expression analysis were obtained from published reports (e.g., Hugo, W. et al. Cell (2016), Chen, P. L. et al. Cancer Discov. (2016), Van Allen, E. M. et al. Science (2015), Cancer Genome Atlas, N. Cell (2015), the contents of each of which are incorporated herein by reference in entirety). For data from Hugo et al. and Van Allen et al., transcriptome sequencing data were aligned using TopHat and normalized gene expression, presented as transcripts per million (TPM), was quantified using DESeq2 (e.g., see Kim, D. et al. Genome Biol. (2013), and Love, M. I. et al. Genome Biol. (2014), the contents of each of which are incorporated herein by reference in entirety) (Table S3). NanoString source data (Chen et al.) for PD-1 responders (n=4) and non-responders (n=8) were compared (on-PD-1/pre-PD-1) and expressed as log-2 fold change. For TCGA analysis, raw RNA-Seq data (BAM files) of TCGA SKCM samples was downloaded from Genomic Data Commons and read counts were summarized (featureCounts) and normalized using edgeR, to generate RPKMs. CCL19 and CXCL13, samples were separated into two groups by kmeans clustering of RPKM values: high group and low group, value of center of each group was used to label high or low. The survival curves were constructed according to Kaplan-Meier method on these two groups (high; n=206 and low; n=257) and survival was compared between groups using the logrank (Mantel-Cox) test (α=0.05). Four-way grouping was performed using median cutoff to define high and low expression. Single sample GSEA (ssGSEA) was performed using immune cell signatures according to methods known in the art (e.g., Bindea, G. et al. Immunity (2013), the content of which is incorporated herein by reference in entirety).

Synthesis of Compound 1, 5-(4-((4-(4-(oxetan-3-yl) piperazin-1-yl)phenyl)amino)-1,3,5-triazin yl)-2-((tetrahydro-2H-pyran-4-yl)oxy)benzonitrile Step 1. To a solution of 2,4-dichloro-1,3,5-triazine (9.5 g, 63 mmol) in N,N-dimethylformamide (150 mL) at 0° C. (flushed with argon balloon) was added a solution of 4-(4-(oxetan-3-yl)piperazin-1-yl)aniline (14.1 g, 60.2 mmol) in N,N-dimethylformamide (100 mL) over 5 minutes via cannula and stirred in an ice-bath for 1 hour. A solution of 40% Methanol/CH$_2$Cl$_2$ (200 mL) was added to the reaction mixture and stirred at room temperature. After 1 hour, the solid formed were filtered and washed twice with diethyl ether. Solids were collected to provide the first lot of product. To the filtrate, diethyl ether (200 mL) was added and stirred overnight at room temperature. The solids were separated by filtration to provide a second lot of product. Both lots were combined to provide a total yield of 20 g (91%) of 4-chloro-N-(4-(4-(oxetan-3-yl)piperazin-1-yl)phenyl)-1,3,5-triazin-2-amine which was used without purification. LCMS-ESI$^+$ (m/z): calculated for C$_{16}$H$_{19}$ClN$_6$O: 346.1; found: 347.1 (M+H).

Step 2. To a mixture of 4-chloro-N-(4-(4-(oxetan-3-yl) piperazin-1-yl)phenyl)-1,3,5-triazin-2-amine (4.6 g, 13.2 mmol), 2-fluoro-5-(4,4,5,5-tetramethyl-1,3,2-dioxaborolan-2-yl)benzonitrile (3.5 g, 14.5 mmol), Pd(dppf)Cl$_2$CH$_2$Cl$_2$ (1.2 g, 1.6 mmol) and potassium carbonate (3.6 g, 26.4 mmol) under argon was added a mixture of de-gassed solvents (1,2-dimethoxyethane (53 mL)/water (27 mL)) and sonicated until all solids went into solution (~5 minutes). The mixture was stirred under argon at 100° C. in a heating block for 1 hour. After cooling to room temperature, water (200 mL) was poured into the reaction mixture and the solids were filtered off and washed with diethyl ether (100 mL). The resulting dark brown solids were suspended in Acetonitrile (20 mL) and stirred at reflux (~2 minutes) and then stirred at room temperature for 2 hours. To this suspension di-ethyl ether (20 mL) was added and the mixture was stirred at room temperature overnight. Solids were taken by filtration to yield crude dark brown product. In 1 g batches, the crude product was suspended in Dichloromethane (150 mL) in a separatory funnel. To the suspension Trifluoroacetic acid was added until all solids had gone into solution. Water was added (150 mL) and mixture was shaken vigorously until black precipitates appeared. The black solids were filtered off. To the filtrate, a saturated aqueous solution of NaHCO$_3$ was added slowly to fully neutralize the mixture. No solids precipitated during this process. The organic phase was dried over MgSO$_4$ and evaporated under reduced pressure to yield a bright yellow material (Total yield 3.1 g, 55% yield). LCMS-ESI$^+$ (m/z): calculated for C$_{23}$H$_{22}$FN$_7$O: 431.1; found: 432.2 (M+H).

Step 3. To a solution of Tetrahydro-2H-pyran-4-ol (4.7 mL, 49 mmol) in THF (200 mL) at 0° C., Potassium t-butoxide (3.8 g, 51 mmol) was added and the reaction mixture was allowed to warm to room temperature. After 30 minutes, solid 2-fluoro-5-[4-([4-[4-(oxetan-3-yl)piperazin-1-yl]phenyl]amino)-1,3,5-triazin-2-yl]benzonitrile (10 g, 23.2 mmol) was added and stirred overnight at 60° C. The reaction mixture was then cooled to 0° C. with a water/ice bath and slowly diluted with water (1.2 L) over 30 minutes and stirred at room temperature for 45 minutes. The solids formed were filtered and dried to give 5-(4-((4-(4-(oxetan-3-yl)piperazin-1-yl)phenyl)amino)-1,3,5-triazin-2-yl)-2-((tetrahydro-2H-pyran-4-yl)oxy)benzonitrile as a yellow solid (10.6 g, 90% yield) LCMS-ESI$^+$ (m/z): calculated for C$_{28}$H$_{31}$N$_7$O$_3$: 513.3; found: 514.5 (M+H) 1H NMR (400 MHz, DMSO-d6) δ 10.23 (d, J=19.4 Hz, 1H), 8.80 (s, 1H), 8.74-8.50 (m, 2H), 7.68 (br, 2H), 7.60 (d, J=9.0 Hz, 1H), 7.11 (br, 2H), 4.99 (m, 1H), 4.91-4.74 (m, 4H), 4.52 (m, 1H), 3.91 (m, 2H), 3.59 (ddd, J=11.6, 8.5, 3.0 Hz, 2H), 3.80-3.30 (m, 4H), 3.30-2.90 (m, 4H), 2.09 (m, 2H), 1.87-1.64 (m, 2H).

In Vitro Characterization of Compound 1.

Biochemical single point inhibition and IC$_{50}$ concentrations for TBK1, IKKε (IKBKE), and off-target kinases were determined at ThermoFisher Scientific using SelectScreen Kinase Profiling Services (Madison, Wis., USA) (Tables S4A and S4B-1-7). To determine cellular potency, the human colorectal cancer carcinoma cell line HCT116 (ATCC, Manassas, Va.) was maintained in T175 flasks in complete RPMI medium; RPMI 1640 supplemented with 10% FBS, 1× Penicillin-Streptomycin solution and 1×MEM (non-essential amino acids). HCT116 cells were grown to 90-95% confluency in T175 flasks containing complete RPMI medium and transfected in bulk using Lipofectamine 2000 (Invitrogen, Carlsbad, Calif.) with 70 µg of ISG54-luciferase reporter plasmid (Elim Biopharmaceuticals Inc., Hayward, Calif.). The reporter plasmid contains a luciferase gene expression cassette under the transcriptional regulation of the promoter of the human interferon stimulated gene 54 (ISG54). Transfection of the cells was allowed to take place for 6 hours, after which the cells were harvested by treatment with 0.25% trypsin EDTA (Corning Inc., Corning, N.Y.). Trypsinized cells were added to 384-well poly-d-lysine treated black clear bottom tissue culture assay plates (Greiner Bio-One GmbH, Kremsmünster, Austria) at a density of 20,000 cells/well in 80 µL of complete RPMI medium and incubated overnight. After 16-18 hours post-transfection, the assay plates were washed with PBS (Corning Inc., Corning, N.Y.), followed by addition of 80 µL/well of serum-free RPMI 1640 medium containing 1× Penicillin-Streptomycin solution, 1×MEM and 350 nL of DMSO or titrations of Compound 1. Compound 1 titrations were generated by 1.5-fold dilution steps in two overlapping serial dilution series to generate a 40-point compound dose range. After incubation at 37° C. for 1 hour, the cells were stimulated with Poly(I:C) (InvivoGen, San Diego, Calif.) at a final concentration of 15 µg/mL in Optimem media (Life Technologies, Rockville, Md.). The assay plates were incubated for 5 hours at 37° C., followed by addition of One-Glo luciferase firefly reagent (Promega, Madison, Wis.) at 1:1 volume/well and luminescence was measured in an EnVision Multilabel Plate Reader (PerkinElmer, Santa Clara, Calif.). The $EC_{50}$ values were calculated from the fit of the dose-response curves to a four-parameter equation. All $EC_{50}$ values represent geometric mean values of a minimum of four determinations.

Interleukin-2 and Interferon Gamma Analysis.

Freshly isolated human CD4+ and CD8+ T cells were obtained from AllCells (Alameda, Calif., USA). Cells were spun down and resuspended in serum free Xvivo15 media (Lonza Walkersville, Inc., Chicago, Ill., USA) supplemented with 5 ng/mL IL-17 and incubated overnight at 37° C. Cells were plated on anti-CD3 coated plates (5 µg/mL OKT3, eBioscience, Dallas, Tex., USA, overnight) with 2 µg/mL anti-CD28 (eBioscience, Dallas, Tex., USA). Cells are treated in replicate plates with a dose-titration of Compound 1 for 24 hours for IL-2 and 96 hours for IFNγ. IL-2 and IFNγ in the supernatant were measured using single- or multi-plex immunoassay (Mesoscale Discovery, Rockville, Md., USA). Jurkat T cell leukemia cells (clone E61 obtained from ATCC) plated on anti-CD3 coated plates were treated with a dose titration of Compound 1 for 24 hours. IL-2 in the supernatant was measured as described above.

In Vivo Compound 1 Combination Treatments.

Combination studies were performed by vivoPharm (Hummelstown, Pa., USA). All procedures used in the performance of these studies were carried out in accordance with vivoPharm's Standard Operating Procedures, with particular reference to US_SOPvP_EF0314 "General Procedures for Efficacy Studies." CT26 colon carcinoma cells ($1\times10^6$ cells/mouse in 100 µL, passage 2-3) were re-suspended in serum-free DMEM and implanted in the upper right flank of 11-12 week old female Balb/c mice (Charles River Laboratories). Mice were randomized into four groups of 10 using a matched pair distribution method based on tumor size for CT26. Treatment was initiated 12 days post-inoculation with mean tumor volume at start of dosing of 125.85 mm³. Vehicle or Compound 1 (40 mg/kg) was administered by oral gavage daily for 26 days and isotype control or a reverse chimera anti-PD-L1 cloned from literature reports (e.g., Deng, R. et al. MAbs (2016), the content of which is incorporated herein by reference in entirety) and placed into a mouse IgG1 framework (10 mg/kg) was administered every 5 days for a total of six doses. Investigators were not blinded to treatment groups. Mice bearing CT26 tumors with exceptional responses to combination therapy with αPD-L1 and Compound 1 were re-implanted with CT26 cells ($1\times10^6$, lower left flank) and EMT6 cells ($0.5\times10^6$, upper left flank) to evaluate development of immunologic memory. MB49 and MC38 in vivo combination studies performed under identical conditions in B6 mice. B16F10 tail vein injection studies were performed in accordance with methods known in the art (e.g., Zhang, J. et al. Cell Rep. (2016), the content of which is incorporated herein by reference in entirety). After tail vein injection ($1\times10^5$ cells in 100 µL), mice were treated with Vehicle or 40 mg/kg Compound 1 daily for 13 days±anti-PD-L1 (10 mg/kg) or isotype control on Days 0, 5, and 10. Mice were sacrificed on Day 13 and lung metastases were quantified (small ≤1 mm, medium >1 mm and ≤3 mm, large >3 mm). No large lung metastases were detected.

Statistical Methods and Data Analysis.

All graphs depict mean±s.d. unless otherwise indicated. Graphs were generated and statistical analysis performed using GraphPad/Prism (v7.0) and R statistical package. Pearson correlation matrix using 21 cell surface markers for MDOTS were calculated with R across tumors and different sized spheroids. Unsupervised hierarchical clustering was performed using GenePattern.

Example 2. Ex Vivo Profiling of PD-1 Blockade Using Organotypic Tumor Spheroids

Existing patient-derived cancer models, including circulating tumor cells (CTCs), organoid cultures, and patient-derived xenografts (PDXs) can guide precision cancer therapy, but take weeks to months to generate and lack the native tumor immune microenvironment. Current approaches to study anti-tumor immune responses in patients are also limited by remote measurements in whole blood or plasma, or static assessment of biopsies. To overcome these challenges and model immune checkpoint blockade (ICB) ex vivo, a 3D microfluidic device was adapted to the short-term culture of murine- and patient-derived organotypic tumor spheroids (MDOTS/PDOTS). Following limited collagenase digestion of fresh tumor specimens, multicellular organotypic spheroids with autologous immune cells were isolated. MDOTS/PDOTS were analyzed by flow cytometry (FIG. 5) or loaded in collagen into the central channel of the device for exposure to anti-PD-1 or anti-CTLA-4 antibodies (FIG. 1A).

Using the MC38 and B16F10 immune competent syngeneic murine tumor models, lymphoid and myeloid immune cell composition of bulk tumor was compared with different spheroid populations (S1>100 µm; S2 40-100 µm; and S3<40 µm). Flow cytometric analysis revealed similar populations across all immune cell fractions examined (FIG. 1B, FIGS. 6A-6C, Tables S2-1 through S2-4). MDOTS (S2) from B16F10 demonstrated fewer CD45+ cells than MC38 and another model, CT26 (Extended Data FIG. 2d), although immune sub-populations were relatively consistent across MC38, B16F10, and CT26 models (FIG. 6E). Since S2 MDOTS were optimally sized for culture in the microfluidic device, this fraction was utilized for subsequent studies.

A large panel of PDOTS (n=40) was immunophenotyped by flow cytometry, enriching for cancers responsive to PD-1 blockade (e.g., melanoma, Merkel cell carcinoma) (FIGS. 1C-1D, Tables 1A and 1B). A range of lymphoid (CD19+ B cells, CD4+ and CD8+ T cells) and myeloid (CD15+ granulocytic, CD14+ monocytic lineages, CD123+ dendritic cells) populations were consistently detected in PDOTS (FIGS. 1C-1D). Variable surface expression of exhaustion markers (PD-1, CTLA-4, TIM-3) was detected on CD4+ and CD8+ T cells (FIG. 6F) and PD-1 ligands (PD-L1 and PD-L2) on myeloid populations, including dendritic cells, myeloid-derived suppressor cells (MDSCs), and tumor-associated macrophages (TAMs) (FIG. 6G). A strong correlation of T-cell profiles was confirmed between PDOTS (S2) and S3 fractions, including antigen-experienced (CD45RO+) (FIG. 1E) and exhausted CD4 and CD8 T cells (FIG. 1F), and overall conservation of immunophenotype regardless of spheroid size (FIGS. 6H-6J). These data demonstrate that PDOTS retain autologous immune cells, including key tumor-infiltrating T lymphocyte populations.

3D microfluidic culture of MDOTS and PDOTS resulted in growth and expansion over time (FIG. 2A) as well as cytokine elaboration in conditioned medium (FIGS. 2B-2C). Tumor/immune cell intermixture in spheroids was further demonstrated by immunofluorescence microscopy (FIGS. 7A-7C). Dynamic cellular interactions were observed by live imaging, and survival of CD45+ immune cells ex vivo in the device was confirmed (FIG. 7D). Thus, short-term culture and cytokine profiling of PDOTS/MDOTS is feasible using this 3D microfluidic device.

MDOTS were exposed to ex vivo PD-1 blockade, starting with MC38 allografts that respond to anti-PD-1 treatment in vivo (FIGS. 2D-2E). MC38 MDOTS were treated with anti-PD-1 antibody (or isotype control) for 3 days or 6 days in the device (FIG. 2F). Dual labeling de-convolution fluorescence microscopy using acridine orange (AO, live cells) and propidium iodide (PI, dead cells) demonstrated >90% viability of MDOTS at the time of spheroid loading (Day 0) and over time in culture with control (FIG. 2G). Treatment with anti-PD-1 resulted in dose- and time-dependent killing of MC38 MDOTS (FIG. 2G, FIG. 2K, FIG. 7E), in contrast to cell line-derived MC38 spheroids lacking autologous immune/stromal cells (FIG. 2H). Modest killing was evident in the intermediately sensitive CT26 model (FIG. 2I), whereas MDOTS derived from the PD-1 resistant B16F10 model exhibited little cell death despite identical treatment (FIGS. 2J-2K). Anti-PD1 induced killing of CT26 MDOTS required CD8+ T cells (FIG. 7F), which varied between tumors of different size, but not between distinct regions from a single tumor (FIG. 7G). These data demonstrate the ability to recapitulate sensitivity and resistance to PD-1 blockade ex vivo using well-defined mouse models.

Responses to PD-1 blockade in PDOTS were evaluated. To perform systematic assessment of ex vivo ICB in PDOTS, acute cytokine production was used as a quantitative measure of early immune activation rather than ex vivo killing, which was more robust in MDOTS. Day 3 cytokine release from PDOTS (n=28)±PD-1 blockade was analyzed, and upregulation of CCL19 and CXCL13 was observed in the majority of samples (23/28) (FIG. 3A, FIG. 3D, FIGS. 8A-8C). CCL19/CXCL13 induction was not observed with isotype IgG control (FIG. 8D), and was comparatively minimal following CTLA-4 blockade (FIG. 4B, FIG. 4E). CCL19/CXCL13 generation was also preserved across a range of spheroid numbers (FIG. 8E) with little intra-assay variability (FIGS. 8F-8G). CCL19 correlated with CXCL13 across PDOTS samples, and required the microfluidic device for robust induction (FIGS. 8H-8I). CCL19/CXCL13 upregulation was also evident following dual PD-1+ CTLA-4 blockade (FIG. 3C, FIG. 3F), and accompanied by induction of additional effector cytokines (e.g., IFN-γ, IL-2, and TNF-α) in select samples (FIG. 9).

In consonance with PDOTS profiling results, CCL19/CXCL13 mRNA expression increased in patients treated with PD-1 blockade (FIGS. 3G-3H, Tables S4A and Tables S4B-1 through S4B-7). Although fold induction of CCL19/CXCL13 did not clearly correlate with response (FIG. 10A), higher absolute levels of CCL19 and CXCL13, and their receptors (CCR7 and CXCR5), was evident in banked samples from melanoma patients with clinical benefit (CB) from checkpoint blockade (FIGS. 3I-3J, FIGS. 10B-10C). Pretreatment CCL19/CXCL13 mRNA expression levels alone failed to correlate with responsiveness to PD-1 or CTLA-4 blockade in melanoma RNAseq datasets (FIGS. 10D-10E). NanoString data from matched formalin-fixed and paraffin-embedded tissue or banked plasma was also insufficient to detect correlation with response (FIGS. 10F-10G).

As PD-1 blockade promotes immune cell infiltration in vivo, gene set enrichment analysis (GSEA) was performed using published immune signatures, which revealed enrichment of diverse immune cell populations in patients with CB to checkpoint blockade (FIG. 3K). To evaluate the clinical significance of CCL19/CXCL13, Cancer Genome Atlas melanoma (SKCM) data were analyzed. Improved patient survival was evident in melanoma specimens with higher expression of CCL19/CXCL13 (FIGS. 3L-3M; p<0.001). Evaluation of TCGA data for other cancers (e.g., bladder cancer, head and neck, and breast) revealed similar a pattern (FIG. 10H). Immune GSEA using melanoma TCGA data confirmed enrichment of diverse immune cell gene sets in melanoma patients with high levels of both CCL19 and CXCL13 (FIG. 3N), consistent with their established roles as chemoattractants.

CCL19/CXCL13 coordinate humoral and cell-mediated adaptive immunity in lymph nodes and tertiary lymphoid structures (TLS), and cancer-associated TLS have been associated with improved prognosis. Histologic review of melanoma biopsy specimens pre- and on-anti-PD1 only identified rare TLS (FIG. 11A) likely due to limited sampling by core biopsy. Expression of CCL19 in the melanoma TME has been linked to cancer-associated fibroblasts (CAFs), and CXCL13 to CD8+ exhausted T cells. CCL19 is also strongly expressed in lymph node high endothelial venules. It was noted that strongest induction of CCL19/CXCL13 by anti-PD1 was independent of the number of total CD45+ cells or other immune subpopulations in PDOTS (FIGS. 11B-11D). Therefore, CD45+ and CD45− cell populations from a sample (MGH-16) marked by robust anti-PD1 induced secretion of CCL19 and CXCL13 were sorted, to determine the cellular source of CCL19 and CXCL13 in PDOTS. Indeed, stromal populations including CD90+CD45− cancer-associated fibroblasts, CD31+ CD144+ endothelial cells, and tumor cells (CD45−) expressed CCL19 in particular, while CXCL13 was also detected in CD45+ cells (FIG. 11E). Immunohistochemical staining confirmed expression of CCL19 and CXCL13 in stromal elements including cancer-associated fibroblasts (αSMA) and endothelial cells (CD31) (FIG. 11F).

To better understand the relationship between anti-PD1 induced PDOTS cytokine profiles and clinical benefit to ICB, unsupervised hierarchical clustering of cytokine profiles from patients specifically treated with anti-PD-1 therapy was performed. PDOTS from patients with mixed response or progression on anti-PD-1 therapy elaborated multiple immune suppressive cytokines/chemokines (e.g., CCL2) in addition to CCL19/CXCL13 (FIG. 3O). Induction of significantly higher levels of CCL20 and CX3CL1 in patients with no clinical benefit (NCB) to PD-1 blockade (FIG. 12A) was noted, consistent with their lack of association with survival (FIG. 12B) and previous association of CX3CL1 induction with anti-PD-L1 resistance. Several of these immune suppressive cytokines/chemokines induced in PDOTS were also components of an innate PD-1 resistance (IPRES) gene expression signature (FIG. 12B), which correlated with nonresponse but missed statistical significance (p=0.08, FIG. 12C). Serial PDOTS profiling from an individual patient revealed that induction of multiple granulocytic and monocytic chemoattractants predicted infiltration of these respective myeloid populations following disease progression on anti-PD-1 therapy in vivo (FIGS. 12D-12E). These data highlight the potential of this assay to identify cytokines changes associated with ineffective anti-tumor immune responses despite CCL19/CXCL13 induction following ICB.

Higher levels of immune suppressive cytokines were also induced in anti-PD1-resistant B16F10 MDOTS relative to MC38 MDOTS (FIG. 12F), as well as the intermediately resistant CT26 MDOTS model, which elaborated particularly high levels of CCL2 (FIG. 12G). Because of its partial sensitivity to anti-PD1, CT26 model was used to determine whether MDOTS profiling could identify novel combination therapies that overcome resistance. However, neutralization of CCL2 alone failed to enhance PD-1 mediated killing of CT26 MDOTS (FIG. 12H-12I), suggesting the need for alternative strategies that more broadly inhibit immune suppressive signaling within the TME and reactivate T cells.

It was noted that the homologous innate immune signaling kinases TBK1 and IKKε not only promote autocrine/paracrine cytokine signaling, but also restrain T cell activation, suggesting that a dual impact of TBK1/IKKε inhibition on the TME could enhance anti-tumor activity of PD-1 blockade (FIG. 4A). A novel potent/selective TBK1/IKKε inhibitor Compound 1 (Cmpd1) was synthesized (FIG. 4B, FIGS. 13A-D, Tables S5-1 and S5-2), which lacks JAK inhibitory activity, in contrast to the multitargeted inhibitor momelotinib (CYT387). Cmpd1 effectively blocked immune suppressive cytokine elaboration by CT26 cell line spheroids, without cytotoxic effects (FIG. 4C, FIG. 13E), and enhanced secretion of IL-2 and IFN-γ from purified CD4+ and CD8+ T cells (FIGS. 4D-4E) and IL-2 from Jurkat cells (FIG. 13F). Decreased levels of CCL4, CCL3, and IL-1β with concomitant induction of cytokines involved in activated innate immune responses (e.g., G-CSF) were observed in CT26 MDOTS treated with Cmpd1±anti-PD-1 (FIG. 4F). Ex vivo combination treatment enhanced killing of CT26 MDOTS (FIGS. 4G-4H), which predicted in vivo response with greater tumour control and longer survival than mice treated with Cmpd1 or anti-PD-L1 alone (FIGS. 4I-4K). Reimplantation of CT26 into mice with exceptional responses to combination therapy showed no growth, suggesting immunologic memory for CT26 tumors (FIG. 13F).

Combination treatment in the PD-1 sensitive MC38 MDOTS model enhanced ex vivo killing and in vivo survival, although neither of these reached significance compared to single-agent PD-1/PD-L1 (FIGS. 14A-14D). The intrinsically resistant B16F10 model could not be sensitized with Cmpd1 treatment (FIGS. 14E-14H), possibly due to the relative paucity of immune cells in B16F10 MDOTS compared to CT26 and MC38 MDOTS. Indeed, downregulation of several immune suppressive chemokines (e.g., CCL2, CCL5) in B16F10 MDOTS was observed, but without concomitant induction of G-CSF and related innate immune response cytokines (FIGS. 14A-14B). However, enhanced response to combination treatment with Cmpd1 was confirmed in vivo using a fourth partially anti-PD1 sensitive syngeneic model (MB49 bladder carcinoma), further validating its activity. Importantly, MDOTS responses in three models (CT26, MC38, and B16F10) effectively recapitulated the in vivo response (or lack thereof) to PD-1 blockade+/−TBK1/IKKε inhibition, highlighting the potential of ex vivo screening in MDOTS to develop combination immunotherapies more generally.

Example 3. Transcriptomic Analysis of MDOTS/PDOTS Following Ex Vivo Treatment

RNA is collected from a subset of the MDOTs within the device after the supernatants have been collected and cDNA libraries for RNA sequencing is generated to evaluate global transcriptome changes associated with treatment regimen on single samples per drug treatment. These types of data may be generated from a variety of clinical specimens. The RNA Advance tissue RNA isolation method (Beckman Coulter) is utilized, which is a bead wash based separation technique, which facilitates elution volumes amenable to sample input for RNA-Seq library preparation. Automated library preparation can be performed using as little as 10 ng of good quality RNA. The RNA Access method from Illumina is utilized, which enriches for the coding region of the genome. Libraries are sequenced on the NextSeq500 platform, as 75 bp Single End to generate approximately 20 million reads per sample. With appropriate adaptors, 24 samples are multiplexed on each NextSeq500 run. The concentration [ng/ul], yield [ng] and quality of RNA (high RIN # by bioanalyzer) derived from the MDOTS are more than sufficient to ensure good quality libraries for subsequent sequencing (FIG. 15).

The STAR RNA sequencing alignment tool (Spliced Transcripts Alignment to a Reference) [STAR_2.5.0a]) is utilized to align the data to the genome (RefSeq gene annotations). DeSeq2 is utilized to perform differential expression analysis (±2-fold, P value <0.05). Overlaps between differentially expressed genes and the annotated Immunological gene sets in the Molecular Signature Database or MSigDB (FDR q-value<0.05) are computed. CIBERSORT (Newman A M et al. Robust enumeration of cell subsets from tissue expression profiles. Nat Methods. 2015 May; 12(5):453-7.) is utilized to provide an estimation of the abundances of member cell types in a mixed cell population, including more than 20 immune subsets, using the transcriptomic data generated.

The additional information garnered from whole transcriptome analysis provides a deeper understanding of the biological response to PD-1 immune blockage on its own and in combination with other immune blockade compounds or a MEK inhibitor. This knowledge complements secretion profiling to identify novel mechanisms of both response and resistance. Moreover, computational methods to evaluate the "immunone" including GSEA and CIBERSORT, permit inference of changes in immune cell populations using established gene signatures.

Tables with Supportive Data for Example 2:

TABLE S2-1

|   |   | Tumor 1.000 | Tumor 2.000 | Tumor 4.000 | Tumor 5.000 | Tumor 6.000 |
|---|---|---|---|---|---|---|
| Tumor | 1 | 1.000 | 0.955 | 0.890 | 0.752 | 0.240 |
| Tumor | 2 | 0.955 | 1.000 | 0.835 | 0.712 | 0.223 |
| Tumor | 4 | 0.890 | 0.835 | 1.000 | 0.907 | 0.495 |
| Tumor | 5 | 0.752 | 0.712 | 0.907 | 1.000 | 0.758 |
| Tumor | 6 | 0.240 | 0.223 | 0.495 | 0.758 | 1.000 |
| S1 | 1 | 0.852 | 0.900 | 0.619 | 0.555 | 0.197 |
| S1 | 2 | 0.975 | 0.963 | 0.852 | 0.699 | 0.129 |
| S1 | 3 | 0.948 | 0.967 | 0.756 | 0.611 | 0.087 |
| S1 | 4 | 0.838 | 0.821 | 0.915 | 0.911 | 0.676 |
| S1 | 5 | 0.558 | 0.549 | 0.708 | 0.802 | 0.860 |
| S1 | 6 | 0.461 | 0.470 | 0.554 | 0.691 | 0.834 |
| S2 | 1 | 0.749 | 0.788 | 0.603 | 0.635 | 0.455 |
| S2 | 2 | 0.948 | 0.936 | 0.865 | 0.816 | 0.367 |
| S2 | 3 | 0.881 | 0.883 | 0.696 | 0.634 | 0.230 |
| S2 | 4 | 0.680 | 0.651 | 0.836 | 0.925 | 0.825 |
| S2 | 5 | 0.308 | 0.310 | 0.540 | 0.713 | 0.925 |
| S2 | 6 | 0.183 | 0.226 | 0.383 | 0.590 | 0.884 |
| S3 | 1 | 0.740 | 0.776 | 0.569 | 0.636 | 0.459 |
| S3 | 2 | 0.827 | 0.856 | 0.664 | 0.688 | 0.407 |
| S3 | 3 | 0.790 | 0.817 | 0.548 | 0.510 | 0.165 |
| S3 | 4 | 0.685 | 0.675 | 0.792 | 0.839 | 0.768 |
| S3 | 5 | 0.300 | 0.278 | 0.518 | 0.567 | 0.793 |
| S3 | 6 | 0.226 | 0.246 | 0.430 | 0.499 | 0.766 |

TABLE S2-2

|   |   | S1 1.000 | S1 2.000 | S1 3.000 | S1 4.000 | S1 5.000 | S1 6.000 |
|---|---|---|---|---|---|---|---|
| Tumor | 1 | 0.852 | 0.975 | 0.948 | 0.838 | 0.558 | 0.461 |
| Tumor | 2 | 0.900 | 0.963 | 0.967 | 0.821 | 0.549 | 0.470 |
| Tumor | 4 | 0.619 | 0.852 | 0.756 | 0.915 | 0.708 | 0.554 |
| Tumor | 5 | 0.555 | 0.699 | 0.611 | 0.911 | 0.802 | 0.691 |
| Tumor | 6 | 0.197 | 0.129 | 0.087 | 0.676 | 0.860 | 0.834 |
| S1 | 1 | 1.000 | 0.854 | 0.932 | 0.745 | 0.546 | 0.553 |
| S1 | 2 | 0.854 | 1.000 | 0.963 | 0.776 | 0.465 | 0.371 |
| S1 | 3 | 0.932 | 0.963 | 1.000 | 0.737 | 0.447 | 0.399 |
| S1 | 4 | 0.745 | 0.776 | 0.737 | 1.000 | 0.897 | 0.803 |
| S1 | 5 | 0.546 | 0.465 | 0.447 | 0.897 | 1.000 | 0.967 |
| S1 | 6 | 0.553 | 0.371 | 0.399 | 0.803 | 0.967 | 1.000 |
| S2 | 1 | 0.908 | 0.692 | 0.778 | 0.800 | 0.677 | 0.672 |
| S2 | 2 | 0.862 | 0.937 | 0.906 | 0.863 | 0.605 | 0.514 |
| S2 | 3 | 0.915 | 0.849 | 0.927 | 0.742 | 0.493 | 0.460 |
| S2 | 4 | 0.590 | 0.598 | 0.547 | 0.957 | 0.928 | 0.835 |
| S2 | 5 | 0.290 | 0.191 | 0.154 | 0.749 | 0.890 | 0.825 |
| S2 | 6 | 0.248 | 0.081 | 0.057 | 0.640 | 0.822 | 0.790 |
| S3 | 1 | 0.908 | 0.685 | 0.776 | 0.767 | 0.654 | 0.666 |
| S3 | 2 | 0.937 | 0.808 | 0.844 | 0.808 | 0.649 | 0.634 |
| S3 | 3 | 0.921 | 0.764 | 0.888 | 0.642 | 0.428 | 0.437 |
| S3 | 4 | 0.663 | 0.605 | 0.580 | 0.959 | 0.958 | 0.889 |
| S3 | 5 | 0.283 | 0.178 | 0.166 | 0.720 | 0.911 | 0.867 |
| S3 | 6 | 0.261 | 0.112 | 0.101 | 0.665 | 0.845 | 0.794 |

TABLE S2-3

|   |   | S2 1.000 | S2 2.000 | S2 3.000 | S2 4.000 | S2 5.000 | S2 6.000 |
|---|---|---|---|---|---|---|---|
| Tumor | 1 | 0.749 | 0.948 | 0.881 | 0.680 | 0.308 | 0.183 |
| Tumor | 2 | 0.788 | 0.936 | 0.883 | 0.651 | 0.310 | 0.226 |
| Tumor | 4 | 0.603 | 0.865 | 0.696 | 0.836 | 0.540 | 0.383 |
| Tumor | 5 | 0.635 | 0.816 | 0.634 | 0.925 | 0.713 | 0.590 |
| Tumor | 6 | 0.455 | 0.367 | 0.230 | 0.825 | 0.925 | 0.884 |
| S1 | 1 | 0.908 | 0.862 | 0.915 | 0.590 | 0.290 | 0.248 |
| S1 | 2 | 0.692 | 0.937 | 0.849 | 0.598 | 0.191 | 0.081 |
| S1 | 3 | 0.778 | 0.906 | 0.927 | 0.547 | 0.154 | 0.057 |
| S1 | 4 | 0.800 | 0.863 | 0.742 | 0.957 | 0.749 | 0.640 |
| S1 | 5 | 0.677 | 0.605 | 0.493 | 0.928 | 0.890 | 0.822 |
| S1 | 6 | 0.672 | 0.514 | 0.460 | 0.835 | 0.825 | 0.790 |
| S2 | 1 | 1.000 | 0.833 | 0.898 | 0.735 | 0.567 | 0.527 |
| S2 | 2 | 0.833 | 1.000 | 0.901 | 0.751 | 0.425 | 0.323 |
| S2 | 3 | 0.898 | 0.901 | 1.000 | 0.616 | 0.290 | 0.184 |
| S2 | 4 | 0.735 | 0.751 | 0.616 | 1.000 | 0.872 | 0.767 |
| S2 | 5 | 0.567 | 0.425 | 0.290 | 0.872 | 1.000 | 0.970 |
| S2 | 6 | 0.527 | 0.323 | 0.184 | 0.767 | 0.970 | 1.000 |
| S3 | 1 | 0.984 | 0.835 | 0.901 | 0.707 | 0.529 | 0.493 |
| S3 | 2 | 0.945 | 0.920 | 0.890 | 0.717 | 0.481 | 0.443 |
| S3 | 3 | 0.893 | 0.816 | 0.976 | 0.517 | 0.217 | 0.139 |
| S3 | 4 | 0.779 | 0.741 | 0.625 | 0.970 | 0.862 | 0.782 |
| S3 | 5 | 0.485 | 0.327 | 0.243 | 0.792 | 0.894 | 0.836 |
| S3 | 6 | 0.510 | 0.298 | 0.201 | 0.747 | 0.929 | 0.920 |

TABLE S2-4

|   |   | S3 1.000 | S3 2.000 | S3 3.000 | S3 4.000 | S3 5.000 | S3 6.000 |
|---|---|---|---|---|---|---|---|
| Tumor | 1 | 0.740 | 0.827 | 0.790 | 0.685 | 0.300 | 0.226 |
| Tumor | 2 | 0.776 | 0.856 | 0.817 | 0.675 | 0.278 | 0.246 |
| Tumor | 4 | 0.569 | 0.664 | 0.548 | 0.792 | 0.518 | 0.430 |
| Tumor | 5 | 0.636 | 0.688 | 0.510 | 0.839 | 0.567 | 0.499 |
| Tumor | 6 | 0.459 | 0.407 | 0.165 | 0.768 | 0.793 | 0.766 |
| S1 | 1 | 0.908 | 0.937 | 0.921 | 0.663 | 0.283 | 0.261 |
| S1 | 2 | 0.685 | 0.808 | 0.764 | 0.605 | 0.178 | 0.112 |
| S1 | 3 | 0.776 | 0.844 | 0.888 | 0.580 | 0.166 | 0.101 |
| S1 | 4 | 0.767 | 0.808 | 0.642 | 0.959 | 0.720 | 0.665 |
| S1 | 5 | 0.654 | 0.649 | 0.428 | 0.958 | 0.911 | 0.845 |
| S1 | 6 | 0.666 | 0.634 | 0.437 | 0.889 | 0.867 | 0.794 |
| S2 | 1 | 0.984 | 0.945 | 0.893 | 0.779 | 0.485 | 0.510 |
| S2 | 2 | 0.835 | 0.920 | 0.816 | 0.741 | 0.327 | 0.298 |
| S2 | 3 | 0.901 | 0.890 | 0.976 | 0.625 | 0.243 | 0.201 |
| S2 | 4 | 0.707 | 0.717 | 0.517 | 0.970 | 0.792 | 0.747 |
| S2 | 5 | 0.529 | 0.481 | 0.217 | 0.862 | 0.894 | 0.929 |
| S2 | 6 | 0.493 | 0.443 | 0.139 | 0.782 | 0.836 | 0.920 |
| S3 | 1 | 1.000 | 0.960 | 0.913 | 0.746 | 0.426 | 0.440 |
| S3 | 2 | 0.960 | 1.000 | 0.874 | 0.763 | 0.387 | 0.394 |
| S3 | 3 | 0.913 | 0.874 | 1.000 | 0.550 | 0.181 | 0.146 |
| S3 | 4 | 0.746 | 0.763 | 0.550 | 1.000 | 0.849 | 0.812 |
| S3 | 5 | 0.426 | 0.387 | 0.181 | 0.849 | 1.000 | 0.955 |
| S3 | 6 | 0.440 | 0.394 | 0.146 | 0.812 | 0.955 | 1.000 |

TABLE S3

| | | Normalized Counts | | | | Transcripts Per Million | |
|---|---|---|---|---|---|---|---|
| | | | | | | CCL19 | CXCL13 |
| ID | Response | CCL19 | CXCL13 | Pt ID | Response | (ENSG00000172724) | (ENSG00000156234) |
| Pt13 | R | 34.698109 | 2519.38443 | Pt13 | R | 1.168351014 | 1.450293862 |
| Pt15 | R | 368.803957 | 958.479364 | Pt15 | R | 7.162930953 | 0.318252625 |
| Pt19 | R | 1958.97151 | 620.707828 | Pt19 | R | 13.49446269 | 0.073098545 |
| Pt2 | R | 290.527532 | 1198.6162 | Pt2 | R | 7.401911739 | 0.522072463 |
| Pt27A | R | 209.760872 | 1416.41918 | Pt27A | R | 7.057272238 | 0.814700951 |
| Pt27B | R | 127.405123 | 460.732479 | Pt27B | R | 4.111967591 | 0.254217624 |
| Pt28 | R | 1952.44983 | 2324.597 | Pt28 | R | 40.56616838 | 0.825706707 |
| Pt35 | R | 95.3399393 | 539.624057 | Pt35 | R | 3.445558222 | 0.333403426 |
| Pt37 | R | 97.0628571 | 349.174174 | Pt37 | R | 2.033195626 | 0.125043823 |

TABLE S3-continued

| | | Normalized Counts | | | | Transcripts Per Million | |
| | | | | | | CCL19 | CXCL13 |
| ID | Response | CCL19 | CXCL13 | Pt ID | Response | (ENSG00000172724) | (ENSG00000156234) |
|---|---|---|---|---|---|---|---|
| Pt38 | R | 9077.47447 | 44808.3318 | Pt38 | R | 292.4756557 | 24.68183797 |
| Pt4 | R | 158.462804 | 383.601214 | Pt4 | R | 2.601765411 | 0.107674982 |
| Pt5 | R | 0.8957807 | 94.056973 | Pt5 | R | 0.038933398 | 0.069888488 |
| Pt6 | R | 1.44330175 | 90.2063594 | Pt6 | R | 0.020724471 | 0.022144073 |
| Pt8 | R | 617.842921 | 243.736198 | Pt8 | R | 12.63014518 | 0.085181314 |
| Pt9 | R | 1131.85131 | 641.694215 | Pt9 | R | 35.53789234 | 0.344448618 |
| Pt1 | NR | 2340.48615 | 479.579124 | Pt1 | NR | 99.54999655 | 0.348730135 |
| Pt10 | NR | 2.70089632 | 2584.08255 | Pt10 | NR | 0.098714409 | 1.614630139 |
| Pt12 | NR | 292.02708 | 93.1555918 | Pt12 | NR | 8.617132617 | 0.046994022 |
| Pt16 | NR | 14.8144533 | 421.153742 | Pt14 | NR | 9.131829845 | 0.112841472 |
| Pt14 | NR | 221.968265 | 160.438202 | Pt16 | NR | 0.360470362 | 0.17519376 |
| Pt20 | NR | 3001.54512 | 6437.79678 | Pt20 | NR | 49.36256271 | 1.810023107 |
| Pt22 | NR | 1426.52919 | 960.941811 | Pt22 | NR | 21.09294252 | 0.242911252 |
| Pt23 | NR | 15.1942229 | 2322.92855 | Pt23 | NR | 0.229044285 | 0.598647058 |
| Pt25 | NR | 944.629262 | 879.267764 | Pt25 | NR | 11.4526496 | 0.182246738 |
| Pt29 | NR | 420.240506 | 1498.70041 | Pt29 | NR | 11.97953537 | 0.73038345 |
| Pt31 | NR | 39.9689397 | 296.01996 | Pt31 | NR | 0.909356479 | 0.115140091 |
| Pt32 | NR | 4.86573555 | 259.830278 | Pt32 | NR | 0.18150561 | 0.165701082 |
| Pt7 | NR | 217.069727 | 429.20605 | Pt7 | NR | 4.459248487 | 0.150737839 |

15 responders
13 non-responders

TABLE S4A

Melanoma Patient Samples - Patient Treatment Details

| Samples | Treatment | Clinical Benefit/Response |
|---|---|---|
| 148-S9 | pre-PD-1-combo (on trial) | NCB (mixed response —> progressive disease) |
| 148-S10 | post-PD-1-combo (on trial) (209 days) | |
| 208-S11 | pre-CTLA-4; pre-PD-1 | NCB (progression) |
| 208-S12 | on-CTLA-4 (42 days); pre-PD-1 | |
| 208-S13 | post-CTLA-4 (182 days); pre-PD-1 | |
| 208-S14 | post-CTLA-4 (245 days); on-PD-1 (63 days) | |
| 27-S1 | post-BRAFi (479 days); pre-PD-1 | NCB (progression) |
| 27-S2 | post-BRAFi (960 days); on-PD-1 (31 days) | |
| 39-S15 | post-BRAFi (393 days); post-IL2 (388 days); post-CTLA-4 (153 days); pre-BRAFi/MEKi; pre-PD-1 | NCB (mixed response —> progressive disease |
| 39-S16 | post-BRAFi (540 days); post-IL2 (535 days); post-CTLA-4 (300 days); post-BRAFi/MEKi (54 days); on-PD-1 (21 days) | |
| 39-S17 | post-BRAFi (607 days); post-IL2 (602 days); post-CTLA-4 (367 days); post-BRAFi/MEKi (121 days); on-PD-1 (88 days) | |
| 42-S3 | post-CTLA-4 (176 days); post-BRAFi/MEKi (64 days); pre-PD-1 | NCB (progression) |
| 42-S4 | post-CTLA-4 (214 days); post-BRAFi/MEKi (102 days); on-PD-1 (38 days) | |
| 42-S5 | post-CTLA-4 (250 days); post-BRAFi/MEKi (138 days); post-PD-1 (74 days) | |
| 62-S6 | pre-CTLA-4; pre-PD-1 | NCB (stable disease —> disease progression) |
| 62-S7 | post-CTLA-4 (235 days); on-PD-1 (3 days) | |
| 62-S8 | post-CTLA-4 (277 days); on-PD-1 (45 days) | |
| 272-S1 | pre-CTLA-4 | CB (near complete response, PD-1 stopped due to irAE, eventual progression off therapy) |
| 272-S2 | post-CTLA-4 (47 days); pre-PD-1 | |
| 272-S3 | post-CTLA-4 (437 days); post-PD-1 (346 days) | |
| 422-S1 | pre-PD-1, pre-CTLA-4 | CB (excellent response after ipi-nivo —> nivo) |
| 422-S2 | on-PD-1, on-CTLA-4 | |
| 51-S1 | pre-PD-L1 | CB (stable disease with a single escape lesion) |
| 51-S2 | post-PD-L1 (224 days) | |
| 98-S1 | post-PD-1 (83 days); pre-CTLA-4 | CB (mixed response —> response) |
| 98-S2 | post-PD-1 (109 days); post-CTLA-4 (25 days) | |
| 98-S3 | post-PD-1 (182 days); post-CTLA-4 (98 days) | |

TABLE S4B-1

| | Samples | | | | | | | |
|---|---|---|---|---|---|---|---|---|
| | 148-S9 | 148-S10 | 208-S11 | 208-S12 | 208-S13 | 208-S14 | 27-S1 | 27-S2 |
| | Treatment | | | | | | | |
| | pre-PD-1-combo (on trial) | post-PD-1-combo (on trial) (209 days) | pre-CTLA-4; pre-PD-1 | on-CTLA-4 (42 days); pre-PD-1 | post-CTLA-4 (182 days); pre-PD-1 | post-CTLA-4 (245 days); on-PD-1 (63 days) | post-BRAFi (479 days); pre-PD-1 | post-BRAFi (960 days); on-PD-1 (31 days) |
| CCL19 | 0.15687084 | 0.41913344 | 1.98815132 | 4.59582353 | 3.45513526 | 8.77085298 | 0.1 | 0.93715502 |
| CXCL13 | 0.26803097 | 2.38711763 | 0.09436038 | 24.7654719 | 2.17496489 | 11.6557472 | 1.27418346 | 0.6404927 |
| CCL2 | 0.1 | 0.1 | 0.1 | 0.1 | 0.1 | 0.1 | 0.1 | 0.1 |
| CCL7 | 0.1 | 0.352523 | 0.13934883 | 0.1 | 0.1 | 0.32786454 | 0.1 | 0.1 |
| CCL8 | 19.5526419 | 29.918033 | 0.90971542 | 3.97934158 | 5.89116018 | 8.66865469 | 0.36852681 | 3.80785605 |
| CCL13 | 24.0118925 | 82.8961538 | 3.06991672 | 9.11382191 | 6.00656079 | 10.3634372 | 0.36047157 | 0.30199656 |
| IL10 | 2.70808608 | 3.17659032 | 0.41855817 | 1.41409955 | 0.68911285 | 1.88752859 | 0.09419912 | 0.23675495 |
| VEGFA | 3.53392266 | 4.83525269 | 1.29428459 | 0.86705549 | 1.65186515 | 1.23934008 | 1.5851421 | 2.89436628 |
| VEGFC | 6.12754266 | 8.3234783 | 0.81574911 | 2.3208504 | 1.85401997 | 1.47147983 | 1.248408 | 2.33787985 |
| CCR7 | 0.43889039 | 0.90613397 | 0.42139498 | 3.5517162 | 0.97129671 | 4.51119789 | 0.11380507 | 0.42904724 |
| CXCR5 | 0.06942884 | 0.13912696 | 0.18331834 | 0.39116295 | 0.20120982 | 0.60384444 | 0.1 | 0.04147717 |
| AXL | 32.5031535 | 60.0635857 | 2.91859483 | 8.55069013 | 6.30519042 | 4.63247743 | 2.56483473 | 3.61622621 |
| GZMA | 2.51550488 | 9.76148303 | 3.16280085 | 53.720088 | 30.132477 | 28.5755234 | 1.53750529 | 13.8827918 |
| GZMB | 3.13000293 | 3.09735564 | 0.7346123 | 33.0483114 | 4.43469902 | 8.64210075 | 3.47191043 | 10.5267372 |
| IFNGR1 | 51.4518655 | 56.8050947 | 54.1265708 | 61.4638002 | 58.8209997 | 82.2106075 | 43.6363806 | 28.2519413 |
| TNF | 0.1 | 0.1 | 0.1 | 0.1 | 0.1 | 0.1 | 0.1 | 0.1 |
| IL2 | 0.13457249 | 0.17977794 | 0.1 | 0.1 | 0.1 | 0.16720274 | 0.1 | 0.1 |
| IFNG | 0.26670627 | 0.23753197 | 0.1 | 3.00525274 | 0.72140516 | 2.09871115 | 0.38036581 | 1.06221195 |
| 0.1 | Below quantification | | | | | | | |

TABLE S4B-2

| | Samples | | | | | | | |
|---|---|---|---|---|---|---|---|---|
| | 39-S15 | 39-S16 | 39-S17 | 42-S3 | 42-S4 | 42-S5 | 62-S6 | 62-S7 |
| | Treatment | | | | | | | |
| | post-BRAFi (393 days); post-IL2 (388 days); post-CTLA-4 (153 days); pre-BRAFi/MEKi; pre-PD-1 | post-BRAFi (540 days); post-IL2 (535 days); post-CTLA-4 (300 days); post-BRAFi/MEKi (54 days); on-PD-1 (21 days) | post-BRAFi (607 days); post-IL2 (602 days); post-CTLA-4 (367 days); post-BRAFi/MEKi (121 days); on-PD-1 (88 days) | post-CTLA-4 (176 days); pre-PD-1 | post-CTLA-4 (214 days); post-BRAFi/MEKi (102 days); on-PD-1 (38 days) | post-CTLA-4 (250 days); post-BRAFi/MEKi (138 days); post-PD-1 (74 days) | pre-CTLA-4; pre-PD-1 | post-CTLA-4 (235 days); on-PD-1 (3 days) |
| CCL19 | 0.1 | 7.17238179 | 0.57691197 | 1.23267021 | 5.18691585 | 6.33513418 | 0.1 | 0.19283266 |
| CXCL13 | 1.62907579 | 2.78518137 | 13.80004 | 0.23401686 | 21.2470659 | 3.96889863 | 0.1 | 0.98842702 |
| CCL2 | 0.1 | 0.1 | 0.1 | 0.1 | 0.1 | 0.1 | 0.1 | 0.1 |
| CCL7 | 0.2830323 | 0.41130796 | 0.48522669 | 0.1 | 0.83895949 | 1.24327654 | 0.1 | 0.1 |
| CCL8 | 3.97261692 | 2.50614458 | 2.32299537 | 2.93296153 | 34.1765182 | 59.2506107 | 7.98116673 | 4.1293583 |
| CCL13 | 2.57546133 | 5.90954174 | 1.08446841 | 3.6412366 | 67.6625745 | 58.3524709 | 5.93524222 | 8.85494803 |
| IL10 | 1.9128064 | 1.50997511 | 6.1537277 | 0.34601269 | 5.87990461 | 2.48959659 | 0.16767663 | 0.64954159 |
| VEGFA | 2.44542296 | 1.59918098 | 1.08303658 | 0.29859241 | 2.57328173 | 0.92074409 | 0.72348459 | 1.68157005 |
| VEGFC | 0.99412394 | 1.76571995 | 1.00996294 | 0.60692541 | 3.9945039 | 0.90110433 | 1.56860848 | 1.77229407 |
| CCR7 | 0.21397451 | 0.8706652 | 0.88040393 | 0.52253673 | 0.9133338 | 0.53710072 | 0.20257569 | 0.09809159 |
| CXCR5 | 0.0372339 | 0.14429073 | 0.17022212 | 0.0909271 | 0.44147241 | 0.0934614 | 0.1 | 0.1 |
| AXL | 3.15217802 | 5.9937903 | 5.59225163 | 2.69996776 | 10.0967011 | 3.89711811 | 4.64898024 | 4.8257931 |
| GZMA | 5.26766769 | 14.8122602 | 18.7958475 | 3.45129418 | 118.364242 | 42.5698517 | 8.66651831 | 5.88984997 |
| GZMB | 3.6058497 | 22.4059016 | 21.3166185 | 3.64372548 | 109.390225 | 31.8348999 | 1.03001359 | 2.13752208 |
| IFNGR1 | 81.0920132 | 110.98998 | 60.1500121 | 79.9433286 | 95.0516258 | 75.0677163 | 0.1 | 35.6153856 |
| TNF | 0.1 | 0.1 | 0.1 | 0.1 | 0.1 | 0.1 | 0.1 | 0.1 |
| IL2 | 0.14433941 | 0.1 | 0.82484505 | 0.1 | 0.1 | 0.36230859 | 0.1 | 0.1 |
| IFNG | 0.66748061 | 0.46190268 | 3.16050183 | 0.11643014 | 7.80107938 | 4.30830872 | 0.56421667 | 0.32784729 |
| 0.1 | Below quantification | | | | | | | |

TABLE S4B-3

| | Samples | | | | | |
|---|---|---|---|---|---|---|
| | 62-S8 | 272-S1 | 272-S2 | 272-S3 | 422-S1 | 422-S2 |
| | Treatment | | | | | |
| | post-CTLA-4 (277 days); on-PD-1 (45 days) | pre-CTLA-4 | post-CTLA-4 (47 days); pre-PD-1 | post-CTLA-4 (437 days); post-PD-1 (346 days) | pre-PD-1, pre-CTLA-4 | on-PD-1, on-CTLA-4 |
| CCL19 | 0.18082453 | 30.8026747 | 81.8439915 | 30.3310126 | 49.1698251 | 569.522382 |
| CXCL13 | 0.20597232 | 143.121621 | 197.444029 | 42.1785257 | 88.565516 | 236.913118 |
| CCL2 | 0.1 | 0.1 | 0.1 | 0.1 | 0.1 | 0.1 |
| CCL7 | 0.1 | 2.26838847 | 2.20958272 | 4.55339377 | 27.1500865 | 0.1 |
| CCL8 | 0.09928753 | 38.0092355 | 21.2212318 | 12.1190886 | 142.838439 | 3.00565688 |
| CCL13 | 1.16540776 | 7.7380948 | 10.0937847 | 4.97652335 | 13.0430495 | 2.22349876 |
| IL10 | 0.22840994 | 10.9175298 | 12.1675798 | 3.6530185 | 2.56684581 | 2.03367129 |
| VEGFA | 1.21549229 | 1.59027526 | 1.89991979 | 4.36289443 | 1.41618926 | 0.51813138 |
| VEGFC | 0.94967388 | 1.66183682 | 2.86889762 | 1.731475 | 1.96825775 | 2.46115994 |
| CCR7 | 0.3219412 | 8.27974664 | 12.7854505 | 4.44863917 | 5.84631976 | 95.5634831 |
| CXCR5 | 0.52019769 | 1.09942208 | 2.21362828 | 0.79868685 | 0.37596741 | 48.1180912 |
| AXL | 2.4522467 | 56.6522478 | 74.8405834 | 13.3027932 | 10.9127259 | 19.1432302 |
| GZMA | 3.58999916 | 80.8064715 | 125.257307 | 46.3160997 | 41.8012 | 37.8345867 |
| GZMB | 7.61677215 | 17.1664256 | 16.4009527 | 3.82328583 | 10.1578792 | 4.1352438 |
| IFNGR1 | 11.8733792 | 57.0563904 | 61.1826911 | 37.3127656 | 44.6747933 | 85.6737313 |
| TNF | 0.1 | 1.26258841 | 1.58476345 | 0.69407351 | 1.36758178 | 2.61714127 |
| IL2 | 0.1 | 0.1 | 0.1 | 0.1 | 0.1 | 0.1 |
| IFNG | 0.20495433 | 10.2969456 | 11.6529517 | 2.83209437 | 2.88850742 | 1.74662482 |
| 0.1 | Below quantification | | | | | |

| | Samples | | | | |
|---|---|---|---|---|---|
| | 51-S1 | 51-S2 | 98-S1 | 98-S2 | 98-S3 |
| | Treatment | | | | |
| | pre-PD-L1 | post-PD-L1 (224 days) | post-PD-1 (83 days); pre-CTLA-4 | post-PD-1 (109 days); post-CTLA-4 (25 days) | post-PD-1 (182 days); post-CTLA-4 (98 days) |
| CCL19 | 31.365808 | 32.4152798 | 0.17967977 | 0.53928875 | 47.9201706 |
| CXCL13 | 16.4200002 | 79.6634246 | 1.33034424 | 1.36021174 | 68.8004261 |
| CCL2 | 0.1 | 0.1 | 0.1 | 0.1 | 0.1 |
| CCL7 | 0.85296606 | 0.06224591 | 0.1511243 | 0.25919012 | 0.48076933 |
| CCL8 | 6.96055707 | 12.0283136 | 1.28256651 | 2.15740095 | 18.2040065 |
| CCL13 | 24.9771521 | 3.04071984 | 0.79614548 | 0.49652815 | 23.4856381 |
| IL10 | 2.3790281 | 1.43340819 | 0.26479124 | 0.55145316 | 2.32656264 |
| VEGFA | 0.97385307 | 0.71259811 | 2.69306142 | 6.84424133 | 0.76154607 |
| VEGFC | 6.2059211 | 0.70448349 | 0.8551934 | 1.01153397 | 5.75394032 |
| CCR7 | 5.96945609 | 8.15050896 | 0.13710131 | 0.05878489 | 4.26465798 |
| CXCR5 | 0.30457195 | 1.75237544 | 0.01988094 | 0.01704869 | 0.92762141 |
| AXL | 2.54442739 | 29.894754 | 0.48020963 | 0.52945552 | 144.038705 |
| GZMA | 10.1174052 | 40.9634229 | 1.79255175 | 1.87878039 | 27.1754305 |
| GZMB | 8.29444931 | 14.8478181 | 2.44928242 | 3.15592022 | 18.753749 |
| IFNGR1 | 184.213974 | 47.254564 | 22.8699314 | 32.4953981 | 124.279512 |
| TNF | 0.33169142 | 0.45183519 | 0.11821037 | 0.04054803 | 0.73206497 |
| IL2 | 0.1 | 0.1 | 0.1 | 0.1 | 0.1 |
| IFNG | 0.12315714 | 4.90717196 | 0.0509142 | 0.04366094 | 10.0962879 |
| 0.1 | | | | | |

TABLE S4B-4

| | FC | | | | | | | | |
|---|---|---|---|---|---|---|---|---|---|
| | 148 | 208a | 208b | 208c | 27 | 39a | 39b | 42a | 42b |
| CCL19 | 2.67 | 2.31 | 1.74 | 4.41 | 9.37 | 71.72 | 5.77 | 4.21 | 5.14 |
| CXCL13 | 8.91 | 262.46 | 23.05 | 123.52 | 0.50 | 1.71 | 8.47 | 90.79 | 16.96 |
| CCL2 | 1.00 | 1.00 | 1.00 | 1.00 | 1.00 | 1.00 | 1.00 | 1.00 | 1.00 |
| CCL7 | 3.53 | 0.72 | 0.72 | 2.35 | 1.00 | 1.45 | 1.71 | 8.39 | 12.43 |
| CCL8 | 1.53 | 4.37 | 6.48 | 9.53 | 10.33 | 0.63 | 0.58 | 11.65 | 20.20 |
| CCL13 | 3.45 | 2.97 | 1.96 | 3.38 | 0.84 | 2.29 | 0.42 | 18.58 | 16.03 |
| IL10 | 1.17 | 3.38 | 1.65 | 4.51 | 2.51 | 0.79 | 3.22 | 16.99 | 7.20 |
| VEGFA | 1.37 | 0.67 | 1.28 | 0.96 | 1.83 | 0.65 | 0.44 | 8.62 | 3.08 |

TABLE S4B-4-continued

| | FC | | | | | | | | |
|---|---|---|---|---|---|---|---|---|---|
| | 148 | 208a | 208b | 208c | 27 | 39a | 39b | 42a | 42b |
| VEGFC | 1.36 | 2.85 | 2.27 | 1.80 | 1.87 | 1.78 | 1.02 | 6.58 | 1.48 |
| CCR7 | 2.06 | 8.43 | 2.30 | 10.71 | 3.77 | 4.07 | 4.11 | 1.75 | 1.03 |
| CXCR5 | 2.00 | 2.13 | 1.10 | 3.29 | 0.41 | 3.88 | 4.57 | 4.86 | 1.03 |
| AXL | 1.85 | 2.93 | 2.16 | 1.59 | 1.41 | 1.90 | 1.77 | 3.74 | 1.44 |
| GZMA | 3.88 | 16.98 | 9.53 | 9.03 | 9.03 | 2.81 | 3.57 | 34.30 | 12.33 |
| GZMB | 0.99 | 44.99 | 6.04 | 11.76 | 3.03 | 6.21 | 5.91 | 30.02 | 8.74 |
| IFNGR1 | 1.10 | 1.14 | 1.09 | 1.52 | 0.65 | 1.37 | 0.74 | 1.19 | 0.94 |
| TNF | 1.00 | 1.00 | 1.00 | 1.00 | 1.00 | 1.00 | 1.00 | 1.00 | 1.00 |
| IL2 | 1.34 | 1.00 | 1.00 | 1.67 | 1.00 | 0.69 | 5.71 | 1.00 | 3.62 |
| IFNG | 0.89 | 30.05 | 7.21 | 20.99 | 2.79 | 0.69 | 4.73 | 67.00 | 37.00 |

TABLE S4B-5

| | FC | | | | | | | |
|---|---|---|---|---|---|---|---|---|
| | 62a | 62b | 272a | 272b | 422 | 51 | 98a | 98b |
| CCL19 | 1.93 | 1.81 | 2.66 | 0.98 | 11.58 | 1.03 | 3.00 | 266.70 |
| CXCL13 | 9.88 | 2.06 | 1.38 | 0.29 | 2.68 | 4.85 | 1.02 | 51.72 |
| CCL2 | 1.00 | 1.00 | 1.00 | 1.00 | 1.00 | 1.00 | 1.00 | 1.00 |
| CCL7 | 1.00 | 1.00 | 0.97 | 2.01 | 0.00 | 0.07 | 1.72 | 3.18 |
| CCL8 | 0.52 | 0.01 | 0.56 | 0.32 | 0.02 | 1.73 | 1.68 | 14.19 |
| CCL13 | 1.49 | 0.20 | 1.30 | 0.64 | 0.17 | 0.12 | 0.62 | 29.50 |
| IL10 | 3.87 | 1.36 | 1.11 | 0.33 | 0.79 | 0.60 | 2.08 | 8.79 |
| VEGFA | 2.32 | 1.68 | 1.19 | 2.74 | 0.37 | 0.73 | 2.54 | 0.28 |
| VEGFC | 1.13 | 0.61 | 1.73 | 1.04 | 1.25 | 0.11 | 1.18 | 6.73 |
| CCR7 | 0.48 | 1.59 | 1.54 | 0.54 | 16.35 | 1.37 | 0.43 | 31.11 |
| CXCR5 | 1.00 | 5.20 | 2.01 | 0.73 | 127.98 | 5.75 | 0.86 | 46.66 |
| AXL | 1.04 | 0.53 | 1.32 | 0.23 | 1.75 | 11.75 | 1.10 | 299.95 |
| GZMA | 0.68 | 0.41 | 1.55 | 0.57 | 0.91 | 4.05 | 1.05 | 15.16 |
| GZMB | 2.08 | 7.39 | 0.96 | 0.22 | 0.41 | 1.79 | 1.29 | 7.66 |
| IFNGR1 | 356.15 | 118.73 | 1.07 | 0.65 | 1.92 | 0.26 | 1.42 | 5.43 |
| TNF | 1.00 | 1.00 | 1.26 | 0.55 | 1.91 | 1.36 | 0.34 | 6.19 |
| IL2 | 1.00 | 1.00 | 1.00 | 1.00 | 1.00 | 1.00 | 1.00 | 1.00 |
| IFNG | 0.58 | 0.36 | 1.13 | 0.28 | 0.60 | 39.84 | 0.86 | 198.30 |

TABLE S4B-6

| | L2FC | | | | | | | | |
|---|---|---|---|---|---|---|---|---|---|
| | 148 | 208a | 208b | 208c | 27 | 39a | 39b | 42a | 42b |
| CCL19 | 1.42 | 1.21 | 0.80 | 2.14 | 3.23 | 6.16 | 2.53 | 2.07 | 2.36 |
| CXCL13 | 3.15 | 8.04 | 4.53 | 6.95 | −0.99 | 0.77 | 3.08 | 6.50 | 4.08 |
| CCL2 | 0.00 | 0.00 | 0.00 | 0.00 | 0.00 | 0.00 | 0.00 | 0.00 | 0.00 |
| CCL7 | 1.82 | −0.48 | −0.48 | 1.23 | 0.00 | 0.54 | 0.78 | 3.07 | 3.64 |
| CCL8 | 0.61 | 2.13 | 2.70 | 3.25 | 3.37 | −0.66 | −0.77 | 3.54 | 4.34 |
| CCL13 | 1.79 | 1.57 | 0.97 | 1.76 | −0.26 | 1.20 | −1.25 | 4.22 | 4.00 |
| IL10 | 0.23 | 1.76 | 0.72 | 2.17 | 1.33 | −0.34 | 1.69 | 4.09 | 2.85 |
| VEGFA | 0.45 | −0.58 | 0.35 | −0.06 | 0.87 | −0.61 | −1.18 | 3.11 | 1.62 |
| VEGFC | 0.44 | 1.51 | 1.18 | 0.85 | 0.91 | 0.83 | 0.02 | 2.72 | 0.57 |
| CCR7 | 1.05 | 3.08 | 1.20 | 3.42 | 1.91 | 2.02 | 2.04 | 0.81 | 0.04 |
| CXCR5 | 1.00 | 1.09 | 0.13 | 1.72 | −1.27 | 1.95 | 2.19 | 2.28 | 0.04 |
| AXL | 0.89 | 1.55 | 1.11 | 0.67 | 0.50 | 0.93 | 0.83 | 1.90 | 0.53 |
| GZMA | 1.96 | 4.09 | 3.25 | 3.18 | 3.17 | 1.49 | 1.84 | 5.10 | 3.62 |
| GZMB | −0.02 | 5.49 | 2.59 | 3.56 | 1.60 | 2.64 | 2.56 | 4.91 | 3.13 |
| IFNGR1 | 0.14 | 0.18 | 0.12 | 0.60 | −0.63 | 0.45 | −0.43 | 0.25 | −0.09 |
| TNF | 0.00 | 0.00 | 0.00 | 0.00 | 0.00 | 0.00 | 0.00 | 0.00 | 0.00 |
| IL2 | 0.42 | 0.00 | 0.00 | 0.74 | 0.00 | −0.53 | 2.51 | 0.00 | 1.86 |
| IFNG | −0.17 | 4.91 | 2.85 | 4.39 | 1.48 | −0.53 | 2.24 | 6.07 | 5.21 |

TABLE S4B-7

| | L2FC | | | | | | | |
|---|---|---|---|---|---|---|---|---|
| | 62a | 62b | 272a | 272b | 422 | 51 | 98a | 98b |
| CCL19 | 0.95 | 0.85 | 1.41 | −0.02 | 3.53 | 0.05 | 1.59 | 8.06 |
| CXCL13 | 3.31 | 1.04 | 0.46 | −1.76 | 1.42 | 2.28 | 0.03 | 5.69 |
| CCL2 | 0.00 | 0.00 | 0.00 | 0.00 | 0.00 | 0.00 | 0.00 | 0.00 |
| CCL7 | 0.00 | 0.00 | −0.04 | 1.01 | −8.08 | −3.78 | 0.78 | 1.67 |
| CCL8 | −0.95 | −6.33 | −0.84 | −1.65 | −5.57 | 0.79 | 0.75 | 3.83 |
| CCL13 | 0.58 | −2.35 | 0.38 | −0.64 | −2.55 | −3.04 | −0.68 | 4.88 |
| IL10 | 1.95 | 0.45 | 0.16 | −1.58 | −0.34 | −0.73 | 1.06 | 3.14 |
| VEGFA | 1.22 | 0.75 | 0.26 | 1.46 | −1.45 | −0.45 | 1.35 | −1.82 |
| VEGFC | 0.18 | −0.72 | 0.79 | 0.06 | 0.32 | −3.14 | 0.24 | 2.75 |
| CCR7 | −1.05 | 0.67 | 0.63 | −0.90 | 4.03 | 0.45 | −1.22 | 4.96 |
| CXCR5 | 0.00 | 2.38 | 1.01 | −0.46 | 7.00 | 2.52 | −0.22 | 5.54 |
| AXL | 0.05 | −0.92 | 0.40 | −2.09 | 0.81 | 3.55 | 0.14 | 8.23 |
| GZMA | −0.56 | −1.27 | 0.63 | −0.80 | −0.14 | 2.02 | 0.07 | 3.92 |
| GZMB | 1.05 | 2.89 | −0.07 | −2.17 | −1.30 | 0.84 | 0.37 | 2.94 |
| IFNGR1 | 8.48 | 6.89 | 0.10 | −0.61 | 0.94 | −1.96 | 0.51 | 2.44 |
| TNF | 0.00 | 0.00 | 0.33 | −0.86 | 0.94 | 0.45 | −1.54 | 2.63 |
| IL2 | 0.00 | 0.00 | 0.00 | 0.00 | 0.00 | 0.00 | 0.00 | 0.00 |
| IFNG | −0.78 | −1.46 | 0.18 | −1.86 | −0.73 | 5.32 | −0.22 | 7.63 |

TABLE S5-1

Project SSBK10488_30712; provides data for Cmpd1 (1000 µM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | TBK1 | | ZLYTE | 91 | 99 | 95 | 8 | Pass | Pass | 0.83 | PV3504/857011 | Pass |
| | CDC7/DBF4 | | LanthaScreen Binding | 100 | 97 | 98 | 3 | Pass | Pass | 0.84 | PV6274/1576890 | |
| | MAPK15 (ERK7) | | LanthaScreen Binding | 100 | 100 | 100 | 0 | Pass | Pass | 0.93 | PV6181/1570972 | |
| Km app | IKBKE (IKK epsilon) | | ZLYTE | 106 | 103 | 105 | 3 | Pass | Pass | 0.8 | PV4875/853377 | Pass |
| Km app | CSF1R (FMS) | | ZLYTE | 91 | 96 | 93 | 6 | Pass | Pass | 0.79 | PV3249/662393 | Pass |
| | STK17A (DRAK1) | | LanthaScreen Binding | 101 | 101 | 101 | 0 | Pass | Pass | 0.9 | PV3783/902537 | |
| | TGFBR2 | | LanthaScreen Binding | 92 | 95 | 93 | 3 | Pass | Pass | 0.79 | PV6122/862447 | |
| | PLK4 | | LanthaScreen Binding | 96 | 95 | 96 | 1 | Pass | Pass | 0.96 | PV6394/1577044 | |
| Km app | LRRK2 | | Adapta | 99 | 100 | 100 | 1 | Pass | Pass | 0.76 | PV4873/1106714 | |
| Km app | STK22D (TSSK1) | | ZLYTE | 99 | 95 | 97 | 3 | Pass | Pass | 0.88 | PV3505/1211826 | Pass |
| Km app | PRKD2 (PKD2) | | ZLYTE | 99 | 97 | 98 | 2 | Pass | Pass | 0.8 | PV3758/34015 | Pass |
| Km app | MKNK1 (MNK1) | | ZLYTE | 99 | 100 | 100 | 1 | Pass | Pass | 0.77 | PV6023/1405297 | Pass |
| Km app | PRKD1 (PKC mu) | | ZLYTE | 100 | 95 | 98 | 5 | Pass | Pass | 0.86 | PV3791/34226 | Pass |
| Km app | MARK4 | | ZLYTE | 96 | 93 | 95 | 3 | Pass | Pass | 0.8 | PV3851/304213 | Pass |
| Km app | MARK3 | | ZLYTE | 98 | 94 | 96 | 4 | Pass | Pass | 0.73 | PV4819/830446 | Pass |
| Km app | PAK4 | | ZLYTE | 91 | 90 | 90 | 1 | Pass | Pass | 0.73 | PV4212/35324 | Pass |
| | MLCK (MLCK2) | | LanthaScreen Binding | 92 | 93 | 93 | 0 | Pass | Pass | 0.56 | PV3835/34028 | |
| | ULK3 | | LanthaScreen Binding | 101 | 104 | 102 | 3 | Pass | Pass | 0.82 | PV6436/1579414 | |
| Km app | IRAK1 | | Adapta | 94 | 96 | 95 | 1 | Pass | Pass | 0.91 | PV4403/880118 | |
| Km app | BRSK1 (SAD1) | | ZLYTE | 92 | 89 | 90 | 4 | Pass | Pass | 0.91 | PV4333/36097 | Pass |
| | SIK3 | | LanthaScreen Binding | 98 | 95 | 96 | 2 | Pass | Pass | 0.73 | PV6403/1577057 | |
| Km app | PRKCN (PKD3) | | ZLYTE | 98 | 96 | 97 | 2 | Pass | Pass | 0.74 | PV3692/1252690 | Pass |
| | STK16 (PKL12) | | LanthaScreen Binding | 95 | 93 | 94 | 2 | Pass | Pass | 0.76 | PV4311/36847 | |
| | ULK2 | | LanthaScreen Binding | 86 | 90 | 88 | 4 | Pass | Pass | 0.9 | PV4433/1579413 | |
| Km app | LRRK2 G2019S | y | Adapta | 99 | 100 | 100 | 1 | Pass | Pass | 0.88 | PV4881/933637 | |
| Km app | LRRK2 G2019S FL | y | Adapta | 100 | 99 | 99 | 1 | Pass | Pass | 0.81 | A15200PT/50078 | |
| Km app | LRRK2 I2020T | y | Adapta | 100 | 98 | 99 | 2 | Pass | Pass | 0.84 | PV5854/902533 | |
| Km app | LRRK2 FL | y | Adapta | 98 | 98 | 98 | 0 | Pass | Pass | 0.88 | A15197PT/1147693 | |
| Km app | LRRK2 R1441C | y | Adapta | 99 | 95 | 97 | 4 | Pass | Pass | 0.8 | PV5858/902531 | |
| | KIT D816H | y | LanthaScreen Binding | 90 | 94 | 92 | 4 | Pass | Pass | 0.82 | PV6196/1570980 | |
| | ULK1 | | LanthaScreen Binding | 91 | 92 | 92 | 1 | Pass | Pass | 0.8 | PV6430/1579415 | |
| | ACVR1 (ALK2) R206H | y | LanthaScreen Binding | 88 | 93 | 91 | 5 | Pass | Pass | 0.88 | PV6232/1578464 | |
| | KIT A829P | y | LanthaScreen Binding | 91 | 90 | 90 | 0 | Pass | Pass | 0.89 | PV6193/1570981 | |
| Km app | AURKA (Aurora A) | | ZLYTE | 91 | 86 | 89 | 5 | Pass | Pass | 0.84 | PV3612/32155 | Pass |
| | EIF2AK2 (PKR) | | LanthaScreen Binding | 90 | 89 | 89 | 1 | Pass | Pass | 0.8 | PV4821/374655 | |
| | STK17B (DRAK2) | | LanthaScreen Binding | 94 | 84 | 89 | 10 | Pass | Pass | 0.6 | PV6328/1575526 | |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| | CLK4 | | LanthaScreen Binding | 87 | 89 | 88 | 2 | Pass | Pass | 0.81 | PV3839/827665 | |
| Km app | SNF1LK2 | | ZLYTE | 88 | 88 | 88 | 0 | Pass | Pass | 0.66 | PV4792/719848 | Pass |
| | MKNK2 (MNK2) | | LanthaScreen Binding | 86 | 88 | 87 | 2 | Pass | Pass | 0.86 | PV5607/811381 | |
| Km app | MAP4K4 (HGK) | | ZLYTE | 86 | 86 | 86 | 0 | Pass | Pass | 0.74 | PV3687/792773 | Pass |
| Km app | MARK1 (MARK) | | ZLYTE | 85 | 87 | 86 | 3 | Pass | Pass | 0.89 | PV4395/1081574 | Pass |
| Km app | FYN | | ZLYTE | 85 | 85 | 85 | 0 | Pass | Pass | 0.7 | P3042/1191778 | Pass |
| | RIPK2 | | LanthaScreen Binding | 84 | 86 | 85 | 1 | Pass | Pass | 0.93 | PV4213/35334 | |
| | ACVR1 (ALK2) | | LanthaScreen Binding | 85 | 84 | 84 | 1 | Pass | Pass | 0.92 | PV4877/676188 | |
| Km app | MARK2 | | ZLYTE | 86 | 82 | 84 | 4 | Pass | Pass | 0.88 | PV3878/877056 | Pass |
| | KIT D816V | y | LanthaScreen Binding | 83 | 83 | 83 | 1 | Pass | Pass | 0.74 | PV6199/1570986 | |
| Km app | NUAK1 (ARK5) | | Adapta | 83 | 83 | 83 | 0 | Pass | Pass | 0.83 | PV4127/1401900 | |
| Km app | PDGFRA V561D | y | ZLYTE | 85 | 81 | 83 | 4 | Pass | Pass | 0.84 | PV4680/1113217 | Pass |
| | TLK2 | | LanthaScreen Binding | 84 | 81 | 83 | 3 | Pass | Pass | 0.91 | PV6424/1578677 | |
| Km app | FLT3 D835Y | y | ZLYTE | 83 | 81 | 82 | 2 | Pass | Pass | 0.81 | PV3967/308809 | Pass |
| Km app | PHKG2 | | ZLYTE | 83 | 79 | 81 | 4 | Pass | Pass | 0.85 | PV4555/37321 | Pass |
| Km app | PDK1 Direct | | ZLYTE | 85 | 74 | 79 | 11 | Pass | Pass | 0.71 | P3001/1394674 | Pass |
| Km app | CHEK1 (CHK1) | | ZLYTE | 78 | 78 | 78 | 1 | Pass | Pass | 0.74 | P3040/28702 | Pass |
| | DMPK | | LanthaScreen Binding | 76 | 79 | 78 | 2 | Pass | Pass | 0.84 | PV3784/802854 | |
| Km app | PAK7 (KIAA1264) | | ZLYTE | 77 | 79 | 78 | 2 | Pass | Pass | 0.84 | PV4405/36846 | Pass |
| Km app | PLK3 | | ZLYTE | 80 | 76 | 78 | 5 | Pass | Pass | 0.8 | PV3812/38812 | Pass |
| Km app | PDGFRA D842V | y | ZLYTE | 77 | 73 | 75 | 4 | Pass | Pass | 0.89 | PV4203/269691 | Pass |
| Km app | JAK3 | | ZLYTE | 73 | 73 | 73 | 1 | Pass | Pass | 0.86 | PV3855/1017963 | Pass |
| | CDK16 (PCTK1)/cyclin Y | | LanthaScreen Binding | 70 | 73 | 71 | 3 | Pass | Pass | 0.81 | PV6379/1577049 | |
| Km app | MAP3K9 (MLK1) | | ZLYTE | 68 | 73 | 70 | 5 | Pass | Pass | 0.84 | PV3787/1095726 | Pass |
| Km app | NEK1 | | ZLYTE | 68 | 70 | 69 | 3 | Pass | Pass | 0.82 | PV4202/880120 | Pass |
| Km app | RET V804L | y | ZLYTE | 71 | 66 | 69 | 5 | Pass | Pass | 0.85 | PV4397/36640 | Pass |
| Km app | MINK1 | | ZLYTE | 66 | 70 | 68 | 4 | Pass | Pass | 0.76 | PV3810/1081579 | Pass |
| | ABL1 M351T | y | LanthaScreen Binding | 65 | 69 | 67 | 4 | Pass | Pass | 0.67 | PV6151/1570962 | |
| Km app | JAK2 | | ZLYTE | 67 | 68 | 67 | 1 | Pass | Pass | 0.8 | PV4210/784633 | Pass |
| | KIT N822K | y | LanthaScreen Binding | 66 | 67 | 66 | 1 | Pass | Pass | 0.71 | PV6310/1576886 | |
| Km app | TYK2 | | ZLYTE | 65 | 64 | 64 | 1 | Pass | Pass | 0.88 | PV4790/884908 | Pass |
| | FLT3 ITD | | LanthaScreen Binding | 64 | 62 | 63 | 2 | Pass | Pass | 0.72 | PV6190/1570961 | |
| Km app | MYLK2 (skMLCK) | | ZLYTE | 65 | 60 | 63 | 5 | Pass | Pass | 0.67 | PV3757/36606 | Pass |
| 100 | BRAF V599E | y | ZLYTE | 63 | 61 | 62 | 2 | Pass | Pass | 0.92 | PV3849/910409 | Pass |
| Km app | FLT4 (VEGFR3) | | ZLYTE | 64 | 60 | 62 | 5 | Pass | Pass | 0.87 | PV4129/38454 | Pass |
| Km app | PLK2 | | ZLYTE | 60 | 64 | 62 | 4 | Pass | Pass | 0.9 | PV4204/38798 | Pass |
| Km app | ABL1 G250E | y | ZLYTE | 60 | 61 | 60 | 1 | Pass | Pass | 0.9 | PV3865/34529 | Pass |
| | ABL1 H396P | y | LanthaScreen Binding | 58 | 60 | 59 | 2 | Pass | Pass | 0.74 | PV6148/1570966 | |
| | MAP3K10 (MLK2) | | LanthaScreen Binding | 58 | 60 | 59 | 2 | Pass | Pass | 0.96 | PV3877/1138344 | |
| | BMPR1B (ALK6) | | LanthaScreen Binding | 56 | 60 | 58 | 3 | Pass | Pass | 0.81 | PV6235/1578462 | |
| Km app | CHUK (IKK alpha) | | Adapta | 65 | 50 | 58 | 15 | Pass | Pass | 0.79 | PV4310/1110228 | |
| | DDR2 T654M | y | LanthaScreen Binding | 56 | 57 | 57 | 1 | Pass | Pass | 0.79 | PV6175/1570973 | |
| | MAP4K1 (HPK1) | | LanthaScreen Binding | 59 | 55 | 57 | 3 | Pass | Pass | 0.72 | PV6355/1575528 | |
| | MAPK8 (JNK1) | | LanthaScreen Binding | 57 | 56 | 57 | 1 | Pass | Pass | 0.83 | PV3319/1354818 | |
| Km app | SRC N1 | | ZLYTE | 54 | 60 | 57 | 6 | Pass | Pass | 0.91 | P2904/21068 | Pass |
| | STK33 | | LanthaScreen Binding | 59 | 55 | 57 | 4 | Pass | Pass | 0.91 | PV4343/798867 | |
| | TGFBR1 (ALK5) | | LanthaScreen Binding | 56 | 58 | 57 | 2 | Pass | Pass | 0.91 | PV5837/562479 | |
| | DAPK2 | | LanthaScreen Binding | 60 | 53 | 56 | 7 | Pass | Pass | 0.64 | PV3614/32159 | |
| | SIK1 | | LanthaScreen Binding | 57 | 54 | 56 | 2 | Pass | Pass | 0.93 | PV6445/1601253 | |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | AMPK A1/B1/G1 | | ZLYTE | 58 | 53 | 55 | 5 | Pass | Pass | 0.9 | PV4672/1046028 | Pass |
| Km app | ABL1 Y253F | y | ZLYTE | 61 | 48 | 54 | 12 | Pass | Pass | 0.92 | PV3863/34531 | Pass |
| | CDK14 (PFTK1)/cyclin Y | | LanthaScreen Binding | 56 | 51 | 54 | 5 | Pass | Pass | 0.56 | PV6382/1577046 | |
| | DYRK2 | | LanthaScreen Binding | 54 | 53 | 54 | 1 | Pass | Pass | 0.57 | PV6331/1578676 | |
| Km app | FGR | | ZLYTE | 53 | 53 | 53 | 0 | Pass | Pass | 0.94 | P3041/26670 | Pass |
| | KIT Y823D | y | LanthaScreen Binding | 47 | 59 | 53 | 12 | Pass | Pass | 0.67 | PV6322/1579412 | |
| Km app | LYN B | | ZLYTE | 56 | 50 | 53 | 6 | Pass | Pass | 0.8 | P2907/21076 | Pass |
| | NUAK2 | | LanthaScreen Binding | 54 | 52 | 53 | 1 | Pass | Pass | 0.65 | PV6376/1607389 | |
| | TEK (TIE2) Y1108F | y | LanthaScreen Binding | 53 | 52 | 53 | 0 | Pass | Pass | 0.6 | PV6229/1570987 | |
| Km app | YES1 | | ZLYTE | 55 | 51 | 53 | 4 | Pass | Pass | 0.84 | A15557/50645 | Pass |
| | BRAF V599E | y | LanthaScreen Binding | 50 | 53 | 52 | 3 | Pass | Pass | 0.89 | PV3849/910409 | |
| Km app | JAK2 JH1 JH2 V617F | | ZLYTE | 54 | 50 | 52 | 4 | Pass | Pass | 0.84 | PV4336/463344 | Pass |
| Km app | KDR (VEGFR2) | | ZLYTE | 51 | 53 | 52 | 2 | Pass | Pass | 0.85 | PV3660/1223246 | Pass |
| Km app | ABL1 E255K | y | ZLYTE | 53 | 50 | 51 | 3 | Pass | Pass | 0.79 | PV3864/34528 | Pass |
| Km app | AURKB (Aurora B) | | ZLYTE | 54 | 48 | 51 | 6 | Pass | Pass | 0.78 | PV6130/857013 | Pass |
| | BMPR1A (ALK3) | | LanthaScreen Binding | 51 | 51 | 51 | 0 | Pass | Pass | 0.82 | PV6038/670004 | |
| Km app | DAPK3 (ZIPK) | | ZLYTE | 52 | 49 | 51 | 3 | Pass | Pass | 0.68 | PV3686/1083962 | Pass |
| | PKN2 (PRK2) | | LanthaScreen Binding | 51 | 52 | 51 | 2 | Pass | Pass | 0.93 | PV3879/555959 | |
| Km app | RET Y791F | y | ZLYTE | 57 | 43 | 50 | 14 | Pass | Pass | 0.91 | PV4396/36639 | Pass |
| | STK38 (NDR) | | LanthaScreen Binding | 51 | 49 | 50 | 2 | Pass | Pass | 0.81 | PV6370/1575531 | |
| Km app | ABL1 | | ZLYTE | 48 | 51 | 49 | 4 | Pass | Pass | 0.88 | P3049/1012910 | Pass |
| | BMPR2 | | LanthaScreen Binding | 50 | 47 | 49 | 3 | Pass | Pass | 0.8 | PV6256/1579470 | |
| | MAPK10 (JNK3) | | LanthaScreen Binding | 48 | 49 | 49 | 1 | Pass | Pass | 0.93 | PV4563/1075329 | |
| Km app | LYN A | | ZLYTE | 48 | 48 | 48 | 0 | Pass | Pass | 0.91 | P2906/827663 | Pass |
| | KIT V559D T670I | y | LanthaScreen Binding | 46 | 49 | 47 | 3 | Pass | Pass | 0.94 | PV6316/1579472 | |
| | MET D1228H | y | LanthaScreen Binding | 46 | 48 | 47 | 2 | Pass | Pass | 0.78 | PV6208/1570985 | |
| | ABL1 Q252H | y | LanthaScreen Binding | 52 | 41 | 46 | 11 | Pass | Pass | 0.76 | PV6154/1570960 | |
| | AMPK (A1/B2/G1) | | LanthaScreen Binding | 49 | 43 | 46 | 5 | Pass | Pass | 0.96 | PV6244/1578463 | |
| Km app | AMPK A2/B1/G1 | | ZLYTE | 47 | 46 | 46 | 2 | Pass | Pass | 0.93 | PV4674/568101 | Pass |
| | BRAF | | LanthaScreen Binding | 44 | 47 | 46 | 2 | Pass | Pass | 0.89 | PV3848/1258788 | |
| Km app | JAK2 JH1 JH2 | | ZLYTE | 46 | 47 | 46 | 1 | Pass | Pass | 0.81 | PV4393/311662 | Pass |
| Km app | NEK9 | | ZLYTE | 46 | 45 | 46 | 1 | Pass | Pass | 0.89 | PV4653/38162 | Pass |
| Km app | SYK | | ZLYTE | 44 | 49 | 46 | 5 | Pass | Pass | 0.85 | PV3857/756818 | Pass |
| | AMPK (A2/B2/G2) | | LanthaScreen Binding | 44 | 45 | 45 | 1 | Pass | Pass | 0.93 | PV6250/1578465 | |
| Km app | FLT3 | | ZLYTE | 42 | 49 | 45 | 7 | Pass | Pass | 0.78 | PV3182/1012909 | Pass |
| Km app | IKBKB (IKK beta) | | ZLYTE | 52 | 39 | 45 | 13 | Pass | Pass | 0.9 | PV3836/1445179 | Pass |
| Km app | SRC | | ZLYTE | 45 | 44 | 45 | 1 | Pass | Pass | 0.89 | P3044/1255538 | Pass |
| | TNIK | | LanthaScreen Binding | 46 | 43 | 45 | 3 | Pass | Pass | 0.8 | PV6427/1578672 | |
| Km app | RET | | ZLYTE | 46 | 42 | 44 | 4 | Pass | Pass | 0.89 | PV3819/853376 | Pass |
| | TAOK1 | | LanthaScreen Binding | 45 | 43 | 44 | 2 | Pass | Pass | 0.82 | PV6415/1576240 | |
| Km app | DAPK1 | | Adapta | 42 | 43 | 43 | 2 | Pass | Pass | 0.83 | PV3969/32654 | |
| Km app | PDGFRA (PDGFR alpha) | | ZLYTE | 43 | 43 | 43 | 0 | Pass | Pass | 0.82 | PV3811/1269727 | Pass |
| Km app | BLK | | ZLYTE | 41 | 42 | 42 | 1 | Pass | Pass | 0.8 | PV3683/33635 | Pass |
| | CDK2/cyclin O | | LanthaScreen Binding | 39 | 42 | 41 | 4 | Pass | Pass | 0.75 | PV6286/1576891 | |
| | TEK (TIE2) R849W | y | LanthaScreen Binding | 40 | 41 | 41 | 1 | Pass | Pass | 0.92 | PV6226/1570990 | |
| Km app | TYRO3 (RSE) | | ZLYTE | 42 | 39 | 41 | 4 | Pass | Pass | 0.9 | PV3828/682475 | Pass |
| Km app | ABL2 (Arg) | | ZLYTE | 40 | 39 | 40 | 1 | Pass | Pass | 0.92 | PV3266/850069 | Pass |
| | AMPK (A1/B1/G2) | | LanthaScreen Binding | 40 | 40 | 40 | 0 | Pass | Pass | 0.97 | PV6238/1578461 | |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
|  | LCK |  | ZLYTE | 41 | 38 | 40 | 3 | Pass | Pass | 0.79 | P3043/850070 | Pass |
|  | LIMK1 |  | LanthaScreen Binding | 40 | 39 | 40 | 1 | Pass | Pass | 0.87 | PV4337/367810 |  |
|  | AMPK (A1/B1/G3) |  | LanthaScreen Binding | 37 | 42 | 39 | 5 | Pass | Pass | 0.92 | PV6241/1578466 |  |
| Km app | MST1R (RON) |  | ZLYTE | 38 | 38 | 38 | 0 | Pass | Pass | 0.83 | PV4314/765277 | Pass |
| Km app | PHKG1 |  | ZLYTE | 39 | 37 | 38 | 2 | Pass | Pass | 0.75 | PV3853/830447 | Pass |
| Km app | CDK2/cyclin A |  | ZLYTE | 38 | 36 | 37 | 1 | Pass | Pass | 0.88 | PV3267/924344 | Pass |
|  | DDR2 N456S | y | LanthaScreen Binding | 33 | 42 | 37 | 9 | Pass | Pass | 0.86 | PV6172/1570968 |  |
| Km app | RPS6KB1 (p70S6K) |  | ZLYTE | 37 | 36 | 37 | 1 | Pass | Pass | 0.84 | PV3815/38944 | Pass |
|  | CDK2/cyclin A1 |  | LanthaScreen Binding | 33 | 39 | 36 | 6 | Pass | Pass | 0.89 | PV6289/1576888 |  |
| Km app | PDGFRA T674I | y | ZLYTE | 40 | 32 | 36 | 8 | Pass | Pass | 0.67 | PV3847/35891 | Pass |
|  | ACVRL1 (ALK1) |  | LanthaScreen Binding | 33 | 38 | 35 | 5 | Pass | Pass | 0.79 | PV4883/511550 |  |
|  | AMPK (A2/B2/G1) |  | LanthaScreen Binding | 35 | 35 | 35 | 0 | Pass | Pass | 0.94 | PV6247/1578460 |  |
|  | FGFR3 K650M | y | LanthaScreen Binding | 33 | 38 | 35 | 5 | Pass | Pass | 0.82 | PV6187/1573650 |  |
| Km app | ITK |  | ZLYTE | 37 | 32 | 34 | 4 | Pass | Pass | 0.71 | PV3875/1430640 | Pass |
|  | STK38L (NDR2) |  | LanthaScreen Binding | 30 | 38 | 34 | 9 | Pass | Pass | 0.54 | PV6373/1575530 |  |
| Km app | CLK1 |  | ZLYTE | 33 | 34 | 33 | 0 | Pass | Pass | 0.88 | PV3315/943590 | Pass |
| Km app | EPHB1 |  | ZLYTE | 34 | 31 | 33 | 3 | Pass | Pass | 0.91 | PV3786/34225 | Pass |
|  | RET V804M | y | LanthaScreen Binding | 35 | 31 | 33 | 4 | Pass | Pass | 0.82 | PV6223/1570988 |  |
|  | TTK |  | LanthaScreen Binding | 33 | 34 | 33 | 1 | Pass | Pass | 0.77 | PV3792/558743 |  |
| Km app | PDGFRB (PDGFR beta) |  | ZLYTE | 34 | 30 | 32 | 4 | Pass | Pass | 0.78 | P3082/27567 | Pass |
|  | WEE1 |  | LanthaScreen Binding | 28 | 36 | 32 | 7 | Pass | Pass | 0.64 | PV3817/784632 |  |
| Km app | CSNK2A2 (CK2 alpha 2) |  | ZLYTE | 32 | 30 | 31 | 2 | Pass | Pass | 0.81 | PV3624/32653 | Pass |
| Km app | EGFR (ErbB1) T790M L858R | y | ZLYTE | 34 | 29 | 31 | 4 | Pass | Pass | 0.9 | PV4879/1189155 | Pass |
| Km app | MET (cMet) |  | ZLYTE | 30 | 33 | 31 | 4 | Pass | Pass | 0.79 | PV3143/625156 | Pass |
| Km app | TXK |  | ZLYTE | 27 | 36 | 31 | 9 | Pass | Pass | 0.86 | PV5860/750657 | Pass |
| Km app | MET M1250T | y | ZLYTE | 26 | 34 | 30 | 8 | Pass | Pass | 0.86 | PV3968/34718 | Pass |
| Km app | NEK2 |  | ZLYTE | 29 | 30 | 30 | 0 | Pass | Pass | 0.81 | PV3360/1086245 | Pass |
|  | SLK |  | LanthaScreen Binding | 29 | 32 | 30 | 4 | Pass | Pass | 0.95 | PV3830/34390 |  |
| Km app | ABL1 T315I | y | ZLYTE | 30 | 29 | 29 | 1 | Pass | Pass | 0.84 | PV3866/39639 | Pass |
|  | ACVR2B |  | LanthaScreen Binding | 27 | 31 | 29 | 4 | Pass | Pass | 0.86 | PV6049/877066 |  |
| Km app | DYRK1A |  | ZLYTE | 30 | 27 | 28 | 4 | Pass | Pass | 0.9 | PV3785/683159 | Pass |
|  | NLK |  | LanthaScreen Binding | 26 | 29 | 28 | 3 | Pass | Pass | 0.88 | PV4309/35323 |  |
| Km app | ROS1 |  | ZLYTE | 30 | 26 | 28 | 4 | Pass | Pass | 0.81 | PV3814/479684 | Pass |
|  | AXL R499C | y | LanthaScreen Binding | 28 | 27 | 27 | 1 | Pass | Pass | 0.89 | PV6253/1578673 |  |
| Km app | CHEK2 (CHK2) |  | ZLYTE | 27 | 27 | 27 | 0 | Pass | Pass | 0.84 | PV3367/1033750 | Pass |
| Km app | EPHA1 |  | ZLYTE | 29 | 24 | 27 | 5 | Pass | Pass | 0.85 | PV3841/1138343 | Pass |
| Km app | HCK |  | ZLYTE | 26 | 28 | 27 | 2 | Pass | Pass | 0.87 | PV6128/862448 | Pass |
| Km app | SGK (SGK1) |  | ZLYTE | 28 | 26 | 27 | 2 | Pass | Pass | 0.88 | PV3818/1088196 | Pass |
|  | CDK2/cyclin A2 |  | LanthaScreen Binding | 24 | 29 | 26 | 5 | Pass | Pass | 0.7 | PV6292/1576892 |  |
|  | MAP3K11 (MLK3) |  | LanthaScreen Binding | 24 | 29 | 26 | 5 | Pass | Pass | 0.93 | PV3788/869925 |  |
|  | MERTK (cMER) A708S | y | LanthaScreen Binding | 24 | 27 | 26 | 3 | Pass | Pass | 0.92 | PV6325/1578675 |  |
| Km app | PRKX |  | ZLYTE | 22 | 30 | 26 | 8 | Pass | Pass | 0.87 | PV3813/34283 | Pass |
| Km app | DYRK3 |  | ZLYTE | 26 | 24 | 25 | 2 | Pass | Pass | 0.89 | PV3837/290370 | Pass |
| Km app | EGFR (ErbB1) T790M | y | ZLYTE | 25 | 25 | 25 | 0 | Pass | Pass | 0.85 | PV4803/1123633 | Pass |
| 100 | MAPK8 (JNK1) |  | ZLYTE | 33 | 18 | 25 | 15 | Pass | Pass | 0.79 | PV3319/1354818 | Pass |
|  | TNK2 (ACK) |  | LanthaScreen Binding | 25 | 26 | 25 | 1 | Pass | Pass | 0.92 | PV4807/407338 |  |
| Km app | AXL |  | ZLYTE | 22 | 25 | 24 | 3 | Pass | Pass | 0.86 | PV3971/873922 | Pass |
|  | LATS2 |  | LanthaScreen Binding | 23 | 25 | 24 | 1 | Pass | Pass | 0.91 | PV6364/1575533 |  |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | MERTK (cMER) | | ZLYTE | 27 | 22 | 24 | 5 | Pass | Pass | 0.82 | PV3627/32658 | Pass |
| | PRKACG (PRKAC gamma) | | LanthaScreen Binding | 28 | 19 | 24 | 9 | Pass | Pass | 0.66 | PV6391/1577047 | |
| Km app | AURKC (Aurora C) | | ZLYTE | 23 | 23 | 23 | 0 | Pass | Pass | 0.66 | PV3856/1078206 | Pass |
| | FGFR1 V561M | y | LanthaScreen Binding | 20 | 25 | 23 | 5 | Pass | Pass | 0.91 | PV6343/1578678 | |
| Km app | MELK | | ZLYTE | 25 | 22 | 23 | 3 | Pass | Pass | 0.85 | PV4823/819467 | Pass |
| Km app | NEK4 | | ZLYTE | 23 | 23 | 23 | 0 | Pass | Pass | 0.88 | PV4315/924342 | Pass |
| | ACVR2A | | LanthaScreen Binding | 23 | 21 | 22 | 2 | Pass | Pass | 0.76 | PV6124/862446 | |
| | ICK | | LanthaScreen Binding | 22 | 22 | 22 | 0 | Pass | Pass | 0.86 | PV6358/1577056 | |
| | MAP3K14 (NIK) | | LanthaScreen Binding | 20 | 24 | 22 | 3 | Pass | Pass | 0.91 | PV4902/1296958 | |
| | MAP3K7/MAP3K7 IP1 (TAK1-TAB1) | | LanthaScreen Binding | 22 | 22 | 22 | 0 | Pass | Pass | 0.89 | PV4394/930475 | |
| Km app | GSK3A (GSK3 alpha) | | ZLYTE | 20 | 22 | 21 | 2 | Pass | Pass | 0.91 | PV6126/862449 | Pass |
| Km app | GSK3B (GSK3 beta) | | ZLYTE | 21 | 21 | 21 | 0 | Pass | Pass | 0.79 | PV3365/371501 | Pass |
| Km app | CDK9/cyclin T1 | | Adapta | 18 | 22 | 20 | 4 | Pass | Pass | 0.88 | PV4131/1370615 | |
| Km app | EPHA4 | | ZLYTE | 18 | 21 | 20 | 2 | Pass | Pass | 0.9 | PV3651/32933 | Pass |
| Km app | HIPK2 | | ZLYTE | 21 | 19 | 20 | 2 | Pass | Pass | 0.93 | PV5275/452552 | Pass |
| 100 | MAPK10 (JNK3) | | ZLYTE | 20 | 21 | 20 | 0 | Pass | Pass | 0.9 | PV4563/1075329 | Pass |
| Km app | CAMK2D (CaMKII delta) | | ZLYTE | 18 | 19 | 19 | 1 | Pass | Pass | 0.91 | PV3373/31647 | Pass |
| | CAMK2G (CaMKII gamma) | | LanthaScreen Binding | 18 | 19 | 18 | 1 | Pass | Pass | 0.77 | PV6268/1576884 | |
| | FYN A | | LanthaScreen Binding | 16 | 21 | 18 | 6 | Pass | Pass | 0.81 | PV6346/1575529 | |
| | KIT D820E | y | LanthaScreen Binding | 18 | 19 | 18 | 2 | Pass | Pass | 0.97 | PV6307/1576885 | |
| | MAP4K3 (GLK) | | LanthaScreen Binding | 16 | 21 | 18 | 6 | Pass | Pass | 0.87 | PV6349/1579471 | |
| | MYO3B (MYO3 beta) | | LanthaScreen Binding | 17 | 20 | 18 | 3 | Pass | Pass | 0.95 | PV6367/1577055 | |
| Km app | NTRK1 (TRKA) | | ZLYTE | 16 | 20 | 18 | 3 | Pass | Pass | 0.73 | PV3144/1347534 | Pass |
| Km app | NTRK3 (TRKC) | | ZLYTE | 17 | 19 | 18 | 3 | Pass | Pass | 0.85 | PV3617/708766 | Pass |
| | RAF1 (cRAF) Y340D Y341D | y | LanthaScreen Binding | 15 | 20 | 18 | 4 | Pass | Pass | 0.91 | PV3805/1293604 | |
| | RET G691S | y | LanthaScreen Binding | 19 | 18 | 18 | 1 | Pass | Pass | 0.8 | PV6214/1570982 | |
| | BRSK2 | | LanthaScreen Binding | 16 | 17 | 17 | 1 | Pass | Pass | 0.87 | PV6259/1576239 | |
| | LIMK2 | | LanthaScreen Binding | 14 | 19 | 17 | 5 | Pass | Pass | 0.95 | PV3860/355434 | |
| | PRKACB (PRKAC beta) | | LanthaScreen Binding | 16 | 18 | 17 | 2 | Pass | Pass | 0.82 | PV6388/1577048 | |
| Km app | CDK1/cyclin B | | ZLYTE | 16 | 15 | 16 | 1 | Pass | Pass | 0.85 | PV3292/873341 | Pass |
| | CDK2/cyclin E1 | | LanthaScreen Binding | 15 | 17 | 16 | 2 | Pass | Pass | 0.66 | PV6295/1576887 | |
| Km app | EPHB2 | | ZLYTE | 14 | 17 | 16 | 3 | Pass | Pass | 0.91 | PV3625/1386867 | Pass |
| Km app | HIPK4 | | ZLYTE | 18 | 14 | 16 | 4 | Pass | Pass | 0.89 | PV3852/719847 | Pass |
| 100 | MAPK9 (JNK2) | | ZLYTE | 12 | 21 | 16 | 9 | Pass | Pass | 0.73 | PV3620/32388 | Pass |
| Km app | PIK3CD/PIK3R1 (p110 delta/p85 alpha) | | Adapta | 22 | 9 | 16 | 12 | Pass | Pass | 0.88 | PV5273/1147693 | |
| Km app | RPS6KA6 (RSK4) | | ZLYTE | 14 | 17 | 16 | 3 | Pass | Pass | 0.63 | PV4557/37496 | Pass |
| Km app | CDK7/cyclin H/MNAT1 | | Adapta | 17 | 14 | 15 | 2 | Pass | Pass | 0.8 | PV3868/1427412 | |
| Km app | EPHB4 | | ZLYTE | 15 | 14 | 15 | 2 | Pass | Pass | 0.73 | PV3251/29241 | Pass |
| 100 | MAP3K8 (COT) | | ZLYTE | 19 | 11 | 15 | 7 | Pass | Pass | 0.89 | PV4313/1111069 | Pass |
| 100 | PDK1 | | ZLYTE | 14 | 16 | 15 | 1 | Pass | Pass | 0.81 | P3001/1394674 | Pass |
| Km app | RPS6KA2 (RSK3) | | ZLYTE | 17 | 13 | 15 | 4 | Pass | Pass | 0.89 | PV3846/34468 | Pass |
| | TLK1 | | LanthaScreen Binding | 13 | 17 | 15 | 4 | Pass | Pass | 0.88 | PV6421/1576241 | |
| | EGFR (ErbB1) d746-750 | y | LanthaScreen Binding | 14 | 13 | 14 | 1 | Pass | Pass | 0.78 | PV6178/1570967 | |
| | EPHA6 | | LanthaScreen Binding | 9 | 20 | 14 | 11 | Pass | Pass | 0.63 | PV6337/1575527 | |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | PRKG2 (PKG2) | | ZLYTE | 16 | 13 | 14 | 3 | Pass | Pass | 0.87 | PV3973/273926 | Pass |
| Km app | RPS6KA3 (RSK2) | | ZLYTE | 17 | 10 | 14 | 7 | Pass | Pass | 0.83 | PV3323/1361669 | Pass |
| Km app | TEK (Tie2) | | ZLYTE | 11 | 17 | 14 | 6 | Pass | Pass | 0.59 | PV3628/34398 | Pass |
| | ALK F1174L | y | LanthaScreen Binding | 12 | 14 | 13 | 2 | Pass | Pass | 0.91 | PV6160/1570964 | |
| Km app | HIPK3 (YAK1) | | ZLYTE | 15 | 11 | 13 | 4 | Pass | Pass | 0.92 | PV4209/1076022 | Pass |
| | MAPK9 (JNK2) | | LanthaScreen Binding | 12 | 14 | 13 | 3 | Pass | Pass | 0.91 | PV3620/32388 | |
| Km app | ROCK2 | | ZLYTE | 12 | 14 | 13 | 2 | Pass | Pass | 0.74 | PV3759/843703 | Pass |
| Km app | RPS6KA1 (RSK1) | | ZLYTE | 15 | 11 | 13 | 4 | Pass | Pass | 0.83 | PV3680/880119 | Pass |
| Km app | STK22B (TSSK2) | | ZLYTE | 12 | 14 | 13 | 1 | Pass | Pass | 0.79 | PV3622/32396 | Pass |
| Km app | BMX | | ZLYTE | 12 | 13 | 12 | 1 | Pass | Pass | 0.89 | PV3371/953336 | Pass |
| Km app | CAMK1D (CaMKI delta) | | ZLYTE | 12 | 13 | 12 | 1 | Pass | Pass | 0.85 | PV3663/1042984 | Pass |
| Km app | CSK | | ZLYTE | 13 | 10 | 12 | 2 | Pass | Pass | 0.88 | P2927/1205898 | Pass |
| Km app | FGFR2 | | ZLYTE | 12 | 11 | 12 | 1 | Pass | Pass | 0.93 | PV3368/31517 | Pass |
| Km app | FRK (PTK5) | | ZLYTE | 11 | 13 | 12 | 2 | Pass | Pass | 0.84 | PV3874/34553 | Pass |
| Km app | HIPK1 (Myak) | | ZLYTE | 11 | 13 | 12 | 1 | Pass | Pass | 0.89 | PV4561/1126221 | Pass |
| | MAP3K3 (MEKK3) | | LanthaScreen Binding | 10 | 13 | 12 | 3 | Pass | Pass | 0.79 | PV3876/702480 | |
| Km app | MAP4K5 (KHS1) | | ZLYTE | 11 | 12 | 12 | 0 | Pass | Pass | 0.65 | PV3682/1383139 | Pass |
| Km app | MUSK | | ZLYTE | 15 | 8 | 12 | 7 | Pass | Pass | 0.67 | PV3834/1217900 | Pass |
| | RET M918T | y | LanthaScreen Binding | 10 | 13 | 12 | 3 | Pass | Pass | 0.64 | PV6217/1570989 | |
| Km app | DYRK1B | | ZLYTE | 14 | 9 | 11 | 5 | Pass | Pass | 0.91 | PV4649/877059 | Pass |
| | EPHA7 | | LanthaScreen Binding | 10 | 12 | 11 | 2 | Pass | Pass | 0.62 | PV3689/33790 | |
| Km app | PLK1 | | ZLYTE | 12 | 9 | 11 | 3 | Pass | Pass | 0.89 | PV3501/39441 | Pass |
| Km app | CAMK2B (CaMKII beta) | | ZLYTE | 11 | 8 | 10 | 3 | Pass | Pass | 0.81 | PV4205/35330 | Pass |
| Km app | CDC42 BPB (MRCKB) | | ZLYTE | 6 | 13 | 10 | 7 | Pass | Pass | 0.88 | PV4399/36845 | Pass |
| | CDK9 (Inactive) | | LanthaScreen Binding | 8 | 13 | 10 | 5 | Pass | Pass | 0.93 | PV6304/1579469 | |
| | CDK9/cyclin K | | LanthaScreen Binding | 11 | 9 | 10 | 2 | Pass | Pass | 0.74 | PV4335/35774 | |
| Km app | CSNK2A1 (CK2 alpha 1) | | ZLYTE | 13 | 7 | 10 | 7 | Pass | Pass | 0.73 | PV3248/1240448 | Pass |
| Km app | JAK1 | | ZLYTE | 11 | 10 | 10 | 2 | Pass | Pass | 0.62 | PV4774/1240449 | Pass |
| | MAP3K2 (MEKK2) | | LanthaScreen Binding | 11 | 9 | 10 | 2 | Pass | Pass | 0.75 | PV3822/1171755 | |
| Km app | PRKCB2 (PKC beta II) | | ZLYTE | 12 | 8 | 10 | 4 | Pass | Pass | 0.82 | P2251/930444 | Pass |
| Km app | PRKCH (PKC eta) | | ZLYTE | 12 | 8 | 10 | 4 | Pass | Pass | 0.62 | P2633/25587 | Pass |
| Km app | ROCK1 | | ZLYTE | 6 | 14 | 10 | 8 | Pass | Pass | 0.78 | PV3691/37178 | Pass |
| Km app | SGK2 | | ZLYTE | 7 | 12 | 10 | 5 | Pass | Pass | 0.78 | PV3858/1099019 | Pass |
| | STK39 (STLK3) | | LanthaScreen Binding | 10 | 9 | 10 | 1 | Pass | Pass | 0.54 | PV6412/1608283 | |
| | ALK C1156Y | y | LanthaScreen Binding | 7 | 12 | 9 | 5 | Pass | Pass | 0.98 | PV6157/1570963 | |
| Km app | EGFR (ErbB1) | | ZLYTE | 10 | 9 | 9 | 2 | Pass | Pass | 0.89 | PV3872/1004026 | Pass |
| Km app | EPHA8 | | ZLYTE | 11 | 7 | 9 | 4 | Pass | Pass | 0.81 | PV3844/36870 | Pass |
| | KIT V654A | y | LanthaScreen Binding | 7 | 10 | 9 | 3 | Pass | Pass | 0.82 | PV4132/35129 | |
| 100 | MAP2K6 (MKK6) | | ZLYTE | 0 | 19 | 9 | 19 | Pass | Pass | 0.85 | PV3318/884909 | Pass |
| Km app | NEK6 | | ZLYTE | 12 | 6 | 9 | 7 | Pass | Pass | 0.76 | PV3353/30778 | Pass |
| Km app | PIK3CG (p110 gamma) | | Adapta | 11 | 8 | 9 | 3 | Pass | Pass | 0.92 | PV4786/1153861 | |
| | CAMKK2 (CaMKK beta) | | LanthaScreen Binding | 7 | 9 | 8 | 2 | Pass | Pass | 0.93 | PV4206/35319 | |
| | CASK | | LanthaScreen Binding | 6 | 10 | 8 | 4 | Pass | Pass | 0.75 | PV6271/1576243 | |
| Km app | FES (FPS) | | ZLYTE | 9 | 7 | 8 | 2 | Pass | Pass | 0.84 | PV3354/35734 | Pass |
| | FGFR3 G697C | y | LanthaScreen Binding | 13 | 4 | 8 | 9 | Pass | Pass | 0.74 | PV6184/1570969 | |
| Km app | FGFR3 K650E | y | ZLYTE | 11 | 6 | 8 | 5 | Pass | Pass | 0.85 | PV4392/36445 | Pass |
| | MAP2K1 (MEK1) S218D S222D | y | LanthaScreen Binding | 10 | 7 | 8 | 2 | Pass | Pass | 0.92 | P3099/38541 | |
| 100 | MAP2K2 (MEK2) | | ZLYTE | 13 | 2 | 8 | 10 | Pass | Pass | 0.92 | PV3615/32519 | Pass |
| Km app | MAPK13 (p38 delta) | | ZLYTE | 7 | 9 | 8 | 2 | Pass | Pass | 0.83 | PV3656/36817 | Pass |

TABLE S5-1-continued

Project SSBK10488_30712; provides data for Cmpd1 (1000 μM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | PAK1 | | ZLYTE | 8 | 8 | 8 | 0 | Pass | Pass | 0.86 | PV3820/35463 | Pass |
| | ZAK | | LanthaScreen Binding | 6 | 10 | 8 | 4 | Pass | Pass | 0.92 | PV3882/34603 | |
| 10 | CAMK1 (CaMK1) | | Adapta | 7 | 8 | 7 | 1 | Pass | Pass | 0.86 | PV4391/36046 | |
| | CDK1/cyclin A2 | | LanthaScreen Binding | 2 | 12 | 7 | 11 | Pass | Pass | 0.73 | PV6280/1579468 | |
| Km app | CLK2 | | ZLYTE | 5 | 9 | 7 | 4 | Pass | Pass | 0.81 | PV4201/873335 | Pass |
| Km app | DCAMKL2 (DCK2) | | ZLYTE | 11 | 3 | 7 | 8 | Pass | Pass | 0.63 | PV4297/869931 | Pass |
| Km app | FER | | ZLYTE | 4 | 9 | 7 | 5 | Pass | Pass | 0.71 | PV3806/38946 | Pass |
| Km app | FRAP1 (mTOR) | | ZLYTE | 2 | 12 | 7 | 10 | Pass | Pass | 0.8 | PV4753/873345 | Pass |
| | MAP2K3 (MEK3) | | LanthaScreen Binding | 5 | 8 | 7 | 4 | Pass | Pass | 0.61 | PV3662/357368 | |
| | MAP3K5 (ASK1) | | LanthaScreen Binding | 7 | 8 | 7 | 1 | Pass | Pass | 0.72 | PV3809/666419 | |
| Km app | PIM1 | | ZLYTE | 11 | 3 | 7 | 9 | Pass | Pass | 0.76 | PV3503/811382 | Pass |
| | CDK3/cyclin E1 | | LanthaScreen Binding | 2 | 9 | 6 | 7 | Pass | Pass | 0.62 | PV6298/1579411 | |
| Km app | EPHA2 | | ZLYTE | 1 | 12 | 6 | 12 | Pass | Pass | 0.77 | PV3688/36904 | Pass |
| Km app | ERBB4 (HER4) | | ZLYTE | 8 | 5 | 6 | 4 | Pass | Pass | 0.74 | PV3626/32657 | Pass |
| Km app | FLT1 (VEGFR1) | | ZLYTE | 7 | 4 | 6 | 3 | Pass | Pass | 0.81 | PV3666/33924 | Pass |
| Km app | IRAK4 | | ZLYTE | 5 | 8 | 6 | 3 | Pass | Pass | 0.78 | PV3362/1088346 | Pass |
| Km app | KIT T670I | y | ZLYTE | 6 | 7 | 6 | 2 | Pass | Pass | 0.71 | PV3869/34504 | Pass |
| Km app | LTK (TYK1) | | ZLYTE | 5 | 7 | 6 | 1 | Pass | Pass | 0.78 | PV4651/768522 | Pass |
| Km app | MAPK1 (ERK2) | | ZLYTE | 6 | 6 | 6 | 0 | Pass | Pass | 0.86 | PV3313/904347 | Pass |
| Km app | MAPKAPK5 (PRAK) | | ZLYTE | 6 | 7 | 6 | 1 | Pass | Pass | 0.78 | PV3301/880117 | Pass |
| Km app | NTRK2 (TRKB) | | ZLYTE | 5 | 7 | 6 | 1 | Pass | Pass | 0.93 | PV3616/35706 | Pass |
| Km app | PAK6 | | ZLYTE | 9 | 4 | 6 | 5 | Pass | Pass | 0.8 | PV3502/625425 | Pass |
| Km app | PRKCI (PKC iota) | | ZLYTE | 5 | 7 | 6 | 2 | Pass | Pass | 0.77 | PV3183/28662 | Pass |
| Km app | PTK2B (FAK2) | | ZLYTE | 8 | 4 | 6 | 4 | Pass | Pass | 0.8 | PV4567/883370 | Pass |
| | TESK2 | | LanthaScreen Binding | 14 | −3 | 6 | 16 | Pass | Pass | 0.74 | PV6418/1576242 | |
| Km app | ADRBK1 (GRK2) | | ZLYTE | 3 | 7 | 5 | 4 | Pass | Pass | 0.88 | PV3361/883372 | Pass |
| Km app | ADRBK2 (GRK3) | | ZLYTE | 6 | 4 | 5 | 2 | Pass | Pass | 0.71 | PV3827/38897 | Pass |
| | ALKL1196M | y | LanthaScreen Binding | 1 | 9 | 5 | 8 | Pass | Pass | 0.92 | PV6166/1570971 | |
| Km app | BTK | | ZLYTE | 3 | 6 | 5 | 3 | Pass | Pass | 0.89 | PV3363/1405298 | Pass |
| Km app | CDK5/p35 | | ZLYTE | 7 | 2 | 5 | 5 | Pass | Pass | 0.89 | PV3000/25348 | Pass |
| Km app | EGFR (ErbB1) L861Q | y | ZLYTE | 6 | 5 | 5 | 1 | Pass | Pass | 0.89 | PV3873/34562 | Pass |
| Km app | FGFR3 | | ZLYTE | 6 | 4 | 5 | 2 | Pass | Pass | 0.84 | PV3145/28459 | Pass |
| | GRK1 | | LanthaScreen Binding | 7 | 2 | 5 | 5 | Pass | Pass | 0.96 | PV6352/1577053 | |
| 100 | MAP2K1 (MEK1) | | ZLYTE | 7 | 3 | 5 | 4 | Pass | Pass | 0.82 | PV3303/1081576 | Pass |
| | MAP2K1 (MEK1) | | LanthaScreen Binding | 6 | 5 | 5 | 1 | Pass | Pass | 0.95 | PV3303/1081567 | |
| | MAP2K2 (MEK2) | | LanthaScreen Binding | 5 | 5 | 5 | 0 | Pass | Pass | 0.94 | PV3615/32519 | |
| | MAP2K6 (MKK6) S207E T211E | y | LanthaScreen Binding | 5 | 5 | 5 | 0 | Pass | Pass | 0.91 | PV3293/877061 | |
| Km app | MAPK11 (p38 beta) | | ZLYTE | 6 | 4 | 5 | 2 | Pass | Pass | 0.85 | PV3679/1131827 | Pass |
| Km app | PAK3 | | ZLYTE | 7 | 2 | 5 | 4 | Pass | Pass | 0.86 | PV3789/34118 | Pass |
| Km app | PI4KB (PI4K beta) | | Adapta | 7 | 3 | 5 | 4 | Pass | Pass | 0.95 | PV5277/943589 | |
| Km app | STK3 (MST2) | | ZLYTE | 5 | 6 | 5 | 1 | Pass | Pass | 0.7 | PV4805/371195 | Pass |
| | STK32B (YANK2) | | LanthaScreen Binding | 1 | 8 | 5 | 7 | Pass | Pass | 0.9 | PV6406/1577058 | |
| Km app | TAOK2 (TAO1) | | ZLYTE | 3 | 6 | 5 | 3 | Pass | Pass | 0.8 | PV3760/1011094 | Pass |
| | ALK R1275Q | y | LanthaScreen Binding | 0 | 7 | 4 | 7 | Pass | Pass | 0.89 | PV6169/1570970 | |
| Km app | CDC42 BPA (MRCKA) | | ZLYTE | 4 | 4 | 4 | 0 | Pass | Pass | 0.7 | PV4398/1314130 | Pass |
| Km app | EGFR (ErbB1) L858R | y | ZLYTE | 6 | 3 | 4 | 3 | Pass | Pass | 0.72 | PV4128/279551 | Pass |
| | EPHA3 | | LanthaScreen Binding | 6 | 3 | 4 | 4 | Pass | Pass | 0.82 | PV3359/673524 | |
| Km app | GRK7 | | ZLYTE | 3 | 5 | 4 | 2 | Pass | Pass | 0.86 | PV3823/34013 | Pass |
| Km app | INSRR (IRR) | | ZLYTE | 5 | 4 | 4 | 1 | Pass | Pass | 0.91 | PV3808/34272 | Pass |
| 100 | MAPK14 (p38 alpha) | | ZLYTE | −1 | 9 | 4 | 10 | Pass | Pass | 0.87 | PV3304/1475037 | Pass |
| | MYLK (MLCK) | | LanthaScreen Binding | 5 | 3 | 4 | 2 | Pass | Pass | 0.91 | PV4339/36152 | |

TABLE S5-1-continued

Project SSBK10488_30712; provides data for Cmpd1 (1000 µM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | PRKCB1 (PKC beta I) | | ZLYTE | 5 | 3 | 4 | 2 | Pass | Pass | 0.71 | P2291/299686 | Pass |
| 100 | RAF1 (cRAF) Y340D Y341D | y | ZLYTE | 5 | 3 | 4 | 2 | Pass | Pass | 0.91 | PV3805/1293604 | Pass |
| Km app | RPS6KA5 (MSK1) | | ZLYTE | 6 | 3 | 4 | 2 | Pass | Pass | 0.84 | PV3681/380935 | Pass |
| Km app | SRMS (Srm) | | ZLYTE | 5 | 3 | 4 | 2 | Pass | Pass | 0.84 | PV4214/1110226 | Pass |
| Km app | ZAP70 | | ZLYTE | 4 | 4 | 4 | 0 | Pass | Pass | 0.86 | P2782/843705 | Pass |
| Km app | AKT2 (PKB beta) | | ZLYTE | 3 | 2 | 3 | 1 | Pass | Pass | 0.81 | PV3184/28770 | Pass |
| Km app | EPHA5 | | ZLYTE | 3 | 4 | 3 | 1 | Pass | Pass | 0.74 | PV3840/34383 | Pass |
| Km app | EPHB3 | | ZLYTE | 3 | 3 | 3 | 0 | Pass | Pass | 0.94 | PV3658/33066 | Pass |
| Km app | FGFR4 | | ZLYTE | 7 | −2 | 3 | 9 | Pass | Pass | 0.65 | P3054/26967 | Pass |
| Km app | KIT | | ZLYTE | 1 | 5 | 3 | 4 | Pass | Pass | 0.76 | P3081/1344384 | Pass |
| Km app | MAPK12 (p38 gamma) | | ZLYTE | 4 | 3 | 3 | 1 | Pass | Pass | 0.87 | PV3654/1140849 | Pass |
| Km app | NEK7 | | ZLYTE | 5 | 2 | 3 | 3 | Pass | Pass | 0.81 | PV3833/34387 | Pass |
| Km app | PAK2 (PAK65) | | ZLYTE | 6 | −1 | 3 | 7 | Pass | Pass | 0.87 | PV4565/924347 | Pass |
| Km app | PIM2 | | ZLYTE | −1 | 7 | 3 | 7 | Pass | Pass | 0.76 | PV3649/32930 | Pass |
| Km app | PRKACA (PKA) | | ZLYTE | 4 | 1 | 3 | 3 | Pass | Pass | 0.8 | P2912/37377 | Pass |
| Km app | PRKG1 | | ZLYTE | 2 | 5 | 3 | 3 | Pass | Pass | 0.9 | PV4340/893283 | Pass |
| Km app | SGKL (SGK3) | | ZLYTE | 3 | 4 | 3 | 1 | Pass | Pass | 0.87 | PV3859/38954 | Pass |
| Km app | AKT1 (PKB alpha) | | ZLYTE | 1 | 3 | 2 | 2 | Pass | Pass | 0.89 | P2999/1159806 | Pass |
| Km app | AKT3 (PKB gamma) | | ZLYTE | 3 | 1 | 2 | 2 | Pass | Pass | 0.88 | PV3185/28771 | Pass |
| Km app | CAMK2A (CaMKII alpha) | | ZLYTE | 4 | 0 | 2 | 4 | Pass | Pass | 0.89 | PV3142/28192 | Pass |
| Km app | CDK5/p25 | | ZLYTE | 3 | 1 | 2 | 2 | Pass | Pass | 0.79 | PV4676/907645 | Pass |
| Km app | CLK3 | | ZLYTE | 1 | 3 | 2 | 1 | Pass | Pass | 0.88 | PV3826/939820 | Pass |
| | DDR1 | | LanthaScreen Binding | 3 | 2 | 2 | 1 | Pass | Pass | 0.95 | PV6047/693053 | |
| Km app | GRK6 | | ZLYTE | 2 | 2 | 2 | 1 | Pass | Pass | 0.84 | PV3661/37437 | Pass |
| | KIT T670E | y | LanthaScreen Binding | 2 | 2 | 2 | 1 | Pass | Pass | 0.9 | PV6313/1575536 | |
| Km app | MAP4K2 (GCK) | | ZLYTE | 6 | −2 | 2 | 8 | Pass | Pass | 0.88 | PV4211/748356 | Pass |
| Km app | MATK (HYL) | | ZLYTE | 1 | 2 | 2 | 0 | Pass | Pass | 0.83 | PV3370/31553 | Pass |
| Km app | MST4 | | ZLYTE | 2 | 3 | 2 | 0 | Pass | Pass | 0.76 | PV3690/1205875 | Pass |
| Km app | PASK | | ZLYTE | 3 | 1 | 2 | 2 | Pass | Pass | 0.68 | PV3972/762487 | Pass |
| Km app | STK23 (MSSK1) | | ZLYTE | 2 | 1 | 2 | 1 | Pass | Pass | 0.86 | PV3880/1214750 | Pass |
| | TAOK3 (JIK) | | LanthaScreen Binding | 3 | 1 | 2 | 2 | Pass | Pass | 0.86 | PV3652/32935 | |
| Km app | ALK | | ZLYTE | 4 | −2 | 1 | 5 | Pass | Pass | 0.86 | PV3867/1542512 | Pass |
| | CDK8/cyclin C | | LanthaScreen Binding | 0 | 3 | 1 | 4 | Pass | Pass | 0.94 | PV4402/1177216 | |
| Km app | CSNK1A1 (CK1 alpha 1) | | ZLYTE | 2 | 1 | 1 | 1 | Pass | Pass | 0.84 | PV3850/1004025 | Pass |
| Km app | CSNK1E (CK1 epsilon) | | ZLYTE | −2 | 4 | 1 | 6 | Pass | Pass | 0.75 | PV3500/866725 | Pass |
| Km app | CSNK1G3 (CK1 gamma 3) | | ZLYTE | 4 | −2 | 1 | 6 | Pass | Pass | 0.85 | PV3838/1140848 | Pass |
| Km app | IGF1R | | ZLYTE | 1 | 2 | 1 | 2 | Pass | Pass | 0.78 | PV3250/924345 | Pass |
| | MAP2K6 (MKK6) | | LanthaScreen Binding | −2 | 4 | 1 | 6 | Pass | Pass | 0.86 | PV3318/884909 | |
| Km app | MAPK14 (p38 alpha) Direct | | ZLYTE | 2 | 1 | 1 | 1 | Pass | Pass | 0.94 | PV3304/1475037 | Pass |
| Km app | PTK2 (FAK) | | ZLYTE | 0 | 2 | 1 | 2 | Pass | Pass | 0.79 | PV3832/1378055 | Pass |
| Km app | RPS6KA4 (MSK2) | | ZLYTE | 0 | 2 | 1 | 3 | Pass | Pass | 0.84 | PV3782/990109 | Pass |
| Km app | STK24 (MST3) | | ZLYTE | −5 | 8 | 1 | 14 | Pass | Pass | 0.7 | PV3650/32932 | Pass |
| | TEC | | LanthaScreen Binding | 0 | 2 | 1 | 2 | Pass | Pass | 0.93 | PV3269/910411 | |
| | WNK2 | | LanthaScreen Binding | −4 | 5 | 1 | 9 | Pass | Pass | 0.86 | PV4341/35976 | |
| | CAMKK1 (CAMKKA) | | LanthaScreen Binding | 2 | −1 | 0 | 2 | Pass | Pass | 0.8 | PV4670/406782 | |
| | DDR2 | | LanthaScreen Binding | 0 | 1 | 0 | 2 | Pass | Pass | 0.94 | PV3870/916220 | |
| Km app | INSR | | ZLYTE | −1 | 1 | 0 | 3 | Pass | Pass | 0.81 | PV3781/1314127 | Pass |
| Km app | MAPK3 (ERK1) | | ZLYTE | 3 | −2 | 0 | 5 | Pass | Pass | 0.86 | PV3311/1255534 | Pass |
| Km app | MAPKAPK2 | | ZLYTE | 0 | −1 | 0 | 1 | Pass | Pass | 0.82 | PV3317/36559 | Pass |
| 10 | PI4KA (PI4K alpha) | | Adapta | 3 | −3 | 0 | 6 | Pass | Pass | 0.81 | PV5689/1131829 | |
| Km app | PRKCD (PKC delta) | | ZLYTE | 4 | −4 | 0 | 8 | Pass | Pass | 0.73 | P2293/39038 | Pass |
| | RIPK3 | | LanthaScreen Binding | −1 | 1 | 0 | 2 | Pass | Pass | 0.84 | PV6397/1610742 | |

TABLE S5-1-continued

Project SSBK10488_30712; provides data for Cmpd1 (1000 µM).

| ATP | Kinase | mutant | Technology | % Inhibition 1 | % Inhibition 2 | % Inhibition Avg | Dup Difference | Donor Interference | Acceptor Interference | Z' | Kinase Part#/Lot# | Dev Reaction Interference |
|---|---|---|---|---|---|---|---|---|---|---|---|---|
| Km app | SPHK1 | | Adapta | 10 | −9 | 0 | 19 | Pass | Pass | 0.77 | PV5214/933639 | |
| Km app | STK4 (MST1) | | ZLYTE | 0 | 0 | 0 | 0 | Pass | Pass | 0.73 | PV3854/38395 | Pass |
| | CDK5 (Inactive) | | LanthaScreen Binding | 1 | −2 | −1 | 3 | Pass | Pass | 0.68 | PV6301/1576893 | |
| Km app | DNA-PK | | ZLYTE | 2 | −4 | −1 | 7 | Pass | Pass | 0.69 | PV5864/1594760 | Pass |
| Km app | DYRK4 | | ZLYTE | −2 | 0 | −1 | 1 | Pass | Pass | 0.82 | PV3871/37361 | Pass |
| Km app | EEF2K | | ZLYTE | −1 | 0 | −1 | 1 | Pass | Pass | 0.87 | PV4559/1075327 | Pass |
| Km app | ERBB2 (HER2) | | ZLYTE | 0 | −3 | −1 | 3 | Pass | Pass | 0.74 | PV3366/1185123 | Pass |
| Km app | PTK6 (Brk) | | ZLYTE | −1 | −1 | −1 | 0 | Pass | Pass | 0.86 | PV3291/1205876 | Pass |
| | STK32C (YANK3) | | LanthaScreen Binding | −4 | 3 | −1 | 6 | Pass | Pass | 0.68 | PV6409/1577045 | |
| Km app | CAMK4 (CaMKIV) | | ZLYTE | −2 | −2 | −2 | 0 | Pass | Pass | 0.84 | PV3310/1103512 | Pass |
| | LATS1 | | LanthaScreen Binding | −5 | 1 | −2 | 6 | Pass | Pass | 0.62 | PV6361/1575532 | |
| 10 | PIK3C2B (PI3K-C2 beta) | | Adapta | 3 | −7 | −2 | 9 | Pass | Pass | 0.87 | PV5374/1223244 | |
| Km app | PRKCA (PKC alpha) | | ZLYTE | 0 | −5 | −2 | 6 | Pass | Pass | 0.71 | P2232/38479 | Pass |
| Km app | SRPK1 | | ZLYTE | −1 | −2 | −2 | 2 | Pass | Pass | 0.94 | PV4215/1182336 | Pass |
| Km app | STK25 (YSK1) | | ZLYTE | 0 | −4 | −2 | 4 | Pass | Pass | 0.8 | PV3657/33163 | Pass |
| | WNK3 | | LanthaScreen Binding | −3 | 0 | −2 | 2 | Pass | Pass | 0.83 | PV4342/36047 | |
| Km app | CSNK1D (CK1 delta) | | ZLYTE | −1 | −5 | −3 | 5 | Pass | Pass | 0.83 | PV3665/843704 | Pass |
| Km app | FGFR1 | | ZLYTE | −5 | −2 | −3 | 3 | Pass | Pass | 0.8 | PV3146/28427 | Pass |
| Km app | GRK5 | | ZLYTE | 5 | −10 | −3 | 15 | Pass | Pass | 0.82 | PV3824/879275 | Pass |
| Km app | MAPKAPK3 | | ZLYTE | 1 | −8 | −3 | 9 | Pass | Pass | 0.86 | PV3299/38895 | Pass |
| Km app | PRKCE (PKC epsilon) | | ZLYTE | 1 | −6 | −3 | 8 | Pass | Pass | 0.83 | P2292/37717 | Pass |
| Km app | SRPK2 | | ZLYTE | −2 | −4 | −3 | 2 | Pass | Pass | 0.91 | PV3829/900365 | Pass |
| | CDK11 (Inactive) | | LanthaScreen Binding | −1 | −7 | −4 | 7 | Pass | Pass | 0.71 | PV6283/1576889 | |
| Km app | GRK4 | | ZLYTE | −4 | −5 | −5 | 1 | Pass | Pass | 0.86 | PV3807/618977 | Pass |
| Km app | PIK3CA/PIK3R1 (p110 alpha/p85 alpha) | | Adapta | −5 | −4 | −5 | 1 | Pass | Pass | 0.79 | PV4788/616250 | |
| Km app | PKN1 (PRK1) | | ZLYTE | −6 | −4 | −5 | 2 | Pass | Pass | 0.68 | PV3790/356552 | Pass |
| Km app | PRKCG (PKC gamma) | | ZLYTE | −9 | −1 | −5 | 8 | Pass | Pass | 0.73 | P2233/39126 | Pass |
| Km app | CSNK1G1 (CK1 gamma 1) | | ZLYTE | −14 | 2 | −6 | 16 | Pass | Pass | 0.77 | PV3825/34360 | Pass |
| Km app | GSG2 (Haspin) | | Adapta | 7 | −20 | −6 | 26 | Pass | Pass | 0.71 | PV5708/869949 | |
| Km app | ACVR1B (ALK4) | | ZLYTE | −10 | −4 | −7 | 6 | Pass | Pass | 0.9 | PV4312/919690 | Pass |
| Km app | PIK3C3 (hVPS34) | | Adapta | −5 | −9 | −7 | 4 | Pass | Pass | 0.91 | PV5126/853378 | |
| Km app | PIK3C2A (PI3K-C2 alpha) | | Adapta | −7 | −9 | −8 | 2 | Pass | Pass | 0.88 | PV5586/1123632 | |
| 10 | SPHK2 | | Adapta | −16 | −2 | −9 | 14 | Pass | Pass | 0.56 | PV5216/1296957 | |
| Km app | CSNK1G2 (CK1 gamma 2) | | ZLYTE | −7 | −16 | −11 | 9 | Pass | Pass | 0.79 | PV3499/1120155 | Pass |
| Km app | PRKCQ (PKC theta) | | ZLYTE | −6 | −17 | −12 | 11 | Pass | Pass | 0.76 | P2996/26231 | Pass |
| 100 | BRAF | | ZLYTE | −18 | −10 | −14 | 8 | Pass | Pass | 0.83 | PV3848/1258788 | Pass |
| Km app | PRKCZ (PKC zeta) | | ZLYTE | −18 | −16 | −17 | 2 | Pass | Pass | 0.7 | P2273/31602 | Pass |

TABLE S5-2

| Technology | ATP | IC50 (nM) | Hill-slope | R2 | fold selectivity (TBK1) | fold selectivity (IKBKE) |
|---|---|---|---|---|---|---|
| ZLYTE | Km app | 1.04 | 1.12 | 0.9966 | 1.0 | 0.2 |
| LanthaScreen Binding | | 2.71 | 0.8 | 0.9917 | 2.6 | 0.5 |
| LanthaScreen Binding | | 4.35 | 1.27 | 0.9998 | 4.2 | 0.8 |
| ZLYTE | Km app | 5.59 | 1.06 | 0.9955 | 5.4 | 1.0 |
| ZLYTE | Km app | 14.2 | 0.55 | 0.9914 | 13.7 | 2.5 |
| LanthaScreen Binding | | 14.8 | 1.25 | 0.9989 | 14.2 | 2.6 |
| LanthaScreen Binding | | 30.9 | 0.84 | 0.9797 | 29.7 | 5.5 |
| LanthaScreen Binding | | 31.5 | 0.88 | 0.9956 | 30.3 | 5.6 |
| Adapta | Km app | 34.9 | 0.99 | 0.9945 | 33.6 | 6.2 |
| ZLYTE | Km app | 35.1 | 1 | 0.9994 | 33.8 | 6.3 |

TABLE S5-2-continued

| Technology | ATP | IC50 (nM) | Hill-slope | R2 | fold selectivity (TBK1) | fold selectivity (IKBKE) |
|---|---|---|---|---|---|---|
| ZLYTE | Km app | 35.8 | 1.11 | 0.9993 | 34.4 | 6.4 |
| ZLYTE | Km app | 41.5 | 1.49 | 0.9978 | 39.9 | 7.4 |
| ZLYTE | Km app | 45.6 | 1.01 | 0.9981 | 43.8 | 8.2 |
| ZLYTE | Km app | 47.7 | 0.84 | 0.9995 | 45.9 | 8.5 |
| ZLYTE | Km app | 55 | 0.96 | 0.9993 | 52.9 | 9.8 |
| ZLYTE | Km app | 59 | 0.69 | 0.9971 | 56.7 | 10.6 |
| LanthaScreen Binding | | 74.1 | 1 | 0.9972 | 71.3 | 13.3 |
| LanthaScreen Binding | | 78.7 | 0.86 | 0.9971 | 75.7 | 14.1 |
| Adapta | Km app | 80.6 | 1 | 0.9983 | 77.5 | 14.4 |
| ZLYTE | Km app | 81.3 | 1.12 | 0.9991 | 78.2 | 14.5 |
| LanthaScreen Binding | | 81.6 | 1.42 | 0.9789 | 78.5 | 14.6 |
| ZLYTE | Km app | 90.9 | 1.11 | 0.9974 | 87.4 | 16.3 |
| LanthaScreen Binding | | 104 | 1.22 | 0.997 | 100.0 | 18.6 |
| LanthaScreen Binding | | 156 | 0.95 | 0.9986 | 150.0 | 27.9 |

REFERENCES

Pitt, J. M. et al. Resistance Mechanisms to Immune-Checkpoint Blockade in Cancer: Tumor-Intrinsic and -Extrinsic Factors. Immunity 44, 1255-1269, doi:10.1016/j.immuni.2016.06.001 (2016).

Zitvogel, L., Pitt, J. M., Daillere, R., Smyth, M. J. & Kroemer, G. Mouse models in oncoimmunology. Nat Rev Cancer 16, 759-773, doi:10.1038/nrc.2016.91 (2016).

Aref, A. R. et al. Screening therapeutic EMT blocking agents in a three-dimensional microenvironment. Integr Biol (Camb) 5, 381-389, doi:10.1039/c2ib20209c (2013).

Yu, M. et al. Cancer therapy. Ex vivo culture of circulating breast tumor cells for individualized testing of drug susceptibility. Science 345, 216-220, doi:10.1126/science.1253533 (2014).

Gao, D. et al. Organoid cultures derived from patients with advanced prostate cancer. Cell 159, 176-187, doi:10.1016/j.cell.2014.08.016 (2014).

Hugo, W. et al. Genomic and Transcriptomic Features of Response to Anti-PD-1 Therapy in Metastatic Melanoma. Cell 165, 35-44, doi:10.1016/j.cell.2016.02.065 (2016).

Chen, P. L. et al. Analysis of immune signatures in longitudinal tumor samples yields insight into biomarkers of response and mechanisms of resistance to immune checkpoint blockade. Cancer Discov, doi:10.1158/2159-8290.CD-15-1545 (2016).

Smyth, M. J., Ngiow, S. F., Ribas, A. & Teng, M. W. Combination cancer immunotherapies tailored to the tumor microenvironment. Nat Rev Clin Oncol 13, 143-158, doi:10.1038/nrclinonc.2015.209 (2016).

Friedman, A. A., Letai, A., Fisher, D. E. & Flaherty, K. T. Precision medicine for cancer with next-generation functional diagnostics. Nat Rev Cancer 15, 747-756, doi:10.1038/nrc4015 (2015).

Zhu, Z. et al. Inhibition of KRAS-driven tumorigenicity by interruption of an autocrine cytokine circuit. Cancer Discov 4, 452-465, doi:10.1158/2159-8290.CD-13-0646 (2014).

Peggs, K. S., Quezada, S. A., Chambers, C. A., Korman, A. J. & Allison, J. P. Blockade of CTLA-4 on both effector and regulatory T cell compartments contributes to the antitumor activity of anti-CTLA-4 antibodies. J Exp Med 206, 1717-1725, doi:10.1084/jem.20082492 (2009).

Curran, M. A., Montalvo, W., Yagita, H. & Allison, J. P. PD-1 and CTLA-4 combination blockade expands infiltrating T cells and reduces regulatory T and myeloid cells within B16 melanoma tumors. Proc Natl Acad Sci USA 107, 4275-4280, doi:10.1073/pnas.0915174107 (2010).

Woo, S. R. et al. Immune inhibitory molecules LAG-3 and PD-1 synergistically regulate T-cell function to promote tumoral immune escape. Cancer Res 72, 917-927, doi:10.1158/0008-5472.CAN-11-1620 (2012).

Ribas, A. et al. Association of Pembrolizumab With Tumor Response and Survival Among Patients With Advanced Melanoma. JAMA 315, 1600-1609, doi:10.1001/jama.2016.4059 (2016).

Nghiem, P. T. et al. PD-1 Blockade with Pembrolizumab in Advanced Merkel-Cell Carcinoma. N Engl J Med 374, 2542-2552, doi:10.1056/NEJMoa1603702 (2016).

Duraiswamy, J., Kaluza, K. M., Freeman, G. J. & Coukos, G. Dual blockade of PD-1 and CTLA-4 combined with tumor vaccine effectively restores T-cell rejection function in tumors. Cancer Res 73, 3591-3603, doi:10.1158/0008-5472.CAN-12-4100 (2013).

Van Allen, E. M. et al. Genomic correlates of response to CTLA-4 blockade in metastatic melanoma. Science 350, 207-211, doi:10.1126/science.aad0095 (2015).

Ribas, A. et al. PD-1 Blockade Expands Intratumoral Memory T Cells. Cancer Immunol Res 4, 194-203, doi:10.1158/2326-6066.CIR-15-0210 (2016).

Bindea, G. et al. Spatiotemporal dynamics of intratumoral immune cells reveal the immune landscape in human cancer. Immunity 39, 782-795, doi:10.1016/j.immuni.2013.10.003 (2013).

Cancer Genome Atlas, N. Genomic Classification of Cutaneous Melanoma. Cell 161, 1681-1696, doi:10.1016/j.cell.2015.05.044 (2015).

Cancer Genome Atlas, N. Comprehensive molecular portraits of human breast tumors. Nature 490, 61-70, doi:10.1038/nature11412 (2012).

Cancer Genome Atlas, N. Comprehensive genomic characterization of head and neck squamous cell carcinomas. Nature 517, 576-582, doi:10.1038/nature14129 (2015).

Cancer Genome Atlas Research, N. Comprehensive molecular characterization of urothelial bladder carcinoma. Nature 507, 315-322, doi:10.1038/nature12965 (2014).

Dieu-Nosjean, M. C. et al. Tertiary lymphoid structures, drivers of the anti-tumor responses in human cancers. Immunol Rev 271, 260-275, doi:10.1111/imr.12405 (2016).

Tirosh, I. et al. Dissecting the multicellular ecosystem of metastatic melanoma by single-cell RNA-seq. Science 352, 189-196, doi:10.1126/science.aad0501 (2016).

Onder, L. et al. Endothelial cell-specific lymphotoxin-beta receptor signaling is critical for lymph node and high endothelial venule formation. J Exp Med 210, 465-473, doi:10.1084/jem.20121462 (2013).

Herbst, R. S. et al. Predictive correlates of response to the anti-PD-L1 antibody MPDL3280A in cancer patients. Nature 515, 563-567, doi:10.1038/nature14011 (2014).

Benci, J. L. et al. Tumor Interferon Signaling Regulates a Multigenic Resistance Program to Immune Checkpoint Blockade. Cell 167, 1540-1554 e1512, doi:10.1016/j.cell.2016.11.022 (2016).

Vanneman, M. & Dranoff, G. Combining immunotherapy and targeted therapies in cancer treatment. Nat Rev Cancer 12, 237-251, doi:10.1038/nrc3237 (2012).

Yu, J. et al. Regulation of T-cell activation and migration by the kinase TBK1 during neuroinflammation. Nat Commun 6, 6074, doi:10.1038/ncomms7074 (2015).

Zhang, J. et al. IkappaB Kinase epsilon Is an NFATc1 Kinase that Inhibits T Cell Immune Response. Cell Rep 16, 405-418, doi:10.1016/j.celrep.2016.05.083 (2016).

Liao, Y., Smyth, G. K. & Shi, W. FeatureCounts: An efficient general purpose program for assigning sequence reads to genomic features. Bioinformatics 30, 923-930, doi: 10.1093/bioinformatics/btt656 (2014).

Robinson, M. D., McCarthy, D. J. & Smyth, G. K. edgeR: a Bioconductor package for differential expression analysis of digital gene expression data. Bioinformatics 26, 139-140, doi:10.1093/bioinformatics/btp616 (2009).

Kim, D. et al. TopHat2: accurate alignment of transcriptomes in the presence of insertions, deletions and gene fusions. Genome Biol 14, R36, doi:10.1186/gb-2013-14-4-r36 (2013).

Love, M. I., Huber, W. & Anders, S. Moderated estimation of fold change and dispersion for RNA-seq data with DESeq2. Genome Biol 15, 550, doi:10.1186/s13059-014-0550-8

Deng, R. et al. Preclinical pharmacokinetics, pharmacodynamics, tissue distribution, and tumor penetration of anti-PD-L1 monoclonal antibody, an immune checkpoint inhibitor. MAbs 8, 593-603, doi:10.1080/19420862.2015.1136043 (2016).

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A method for evaluating primary patient-derived tumor cell spheroids in a three-dimensional microfluidic device, the method comprising:
   obtaining primary patient-derived tumor cell spheroids from an enzyme treated tumor sample,
   suspending a first aliquot of the primary patient-derived tumor cell spheroids in a biocompatible gel,
   suspending a second aliquot of the primary patient-derived tumor cell spheroids in a biocompatible gel,
   placing the first aliquot of the primary patient-derived tumor cell spheroids in the biocompatible gel in a first three-dimensional microfluidic device,
   contacting the first aliquot with a first fluorophore dye selective for dead cells, the first fluorophore dye emitting fluorescence at a first wavelength when bound to a dead cell,
   contacting the first aliquot with a second fluorophore dye selective for live cells, the second fluorophore dye emitting fluorescence at a second wavelength different from the first wavelength when bound to a live cell,
   quantitating total fluorescence using a camera emitted by each of the first and second fluorophore dyes in the primary patient-derived tumor cell spheroids in the first aliquot within the first three-dimensional microfluidic device,
   placing the second aliquot of the primary patient-derived tumor cell spheroids in the biocompatible gel in a second three-dimensional microfluidic device,
   contacting the second aliquot with the first fluorophore dye,
   contacting the second aliquot with the second fluorophore dye, wherein the contacting of the second aliquot with the first fluorophore dye and the second fluorophore dye is carried out at least 24 hours after the contacting of the first aliquot with the first fluorophore dye and the second fluorophore dye,
   quantitating total fluorescence using a camera emitted by each of the first and second fluorophore dyes in the primary patient-derived tumor cell spheroids in the second aliquot within the second three-dimensional microfluidic device, and,
   assessing a ratio of live cells to dead cells in each of the aliquots based on the total fluorescence quantitated in each of the three-dimensional microfluidic devices.

2. The method of claim 1, wherein the total fluorescence emitted by each of the first and second fluorophore dyes is quantitated using a camera at a resolution of at least 2× from directly above or below each of the three-dimensional devices using a moveable stage.

3. The method of claim 1, wherein the second aliquot is contacted with at least a first test compound during the placing of the second aliquot in the biocompatible gel in the second three-dimensional microfluidic device, and wherein said contacting of the second aliquot with the first test compound occurs for at least 24 hours, at least two days, at least three days, at least four days, at least five days, or at least 6 days.

4. The method of claim 3, wherein the first test compound is a small molecule, a nucleic acid molecule, an RNAi compound, an aptamer, a protein or a peptide, an antibody or antigen-binding antibody fragment, a ligand or receptor-binding protein, a gene therapy vector, or a combination thereof.

5. The method of claim 3, wherein the first test compound is a chemotherapeutic compound, an immunomodulatory compound, or radiation.

6. The method of claim 5, wherein the first test compound is an alkylating compound, an antimetabolite, an anthracycline, a proteasome inhibitor, or an mTOR inhibitor.

7. The method of claim 3, wherein the first test compound is an immune modulator.

8. The method of claim 1, wherein the second aliquot is contacted with at least a first test compound and a second test compound during the placing of the second aliquot in the biocompatible gel in the second three-dimensional microfluidic device, and wherein said contacting of the second aliquot with the first test compound and the second test compound occurs for at least 24 hours.

9. The method of claim 1, wherein the first and the second aliquots each contains between about 15 and 30 spheroids.

10. The method of claim 1, wherein the first aliquot is placed in the first three-dimensional microfluidic device, said culturing being for less than 6 hours, less than 3 hours, less than 2 hours, or less than 1 hour prior to contacting the first aliquot with the first and second fluorophore dyes.

11. The method of claim 10, wherein the first aliquot in the first three-dimensional microfluidic device is not cultured prior to contacting the first aliquot with the first and second fluorophore dyes.

12. The method of claim 1, wherein the primary patient-derived tumor cell spheroids are obtained from a tumor sample treated with collagenase.

13. The method of claim 1, wherein the first fluorophore dye is a DNA-dependent stain, and/or the second fluorophore dye is either a DNA-dependent stain or a non-DNA-dependent fluorophore dye.

14. The method of claim 1, wherein the primary patient-derived tumor cell spheroids are obtained by
   mincing a primary tumor sample in a medium supplemented with serum;
   treating the minced primary tumor sample with an enzyme; and
   harvesting tumor cell spheroids from the enzyme treated sample.

15. The method of claim 1, wherein the biocompatible gel is collagen, a gel formed from basement membrane matrix, or fibrin hydrogel.

16. The method of claim 1, wherein the tumor sample is derived from murine tissue of a Bladder MBT-2, Breast 4T1, EMT6, Colon, Colon26, CT-26, MC38, Fibrosarcoma WEHI-164, Kidney Renca, Leukemia C1498, L1210, Liver H22, KLN205, LL/2, LewisLung, Lymphoma A20 S, E.G7-OVA, EL4, Mastocytoma P815, Melanoma B16-BL6, B16-F10, S91, Myeloma MPC-11, Neuroblastoma Neuro-2a, Ovarian: IDB, Pancreatic Pan02, Plasmacytoma J558, or Prostate RM-1 murine model.

17. The method of claim 1, wherein the tumor sample is a patient derived xenograft (PDX).

18. The method of claim 1, wherein the first three-dimensional microfluidic device and/or the second three-dimensional microfluidic device comprises:
   one or more fluid channels flanked by one or more gel cage regions, wherein the one or more gel cage regions comprises the biocompatible gel in which the tumor cell spheroids are suspended.

19. The method of claim 1, wherein the first three-dimensional microfluidic device and/or the second three-dimensional microfluidic device comprises:
   a substrate comprised of an optically transparent material and further comprising
   i) one or more fluid channels;
   ii) one or more fluid channel inlets;

iii) one or more fluid channel outlets;
iv) one or more gel cage regions; and
v) a plurality of posts;

wherein all or a portion of each of the one or more gel cage regions is flanked by all or a portion of the one or more fluid channels, thereby creating one or more gel cage region-fluid channel interface regions; each of the one or more gel cage regions comprises at least one row of posts which forms the gel cage region; and each of the one or more gel cage regions has a height of less than 500 μm.

20. The method of claim 1, wherein the first fluorophore dye is propidium iodide and the second fluorophore dye is acridine orange.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
gaggcagatg gaacttgagc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
ctggggatct tcgaatgcta                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ccaactctga gtggcaccaa                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
tgaacactac agcaggcacc                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
cgcagaagag gaggaggatt                                                    20

<210> SEQ ID NO 6
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 6
gaggaaaggg gcagttgagt                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
ctctgcttct catgctgctg                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
tgagggtcca cacacacaat                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
atccctgggt acatcgtgag                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
gcttcatctt ggctgaggtc                                          20

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 11
cagattggct acccaactgt t                                        21

<210> SEQ ID NO 12
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 12
ggaaggtgta atccgtctcc ac                                       22